US007541184B2

(12) United States Patent
Berenson et al.

(10) Patent No.: US 7,541,184 B2
(45) Date of Patent: *Jun. 2, 2009

(54) ACTIVATION AND EXPANSION OF CELLS

(75) Inventors: Ronald J. Berenson, Mercer Island, WA (US); Che Law, Shoreline, WA (US); Mark Bonyhadi, Issaquah, WA (US); Narinder Saund, Seattle, WA (US); Stewart Craig, Issaquah, WA (US); Alan Hardwick, Seattle, WA (US); Dale Kalamasz, Redmond, WA (US); David McMillen, Seattle, WA (US); Harjinder Singh Chana, Issaquah, WA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/762,210

(22) Filed: Jan. 20, 2004

(65) Prior Publication Data
US 2004/0241162 A1 Dec. 2, 2004

Related U.S. Application Data

(63) Continuation-in-part of application No. 10/350,305, filed on Jan. 22, 2003, which is a continuation-in-part of application No. 10/187,467, filed on Jun. 28, 2002, which is a continuation-in-part of application No. 10/133,236, filed on Apr. 26, 2002, now Pat. No. 6,867,041, which is a continuation-in-part of application No. 09/960,264, filed on Sep. 20, 2001, now Pat. No. 6,797,514, which is a continuation-in-part of application No. 09/794,230, filed on Feb. 26, 2001, now Pat. No. 6,905,874.

(60) Provisional application No. 60/249,902, filed on Nov. 17, 2000, provisional application No. 60/184,788, filed on Feb. 24, 2000.

(51) Int. Cl.
C12N 5/00 (2006.01)
(52) U.S. Cl. .............. 435/375; 435/325; 435/372.3
(58) Field of Classification Search ............ 435/325, 435/326, 375, 377, 372.3; 436/526
See application file for complete search history.

(56) References Cited

U.S. PATENT DOCUMENTS

| 4,464,456 A | 8/1984 | Fujikawa et al. ............ 430/281 |
|---|---|---|
| 4,654,210 A | 3/1987 | Kung et al. .................... 424/85 |
| 4,844,893 A | 7/1989 | Honsik et al. ............... 424/85.8 |
| 5,057,423 A | 10/1991 | Hiserodt et al. ......... 435/240.23 |
| 5,081,029 A | 1/1992 | Zarling et al. ............ 435/172.3 |
| 5,106,746 A | 4/1992 | Ho ......................... 435/240.25 |
| 5,116,964 A | 5/1992 | Capon et al. .................... 536/27 |
| 5,166,320 A | 11/1992 | Wu et al. ...................... 530/395 |
| 5,190,878 A | 3/1993 | Wilhelm ....................... 435/285 |
| 5,223,426 A | 6/1993 | Skibbens et al. ......... 435/240.27 |
| 5,260,422 A | 11/1993 | Clark et al. .................. 530/403 |
| 5,336,603 A | 8/1994 | Capon et al. ................ 435/69.7 |
| 5,434,131 A | 7/1995 | Linsley et al. ................... 514/2 |
| 5,443,983 A | 8/1995 | Ochoa et al. ............. 435/240.2 |
| 5,468,635 A | 11/1995 | Komiya et al. .......... 435/240.21 |
| 5,470,730 A | 11/1995 | Greenberg et al. ........ 435/172.3 |
| 5,521,288 A | 5/1996 | Linsley et al. ............. 530/387.3 |
| 5,529,921 A | 6/1996 | Peterson et al. ........... 435/240.2 |
| 5,547,963 A | 8/1996 | Poindron et al. ............. 514/317 |
| 5,554,512 A | 9/1996 | Lyman et al. ............... 435/69.5 |
| 5,595,881 A | 1/1997 | Kendrick et al. ........... 435/7.21 |
| 5,635,354 A | 6/1997 | Kourilsky et al. ............... 435/6 |
| 5,648,219 A | 7/1997 | MacKay et al. ................. 435/6 |
| 5,672,505 A | 9/1997 | Jones et al. |
| 5,674,704 A | 10/1997 | Goodwin et al. ........... 435/69.1 |
| 5,677,139 A | 10/1997 | Johnson et al. ................ 435/29 |
| 5,688,915 A | 11/1997 | Ron et al. ..................... 530/380 |
| 5,724,551 A | 3/1998 | Greenstein et al. ........... 435/375 |
| 5,728,388 A | 3/1998 | Terman .................... 424/237.1 |
| 5,735,279 A | 4/1998 | Klaveness et al. ............ 128/654 |
| 5,738,852 A | 4/1998 | Robinson et al. ......... 424/199.1 |
| 5,759,546 A | 6/1998 | Weinberg et al. ......... 424/179.1 |
| 5,766,944 A | 6/1998 | Ruiz | |

(Continued)

FOREIGN PATENT DOCUMENTS

CA 2 304 268 4/1999

(Continued)

OTHER PUBLICATIONS

Bonyhadi, M. et al., "Autologous T Cell Therapy for B-CLL," *Blood* 100(11), Abstract No. 774, Nov. 16, 2002.

(Continued)

Primary Examiner—L Blaine Lankford
Assistant Examiner—Taeyoon Kim
(74) Attorney, Agent, or Firm—Seed IP Law Group PLLC

(57) ABSTRACT

The present invention relates generally to methods for activating and expanding cells, and more particularly, to a novel method to activate and/or stimulate cells that maximizes the expansion of such cells to achieve dramatically high densities. In the various embodiments, cells are activated and expanded to very high densities in a short period of time. In certain embodiments, cells are activated and expanded to very high numbers of cells in a short period of time. Compositions of cells activated and expanded by the methods herein are further provided.

2 Claims, 52 Drawing Sheets

U.S. PATENT DOCUMENTS

| | | | |
|---|---|---|---|
| 5,766,947 A | 6/1998 | Rittershaus et al. | 435/334 |
| 5,773,573 A | 6/1998 | Holms | 530/327 |
| 5,776,966 A | 7/1998 | North | 514/410 |
| 5,788,963 A | 8/1998 | Murphy et al. | 424/93.21 |
| 5,804,442 A | 9/1998 | Romet-Lemonne et al. | 435/374 |
| 5,827,642 A | 10/1998 | Riddell et al. | 435/2 |
| 5,830,462 A | 11/1998 | Crabtree et al. | 424/93.21 |
| 5,830,473 A | 11/1998 | Thierfelder | 424/172.1 |
| 5,837,447 A | 11/1998 | Gorski | 435/6 |
| 5,837,477 A | 11/1998 | Germain et al. | |
| 5,843,435 A | 12/1998 | Slavin | 424/93.71 |
| 5,843,635 A | 12/1998 | Schlossman et al. | 425/5 |
| 5,849,589 A | 12/1998 | Tedder et al. | 435/377 |
| 5,851,756 A | 12/1998 | Steinman et al. | 435/2 |
| 5,853,719 A | 12/1998 | Nair et al. | 424/93.21 |
| 5,858,358 A | 1/1999 | June et al. | 424/130.1 |
| 5,861,486 A | 1/1999 | Devore et al. | 530/356 |
| 5,869,270 A | 2/1999 | Rhode et al. | 435/7.24 |
| 5,869,337 A | 2/1999 | Crabtree et al. | 435/372.3 |
| 5,871,728 A | 2/1999 | Thomson et al. | 424/93.7 |
| 5,871,753 A | 2/1999 | Crabtree et al. | 424/280.1 |
| 5,872,222 A | 2/1999 | Chang | 530/391.1 |
| 5,874,307 A | 2/1999 | Ohno et al. | 435/372.3 |
| 5,877,397 A | 3/1999 | Lonberg et al. | 800/2 |
| 5,883,223 A | 3/1999 | Gray | 530/328 |
| 5,888,511 A | 3/1999 | Skurkovich et al. | 424/145.1 |
| 5,888,807 A | 3/1999 | Palsson et al. | 435/293.2 |
| 5,910,403 A | 6/1999 | Hellerstein | 435/4 |
| 5,928,639 A | 7/1999 | Slavin | 424/93.71 |
| 5,935,575 A | 8/1999 | Lenardo et al. | 424/184.1 |
| 5,942,607 A | 8/1999 | Freeman et al. | |
| 5,962,318 A | 10/1999 | Rooney et al. | 435/325 |
| 5,962,319 A | 10/1999 | Ogawa et al. | 435/325 |
| 5,962,320 A | 10/1999 | Robinson | 435/366 |
| 5,962,406 A | 10/1999 | Armitage et al. | 514/8 |
| 5,972,721 A | 10/1999 | Bruno et al. | |
| 5,976,533 A | 11/1999 | Skibbens et al. | 424/144.1 |
| 5,980,892 A | 11/1999 | Skibbens et al. | 424/144.1 |
| 5,981,724 A | 11/1999 | Armitage et al. | 536/23.5 |
| 5,985,552 A | 11/1999 | Howell et al. | 435/6 |
| 5,985,653 A | 11/1999 | Armstrong et al. | 435/303.1 |
| 5,989,546 A | 11/1999 | Lenardo | 424/184.1 |
| 5,994,126 A | 11/1999 | Steinman et al. | 435/325 |
| 6,001,365 A | 12/1999 | Peterson et al. | 424/193.1 |
| 6,004,807 A | 12/1999 | Banchereau et al. | 435/325 |
| 6,004,942 A | 12/1999 | Firestein et al. | 514/44 |
| 6,008,188 A | 12/1999 | Oishi et al. | 514/2 |
| 6,011,018 A | 1/2000 | Crabtree et al. | 514/14 |
| 6,017,527 A | 1/2000 | Maraskovsky et al. | 424/93.71 |
| 6,040,177 A | 3/2000 | Riddell et al. | 435/372.3 |
| 6,043,082 A | 3/2000 | Crabtree et al. | 435/320.1 |
| 6,046,047 A | 4/2000 | Crabtree et al. | 435/320.1 |
| 6,048,526 A | 4/2000 | Skibbens et al. | 424/144.1 |
| 6,063,625 A | 5/2000 | Crabtree et al. | 435/375 |
| 6,074,635 A | 6/2000 | Abrignani | 424/85.1 |
| 6,080,409 A | 6/2000 | Laus et al. | 424/192.1 |
| 6,083,503 A | 7/2000 | Lenardo | 424/184.1 |
| 6,090,387 A | 7/2000 | Howell et al. | 424/185.1 |
| 6,096,532 A | 8/2000 | Armstrong et al. | 435/286.5 |
| 6,113,901 A | 9/2000 | Bluestone | 424/154.1 |
| 6,117,982 A | 9/2000 | Chang | 530/391.1 |
| 6,120,766 A | 9/2000 | Hale et al. | 424/130.1 |
| 6,121,044 A | 9/2000 | Peshwa et al. | 435/325 |
| 6,126,945 A | 10/2000 | Terman et al. | 424/237.1 |
| 6,129,916 A | 10/2000 | Chang | 424/179.1 |
| 6,140,120 A | 10/2000 | Crabtree et al. | 435/372.3 |
| 6,143,291 A | 11/2000 | June et al. | 424/93.21 |
| 6,143,292 A | 11/2000 | Slavin | 424/93.7 |
| 6,143,297 A | 11/2000 | Bluestone | 424/184.1 |
| 6,159,461 A | 12/2000 | Besmer et al. | 424/85.1 |
| 6,165,785 A | 12/2000 | Ogle et al. | 435/347 |
| 6,165,787 A | 12/2000 | Crabtree et al. | 435/372.3 |
| 6,171,799 B1 | 1/2001 | Skibbens et al. | 435/7.1 |
| 6,180,097 B1 | 1/2001 | Terman | 424/93.1 |
| 6,184,043 B1 | 2/2001 | Fodstad et al. | |
| 6,190,655 B1 | 2/2001 | Lyman et al. | 424/85.1 |
| 6,194,207 B1 | 2/2001 | Bell et al. | 435/377 |
| 6,197,298 B1 | 3/2001 | Chang | 424/179.1 |
| 6,200,806 B1 | 3/2001 | Thomson | 435/366 |
| 6,203,487 B1 | 3/2001 | Consigny | 600/12 |
| 6,210,669 B1 | 4/2001 | Aruffo et al. | 424/144.1 |
| 6,221,351 B1 | 4/2001 | Terman | 424/93.71 |
| 6,221,352 B1 | 4/2001 | Howell et al. | 424/139.1 |
| 6,225,118 B1 | 5/2001 | Grant et al. | 435/347 |
| 6,232,445 B1 | 5/2001 | Rhode et al. | 530/387.3 |
| 6,251,385 B1 | 6/2001 | Terman | 424/93.7 |
| 6,258,357 B1 | 7/2001 | Spaner | 424/93.71 |
| 6,284,879 B1 | 9/2001 | Faustman | 536/23.1 |
| 6,290,955 B1 | 9/2001 | Thierfelder | 424/130.1 |
| 6,309,645 B1 | 10/2001 | Rhode et al. | 424/192.1 |
| 6,316,257 B1 | 11/2001 | Flyer et al. | 435/372.3 |
| 6,333,032 B1 | 12/2001 | Skurkovich et al. | 424/130.1 |
| 6,338,845 B1 | 1/2002 | Terman | 424/93.1 |
| 6,340,461 B1 | 1/2002 | Terman | 424/193.1 |
| 6,352,694 B1 | 3/2002 | June et al. | 424/93.71 |
| 6,355,479 B1 | 3/2002 | Webb et al. | 425/325 |
| 6,355,779 B1 | 3/2002 | Goodwin et al. | 530/388.23 |
| 6,362,694 B1 | 3/2002 | Doberenz | 331/57 |
| 6,399,054 B1 | 6/2002 | Casorati et al. | 424/93.21 |
| 6,406,699 B1 | 6/2002 | Wood | 424/184.1 |
| 6,447,765 B1 | 9/2002 | Horwitz | 424/85.1 |
| 6,455,299 B1 | 9/2002 | Steinman et al. | 435/235.1 |
| 6,461,806 B1 | 10/2002 | Hellerstein | 435/4 |
| 6,464,973 B1 | 10/2002 | Levitsky et al. | 424/93.21 |
| 6,465,251 B1 | 10/2002 | Schultze et al. | 435/377 |
| 6,488,933 B2 | 12/2002 | Cohen et al. | 424/185.1 |
| 6,534,055 B1 | 3/2003 | June et al. | 424/93.71 |
| 6,544,787 B1 | 4/2003 | Slavin | 435/372 |
| 6,544,788 B2 | 4/2003 | Singh | |
| 6,566,082 B1 | 5/2003 | Weinberg et al. | 435/7.24 |
| 6,576,428 B1 | 6/2003 | Assenmacher et al. | 435/7.1 |
| 6,576,466 B2 | 6/2003 | Jungfer et al. | 435/372.3 |
| 6,602,709 B1 | 8/2003 | Albert et al. | 435/372 |
| 6,610,542 B1 | 8/2003 | Bell et al. | 435/377 |
| 6,656,471 B1 | 12/2003 | Sastry et al. | 424/188.1 |
| 6,689,605 B1 | 2/2004 | Mountz et al. | 435/320.1 |
| 6,692,746 B1 | 2/2004 | Terman et al. | 424/184.1 |
| 6,719,972 B1 | 4/2004 | Gribben et al. | 424/154.1 |
| 6,867,041 B2 | 3/2005 | Berenson et al. | 435/377 |
| 6,887,466 B2 | 5/2005 | June et al. | 424/93.71 |
| 6,905,680 B2 | 6/2005 | June et al. | 424/93.71 |
| 6,905,874 B2 | 6/2005 | Berenson et al. | 435/375 |
| 7,232,566 B2 | 6/2007 | June et al. | 424/93.71 |
| 2001/0012514 A1 | 8/2001 | Skurkovich et al. | 424/143.1 |
| 2001/0028879 A1 | 10/2001 | Spaner | 424/93.7 |
| 2001/0031253 A1 | 10/2001 | Gruenberg | 424/93.1 |
| 2001/0051151 A1 | 12/2001 | Lamb, Jr. | 424/93.7 |
| 2002/0004041 A1 | 1/2002 | Albert et al. | 424/93.21 |
| 2002/0006409 A1 | 1/2002 | Wood | 424/184.1 |
| 2002/0009448 A1 | 1/2002 | Weiner et al. | 424/154.1 |
| 2002/0031496 A1 | 3/2002 | Firestein et al. | 424/93.6 |
| 2002/0034513 A1 | 3/2002 | Rhode et al. | 424/184.1 |
| 2002/0034517 A1 | 3/2002 | Brasel et al. | 424/192.1 |
| 2002/0037860 A1 | 3/2002 | D'Andrea et al. | 514/19 |
| 2002/0039569 A1 | 4/2002 | Jungfer et al. | 424/85.2 |
| 2002/0058019 A1 | 5/2002 | Berenson et al. | 424/93.7 |
| 2002/0076407 A1 | 6/2002 | June et al. | 424/143.1 |
| 2002/0081635 A1 | 6/2002 | Thomas et al. | |
| 2002/0090362 A1 | 7/2002 | Strauss | 424/93.21 |
| 2002/0091079 A1 | 7/2002 | Rhode et al. | 514/12 |
| 2002/0115214 A1 | 8/2002 | June et al. | 435/372.3 |
| 2002/0119568 A1 | 8/2002 | Berenson et al. | 435/446 |
| 2002/0119571 A1 | 8/2002 | Ritter et al. | 435/456 |
| 2002/0123472 A1 | 9/2002 | Faustman | 514/44 |

| Publication No. | Date | Inventor | Class |
|---|---|---|---|
| 2002/0146396 A1 | 10/2002 | Albert et al. | 424/93.21 |
| 2002/0155604 A1 | 10/2002 | Ledbetter et al. | 435/372.3 |
| 2002/0164331 A1 | 11/2002 | Exley et al. | 424/144.1 |
| 2002/0176850 A1 | 11/2002 | Slavin | 424/93.21 |
| 2002/0177554 A1 | 11/2002 | Verheijden et al. | 514/12 |
| 2002/0182730 A1 | 12/2002 | Gruenberg | 435/375 |
| 2002/0197716 A1 | 12/2002 | Flyer et al. | 435/372 |
| 2003/0039650 A1 | 2/2003 | Gruenberg | 424/144.1 |
| 2003/0099643 A1 | 5/2003 | June et al. | 424/144.1 |
| 2003/0113328 A1 | 6/2003 | Roifman et al. | 424/146.1 |
| 2003/0113341 A1 | 6/2003 | Lynch et al. | 424/185.1 |
| 2003/0118659 A1 | 6/2003 | August et al. | 424/491 |
| 2003/0119185 A1 | 6/2003 | Berenson et al. | 435/372 |
| 2003/0134341 A1 | 7/2003 | Gruenberg | 435/7.21 |
| 2003/0134415 A1 | 7/2003 | Gruenberg | 435/372 |
| 2003/0165531 A1 | 9/2003 | Lynch et al. | 424/192.1 |
| 2003/0170238 A1 | 9/2003 | Gruenberg | 424/144.1 |
| 2003/0175242 A1 | 9/2003 | Gruenberg | 424/93.2 |
| 2003/0175272 A1 | 9/2003 | Gruenberg | 424/144.1 |
| 2003/0176378 A1 | 9/2003 | Weiner et al. | 514/44 |
| 2003/0190323 A1 | 10/2003 | Cohen et al. | 424/185.1 |
| 2003/0194395 A1 | 10/2003 | Gruenberg et al. | 424/93.7 |
| 2003/0219463 A1 | 11/2003 | Falkenburg et al. | 424/277.1 |
| 2003/0235908 A1 | 12/2003 | Berenson et al. | 435/372 |
| 2004/0023377 A1 | 2/2004 | Assenmacher et al. | 435/372 |
| 2004/0037845 A1 | 2/2004 | Brasel et al. | 424/185.1 |
| 2004/0072749 A1 | 4/2004 | Zochoer et al. | 514/12 |
| 2004/0156860 A1 | 8/2004 | Weiner et al. | 424/185.1 |
| 2004/0157792 A1 | 8/2004 | Mountz et al. | 514/44 |
| 2004/0161433 A1 | 8/2004 | Teshigawara et al. | 424/277.1 |
| 2004/0175373 A1 | 9/2004 | Berenson et al. | 424/93.71 |
| 2004/0180050 A1 | 9/2004 | Hoffman | 424/144.1 |
| 2004/0180808 A1 | 9/2004 | Nye et al. | 514/2 |
| 2004/0185048 A1 | 9/2004 | Strom et al. | 424/145.1 |
| 2004/0241162 A1 | 12/2004 | Berenson et al. | 424/144.1 |
| 2005/0003484 A1 | 1/2005 | Hirano et al. | 435/69.1 |
| 2005/0084967 A1 | 4/2005 | Berenson et al. | 435/372 |
| 2005/0153447 A1 | 7/2005 | Berenson et al. | 435/372 |
| 2005/0214942 A1 | 9/2005 | Berenson et al. | 435/372 |
| 2005/0226857 A1 | 10/2005 | Bonyhadi et al. | 424/93.7 |
| 2006/0039909 A1 | 2/2006 | Hunig | 424/144.1 |
| 2006/0121005 A1 | 6/2006 | Berenson et al. | 424/93.7 |
| 2006/0246587 A1 | 11/2006 | June et al. | 435/456 |
| 2006/0286089 A1 | 12/2006 | Berenson et al. | 424/131.1 |
| 2007/0212767 A1 | 9/2007 | Bonyhadi et al. | 435/173.8 |
| 2007/0274974 A1 | 11/2007 | Bonyhadi et al. | 424/93.71 |

FOREIGN PATENT DOCUMENTS

| | | |
|---|---|---|
| DE | 197 22 888 A1 | 12/1998 |
| EP | 0 242 216 | 10/1987 |
| EP | 0 336 379 | 10/1989 |
| EP | 0 448 057 | 9/1991 |
| EP | 0 521 897 | 6/1995 |
| EP | 440373 B1 | 4/1997 |
| EP | 0 240 109 | 5/1997 |
| EP | 0 018 795 | 4/1999 |
| EP | 0 922 758 A2 | 6/1999 |
| EP | 633930 B1 | 4/2000 |
| EP | 0 690 125 B1 | 4/2003 |
| WO | WO 86/04334 | 7/1986 |
| WO | WO 89/05657 | 6/1989 |
| WO | WO 90/05541 | 5/1990 |
| WO | WO 90/10449 | 9/1990 |
| WO | WO 91/06319 | 5/1991 |
| WO | WO 91/15236 | 10/1991 |
| WO | WO 91/18629 | 12/1991 |
| WO | WO 92/00092 | 1/1992 |
| WO | WO 92/06117 | 4/1992 |
| WO | WO 92/09628 | 6/1992 |
| WO | WO 92/15671 | 9/1992 |
| WO | WO 93/02690 | 2/1993 |
| WO | WO 93/14789 | 8/1993 |
| WO | WO 93/19605 | 10/1993 |
| WO | WO 93/19767 | 10/1993 |
| WO | WO 93/20185 | 10/1993 |
| WO | WO 93/20186 | 10/1993 |
| WO | WO 93/24127 | 12/1993 |
| WO | WO 93/24136 | 12/1993 |
| WO | WO 94/02156 | 2/1994 |
| WO | WO 94/03202 | 2/1994 |
| WO | WO 94/12196 | 6/1994 |
| WO | WO 94/18317 | 8/1994 |
| WO | WO 94/19009 | 9/1994 |
| WO | WO 94/23734 | 10/1994 |
| WO | WO 94/28912 | 12/1994 |
| WO | WO 94/28926 | 12/1994 |
| WO | WO 94/29436 | 12/1994 |
| WO | WO 95/00642 | 1/1995 |
| WO | WO 95/03408 | 2/1995 |
| WO | WO 95/09652 | 4/1995 |
| WO | WO 95/13082 | 5/1995 |
| WO | WO 95/16775 | 6/1995 |
| WO | WO 95/20649 | 8/1995 |
| WO | WO 95/21251 | 8/1995 |
| WO | WO 95/24910 | 9/1995 |
| WO | WO 95/32729 | 12/1995 |
| WO | WO 95/32735 | 12/1995 |
| WO | WO 95/33770 | 12/1995 |
| WO | WO 95/33823 | 12/1995 |
| WO | WO 96/06929 | 3/1996 |
| WO | WO 96/14874 | 5/1996 |
| WO | WO 96/15153 | 5/1996 |
| WO | WO 96/30030 | 10/1996 |
| WO | WO 96/33265 | 10/1996 |
| WO | WO 96/34622 | 11/1996 |
| WO | WO 96/37208 | 11/1996 |
| WO | WO 96/38158 | 12/1996 |
| WO | WO 97/00270 | 1/1997 |
| WO | WO 97/01304 | 1/1997 |
| WO | WO 97/02016 | 1/1997 |
| WO | WO 97/02045 | 1/1997 |
| WO | WO 97/05233 | 2/1997 |
| WO | WO 97/05239 | 2/1997 |
| WO | WO 97/10361 | 3/1997 |
| WO | WO 97/12633 | 4/1997 |
| WO | WO 97/29182 | 8/1997 |
| WO | WO 97/29183 | 8/1997 |
| WO | WO 97/32970 | 9/1997 |
| WO | WO 97/34472 | 9/1997 |
| WO | WO 97/34618 | 9/1997 |
| WO | WO 97/37004 | 10/1997 |
| WO | WO 97/39722 | 10/1997 |
| WO | WO 97/44667 | 11/1997 |
| WO | WO 97/46256 | 12/1997 |
| WO | WO 98/13382 | 4/1998 |
| WO | WO 98/21314 | 5/1998 |
| WO | WO 98/23728 | 6/1998 |
| WO | WO 98/33891 | 8/1998 |
| WO | WO 98/41090 | 9/1998 |
| WO | WO 98/46083 | 10/1998 |
| WO | WO 98/51820 | 11/1998 |
| WO | WO 98/52615 | 11/1998 |
| WO | WO 98/53048 | 11/1998 |
| WO | WO 98/56819 | 12/1998 |
| WO | WO 98/56823 | 12/1998 |
| WO | WO 98/58541 | 12/1998 |
| WO | WO 99/00137 | 1/1999 |
| WO | WO 99/00143 | 1/1999 |
| WO | WO 99/13904 | 3/1999 |
| WO | WO 99/21572 | 5/1999 |
| WO | WO 99/21576 | 5/1999 |
| WO | WO 99/24045 | 5/1999 |
| WO | WO 99/25812 | 5/1999 |
| WO | WO 99/29865 | 6/1999 |
| WO | WO 99/29883 | 6/1999 |

| | | |
|---|---|---|
| WO | WO 99/34827 | 7/1999 |
| WO | WO 99/36093 | 7/1999 |
| WO | WO 99/38953 | 8/1999 |
| WO | WO 99/42564 | 8/1999 |
| WO | WO 99/51247 | 10/1999 |
| WO | WO 99/52928 | 10/1999 |
| WO | WO 99/55843 | 11/1999 |
| WO | WO 99/58977 | 11/1999 |
| WO | WO 00/02520 | 1/2000 |
| WO | WO 00/06588 | 2/2000 |
| WO | WO 00/15767 | 3/2000 |
| WO | WO 00/22124 | 4/2000 |
| WO | WO 00/28000 | 5/2000 |
| WO | WO 00/29008 | 5/2000 |
| WO | WO 00/31138 | 6/2000 |
| WO | WO 00/44893 | 8/2000 |
| WO | WO 00/47719 | 8/2000 |
| WO | WO 00/50570 | 8/2000 |
| WO | WO 00/51432 | 9/2000 |
| WO | WO 00/52046 | 9/2000 |
| WO | WO 00/53209 | 9/2000 |
| WO | WO 00/56356 | 9/2000 |
| WO | WO 00/57705 | 10/2000 |
| WO | WO 00/59538 | 10/2000 |
| WO | WO 00/61157 | 10/2000 |
| WO | WO 00/66764 | 11/2000 |
| WO | WO 00/73432 | 12/2000 |
| WO | WO 00/78348 | 12/2000 |
| WO | WO 01/22970 | 4/2001 |
| WO | WO 01/24771 | 4/2001 |
| WO | WO 01/29192 | 4/2001 |
| WO | WO 01/43694 | 6/2001 |
| WO | WO 01/43695 | 6/2001 |
| WO | WO 01/49743 | 7/2001 |
| WO | WO 01/52664 | 7/2001 |
| WO | WO 01/62895 | 8/2001 |
| WO | WO 01/62895 A2 | 8/2001 |
| WO | WO 01/70938 | 9/2001 |
| WO | WO 001/85920 | 11/2001 |
| WO | WO 01/87333 | 11/2001 |
| WO | WO 01/88116 | 11/2001 |
| WO | WO 01/88159 | 11/2001 |
| WO | WO 01/98357 | 12/2001 |
| WO | WO 02/09674 | 2/2002 |
| WO | WO 02/16414 | 2/2002 |
| WO | WO 02/22790 | 3/2002 |
| WO | WO 02/22805 | 3/2002 |
| WO | WO 02/28385 | 4/2002 |
| WO | WO 02/060376 | 8/2002 |
| WO | WO 02/072799 | 9/2002 |
| WO | WO 02/087627 | 11/2002 |
| WO | WO 02/092793 | 11/2002 |
| WO | WO 02/098361 | 12/2002 |
| WO | WO 03/006632 | 1/2003 |
| WO | WO 03/020904 | 3/2003 |
| WO | WO 03/024312 | 3/2003 |
| WO | WO 03/024989 | 3/2003 |
| WO | WO 03/025158 | 3/2003 |
| WO | WO 03/034820 | 5/2003 |
| WO | WO 03/043643 | 5/2003 |
| WO | WO 03/077658 | 9/2003 |

OTHER PUBLICATIONS

Frohlich, M.W. et al. "Ex Vivo Activation and Expansion of T Cells from the Peripheral Blood of Multiple Myeloma Patients Using the Xcellerate™ Process," *Blood 100*(11), Abstract No. 5259, Nov. 16, 2002.

Grosmaire, L. et al., "Ligation of CD2 Amplifies Anti-CD3 X Anti-CD28-Mediated Ex Vivo Activation and Expansion of T Cells," *Blood 96*(11 part 2): 40b, Abstract No. 3834, Nov. 16, 2000.

Hou, J.W. et al., "Naïve (CD45RA+) vs Memory (CD45RO+) Status of Human CD4 Cells Greatly Influences Th1/Th2 Polarization Potential," *Blood 100*(11), Abstract No. 944, Nov. 16, 2002.

Larsen, A.C. et al., "The ratio of anti-CD3 and anti-CD28 stimulation determines proliferation and IL-2R expression in T cells," *Tissue Antigens 55*(Suppl. 1): 109, 2000.

Long, S.A. et al., "Modulating T Cell Signals Using Xcyte™ Dynabeads® Leads to Selective Expansion of Antigen-Specific T Cells," *Blood 102*(11): 55b, Abstract No. 3922, Nov. 16, 2003.

Patel and Rickwood, "Optimization of conditions for specific binding of antibody-coated beads to cells," *Journal of Immunological Methods 184*: 71-80, 1995.

"CD4+ T Cell Diversity Not Immediately Restored by Therapy," NIAID AIDS Agenda, Aug. 1997, accessed on Jul. 8, 2002. Available at http://www.niaid.nih.gov/publications/agenda/1097/page3.htm.

Arenz, M. et al., "Antigen-independent in vitro expansion of T cells does not affect the T cell receptor Vβ repertoire," *J. Mol. Med. 75*: 678-686, 1997.

Baroja, M.L. et al., "The Anti-T Cell Monoclonal Antibody 9.3 (Anti-CD28) Provides a Helper Signal and Bypasses the Need for Accessory Cells in T Cell Activation with Immobilized Anti-CD3 and Mitogens," *Cellular Immunology 120*: 205-217, 1989.

Bergstresser, P.R. et al., "T Cell-Mediated Terminal Maturation of Dendritic Cells," in *Dendritic Cell in Fundamental and Clinical Immunology*, Ricciardi-Castognoli (Ed.), Plenum Press, New York, 1997, pp. 65-69.

Bonyhadi, M. et al., "Xcellearate: An Autologous T Cell Immunotherapy Approach for Treatimg B-Cell Lymphocytic Leukemia (B-CLL)," in *Proceedings of the 42nd Annual Meeting of the American Society of Hematology*, San Francisco, Dec. 1-5, 2000, vol. 96, No. 11, part 1, Abstract # 3616.

Bretscher, P., "The two-signal model of lymphocyte activation twenty-one years later," *Immunology Today 13*(2): 74-76, 1992.

Carlens, S. et al., "Ex vivo T lymphocyte expansion for retroviral transduction: Influence of serum-free media on variations in cell expansion rates and lymphocyte subset distribution," *Experimental Hematology 28*: 1137-1146, 2000.

Chapman, A.L.N. et al., "Epstein-Barr Virus-specific Cytotoxic T Lymphocyte Responses in the Blood and Tumor Site of Hodgkin's Disease Patients: Implications for a T-cell-based Therapy," *Cancer Research 61*: 6219-6226, Aug. 15, 2001.

Cohen, P.A. et al., "T-Cell Adoptive Therapy of Tumors: Mechanisms of Improved Therapeutic Performance," *Critical Reviews in Immunology 21*: 215-248, 2001.

Creson, J. et al., "The Mode and Duration of Anti-CD28 Costimulation Determine Resistance to Infection by Macrophage-Tropic Strains of Human Immunodeficiency Virus Type I in Vitro," *Journal Of Virology*, 73(11):9337-9347, Nov. 1999.

Dietrich, P-Y et al., "TCR analysis reveals significant repertoire selection during in vitro lymphocyte culture," *International Immunology 9*(8): 1073-1083, 1997.

Garland et al., "The use of Teflon cell culture bags to expand functionally active CD8+ cytotoxic T lymphocytes," *Journal of Immunological Methods 227*: 53-63, 1999.

Groh, V. et al., "Stimulation of T cell autoreactivity by anomalous expression of NKG2D and its MIC ligands in rheumatoid arthritis," *Proceedings of the National Academy of Sciences 100*(16): 9452-9457, Aug. 5, 2003.

Haanen et al., "Selective Expansion of Cross-reactive CD8+ Memory T Cells by Viral Variants," *J. Exp. Med. 190*(9): 1319-1328, Nov. 1, 1999.

Hami, L. et al., "Xcellerate™: A Platform Process for the GMP Manufacture of Activated T Cells for the Treatment of Patients with Cancer and Immune Dysfunction," in *Proceedings of the 42nd Annual Meeting of the American Society of Hematology*, San Francisco, Dec. 1-5, 2000, vol. 96, No. 11, part 1, abstract # 3630.

Heitger, A. et al., "Defective T-helper cell function after T-cell-depleting therapy affecting naïve and memory populations," *Blood 99*(11): 4053-4062, Jun. 2002.

Husebekk, A. et al., "Selection and expansion of T cells from untreated patients with CLL: source of cells for immune reconstitution," *Cytotherapy 2*(3): 187-193, 2000.

Iezzi et al., "The Duration of Antigenic Stimulation Determines the Fate of Naive and Effector T Cells," *Immunity 8*: 89-95, Jan. 1998.

Jason, J. et al., "The Effect of Mitogens, IL-2 and Anti-CD3 Antibody on the T-Cell Receptor Vβ Repertoire," *Scand. J. Immunol. 43*: 652-661, 1996.

June et al., "The B7 and CD28 receptor families," *Immunology Today 15*(7): 321-331, 1994.

Kalamasz, D. et al., "Storage Shipment of Freshly Harvested or Cryopreserved Xcellerate™ Activated T Cells for Clinical Applications," in *Proceedings of the 42nd Annual Meeting of the American Society of Hematology*, San Francisco, Dec. 1-5, 2000, vol. 96, No. 11, part 2, abstract # 5113.

Kato et al., "Gene Transfer of CD40-Ligand Induces Autologous Immune Recognition of Chronic Lymphocytic Leukemia B Cells," *J. Clin. Invest. 101*(5): 1133-1141, Mar. 1998.

Kluin-Nelemans, H.C. et al., "Correction of Abnormal T-Cell Receptor Repertoire During Interferon-α Therapy in Patients With Hairy Cell Leukemia," *Blood 91*(11): 4224-4231, Jun. 1998.

Krawczyk et al., "Cbl-b Is a Negative Regulator of Receptor Clustering and Raft Aggregation in T Cells," *Immunity 13*: 463-473, Oct. 2000.

Lanzavecchia, A., "The Role of Dendritic Cells in the Generation of Effector and Memory T Cell Responses," from *The Midwinter Conference of Immunologists*, Jan. 22-25, 2000, available at www.midwconfimmunol.org/Midwinter00/sessions/lanzavecchia.html.

Larsson, S. et al., "Productive Cytomegalovirus (CMV) Infection Exclusively in CD13-Positive Peripheral Blood Mononuclear Cells from CMV-Infected Individuals," *Transplantation*, 65(3):411-415, Feb. 15, 1998.

Levings, M.K. et al., "Human $CD25^{30}$ $CD4^+$ T regulatory cells suppress naive and memory T cell proliferation and can be expanded in vitro without loss of function," *J. Exp. Med. 193*(11): 1295-1301, Jun. 2001.

Li, Q. et al., "Expanded Tumor-reactive $CD4^+$ T-Cell Responses to Human Cancers Induced by Secondary Anti-CD3/Anti-CD28 Activation," *Clinical Cancer Research 5*: 461-469, Feb. 1999.

Li, Q. et al., "Immunological Effects of BCG as an Adjuvant in Autologous Tumor Vaccines," *Clinical Immunology 94*(1): 64-72, Jan. 2000.

Liebowitz et al., "Costimulatory approaches to adoptive immunotherapy," *Current Opinion in Oncology 10*: 533-541, 1998.

Lin and Welsh, "Stability and Diversity of T Cell Receptor Repertoire Usage during Lymphocytic Choriomenigitis Virus Infection of Mice," *Journal of Experimental Medicine 188*(11): 1993-2005, Dec. 7, 1998.

Lopez, R.D. et al., "CD58/LFA-3 and IL-12 provided by activated monocytes are critical in the in vitro expansion of $CD56^+$ T cells," *Cancer Immunol. Immunother. 49*: 629-640, 2001.

Mariani, S. et al., "Severe and long-lasting disruption of T-cell receptor diversity in human myeloma after high-dose chemotherapy and autologous blood progenitor cell infusion," *British Journal of Hematology 113*: 1051-1059, 2001.

Marijt and Falkenburg, "Specific T Cell Therapy in Leukemia," *Journal of Hematotherapy & Stem Cell Research 10*: 493-500, 2001.

Moebius, U. et al., "T cell receptor gene rearrangements of T lymphocytes infiltrating the liver in chronic active hepatitis B and primary biliary cirrhosis (PBC): oligoclonality of PBC-derived T cell clones," *Eur. J. Immunol. 20*: 889-896, 1990.

Nijhuis, M. et al., "Stochastic processes strongly influence HIV-1 evolution during suboptimal protease-inhibitor therapy," *Proc. Natl. Acad. Sci. USA 95*: 14441-14446, Nov. 1998.

Polanski, M. et al., "Xcellerate( : A Closed, Scalable Process for the GMP Manufacture of Stable Activated T Cells," in *Proceedings of the 15th Annual Scientific Meeting of the Society for Biological Therapy*, Seattle, Oct. 26-29, 2000, and *Journal of Immunotherapy*, (23)5:599, Sep. 2000.

Ranheim and Kipps, "Activated T Cells Induce Expression of B7/BB1 on Normal or Leukemic B Cells through a CD40-dependent Signal," *J. Exp. Med. 177*: 925-935, Apr. 1993.

Ria, F. et al., "Molecular Characterization of the T Cell Repertoire Using Immuno-scope Analysis and its Possible Implentation in Clinical Practice," *Current Molecular Medicine 1*: 297-304, 2001.

Riddell, S.R. et al., "T-Cell Therapy of Leukemia," *Cancer Control 9*(2): 114-122, Mar./Apr. 2002.

Shimizu, N. et al., "Large-Scale ex Vivo Expansion of Primary T Lymphocytes in Late-Stage AIDS Patients, *AIDS Research and Human Retroviruses 16*(6): 611-612, 2000.

Stohl, W. et al., "Polyclonal in Vitro T Cell Proliferation and T Cell-Dependent B Cell Differentiation Supported By Activated Autologous B Cells," *Clinical Immunology and Immunopathology 72*(1): 44-52, Jul. 1994.

Tao, Q. et al., "Conservation of Epstein-Barr Virus Cytotoxic T-Cell Epitopes in Posttransplant Lymphomas. Implications for Immune Therapy," *American Journal of Pathology 160*(5): 1839-1845, May 2002.

Ten Berge et al., "Selective Expansion of a Peripheral Blood $CD8^+$ Memory T Cell Subset Expressing Both Granzyme B and $_L$-Selectin During Primary Viral Infection in Renal Allograft Recipients," *Transplantation Proceedings 30*: 3975-3977, 1998.

Vathsala, A. et al., "Inhibition of Apoptosis in Anti-CD3-Treated Peripheral Blood Lymphocytes by Immunosuppressive Drugs," *Transplantation Proceedings 32*: 1992-1994, 2000.

Yamada, O. et al., "Clonal T-cell proliferation causing pure red cell aplasia in chronic B-cell lymphocytic leukaemia: successful treatment with cyclosporine following in vitro abrogation of erythroid colony-suppressing activity," *British Journal of Haematology 101*: 335-337, 1998.

Zou, J.-P. et al., "Tumor-Bearing Mice Exhibit A Progressive Increase in Tumor Antigen-Presenting Cell Function and A Reciprocal Decrease in Tumor Antigen-Responsive $CD4^+$ T Cell Activity," *The Journal of Immunology 148* (2): 648-655, Jan. 15, 1992.

Jackson et al., Small-Scale Monoclonal Antibody Production In Vitro: Methods And Resources, Proceedings of the Production of Monoclonal Antibodies Workshop, Aug. 29, 1999, Bologna, Italy, http://altweb.jhsph.edu/topics/mabs/ardf/jackson.htm, accessed Apr. 17, 2007.

U.S. Appl. No. 08/253,964, filed Jun. 3, 1994, June et al.

U.S. Appl. No. 60/375,733, filed Apr. 4, 2002, Bonyhadi et al.

Abbas et al., *Cellular and Molecular Immunology*, 3rd Ed., W.B. Saunders Co., Philadelphia, PA, 1997, pp. 149, 155, 250, 266 and 413.

Allegretta et al., "Homologies between T Cell Receptor Junctional Sequences Unique to Multiple Sclerosis and T Cells Mediating Experimental Allergic Encephalomyelitis," *J. of Clin. Invest.*, 94:105-109, Jul. 1994.

Altman et al., "Phenotypic Analysis of Antigen-Specific T Lymphocytes," *Science*, 274:94-63, Oct. 4, 1996.

Anderton et al., "Therapeutic potential of TCR antagonists is determined by their ability to modulate a diverse repertoire of autoreactive T cells," *Eur. J. Immunol.*, 29:1850-1857, 1999.

"Attack on Cancer Soups Up Body's Immune Cells," *Cancer Weekly Plus*, Dec. 21, 1998.

Azuma et al., "B70 antigen is a second ligand for CTLA-4 and CD28," *Nature*, 366:76-79, Nov. 4, 1993.

Azuma et al., "Induction of apoptosis of activated murine splenic T cells by Cycloprodigiosin hydrochloride, a novel immunosuppressant," *Immunopharmacol.*, 46:29-37, 2000.

Bender et al., "T Cell Receptor Repertoire in Polymyositis: Clonal Expansion of Autoaggressive $CD8^+T$ Cells," *J. Exp. Med.*, 181:1863-1868, May 1995.

Bennett et al., "Help for cytotoxic-T-cell responsed is mediated by CD40 signalling," *Nature*, 393:478-480, Jun. 4, 1998.

Berenson et al., "Engraftment After Infusion of $CD34^+$Marrow Cells in Patients With Breast Cancer or Neuroblastoma," *Blood*, 77(8):1717-1722, Apr. 15, 1991.

Berstein et al., "Immune reconstitution following autologous transfers of CD3/CD28 stimulated CD4+ T cells to HIV-infected persons," *Clin. Immunol.*, 111:262-274, 2004.

Bishop et al., "High-Dose Therapy and Peripheral Blood Progenitor Cell Transplantation: Effects of Recombinant Human Granulocyte-Macrophage Colony-Stimulating Factor on the Autograft," *Blood*, 83(2):610-616, Jan. 15, 1994.

Bishop et al., "Assessing Apoptosis of Developing T Cells by Flow Cytometry" in *Methods in Molecular Biology, vol. 134: T Cell Protocols: Development And Activation*, Kearse Ed., Humana Press, Tolowa, NJ, 1999, pp. 117-131.

Boehncke et al., "T-Cell-Receptor Repertoire in Chronic Plaque-Stage Psoriasis Is Restricted and Lacks Enrichment of Superantigen-Associated Vβ Regions," *J. Invest. Dermatol.*, 104:725-728, May 1995.

Boerner et al., "Production of an Antigen-Specific Human Monoclonal Antibodies from in Vitro-Primed Human Splenocytes," *J. Immunol.*, 147(1):86-95, Jul. 1991.

Borthwick et al., "Loss of CD28 expression on CD8$^+$T cells is induced by IL-2 receptor γ chain signaling cytokines and type I IFN, and increases susceptibility to activation-induced apoptosis," *Int. Immunol.*, 12(7): 1005-1013, 2000.

Bour et al., "T-Cell Repertoire Analysis in Chronic Plaque Psoriasis Suggests an Antigen-Specific Immune Response," *Human Immunol.*, 60:665-676, 1999.

Broder et al., "The Suppressor-Cell Network in Cancer," *New Eng. J. Med.*. 299(23): 1281-1284, Dec. 7, 1978.

Brooméet al., "Preferential Vβ3 usage by hepatic T lymphocytes in patients with primary sclerosing cholangitis," *J. Hepatol.*, 26:527-537, 1997.

Brüggemann et al., "Production of human antibody repertoires in transgenic mice," *Curr. Opin. Biotechnol.*, 8:455-458, 1997.

Bruserud et al., "Cyclosporine A and FK506 Show Similar Immunosuppressive Effects on Long-term *in Vitro* T-Cell Proliferation," *Int. J. Immunopharmac.*, 15(2):93-97, 1993.

Bulfone-Paus et al., "An Interleukin-2-2IgG-Fas Ligand Fusion Protein Suppresses Delayed-Type Hypersensitivity in Mice by Triggering Apoptosis in Activated T Cells as a Novel Strategy for Immunosuppression," *Transplantation*, 69(7): 1386-1391, Apr. 15, 2000.

Carpenter et al., "Non-FcR-Binding, Humanized Anti-CD3 Antibody Hu291 Induces Apoptosis of Human T Cells More Effectively Than OKT3 and Is Immunosuppressive In Vivo," *Transplant. Proc.*, 32(7): 1545-1546, Nov. 2000.

Carpenter et al., "Non-Fc Receptor-Binding Humanized Anti-CD3 Antibodies Induce Apoptosis of Activated Human T Cells," *J. Immunol.*, 165:6205-6213, 2000.

Carroll et al., "Accelerating the induction of Fas-mediated T cell apoptosis: a strategy for transplant tolerance?," *Clin. Exp. Immunol.*, 126:589-597, 2001.

Cella et al., "Ligation of CD40 om Dendritic Cells Triggers Production of High Levels of Interleukin-12 and Enhances T Cell Stimulatory CapacityL T-T Help vai APC Activation," *J. Exp. Med.*, 184:747-752, Aug. 1996.

Chen et al., "Ex vivo expansion of dendritic-cell-activated antigen-specific CD4(+) T cells with anti-CD3/CD28, interleukin-7, and interleukin-15: Potential for adoptive T cell immunotherapy," *Clin. Immunol.*, 119:21-31, 2006.

Christen et al., "Apoptosis of Autoreactive CD8 Lymphocytes as a Potential mechanism for the Abrogation of Type 1 Diabetes by Islet-Specific TNF-α Expressionat a Time When the Autoimmune Process Is Already Ongoing," *Ann. N.Y. Acad. Sci.*, 958:166-169, 2002.

Cioca et al., "Apoptosis of Peripheral Blood Lymphocytes is Induced by Catecholamines," *Jpn. Heart J.*, 41:385-398, 2000.

Claret et al., "Characterization of T Cell Repertoire in Patients with Graft-Versus-Leukemia After Donor Lymphocyte Infusion," *J. Clin. Invest.*, 100(4):855-866, Aug. 1997.

Combadière et al., "Selective Induction of Apoptosis in Mature T Lymphocytes by Variant T Cell Receptor Ligands," *J. Exp. Med.*, 187(3):349-355, Feb. 2, 1998.

Dalum et al., "Therapeutic antibodies elicited by immunization against TNF-α" *Nat. Biotechnol.*, 17:666-669, Jul. 1999.

Dao et al., "Natural Human Interferon-α Augments Apoptosis in Activated T Cell Line," *Cellular Immunol.*, 155:304-311, 1994.

Davey et al., "TCRB Clonotypes Are Present in CD4+ T Cell Populations Prepared Directly from Rheumatoid Synovium," *Human Immunol.*, 55:11-21, 1997.

Davies, "A New Role for Methimazole in Autoimmune Thyroid Disease: Inducing T Cell Apoptosis," *Thyroid*, 10(7):525-526, Jul. 2000.

Di Renzo et al., "Enhanced apoptosis of T cells in common variable immunodeficiency (CVID): role of defective CD28 co-stimulation," *Clin. Exp. Immunol.*, 120:503-511, 2000.

Di Sabatino et al., "Apoptosis and peripheral blood lymphocyte depletion in coeliac disease," *Immunol.*, 103:435-440, 2001.

Ebata et al., "Rapid induction oc CD95 ligand and CD4$^+$ T cell-mediated apoptosis by CD137 (4-IBB) costimulation," *Eur. J. Immunol.*, 31:1410-1416, 2001.

Ebert et al., "Lymphocyte apoptosis: induction by gene transfer techniques," *Gene Ther.*, 4:296-302, 1997.

Epperson et al., "Oligoclonal T cell expansion in myelodysplastic syndrome: evidence for an autoimmune process," *Leukemia Res.*, 25:1075-1083, 2001.

Freedman et al., "B7, A B Cell-Restricted Antigen that Identifies Reactivated B Cells," *J. Immunol.*, 139(10):3260-3267, Nov. 15, 1987.

Freeman et al., "B7, A New Member of the Ig Superfamily with Unique Expression on Activated and Neoplastic B Cells," *J. Immunol.*, 143(8):2714-2722, Oct. 15, 1989.

Freeman et al., "Cloning of B7-2: A CTLA-4 Counter-receptor that Costimulates Human T Cell Proliferation," *Science*, 262:909-911, Nov. 5, 1993.

Freeman et al., "Structure, Expression, and T Cell Costimulatory Activity of the Murine Homologue of the Human B Lymphocyte Activation Antigen B7," *J. Exp. Med.*, 174:625-631, Sep. 1991.

Freeman et al., "Murine B7-2, an Alternative CTLA4 Counter-receptor that Costimulates T Cell Proliferation and Interleukin 2 Production," *J. Exp. Med.*, 178:2185-2192, Dec. 1993.

Freudenthal et al., "The distinct surface of human blood dendritic cells, as observed after an improved isolation method," *Pro. Natl. Acad. Sci. USA*, 87:7698-7702, Oct. 1990.

Gailit et al., "Wound repair in the context of extracellular matrix," *Curr. Opin. Cell Biol.*, 6:717-725, 1994.

Gong et al., "Reversal of tolerance to human MUC1 antigen in MUC1 transgenic mice immunized with fusions of dendritic and carcinoma cells," *Proc. Natl. Acad. Sci. USA*, 95:6279-6283, May 1998.

Gorochov et al., Perturbation of CD4$^+$and CD8$^+$T-Cell repertoires during progression to AIDS and regulation of the CD4$^+$repertoire during antiviral therapy, Nat, Med., 4(2):215-221, Feb. 1998.

Hami et al., "Optimizing the Efficiency, Reproducibility and Cost of the Xcellerate™ Process for Clinical Delivery of Activated T Cells," *Blood*, 98(11 Part 2):336b-337b, Abstract 5112, 2001.

Hancock et al., "Keratinocyte Growth Regulation by the Products of Immune Cells," *J. Exp. Med.*, 168:1395-1402, Oct. 1988.

Hersh et al., "Impaired in Vitro Lymphocyte Transformation in Hodgkin's Disease," *New Eng. J. Med.*, 273(19):1006-1012, Nov. 4, 1965.

Hewitt, "Xcellerating cancer treatment," *Bio Venture View*, 18(7):19, Apr. 8, 2003.

Imura et al., "The Human OX40gp34 System Directly Meditates Adhesion of Activated T Cells to Vascular Endothelial Cells," *J. Exp. Med*, 183:2185-2195, May 1996.

Iruela-Arispe et al., "Thrombospondin exerts and antiangiogenic effect on cord formation by endothelial cells *in vitro*," *Proc. Nat.l Acad. Sci. USA*, 88:5026-5030, Jun. 1991.

Izumi et al., "Transforming Growth Factor $β_1$ Stimulates Type II Collagen Expression in Cultured Periosteum-Derived Cells," *J. Bone and Min. Res.*, 7(1):115-121, 1992.

Jakobovits et al., "Production of Antigen-Specific Human Antibodies from Mice Engineered with Human Heavy and Light Chain YACs[a]," *Ann. N.Y. Acad. Sci.*, 764:525-535, Sep. 29, 1995.

Janeway et al., *Immunobiology: The Immune System in Health and Disease*, Garland Publishing Inc., London, 1994, pp. 11:19-11:31.

Jin et al., "Cotimulation of T Cells with Immobilized Anti-CD3/Anti-CD28 (OKT3/9.3) Induces and Maintains Non-MHC Restricted Cytotoxicity," *Blood*, 88(10):41b, Abstract 2892, 1996.

Jingushi et al., "Acidic Fibroblast Growth Factor (aFGF) Injection Stimulates Cartilage Enlargement and Inhibits Cartilage Gene Expression in Rat Fracture Healing," *J. Orthopaedic Res.*, 8:364-371, 1990.

Joyce et al., "Transforming Growth Factor-β and the Initiation of Chondrogenesis and Osteogenesis in the Rat Femur," *J. Cell. Biol.*, 110:2195-2207, Jun. 1990.

Kern et al., "Cancer Cachexia," *J. Parenteral and Enteral Nutrition*, 12(3):286-298, 1998.

Kitajima et al., "T Cell-Mediated Terminal Maturation of Dendritic Cells: Loss of Adhesive and Phagocytotic Capacities," *J. Immunol.*, 157:2340-2347, 1996.

Knight et al., "Dendritic Cells and HIV Infection," in *Accessory Cells in HIV and Other Retroviral Infections*, Racz et al. Eds., Basel Krager, 1991, pp. 145-154.

Kugler et al., "Regression of human metastatic renal cell carcinoma after vaccination with tumor cell-dendritic cell hybrids," *Nat. Med.*, 6(3):332-336, Mar. 2000.

Låhdevirta et al., "Elevated Levels of Circulating Cachectin/Tumor Necrosis Factor in Patients with Acquired Immunodeficiency Syndrome," *Am. J. Med.*, 85:289-291, 1988.

Leporrier, "Role of fludarabine as monotherapy in the treatment of chronic lymphocytic leukemia," *Hematol. J.*, 5(Supp.1):S10-9, 2004. [Abstract Only].

Li et al., "CDR3 Sequence Motifs Shared by Oligoclonal Rheumatoid Arthritis Synovial T Cells. Evidence for an Antigen-driven Response," *J. Clin. Invest.*, 94:2525-2531, Dec. 1994.

Lim et al., "Spread of Clonal T-Cell Expansions in Rheumatoid Arthritis Patients," *Human Immunol.*, 48:77-83, 1996.

Liuzzo et al., "Monoclonal T-Cell Proliferation and Plaque Instability in Acute Coronary Syndromes," *Circulation*, 102:2883-2888, Jun. 27, 2000.

Mantegazza et al., "Analysis of T Cell Receptor Repertoir of Muscle-infiltrating T Lymphocytes in Polymyositis. Restricted $V\alpha/\beta$ Rearrangements May Indicate Antigen-driven Selection," *J. Clin. Invest.*, 91:2880-2886, Jun. 1993.

Martin et al., "Diversity in Fine Specificity and T Cell Receptor Usage of the Human CD4 Cytotoxic T Cell Response Specific for the Immunodominant Myelin Basic Protein Peptide 87-106," *J. Immunol.*, 148(5):1359-1366, Mar. 1, 1992.

Martin et al., "T-Cell Receptors and Autoimmune Thyroid Disease - Signposts for T-Cell-Antigen Driven Disease," *Intern. Rev. Immunol.*, 18:111-140, 1999.

Meuer et al., "An Alternative pathway of T-Cell Activation: A Functional Role for the 50kd T11 Sheep Erythrocyte Receptor Protein," *Cell*, 36:897-906. Apr. 1984.

Monji et al., "Activated T Cells and Their Culture Supernatants Mediate Differentiation and Maturation of Monocyte-Derived Dendritic Cells," *Blood*, 98(11 part 1):231a, Abstract 965, Nov. 16, 2001.

"New Approach Shows Promise to Use Patient's Own T Cells to Treat Cancer," *PR Newswire*, pp. 1774, Dec. 7, 1998.

Ogata, "Parathyroid Hormone-Related Protein as a Potential Target of THerapy for Cancer-Associated Morbidity," *Cancer Supplement*, 88(12):2909-2911, Jun. 15, 2000.

Racioppi et al., "Defective dendritic cell maturation a child with nucleotide excision repair deficiency and CD4 lymphopenia," *Clin. Exp. Immunol.*, 126:511-518, 2001.

Ramsauer et al., "Imunohistochemical Study of Langerhans' Cells in the Skin of HIV-1-Infected Patients with and without Kaposi's Sarcoma," *Accessory Cells in HIV and Other Retroviral Infections*, In Racz et al. Eds., Basel Krager, 1991, pp. 155-161.

Reddy et al., "Monocyte Conditioned Medium Is More Effective Than Deifned Cytokines in Mediating the Terminal Maturation of Human Dendritic Cells," *Blood*, 90(9):3640-3646, Nov. 1, 1997.

Ridge et al., "A conditioned dendritic cell can be a temporal bridge between a CD4 T-helper and T-killer cell," *Nature*, 393:474-478, Jun. 4, 1998.

Rissoan et al., "Reciprocal Control of T Helper C ell and Dendritic Cell Differentiation," *Science*, 283:1183-1186, Feb. 19, 1999.

Rosenberg et al., "Use of Tumor-Infiltrating Lymphocytes and Interleukin-2 in the Immunotherapy of Patients With Metastatic Melanoma: A Preliminary Report," *New Eng. J. of Med.*, 319(25):1676-1680, Dec. 22, 1988.

Sage et al., "Collagen Synthesis by Bovine Aortic Endothelial Cells in Culture," *Biochem.*, 18(24):5433-5442, Nov. 24, 1979.

Scanlan et al., "Molecular cloning of fibroblast activation protein α, a member of the serine protease family selectively expressed in stromal fibroblast of epithelial cancers," *Proc. Natl. Acad. Sci. USA*, 91:5657-5661, Jun. 1994.

Schoenberger et al., "T-cell help for cytotoxic T lymphocytes is mediated by CD40-CD40L interactions," *Nature*, 393:480-483, Jun. 4, 1998.

Schuurhuis et al., "Immature Dendritic Cells Acquire CD8 Cytotoxic T Lymphocyte Priming Capacity Upon Activation by T Helper Cell-Independent or -Dependent Stimuli," *J. Exp. Med.*, 192(1):145-150, Jul. 3, 2000.

Smith, "Technology evaluation: C242-DM1, ImmunoGen Inc.," *Curr. Opin. Mol. Therapeutics*, 3(2):198-203, 2001.

Staiano-Coico et al., "Human Keratinocyte Culture. Indentification and Staging of Epidermal Cell Subpopulations," *J. Clin. Invest.*, 77(2):396-404, Feb. 1986.

Takashima et al., "T Cell-Mediated Terminal Maturation of Dendritic Cells, a Critical Transition into Fully Potent Antigen Presenting Cells," *Pathologie Biologie (Paris)*, 46(1):53-60, Jan. 1998.

Thomson et al., "Embryonic Stem Cell Lines Derived From Human Blastocysts," *Science*, 282:1145-1147, Nov. 6, 1998.

Tolsma et al., "Peptides Derived From Two Separate Domains of the Matrix Protein Thrombospondin-1 Have Anti-Angiogenic Activity," *J. Cell. Biol.*, 122(2):497-511, Jul. 1993.

Vogel et al., "Modulation of Endothelial Cell Proliferation, Adhesion, and Motility by Recombinant Heparin-Binding Domain and Synthetic Peptides From the Type I Repeats of Thrombospondin," *J. Cell. Biochem.*, 53:74-84, 1993.

Weishaupt et al., "Antigen therapy eliminates T cell inflammation by apoptosis: Effective treatment of experimental autoimmune neuritis with recombinant myelin protein P2," *Proc. Natl. Acad. Sci. USA*, 94:1338-1343, Feb. 1997.

Weishaupt et al., "Glucocorticosteroids modulate antigen-induced T cell apoptosis in experimental autoimmune neuritis and cause T cell proliferation in situ," *Acta Neuropathologica*, 102(1):75-82, Jul. 2001.

White et al., "The roles of Fas, Fas ligand and Bcl-2 in T cell apoptosis in the central nervous system in experimental autoimmune encephalomyelitis," *J. Neuroimmunol.*, 82:47-55, 1998.

Wong et al., "Analysis of the Peripheral T-Cell Receptor $V\beta$ Repertoire in Newly Diagnosed Patients with Type I Diabetes," *Autoimmunity*, 154:3603-3610,1995.

Wu et al., "TCR Gene Usage in Experimental Autoimmune Myasthenia Gravis Pathogenesis," *J. Immunol.*, 154:3603-3610, 1995.

Wu et al., "Conserved T-cell receptor β-chain CDR3 sequences in IgA nephropathy biopsies," *Kidney Int.*, 55:109-119, 1999.

Wucherpfennig et al., "T Cell Recptor $V_\alpha$-$V_\beta$ Repertoire and Cytokine Gene Expression in Active Multiple Sclerosis Lesions," *J. Exp. Med.*, 175:993--1002, Apr. 1992.

Xiao et al., "Mechanisms of Recovery from experimental allergic encephalomyelitis induced with myelin basic protein peptide 68-86 in Lewis rats: a role for dendritic cells in iducing apoptosis of CD4+ T cells," *J. Neuroimmunol.*, 97:25-36, 1999.

Yang et al., "A Common Pathway for T Lymphocyte Activation Involving Both the CD3-Ti Complex and CD2 Sheep Erytho Receptor Determinants,"*J. Neuroimmunol.*, 97:25-36, 1999.

Yang et al., "Apoptosis of infiltrating cells in experimental autoimmune ureoretinitis," *Chinese Med. J.*, 113(7):643-646, 2000.

Young et al., "Dendritic cells: expansion and differentiation with hematopoietic growth factors," *Curr. Opin. Hematol.*, 6:135-144, 1999.

Yu et al., "Apoptosis of CD4 T cells occurs in experimental autoimmune anterior uveitis (EAAU)," *Clin. Exp. Immunol.*, 118:357-363, 1999.

Zipp et al., "Dual effect of glucocortocoids on apoptosis of human autoreactive and foreign antigen-specific T cells" *J. Neuroimmunol.*, 110(1-2):214-222, Oct. 2000.

Bonini et al., "HSV-TK Gene Transfer into Donor Lymphocytes for Control of Allogeneic Graft-Versus-Leukemia," *Science*, 276:1719-1724, Jun. 13, 1997.

Bruno et al., "Positive selection of CD34+cells by immunoadsorption: factors affecting the final yield and hematopoietic recovery in patients with hematological malignancies and solid tumors," *Transfusion and Apheresis Science*, 26: 103-110, 2002.

Dal Porto et al., "A soluble divalent class I major histocompatibility complex molecule inhibits alloreactive T cells at nanomolar concentrations," *Proc. Natl. Acad. Sci. USA*, 90: 6671-6675, Jul. 1993.

Fishman-Lobell et al., "CD4 mAb induced apoptosis of peripheral T cells: multiparameter subpopulation analysis by flow cytometry using Attractors™," *J. Immunol. Meth.*, 257:71-82, 2001.

Flens et al., "Efficient expansion of tumor-infiltrating lymphocytes from solid tumors by stimulation with combined CD3 and CD28 monoclonal antibodies," *Cancer Immunol. Immunother.*, 37:323-328, 1993.

Friedman et al., "Repertoire Analysis of CD8 T Cell Responses to Minor Histocompatibility Antigens Involved in Graft-Versus-Host Disease," *J. Immunol.*, 161:41-48, 1998.

Fukumoto et al., "Activation-induced apoptosis of peripheral lymphocytes treated with 7-hydroxystaurosporine, UCN-01," *Investigational New Drugs*, 17:335-341, 1999.

Fuss et al., "Anti-Interleukin 12 Treatment Regulates Apoptosis of Th1 T Cells in Experimental Colitis in Mice," *Gastroenterol.*, 117:1078-1088, 1999.

Fyhr et al., "T cell receptor β-chain repertoire in inclusion body myositis," *J. Neuroimmunol.*, 91:129-134, 1998.

Goronzy et al., "T Cell Receptor Repertoire in Rheumatoid Arthritis," *Int. Rev. Immunol.*, 17:339-363, 1998.

Goronzy et al., "Thymic function and peripheral T-cell homeostasis in rheumatoid arthritis," *TRENDS in Immunol.*, 22(5):251-255, May 2001.

Greer et al., "T Cell and NK Cell Lymphoproliferative Disorders," *Hemotology: Am. Soc. Hematol. Educ. Program.*, 2001:259-281.

Haegert et al., "Does a shift in the T-cell receptor repertoire precede the onset of MS?," *Neurol.*, 53:485-490, 1999.

Hall et al., "TCRβ spectratyping in RA: evidence of clonal expansions in peripheral blood lymphocytes," *Ann. Rheum. Dis.*, 57:319-322, 1998.

Hashimoto et al., "Novel immunosuppressive effect of FK506 by augmentation of T Cell apoptosis," *Clin. Exp. Immunol.*, 125:19-24, 2001.

Hayashi et al., "Implications of altered apoptosis in diabetes mellitus and autoimmune disease," *Apoptosis*, 6:31-45, 2001.

Hildeman et al., "Reactive Oxygen Species Regulate Activation-Induced T Cell Apoptosis," *Immunity*, 10:7335-744, Jun. 1999.

Holbrook et al., "Restrictions of T cell receptor β chain repertoire in the peripheral blood of patients with systemis lupus erythematosus," *Ann. Rheum. Dis.*, 55:627-631, 1996.

Holtzman et al., "Regulation of T cell apoptosis," *Apoptosis*, 5:459-471, 2000.

Inada et al., "T Cell Repertoire in the Liver of Patients with Primary Biliary Cirrhosis," *Human Immunol.*, 61:675-683, 2000.

Ino et al., "Activation-induced T cell Apoptosis by Monocytes from stem cell products," *Int. Immunopharmacol.*, 1:1307-1319, 2001.

Kallan et al., "Th1-like Cytokine Production Profile and Individual Specific Alterations in TCRBV-gene Usage of T cells from Newly Diagnosed Type 1 Diabetes Patients after Stimulation with β-cell Antigens," *J. Autoimmunity*, 10(6):589-598, Dec. 1997.

Kang et al., "Clonal Expansion of Infiltrating T Cells in the Spinal Cords of SJL/J Mice Infected with Theiler's Virus," *J. Immunol.*, 165:583-590, 2000.

Karadimitris et al., "Abnormal T-cell repertoire is consistent with immune process underlying the pathogenesis of paroxysmal nocturnal hemoglobinuria," *Blood*, 96:2613-2620, 2000.

Kay et al., "Interleukin 4 content in chronic lymphocytic leukemia (CLL) B cells and blood CD8 T cells from B-CLL patients; impact on clonal B-cell apoptosis," *British J. Haematol.*, 112:760-767, 2001.

Kim et al., "CDR3 Size Spectratyping and Sequencing of Spectratype-Derived TCR of Spinal Cord T Cells in Autoimmune Encephalomyelitis," *J. Immunol.*, 160:509-513, 1998.

Kirsch et al., "Apoptosis of human T-cells: induction by glucocorticoids of surface receptor ligation in vitro and ex vivo," *J. Biol. Regul. Homeost. Agents*, 13(2):80-89, Apr.-Jun. 1999.

Koeta et al., "T cell Homeostasis in patients with rheumatoid arthritis," *Proc. natl. Acad. Sci. USA*, 97(16):9203-9208, Aug. 1, 2000.

Kolowos et al., "Detection of Restricted junctional diversity of peripheral T cells in SLE patients by spectratyping," *Lupus*, 6:701-707, 1997.

Kornacker et al., "Survivin expression correlates with apoptosis resistance after lymphocyte activation and is found preferentially in memory T cells," *Immunol. Letters*, 76:169-173, 2001.

Krawcyzk et al.,"Cbi-b Is a Negative Regulator of Receptor Clustering and Raft Aggregation in T Cells," *Immunity*, 13:463-473, Oct. 2000.

Lamy et al., "Large GRanular Lymphocyte Leukemia," *Cancer Control.*, 5(1):25-33, Jan. 5, 1998. Available at www.moffitt.usf.edu.

Lanzavecchia et al., "In *vitro* selective expansion of allergen specific T cells from atopic patients," *Clinical Exp. Immunol.*, 52:21-28, 1983.

Laport et al., "Adoptive transfer of costimulated T cells induces lymphocytosis in patients with relapsed/refactory non-Hodgkin lymphoma following CD34+ selected hematopoietic cell transplantation," *Blood*, 102(6):2004-2013, Sep. 15, 2003.

Laytragoon-Lewin et al., "Alteration of Cellular Mediated Cytotoxicity, T Cell Receptor Zeta (TcRξ) and Apoptosis Related Gene Expression in Nasopharyngeal Carcinoma (NPC) Patients: Possible Clinical Relevance," *Anticancer Res.*, 20:1093-1100, 2000.

Lehmann et al., "Determinant spreading and the dynamics of the autoimmune T-cell repertoire," *Immunol. Today*, 14(5):203-208, 1993.

McCarty, "Upregulation of lymphocyte apoptosis as a strategy for preventing and treating autoimmune disorders: a role for whole-food vegan diets, fish oil and dopamine agonists," *Med. Hyposthesis*, 57(2):258-275, 2001.

McFarland et al., "Amelioration of Autoimmune Reactions by Antigen-Induced Apoptosis of T Cells," *Adv. Exp. Med. Biol.*, 383:157-166, 1995.

McIntosh et al., "Analysis of the T Cell Receptor Vα Repertoire in Hashimoto's Thyroiditis: Evidence for the Restricted Accumulation of CD8 T Cells in the Absense of CD4 T Cell Restriction," *J. Clin. Endocrinol. and Metabol.*, 82(4):140-1146,1997.

McIntosh et al., "Induction of Apoptosis in Activated T Cell Blasts by Suppressive Macrophages: A Possible Immunotherapeutic Approach for Treatment of Autoimmune Disease," *Cellular Immunol.*, 193:24-35, 1999.

Melms et al., "Specific immune complexes augment in vitro acetylocholine receptor-specific T-cell proliferation," *Neurol.*, 43:583-588, 1993.

Migita et al., "FK506 Markedly Enhances Apoptosis of Antigen-Stimulated Peripheral T Cells By Down-Rugi;ation of Bcl-$x_L$," *Transplantation*, 68(7):1018-1023, Oct. 15, 1999.

Murata et al., "Limited TCR Repertoire of Infiltrating T Cells in the Kidneys of Sjögren's Syndrome Patients with Interstitial Nephritis," *J. Immunol.*, 155:4084-4089, 1995.

Murphy et al., "Clinical Clearing of Psoriasis by 6-Thioguanine Correlates With Cutaneous T- Cell Depletion via Apoptosis," *Arch. Dermatol.*, 135:1495-1502, 1999.

Musette et al., "Expansion of a recurrent Vβ5.3 T-cell population in newly diagnosed and untreated HLA-DR2 multiple sclerosis patients," *Proc. Natl. Acad. Sci. USA*, 93:12461-12466, Oct. 1996.

Nagahara et al., "Evidence that FTY 720 induces T cell apoptosis in vivo," *Immunopharmacol.*, 48:75-85, 2000.

Nakashima et al., "The Role of T Cells Expressing TcR Vβ13 in Autoimmune Thyroiditis Induced by Transfer of Mouse Thyroglobulin-Activated Lymphocytes: Identification of Two Coomon CDR3 Motifs," *Clin. Immunol. and Immunopathol.*, 80(2):204-210, Aug. 1996.

Namekawa et al., "Killer Cell Activating Receptors Function as Costimulatory Molecules on CD4 $CD28^{null}$ T Cells clonally Expanded in Rheumatoid Arthritis," *J. Immunol.*, 165:1138-1145, 2000.

Nikolic-paterson, "T-Cell Specific Therapy in Autoimmune Glomerulonephritis," *Am. J. Kidney Dis.*, 38(6):1321-1328, Dec. 2001.

Nomura et al., "Twenty-five types of T-cell receptor Vβ family repertoire in patients with Kawasaki syndrome," *Eur. J. Pediatr.*, 157:981-986, 1998.

O'Reilly et al., "Apoptosis and autoimmune disease," *Inflamm. Res.*, 48:5-21, 1999.

Ogura et al., "Induction of apoptosis by novel synthesized acylamides of human lymphocytes," *Biochimica et Biophysica Acta*, 1483:111-118, 2000.

Okamoto et al., "T Cell Repertoir in Primary Biliary Cirrhosis: A Common T Cell Clone and Repertoire Change After Treatment,"*J. Clin. Immunol.*, 21(4):278-285, 2001.

Olive et al., "Resticted junctional diversity of T cell receptor δ gene rearrangements expressed in systemic lupus erythematosus (SLE) patients," *Clin. Exp. Immunol.*, 97:430-438, 1994.

Paillot et al., "Activation-Dependent Lymphocyte Apoptosis Induced by Methotrexate," *Transplan. Proc.*, 20:2348-2350, 1998.

Perkins et al., "Restriction of the TCR Repertoire Inhibits the Development of Memory T Cells and Prevents Autoimmunity in *lpr* Mice," *J. Immunol.*, 156:4961-4968, 1996.

Pinkoski et al., "Lymphocyte apoptosis: refining the paths to perdition," *Curr. Opin. Hematol.*, 9:43-49, 2002.

Planey et al., "Glucocorticoid-Induced Apoptosis in Lymphocytes," *Biochem. Biophys. Res. Coomun.*, 279:307-312, 2000.

Prinz et al., "T cell clones from psoriasis skin lesions can rptomote keratinocyte proliferation *in vitro* via secreted products," *Eur. J. Immunol.*, 24:593-598, 1994.

Prinz et al., "Selection of conserved TCR VDJ rearrangements in chronic psoriatic plaques indicates a common antigen in psoriasis vulgaris," *Eur. J. Immunol.*, 29:3360-3368, 1999.

Qiao et al., "T cell repertoire amd mitotic responses of lamina propria T lymphocytes in inflammatory bowel disease," *Clin. Exp. Immunol.*, 97:303-308, 1994.

Ravirajan et al., "Apoptosis in Human Autoimmune Disease," *Intern. Rev. Immunol.*, 18:563-589, 1999.

Rawling et al., "Spontaneous Apoptosis in Lymphocytes From Patients With Wiscott-Aldrich Syndrome: Correlation of Accelerated Cell Death and Attenuated Bcl-2 Expression," *Blood*, 94(11):3872-3882, Dec. 1, 1999.

Renz et al., "T cell recptor-Vβ repertoire in allergen-specific sensitization and increased airway responsiveness," *Allergy*, 50(suppl. 25):15-19, 1995.

Riddell, S.R. et al., "The use of anti-CD3 and anti-CD28 monoclonal antibodies to clone and expand human atigen-specific T cells," *J. Immunological Meth.*, 128:189-201, 1990.

Rodriguez-Palmero et al., "Triggering of T cell proliferation through CD28 induces GATA-3 and promotes T helper type 2 differentiation in vitro and in vivo," *Eur. J. Immunol.*, 29:3914-3924, 1999.

Sasajima et al., "Detection of T cell Apoptosis after Major Operations," *Eur. J. Surg.*, 165:1020-1023, 1999.

Schmidt et al., "The Repertoire of CD4 CD28 T Cells in Rheumatoid Arthritis," *Molecular Med.*, 2(5):608-618, Sep. 1996.

Schmidt et al., "T-cell apoptosis in *situ* in experimental autoimmune encephalomyclitis following methylprednisolone pulse therapy, " *Brain*, 123:1431-1441, 2000.

Schneider et al., "Experimental autoimmune myositis in the Lewis rat: lack of spontaneous T-cell apoptosis and therapeutic response to glucocorticosteroid application," *J. Neuroimmunol.*, 107:83-87, 2000.

Smith et al., "In vitro T cell proliferation from kidney allograft biopsies with unremarkable pathology: new strategies for an old problem," *Transplantation*, 73(1):142-145, Jan. 15, 2002.

Snyder et al., "Formation of the Killer Ig-Like Receptor Repertoire on CD4 CD28$^{null}$ T Cells," *J. Immunol.*, 168:3839-3846, 2002.

Söderström et al., "Autoimmune T cell repertoire in optic neuritis and multiple sclerosis: T cells recognizing multiple myelin proteins are accumulated in cerebrospinal fluid," *J. Neurol., Neurosurg., and Pysch.*, 57:544-551, 1994.

Stahnke et al., "Activation of apoptosis pathways in peripheral blood lymphocytes by in vivo chemotherapy," *Blood*, 98(10):3066-3073, Nov. 15, 2001.

Strauss et al., "Induction of apoptosis and modulation activation and effector function in T cells by immunosuppressive drugs," *Clin Exp. Immunol.*, 128:255-266, 2002.

Takemura et al., "T Cell Activation in Rheumatoid Synovium Is B Cell Dependent," *J. Immunol.*, 167:4710-4718, 2001.

Tokushige et al., "Abnormal T Cell Activation and Skewed T Cell Receptor Vβ Repertoire Usage in Japanese Patients with Idiopathic Portal Hypertension," *Clin. Immunol. and Immunopathol.*, 75(3): 206-213, 1995.

Trickett et al., "Ex vivo expansion of functional T lymphocytes from HIV-infected individuals," *J. Immunological Meth.*, 262:71-83, 2002.

Vavassori et al., "Restricted TCR Repertoire and Long-Term Persistence of Donor-Derived Antigen-Experienced CD4 T Cells in Allogenic Bone Marrow Transplantation Recipients,"*J. Immunol.*, 157:5739-5747, 1996.

Venuprasad et al., "Human Neutrophil-Expressed CD28 Interacts with Macrophage B7 to Induce Phosphatidylinositol 3-Kinase-Dependent INF-γ Secretion and Restriction of *Leishmania* Growth," *J. Immunol.*, 169:920-928, 2002.

Warrington et al., "CD4+, CD28- T Cells in Rheumatoid Arthritis Patients Combine Features of the Innate and Adaptive Immune Systems," *Arthritis & Rheumatism*, 44()1:13-20, Jan. 2001.

Brodie et al., "In vivo migration and function of transferred HIV-1-specific cytotoxic T cells," *Nature Medicine* 5(1): 34-41, Jan. 1999.

Cohen et al., "Propagation of mouse and human T cells with defined antigen specificity and function," *CIBA Foundation Symposium*, 187;179-197, 1994.

Curtsinger et al., "CD8 Memory T Cells (CD44$^{high}$, Ly-6C) Are More Sensitive than Naïve Cells (CD44$^{low}$, Ly-6C) to TCR/CD8 Signaling in Response to Antigen,"*J. Immunol.*, 160:3326-3243, 1998.

Dahl et al., "Expression of Bcl-$X_L$ Restores Cell Survival, but Not Proliferation and Effector Differentiation, in CD28-deficient T Lymphocytes,"*J. Exp. Med.*, 191(12):2031-2037, Jun. 19, 2000.

DeBenedette et al., "Costimulation of CD28 T Lymphocytes by 4-1BB Ligand," *J. Immunol.*, 158(2):551-559, Jan. 15, 1997.

Deeths et al., "B7-1-depedent co-stimulation results in qualitatively and quantitatively different response by CD4 and CD8 T cells," *Eur. J. immunol.*, 27(1):598-608, Jan. 1997.

Deeths et al., "CD8 T Cells Become Nonresponsive (Anergic) Following Activation in the Presence of Costimulation," *J. Immunol.*, 163:102-110, 1999.

Dong et al., "B7-H1, a thrid member of the family, co-stimulates T-cell proliferation and interleukin-10 secretion," *Nature Medicine* 5(12):1365-1369, Dec. 1999.

Dunbar et al., "Direct isolation, phenotyping and cloning of low-frequency antigen-specific cytotoxic T lymphocytes from peripheral blood," *Current Biology*, 8(7):413-416, Mar. 26, 1998.

Fanger et al., "Type I (CD64) and Type II (CD32) Fcγ Receptor-Mediated Phagocytosis by Human Blood Dendritic Cells," *J. Immunol.*, 157(2):541-548, Jul. 15, 1996.

Fowler et al., "Donor CD-4 Enriched Cells of Th2 Cytokine Phenotype Regulate Graft-Versus-Host Disease Without Impairing Allogeneic Engraftment in Sublethally Irradiated Mice," *Blood*, 84(10):3540-3549, Nov. 15, 1994.

Fraser et al., "Regulation of Interleukin-2 Gene Enhancer Activity by the T Cell Accessory Molecule CD28," *Science*, 251:313-316, Jan. 18, 1991.

Freeman et al., "Engagement of the PD-1 Immunoinhibitory Receptor by a Novel B7 Family Member Leads to Negative Regulation of Lymphocyte Activation," *J. Exp. Med.*, 192(7):1027-1034, Oct. 2, 2000.

Gett et al., "Cell division regulates the T cell cytokine repertoire, revealing a mechanism underlying immune class regulation," *Proc. Natl. Acad. Sci. USA*, 95:9488-9493, Aug. 1998.

Gett et al., "A cellular calculus for signal integration by T cells," *Nature Immunology*, 1(3):239-244, Sep. 2000.

Gillis et al., "Long term culture of tumour-specific cytoxic T cells," *Nature*, 268(14):154-156, Jul. 14, 1977.

Gimmi et al., "B-cell surface antigen B7 provides a costimulatory signal that includes T cells to proliferate and secrete interleukin 2," *Proc. Natl. Acad. Sci. USA*, 88:6576-6579, Aug. 1991.

Goodwin et al., "Molecular cloning of a ligand for the inducible T cell gene 4-1BB: a member of an emerging family of cytokines with homology to tumor necrosis factor," *Eur. J. Immunol.*, 23(10):2631-2641, Oct. 1993.

Green et al., "Antigen-specific human monoclonal antibodies from mice engineered with human 1g heavy and light chain YACs," *Nat. Genet.*, 7(1):13-21, May 1994.

Groux et al., "CD3-mediated apoptosis of human medullary thymocytes and activated peripheral T cells: respective roles of interleukin-1, interleukin-2, interferon-γ and accessory cells," *Eur. J. Immunol*, 23(7):1623-1629, Jul. 1993.

Guinn et al., "4-1BBL Cooperates with B7-1 and B7-2 in Converting a B Cell Lymphoma Cell Line into a Long-Lasting Antitumor Vaccine," *J. Immunol.*, 162:5003-5010, 1999.

Hansen et al., "Monoclonal Antibodies Identifying a Novel T-Cell Antigen and Ia Antigens of Human Lymphocytes," *Immunogenetics*, 10(3):247-260, Mar. 1, 1980.

Harding et al., "CD28-mediated signalling co-stimulates murine T cells and prevents induction of anergy in T-cell clones," *Nature* 356:607-609, Apr. 16, 1992.

Heimfeld et al., "Improvements in Gene Therapy: Rapid Purification of Specific Target Cells Using the Ceprate® System," *British J. Haematol.*, 87(1):193, Abstract No. 754, 1994.

Henderson et al., "Comparison of the effect of FK-506, cyclosporin A and rapamycin on IL-2 producton," *Immunol.*, 73(3):316-321, Jul. 1991.

Heslop et al., "Long-term restoration of immunity against Epstein-Barr Virus Infection by adoptive transfer of gene-modified virus-specific T lymphocytes," *Nature Medicine* 2(5):551-555, May 1996.

Hurtado et al., "Potential Role of 4-1BB in T Cell Activation," *J. Immunol.* 155(7):3360-3367, Oct. 1, 1995.

Hurtado et al., "Signals Through 4-1BB are Costimulatory to Previously activated Splenic T Cells and Inhibit Activation-Induced Cell Death," *J. Immunol.* 158(6):2600-2609, Mar. 15, 1997.

Jelley-Gibbs et al.,"Two Distinct Stages in the Transition from Naive CD4 T Cells to Effectors, Early Antigen-Dependent and late Cytokine-Driven Expansion and Differentiation," *J. Immunol.*, 165:5017-5026, 2000.

Kenikns et al., "Molecules involved in T-cell costimulation," *Curr. Opin, Immunol.*, 5(3):361-367, Jun. 1993.

June et al., "T-Cell Proliferation Involving the CD28 Pathway Is Associated with Cyclosporine-Resistant Interleukin 2 Gene Expression," *Mol. Cell. Biol.*, 7(12): 4472-4481, Dec. 1987.

Kabelitz et al., "Life and Death of a superantigen-reactive human CD4+ T cell clone: staphylococcal enterotoxins induce death by apoptosis but simultaneously trigger a proliferative response in the presence of HLA-DR+ antigen-presenting cells," *Int. Immunol.*, 4(12):1381-1388, Dec. 1992.

Kawabe et al., "Programmed cell death and extrathymic reduction of Vβ CD4 T cells in mice tolerant to *Staphylococcus aureus* enterotoxin B," *Nature*, 349:245-248, Jan. 17, 1991.

Ku et al., "Control of Homeostasis of CD8 memory T Cells by Opposing Cytokines," *Science*, 288:675-678, Apr. 28, 2000.

Kung et al., "Monoclonal Antibodies Defining Distinctive Human T Cell Surface Antigens," *Science*, 20:347-349, Oct. 19, 1979.

Kurys et al., "The Long Signal Peptide Isoform and Its Alternative Processing Direct the Intracellular Trafficking of Interleukin-15," *J. Biol. Chem.*, 275(39):30653-20659, Sep. 29, 2000.

Lanzavecchia, A., "Licence to Kill," *Nature*, 393:413-414, Jun. 4, 1998.

Latouche et al., "Induction of human cytotoxic T lymphocytes by artificial antigen- presenting cells," *Nature Biotechnology*, 18(4):405-409, Apr. 2000.

Laux et al., "Response Differences between Human CD4 and CD8 T-Cells during CD28 Costimulation: Implications for Immune Cell-Based Therapies and Studies Related to the Expansion of Double-Positive T-Cells during Aging," *Clin. Immunol.*, 96(3):187-197, Sep. 2000.

Lenschow et al., "Long-Term Survival of Xeogeneic Pancreatic Islet Grafts Induced by CTLA4Ig," *Science*, 257:789-792, Aug. 7, 1992.

Levine et al., "CD28 ligands CD80 (B7-1) and CD86 (B7-2) induce long-term autocrine growth of CD4+ T cells and induce similar patterns of cytokine secretion *in vitro*," *Int. Immunol.*, 7(6):891-904, 1995.

Lindsten et al., "Regulation of Lymphokine Messenger RNA Stability by a Surface-Mediated T Cell Activation Pathway," *Science*, 244:339-343, Apr. 21, 1989.

Linsley et al., "The Role of the CD28 Receptor During T Cell Responses to Antigen," *Annu. Rev. Immunol.*, 11:191-212, 1993.

Liu et al., "Calcineurin is a Common Target of Cyclophilin-Cyclosporin A and FKBP-FK506 Complexes," *Cell*, 66(4):807-815, Aug. 23, 1991.

Liuzzo et al., "Perturbation of the T-Cell Repertoire in Patients With Unstable Angina," *Circulation*, 100(21):2135-2139, Nov. 23, 1999.

Lord et al., "The IL-2 Receptor Promotes Proliferation, bcl-2 and bcl-x Induction, But Not Cell Viability Through the Adapter Molecule She," *J. Immunol.*, 161:4627-4633, 1998.

Malefyt et al., "Direct Effects of IL-10 on Subsets of Human CD4 T Cell Clones and Resting T Cells," *J. Immunol.* ,150(11):4754-4765, Jun. 1, 1993.

Marks-Konczalik et al., "IL-2-induced activation-induced cell death is inhibited in IL-15 transgenic mice," *Proc. Natl. Acad. Sci. USA*, 97(21): 11445-11450, Oct. 10, 2000.

Melero et al., Monoclonal antibodies against the 4-1BB T-cell activation molecule eradicate established tumors, *Nature Medicine*, 3(6):682-685, Jun. 1997.

Melero et al., "Amplification of tumor immunity by gene transfer of the co-stimulatory 4-1BB ligand: synergy with the CD28 co-stimulatory pathway," *Eur. J. of Immunol.* 28(3):1116-1121, Mar. 1998.

Melief et al., "T-Cell Immunotherapy of Tumors by Adoptive Transfer of Cytotoxic T Lymphocytes and by Vaccination with minimal Essential Epitopes," *Immunological Reviews*, 146:167-177, 1995.

Musso et al., "Human Monocytes Constitutively Express Membrane-Bound, Biologically Active, and Interferon -γ- Upregulated Interleukin-15," *Blood*, 93(10):3531-3539, May 15, 1999.

Pollok et al., "Inducible T Cell Antigen 4-1BB: Analysis of Expression and Function," *J. Immunol.*, 150(3):771-781, Feb. 1, 1993.

Rabinovitch, "Regulation of human fibroblast growth rate by both noncycling cell fraction and transition probability is shown by growth in 5-bromodeoxyuridine followed by Hoechst 33258 flow cytometry," *Proc. Natl. Acad. Sci. USA*, 80:2951-2955, May 1983.

Refaeli et al., "Biochemical Mechanisms of IL-2-Regulated Fas-Mediated T Cell Apoptosis," *Immunity*, 8(5):615-623, May 1998.

Riddell et al., "The Fred Hutchinson Cancer Research Center and the University of Washington School of Medicine, Department of Medicine, Division of Oncology: Phase I Study of Cellular Adoptive Immunotherapy Using Genetically Modified CD8 HIV- Specific t Cells for HIV Seropositive Patients Undergoing Allogeneic Bone Marrow Transplant," *Humane Gene Therapy*, 3(3):319-338, Jun. 1992.

Riddell et al., "Restoration of Viral Immunity in Immunodeficient Humans by the Adoptive Transfer of T Cell Clones," *Science*, 257:238-241, Jul. 10, 1992.

Riddell et al., "Principles for Adoptive T Cell Therapy of Human Viral Disease," *Ann. Rev. Immunol.*, 13:545-586, 1995.

Rooney et al., "Infusion of Cytotoxic T Cells for the Prevention and Treatment of Epstein-Barr Virus-Induced Lymphoma in Allogeneic Transplant Recipients," *Blood*, 92(5):1549-1555, Sep. 1, 1998.

Rosenberg et al., "Gene Transfer into Humans - Immunotherapy of Patients with Advanced Melanoma, using Tumor-Infiltrating Lymphocytes Modified by Retroviral Gene Transduction," *N. Engl. J. Med.*, 323(9)570-578, Aug. 30, 1990.

Sagerström et al., "Activation and Differentiation requirements of primary T cells *in vitro*," *Proc. Natl. Acad. Sci. USA*, 90:8987-8991, Oct. 1993.

Salomon et al., "B7/CD28 Costimulation is Essential for the Homeostasis of the CD4 CD5 Immunoregulatory T Cells that Control Autoimmune Diabetes," *Immunity*, 12(4):431-440, Apr. 2000.

San Jose et al., "Assembly of the TCR/CD3 complex: CD3εδ CDεγ dimers associate indistinctly with both TCRα TCRβ chains. Evidence for a double TCR heterodimer model," *Eur. J. Immunol.*, 28:12-21, 1998.

Saoulli et al., "CD28-independent TRAF2-dependent Costimulation of Resting T Cells by 4-1BB Ligand," *J. Exp. Med.*, 187(11):1849-1862, Jun. 1, 1998.

Schwartz, R.H., "Costimulation of T Lymphocytes: The Role of CD28, CTLA-4, and B7/BB1 in Interleukin-2 Production and Immunotherapy," *Cell*, 71:1065-1068, Dec. 24, 1992.

Shevach, "Regulatory T Cells in Autoimmunity," *Annu. Rev. Immunol.* 18:423-229, 2000.

Shuford et al., "4-1BB Costimulatory Signals Perferentially Induce CD8 T Cell Proliferation and Lead to the Amplification In Vivo of Cytotoxic T Cell Responses," *J. Exp. Med.*, 186(1):47-55, Jul. 7, 1997.

Smith et al., "T-Cell Growth Factor-Mediated T-Cell Proliferation," *Ann. N.Y. Acad. Sci.*, 332:423-432, 1979.

Springer et al., "The Lymphocytes Function-Associated LFA-1, CD2, and LFA-3 Molecules: Cell Adhesion Receptors of the Immune System," *Ann. Rev. Immunol.*, 5:223-252, 1987.

Tagaya et al., "Generation of secretable and nonsecretable interleukin 15 isoforms through alernate usage of signal peptides," *Proc. Natl. Acad. Sci. USA*, 94:14444-14449, Dec. 1997.

Takahashi et al., "Cutting Edge: 4-1BB Is a Bona Fide CD8 T Cell Survival Signal," *j. Immunol.*, 162:5037-5040, 1999.

Tan et al., "4-1BB Costimulation Is Required for the Protective Anti-Viral Immunity After Peptide Vaccination," *J. Immunol.*, 164:2320-2325, 2000.

Turka et al., "T-cell actication by the CD28 ligand B7 is required for cardiac allograft rejection *in vivo*," *Proc. Natl. Acad. Sci. USA*, 89:11102-11105, Nov. 1992.

van de Winkel et al., "Human IgG Fc receptor heterogeniety: molecular aspects and clinical implications," *Immunol. Today*, 14(5):215-221, 1993.

Voltz et al., "A Serologic Marker of Paraneoplastic Limbic and Brain-Stem Encephalitis in Patients with Testicular Cancer," *N. Eng. J. Med.*, 340(23):1788-1795, Jun. 10, 1999.

Wang et al., "Naïve CD8 T-Cells Do Not Require Costimulation for Proliferation and Differentiation into Cytotoxic Effector Cells," *J. of Immunol.*, 164:1216-1222, 2000.

Webb et al., "Extrathymic Tolerance of Mature T Cells: Clonal Elimination as a Consequence of Immunity," *Cell*, 63:1249-1256, Dec. 21, 1990.

Wells et al., "Following the Fate of Individual T Cells Throughout Activation and Clonal Expansion," *J. Clin. Invest.*, 100(12):3173-3183, Dec. 1997.

Wells et al., "T Cell Effector Function and Anergy Avoidance Are Quantitatively Linked to Cell Division," *J. Immunol.*, 165:2432-2443, 2000.

Weyand et al., "Functional properties of CD4 Cd28 T cells in the aging immune system," *Mechanisms of Aging and Development*, 102(2, 3):131-147, May 15, 1998.

Yee et al., "Isolation of high Avidity Melanoma-Reactive CTl from Heterogeneous Populations Using Peptide-MHC Tetramers," *J. immunol.*, 162:2227-2234, 1999.

Yotnda et al., "Cytotxic T Cell Response Against the Chimeric p210 BCR-ABL Protein in Patients with Chronic Myelogenous Leukemia," *J. Clin. Invest.*, 101(10):2290-2296, May 2, 1998.

Zamai et al., "Lymphocyte binding to K562 cells: effect of target cell irradiation and correlation with ICAM-1 and LFA-3 expression," *Eur. J. Histochem.*, 38(Supp. 1):53-60, 1994.

Anonymous, "Xcyte Therapies Presents Clinical Results From Clinical Trials In Chronic Lymphocytic Leukemia And Multiple Myeoloma At The American Society of Hematology (ASH)," Biospace Beat, URL=http://www.biospace.com/news_story.aspx?StoryID=14618620&full=1>, download date Sep. 25, 2008.

Bonyhadi et al., "Expansion of Antigen-Specific CTL Using CD3/CD28 Paramagnetic Microbeads (Xcellerate™ Beads) for Adoptive Cellular Therapy of Melanoma," *Blood*, 98(11): 32B-33B, Nov. 16, 2001.

Drobyski et al., "Ex Vivo Anti-CD3 Antibody-Activated Donor T Cells Have a Reduced Ability to Cause Lethal Murine Graft-Versus-Host Disease but Retain Thier Ability to Facilitate Alloengraftment," *J. Immunol.*, 161(5):2610-2619, Sep. 1, 1998.

Jones et al., "Post-Hematopoietic Cell Transplantation Control of Graft-versus-Host Disease by Donor CD4+25+ T Cells to Allow an Effective Graft-versus-Leukemia Response," *Biol. of Blood and Marrow Transplantation*, 9:243-256, 2003.

Marktel et al., "Immunologic potential of donor lymphocytes expressing a suicide gene for early immune reconstitution after hematopoietic T-cell-depleted stem cell transplantation," *Blood*, 101(4):1290-1298, Feb. 15, 2003.

Muller et al., "Induction of Apoptosis and Anergy In Resting Human T-Lymphocytes After CD-3 Triggering and Its Modulation by CD28 and Cytokines," *European J. Cancer*, 31(1003):S34, Oct. 1995.

Muller et al., "Reduction of CD3-Mediated Apoptosis In Human T Cells By CD28-Costimulation: Possible Mechanisms," *European J. of Cancer*, 33:S35, Jun. 1997.

Napoles et al., "Mesenchymal Stem Cells Can Reduce Conditioning Requirements For Allogeneic Engraftment," *Am. J. Transplantation*, 4(s8):470, Mar. 2004.

Parmar et al., "Ex vivo expanded umbilical cord blood T cells maintain naive phenotype and TCR diversity," *Cytotherapy*, 8(2):149-157, 2006.

Porter et al., "Graft-Versus-Tumor Induction With Donor Leukocyte Infusions as Primary Therapy for Patients With Malignancies," *J. Clin. Oncol.*, 17(4):1234-1243, Apr. 1999.

Porter et al., "A phase 1 trial of donor lymphocyte infusions expanded and activated ex vivo via CD3/CD28 Costimulation," *Blood*, 107:1325-1331, Nov. 3, 2005.

Rapoport et al., "Molecular remission of CML after autotransplantation followed by adoptive transfer of costimulated autologous T cells," *Bone Marrow Transplantation*, 33:53-60, 2004.

Rapoport et al., "Restoration of immunity in lymphopenic individuals with cancer by vaccination and adoptive T-cell transfer," *Nature Medicine*, 11(11):1230-1237, Nov. 2005.

Rettig et al., "Kinetics of In Vivo Elimination of Suicide Gene-Expressing T Cells Affects Engraftment, Graft-versus-Host Disease, and Graft-versus-Leukemia after Allogeneic bone Marrow Transplantation," *J. Immunol.*, 173:3620-3630, 2004.

Rettig et al., "Comparison of the Proliferative Kinetics, GVHD Potential and GVC Sensitivity of Naive and Transduced and Selected Murine T Cells after Allogeneic BMT," *Blood* (ASH Annual Meeting Abstracts), 106: Abstract 5257, 2005.

Shibuya et al., "Anti-CD3/Anti-CD28 Bead Stimulation Overcomes CD3 Unresponsiveness in Patients With Head and Neck Squamous Cell Carcinoma," *Arch. Otolaryngol. Head Neck Surg.*, 126:473-479, 2000.

Siegel et al., "A Phase I/II Study of Xcellerated T Cells™ after Autologous Peripheral Blood Stem Cell Transplantation in Patients with Multiple Myeloma," *Blood* (ASH Annual Meeting Abstracts), 104: Abstract 925, 2004.

Slavin et al., "Immunotherapy of cancer with alloreactive lymphocytes," *Lancet Oncol.*, 2:491-498, Aug. 2001.

Stefanski et al., "Transduction and Expansion of T Lymphocytes Genetically Engineered To Target the CD19 Antigen for the Treatment of CLL Using Xcyte™ Dynabeads®," *Molecular Therapy*, 11(Supp. 1):S274, May 2005.

Tang et al., "In Vitro-expanded Antigen-specifc Regulatory T Cells Suppress Autoimmune Diabetes," *J. Exp. Med.*, 199(11):1455-1465, Jun. 7, 2004.

Taylor et al., "The infusion of ex vivo activated and expanded CD4=CD25= immune regulatory cells inhibits graft-versus-host disease lethality," *Blood*, 99:3493-3499, 2002.

Taylor et al., "L-Selectinhi but not the L-selectinlo CD4=25= T-regulatory cells are potent inhibitors of GVHD and BM graft rejection," *Blood*, 104:3804-3812, Aug. 3, 2004.

Thompson et al., "A Phase I Trial of CD3/CD28-activated T Cells (Xcellerated T Cells) and Interleukin-2 in Patients with Metastatic Renal Cell Carcinoma," *Clin. Cancer Res.*, 9:3562-3570, Sep. 1, 2003.

Thornton et al., "Activation requirments for the induction of CD4+CD25+ T cell suppressor function," *European J. Immunol.*, 34:366-376, 2004.

Trenado et al., "Ex Vivo-Expanded CD4+ CD25+ Immunoregulatory T Cells Prevent Graft-versus-Host-Disease by Inhibiting Activation/Differentiation of Pathogenic T Cells," *J. Immunol.*, 176:1266-1273, 2006.

Van Rijn et al., "Quantitative Assessment of Human T Lymphocytes in RAG2-/-yc-/-Mice: The Impact of Ex Vivo Manipulation on In Vivo Functionality," *Exper. Hematol.*, 35:117-127, 2007.

Vij et al., "A Phase I/II Study of Xcellerated T Cells™ after Autologous Peripheral Blood Stem Cells Transplantation in Patients with Multiple Myeoloma," *Blood* (ASH Annual Meeting Abstracts), 102(11): Abstract 139, 2003.

Vij et al., "A Randomized Phase II Study of Xcellerated T Cells™ with or without Prior Fludarabine Therapy in Patients with Multiple Myeolma (MM)," ASCO Annual Meeting Proceedings, 23(16S):2582, Jun. 1, 2005.

Wei et al., "Mapping the sensitivity of T cells with an optical trap: Polarity and minimal number of receptors for Ca2+ signaling," Proc. Natl. Acad. Sci. USA, 96:8471-8476, Jul. 1999.

Xia et al., "Targeting Acute Allograft Rejection by Immunotherapy With Ex Vivo-Expanded Natural CD4+CD25+ Regulatory T Cells," Transplantation, 82(12):1749-1755, Dec. 27, 2006.

Zapata-Sirvent et al., "Temporal analysis of human leucocyte surface antigen expression and neutrophil respiratory burst activity after thermal injury," Burns, 19(1):5-11, 1993.

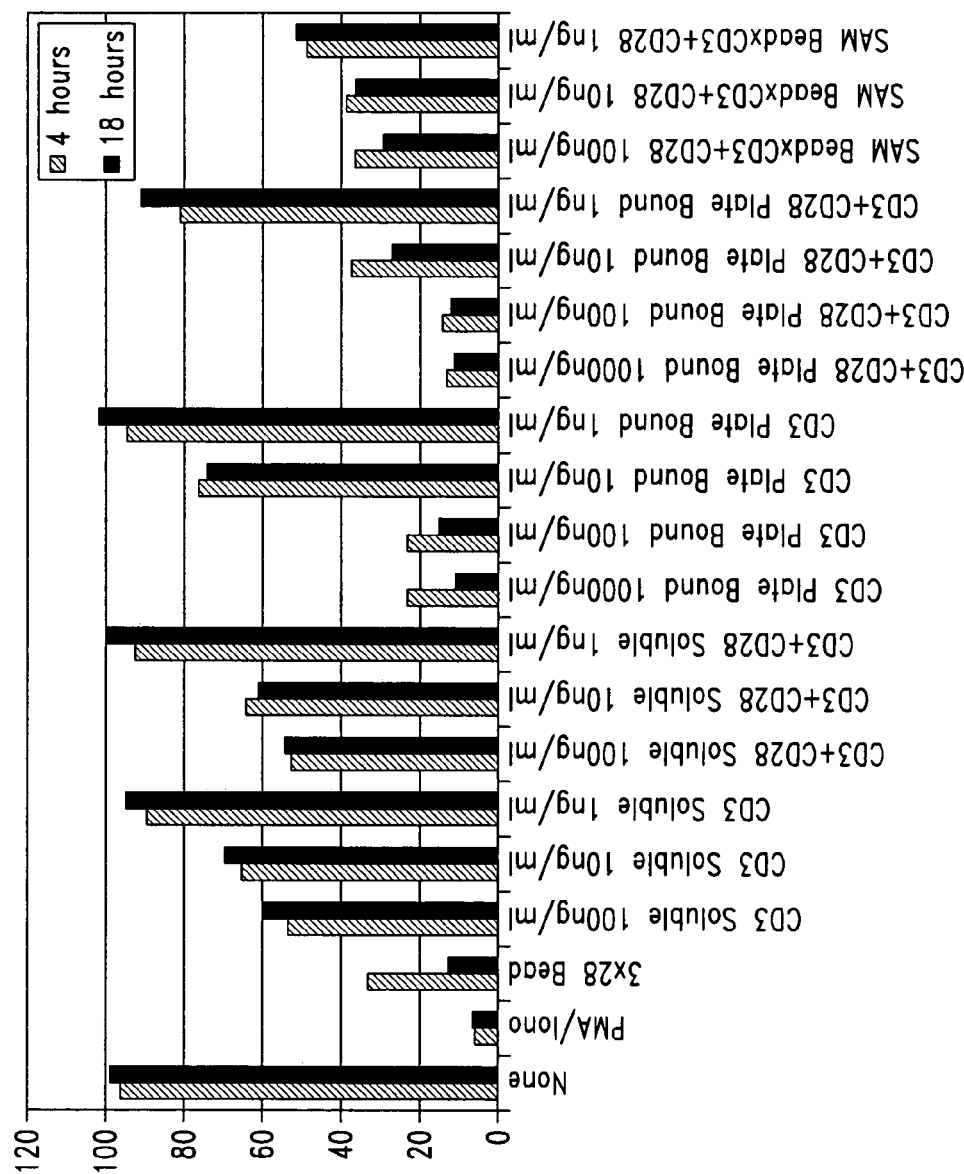

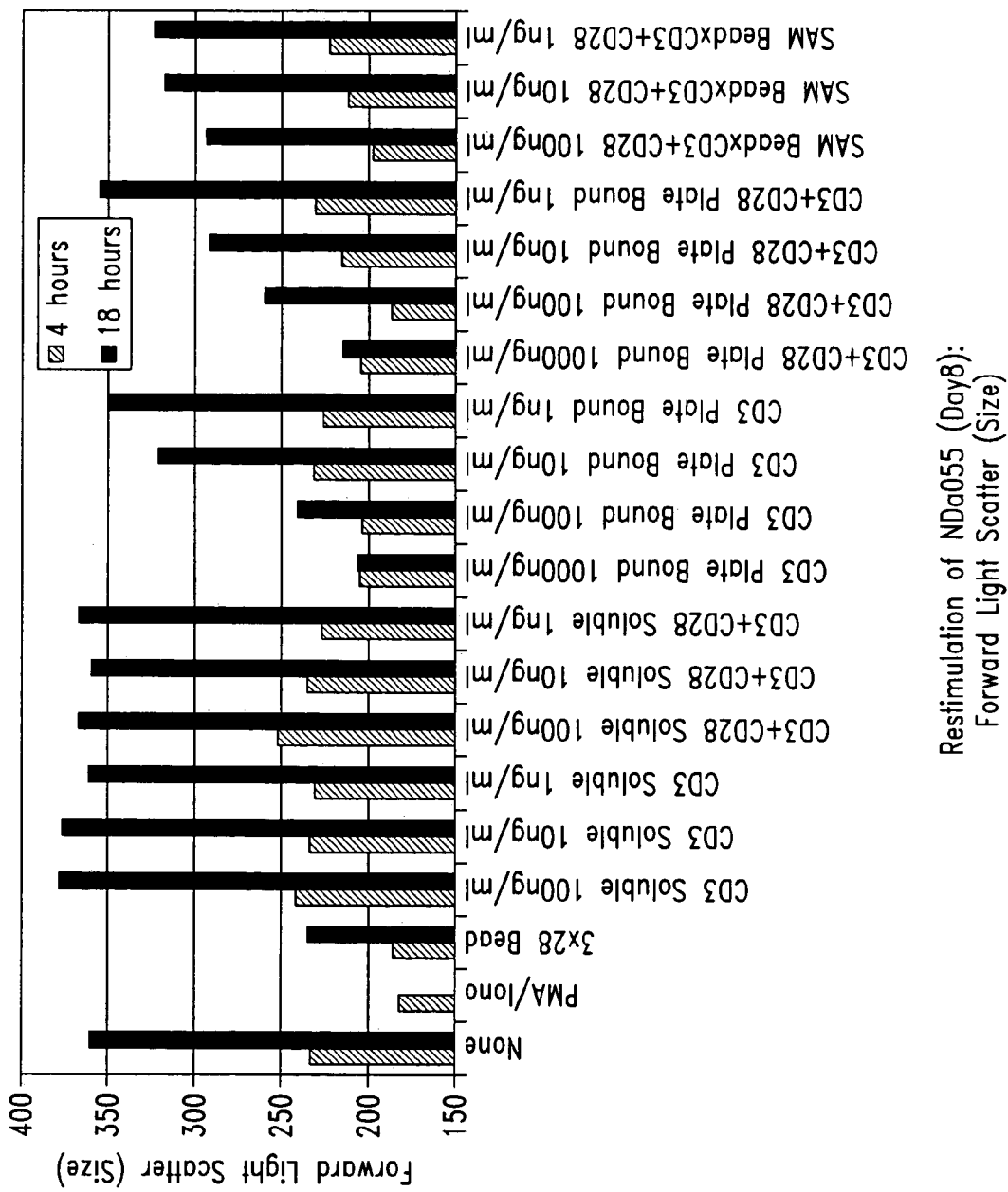

ACTIVATION AND EXPANSION OF CELLS

BACKGROUND OF THE INVENTION

1. Field of the Invention

The present invention relates generally to methods for stimulating and activating cells, and more particularly, to methods to activate and expand cells to very high densities and to expand cells to very high numbers. The present invention also relates to compositions of cells, including activated and expanded T cells at high concentrations and expanded to high numbers.

2. Description of the Related Art

The T cell antigen receptor (TCR) is a multisubunit immune recognition receptor that associates with the CD3 complex and binds to peptides presented by the major histocompatibility complex (MHC) class I and II proteins on the surface of antigen-presenting cells (APCs). Binding of TCR to the antigenic peptide on the APC is the central event in T cell activation, which occurs at an immunological synapse at the point of contact between the T cell and the APC.

To sustain T cell activation, T lymphocytes typically require a second co-stimulatory signal. Co-stimulation is typically necessary for a T helper cell to produce sufficient cytokine levels that induce clonal expansion. Bretscher, *Immunol. Today* 13:74, 1992; June et al., *Immunol. Today* 15:321, 1994. The major co-stimulatory signal occurs when a member of the B7 family ligands (CD80 (B7.1) or CD86 (B7.2)) on an activated antigen-presenting cell (APC) binds to CD28 on a T cell.

Methods of stimulating the expansion of certain subsets of T cells have the potential to generate a variety of T cell compositions useful in immunotherapy. Successful immunotherapy can be aided by increasing the reactivity and quantity of T cells by efficient stimulation.

The various techniques available for expanding human T cells have relied primarily on the use of accessory cells and/or exogenous growth factors, such as interleukin-2 (IL-2). IL-2 has been used together with an anti-CD3 antibody to stimulate T cell proliferation, predominantly expanding the CD8$^+$ subpopulation of T cells. Both APC signals are thought to be required for optimal T cell activation, expansion, and long-term survival of the T cells upon re-infusion. The requirement for MHC-matched APCs as accessory cells presents a significant problem for long-term culture systems because APCs are relatively short-lived. Therefore, in a long-term culture system, APCs must be continually obtained from a source and replenished. The necessity for a renewable supply of accessory cells is problematic for treatment of immunodeficiencies in which accessory cells are affected. In addition, when treating viral infection, if accessory cells carry the virus, the cells may contaminate the entire T cell population during long-term culture.

In the absence of exogenous growth factors or accessory cells, a co-stimulatory signal may be delivered to a T cell population, for example, by exposing the cells to a CD3 ligand and a CD28 ligand attached to a solid phase surface, such as a bead. See C. June, et al (U.S. Pat. No. 5,858,358); C. June et al. WO 99/953823. While these methods are capable of achieving therapeutically useful T cell populations, increased robustness and ease of T cell preparation remain less than ideal.

In addition, the methods currently available in the art have not focused on short-term expansion of T cells or obtaining a more robust population of T cells and the beneficial results thereof. Furthermore, the applicability of expanded T cells has been limited to only a few disease states. For maximum in vivo effectiveness, theoretically, an ex vivo- or in vivo-generated, activated T cell population should be in a state that can maximally orchestrate an immune response to cancer, infectious disease, or other disease states. The present invention provides methods to generate an increased number of more highly activated and more pure T cells that have surface receptor and cytokine production characteristics that appear more healthy and natural than other expansion methods.

In addition, the present invention provides compositions of cell populations of any target cell, including T cell populations and parameters for producing the same, as well as providing other related advantages.

BRIEF SUMMARY OF THE INVENTION

The present invention provides methods for activating and expanding a population of T cells by cell surface moiety ligation, comprising: a) providing a population of cells wherein at least a portion thereof comprises T cells; b) contacting said population of cells with a surface, wherein said surface has attached thereto one or more agents that ligate a cell surface moiety of at least a portion of the T cells and stimulates said T cells, and wherein said T cells expand to a concentration of about between $6\times10^6$ cells/ml and about $90\times10^6$ cells/ml in less than about two weeks. In one embodiment, the T cells are derived from a single individual and the T cells expand from a starting number of cells of about 100-$500\times10^6$ to a total of about 100-$500\times10^9$ cells in less than about two weeks. The method of claim 1 wherein said T cells reach a concentration of about $50\times10^6$ cells/ml in less than about two weeks. In one embodiment, the T cells reach a concentration of about 40-$60\times10^6$ cells/ml by about day 7 to about day 12. In a further embodiment, the T cells expand by at least about 1.5 fold in about 24 hours from about day 5 to about day 12. In another embodiment, the population of T cells is seeded into a culture container that holds from about a 0.1 liter volume to about a 200 liter volume. In a related embodiment, the culture container comprises at least one inlet filter and one outlet filter. In yet another embodiment, the population of T cells is seeded at an initial concentration of about $0.2\times10^6$ cells/ml to about $5\times10^6$ cells/ml.

In one embodiment, the expansion of the cells of the present invention occurs in a closed system. In one embodiment, the closed system comprises a container comprising at least one inlet filter, one outlet filter, and a sampling port. In another embodiment, the culture medium is perfused through the closed system. In certain embodiments perfusion is initiated on about day 4-day 8 at a rate from about 0.5 ml/minute to about 3 ml/minute. Illustrative media includes, but is not limited to, RPMI 1640, AIM-V, DMEM, MEM, α-MEM, F-12, X-Vivo 15, and X-Vivo 20. In further embodiments, the media can comprise a cytokine, such as IL-2, IFN-γ, IL-4, GM-CSF, IL-10, IL-12, TGFβ, and TNF-α, or a vitamin. In further embodiments, the medium comprises surfactant, an antibody, plasmanate or a reducing agent (e.g. N-acetyl-cysteine, 2-mercaptoethanol).

In further embodiments, the closed system of the present invention comprises a bioreactor culture container positioned on a platform capable of rocking. In certain embodiments, the speed and the angle of the rocking platform are variable. In further embodiments, the rocking of said platform is initiated on about day 3 at about 5-15 rocks/minute. In yet other embodiments, the platform further comprises a variable heating element, a magnet, and a gas manifold In certain embodiments, the closed system further comprises a syringe pump and control for sterile transfer to and from said closed system.

In a further embodiment, the methods of the present invention provide for a surface that has attached thereto a first agent that ligates a first T cell surface moiety of a T cell, and the same or a second surface has attached thereto a second agent that ligates a second moiety of said T cell, wherein said ligation by the first and second agent induces proliferation of said T cell. In a related embodiment, the same or a third surface has attached thereto a third agent that ligates a third moiety of said T cell wherein said ligation by the first, second, and third agents induces proliferation of said T cell. In certain embodiments, at least one agent is an antibody or an antibody fragment. In other embodiments, the first agent is an antibody or a fragment thereof, and the second agent is an antibody or a fragment thereof. In yet another embodiment, the first and the second agents are different antibodies. In certain embodiments, the first agent is an anti-CD3 antibody, an anti-CD2 antibody, or an antibody fragment of an anti-CD3 or anti-CD2 antibody and the second the second agent is an anti-CD28 antibody or antibody fragment thereof. In another embodiment, the first agent is an anti-CD3 antibody and the second agent is an anti-CD28 antibody. In further embodiments, the anti-CD3 antibody and the anti-CD28 antibody are present at a ratio of about 1:1 to about 1:100. In certain embodiments, the first agent is an anti-CD3 antibody and the second agent is a ligand for CD28, such as the natural ligand, B7. In further embodiments, the third agent is an antibody or antibody fragment thereof. In another embodiment, the third agent is an anti-4-1BB antibody or antibody fragment thereof.

The present invention also provides for populations of T cells produced according to the methods as described herein.

One aspect of the present invention provides for an apparatus, comprising a closed culture container comprising at least one outlet filter and one inlet filter; said closed culture container having inside a volume of culture medium comprising expanded T cells at a density of from about $6 \times 10^6$ cells/ml to about $90 \times 10^6$ cells/ml. In certain embodiments the expanded T cells are at a density of from about $10\text{-}50 \times 10^6$ cells/ml. In further embodiments, the medium of the apparatus further comprises a surface wherein said surface has attached thereto a first agent that ligates a first cell surface moiety of a T cell, and the same or a second surface has attached thereto a second agent that ligates a second moiety of said T cell.

One aspect of the present invention provides for compositions comprising a total of $100 \times 10^9$ activated and expanded T cells from a single individual.

Another aspect of the present invention provides for methods for expanding a population of cells by cell surface moiety ligation, comprising: providing a population of cells; contacting said population of cells with a surface, wherein said surface has attached thereto one or more agents that ligate a cell surface moiety of at least a portion of the cells and stimulates said cells, and wherein said cells expand to a concentration of about between $6 \times 10^6$ cells/ml and about $90 \times 10^6$ cells/ml in less than about two weeks. In certain embodiments of the methods, at least a portion of said population of cells comprises B cells, NK cells, dendritic cells, stem cells, liver cells, neurons, mesenchymal cells, LAK cells, or lung cells.

Another aspect of the present invention provides for methods for expanding a population of T cells by cell surface moiety ligation, comprising: providing a population of cells wherein at least a portion thereof comprises T cells; contacting said population of cells with a surface, wherein said surface has attached thereto a first agent that ligates a first cell surface moiety of a T cell, and the same or a second surface has attached thereto a second agent that ligates a second moiety of said T cell, wherein said ligation by the first and second agent induces proliferation of said T cell; following contact with said surface for a period of time of about between 0 and 5 days, seeding said population of cells at a concentration of between about $0.2 \times 10^6$ and $5.0 \times 10^6$ cells/ml in a closed system comprising a disposable bioreactor bag comprising at least one inlet filter and one outlet filter; perfusing medium through said closed system at about 1 ml/minute; rocking said bioreactor bag on a rocking platform at about 5-15 rocks/minute; and wherein said T cells expand to a concentration of about between $6 \times 10^6$ cells/ml to about $90 \times 10^6$ cells/ml in less than about two weeks.

The present invention also provides populations of T cells wherein said T cells are proliferating and wherein said population is at a concentration of between about $6 \times 10^6$ cells/ml and about $90 \times 10^6$ cells/ml. In one embodiment, the population of T cells reaches a total cell number of between about $100 \times 10^9$ and about $500 \times 10^9$ in less than 2 weeks in culture.

The present invention further provides method for activating and expanding a population of T cells by cell surface moiety ligation, comprising providing a population of cells wherein at least a portion thereof comprises T cells, contacting said population of cells with a surface, wherein said surface has attached thereto one or more agents that ligate a cell surface moiety of at least a portion of the T cells and stimulates said T cells, wherein said surface is present at a ratio of said surface to said cells such that at least one population of antigen-specific T cells is expanded at least about 10 fold in about 8 days. In one embodiment, the ratio is from about 1:1 to about 1:10. In a further embodiment, the ratio is about 1:5.

One aspect of the present invention provides a method for activating and expanding a population of T cells by cell surface moiety ligation, comprising: providing a population of cells wherein at least a portion thereof comprises T cells; contacting said population of cells with a surface, wherein said surface has attached thereto a first agent that ligates a first T cell surface moiety of a T cell, and the same or a second surface has attached thereto a second agent that ligates a second moiety of said T cell, wherein said ligation by the first and second agent induces proliferation of said T cell, and wherein said surface is present at a ratio of said surface to said cells such that at least one population of antigen-specific T cells is expanded at least about 10 fold in about 8 days. In one embodiment, the ratio is from about 1:1 to about 1:100, and all integers therebetween. In another embodiment, the ratio is from about 1:5 to about 1:6, 1:7, 1:8, 1:9, or 1:10.

In a further embodiment, said same or a third surface has attached thereto a third agent that ligates a third moiety of said T cell wherein said ligation by the first, second, and third agents induces proliferation of said T cell. In an additional embodiment the third agent is an antibody or antibody fragment thereof. In yet another embodiment, the third agent is an anti-4-1BB antibody or antibody fragment thereof. In another embodiment, at least one agent is an antibody or an antibody fragment. In a further embodiment, the first agent is an antibody or a fragment thereof, and the second agent is an antibody or a fragment thereof and in certain embodiments, the first and the second agents are different antibodies. The the first agent may be an anti-CD3 antibody, an anti-CD2 antibody, or an antibody fragment of an anti-CD3 or anti-CD2 antibody. The second agent may be an anti-CD28 antibody or antibody fragment thereof. In a further embodiment, the first agent is an anti-CD3 antibody and the second agent is an anti-CD28 antibody. In another embodiment, the anti-CD3 antibody and the anti-CD28 antibody are present at a ratio of about 1:1 to about 1:100. In yet a further embodiment, the first agent is an anti-CD3 antibody and the second agent is a ligand for CD28. In certain embodiments, the ligand is a natural ligand for CD28, such as B7.

Another aspect of the present invention provides population of T cells produced according to any of the methods described herein. A further embodiment provides for a method for the treatment of cancer comprising administering to a patient the population of T cells according to the methods described herein. Cancers that can be treated include but are not limited to melanoma, non-Hodgkin's lymphoma, cutaneous T cell lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL).

Another aspect of the present invention provides a method for activating and expanding a population of regulatory T cells by cell surface moiety ligation, comprising: providing a population of cells wherein at least a portion thereof comprises regulatory T cells; contacting said population of cells with a surface, wherein said surface has attached thereto a first agent that ligates a first T cell surface moiety of a regulatory T cell, and the same or a second surface has attached thereto a second agent that ligates a second moiety of said regulatory T cell, wherein said ligation by the first and second agent induces proliferation of said regulatory T cell. In one embodiment, the first agent is an anti-CD3 antibody and the second agent is an anti-CD28 antibody.

A further aspect of the present invention provides a composition comprising a population of T cells activated and expanded according to the following method: providing a population of cells wherein at least a portion thereof comprises T cells; contacting said population of cells with a surface, wherein said surface has attached thereto a first agent that ligates a first T cell surface moiety of a T cell, and the same or a second surface has attached thereto a second agent that ligates a second moiety of said T cell, wherein said ligation by the first and second agent induces proliferation of said T cell, thereby activating and expanding said population of T cells; wherein said population of cells of part (a) is collected from a healthy individual for use at a later time point for the treatment of cancer, or other disease where activated and expanded T cells is beneficial, in said individual.

Another aspect of the present invention provides a composition comprising a population of T cells according to any one of claims 1-16 and 22 wherein said population of cells wherein at least a portion thereof comprises T cells is collected from a healthy individual for use at a later time point for the treatment of cancer in said individual. In this regard, a cancer may include, but is not limited to, melanoma, non-Hodgkin's lymphoma, cutaneous T cell lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL).

These and other aspects of the present invention will become evident upon reference to the following detailed description and attached drawings.

BRIEF DESCRIPTION OF THE SEVERAL VIEWS OF THE DRAWINGS

FIG. 6A, depicts CD25 expression on CD4$^+$ cells, while FIG. 6B depicts CD25 expression on CD8$^+$ cells.

FIG. 7A, depicts CD154 expression on CD4$^+$ cells, while FIG. 7B depicts CD154 expression on CD8$^+$ cells.

FIG. 11A represents the expression profile of CD25 on CD4$^+$ cells, while FIG. 11B represents the expression profile of CD25 on CD8$^+$ cells.

FIG. 13A represents the expression profile of CD25 on CD4$^+$ cells, while FIG. 13B represents the expression profile of CD25 on CD8$^+$ cells.

FIG. 14A represents the expression profile of CD154 on $CD4^+$ cells, while FIG. 14B represents the expression profile of CD154 on $CD8^+$ cells.

FIG. 16A represents the expression of CD54 on $CD4^+$ cells, while FIG. 16B represents the expression of CD54 on $CD8^+$ cells.

FIGS. 17A and 17B represent $CD4^+$ and $CD8^+$ cells present in samples 13 days post-stimulation with anti-CD3 and anti-CD28 coupled beads (17A) and 18 days post-primary stimulation and 7 days post-secondary stimulation with anti-CD3 and anti-CD28 coupled beads (17B). FIGS. 17C and 17D are flow cytometry data plots representing CD154 and CD137 expression after secondary stimulation of cells obtained from a patient with B-cell chronic lymphocytic leukemia.

FIGS. 26A-26L are bar graphs representing flow cytometry data of CD62L expression (mean fluorescence intensity, MFI) (26A), CD49d (MFI) (26B), CD25 (MFI) (26C), CD69 (MFI) (26D), CD154 (MFI) (26E), forward light scatter (size) (26F), viability (% live gate) (26G); all following stimulation with anti-CD3 and anti-CD28 co-immobilized beads and re-stimulation with the same at day 8. FIGS. 26H-26L depict CD62L, CD69, CD49d, CD154, and CD25 at 4 and 18 hours post-stimulation, respectively.

DETAILED DESCRIPTION OF THE INVENTION

Figure 1:
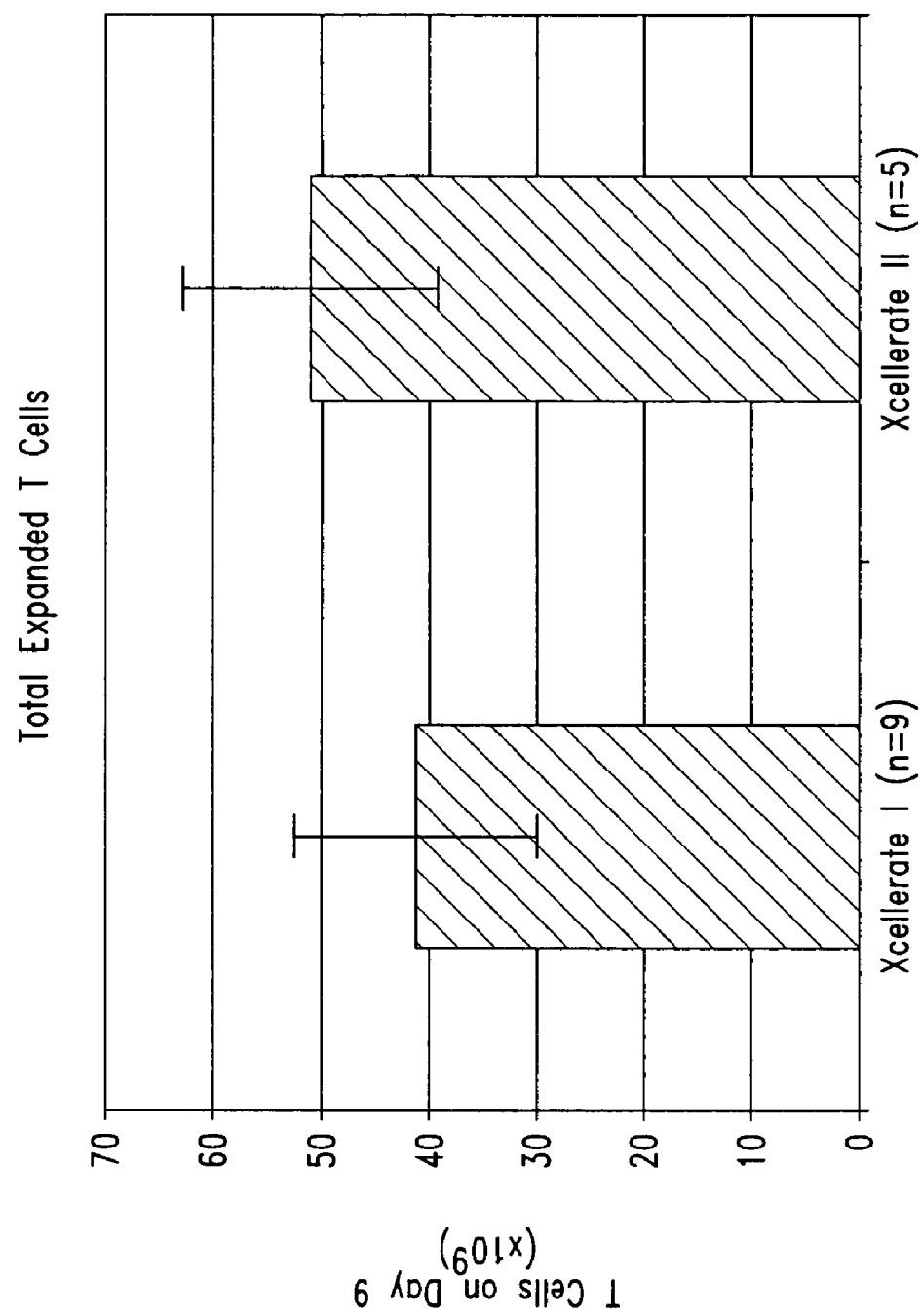
FIG. 1 is a plot comparing the total numbers of activated and expanded T cells measured at day 8 starting with about $0.5 \times 10^9$ T cells with (XCELLERATE II™) or without (XCELLERATE I™) magnetic concentration and stimulation.

Prior to setting forth the invention, it may be helpful to an understanding thereof to set forth definitions of certain terms that will be used hereinafter.

The term "biocompatible", as used herein, refers to the property of being predominantly non-toxic to living cells.

The term "stimulation", as used herein, refers to a primary response induced by ligation of a cell surface moiety. For example, in the context of receptors, such stimulation entails the ligation of a receptor and a subsequent signal transduction event. With respect to stimulation of a T cell, such stimulation refers to the ligation of a T cell surface moiety that in one embodiment subsequently induces a signal transduction event, such as binding the TCR/CD3 complex. Further, the stimulation event may activate a cell and upregulate or down-regulate expression or secretion of a molecule, such as down-regulation of TGF-β. Thus, ligation of cell surface moieties, even in the absence of a direct signal transduction event, may result in the reorganization of cytoskeletal structures, or in the coalescing of cell surface moieties, each of which could serve to enhance, modify, or alter subsequent cell responses.

The term "activation", as used herein, refers to the state of a cell following sufficient cell surface moiety ligation to induce a noticeable biochemical or morphological change.

Within the context of T cells, such activation, refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process.

The term "force", as used herein, refers to an artificial or external force applied to the cells to be stimulated that induces cellular concentration and concentration of cells with the agent that binds a cell surface moiety. For example, the term "force" includes any force greater than gravity (i.e., in addition to gravity and not solely gravitational force) that induces cell concentration and/or cell surface moiety aggregation. Such forces include transmembrane pressure such as filtration, a hydraulic force, an electrical force, an acoustical force, a centrifugal force, or a magnetic force. Ideally, the force utilized drives the concentration of the target cell of interest with an agent that ligates a cell surface moiety. In various contexts, the force can be pulsed, i.e., applied and reapplied (e.g., a magnetic force could be turned off and on, pulsing the population of cells in combination with a paramagnetic particle).

The term "simultaneous", as used herein, refers to the fact that inherently upon concentrating cells at a surface that has cell surface moiety binding agents attached thereto, results in concentration of cells with each other and with the surface, thus ligands (i.e., agents). However, the use of the term "simultaneous" does not preclude previous binding of the target cells with a surface having cell surface moiety binding agents attached thereto, as concentration and further ligand binding occurs simultaneously at the concentration surface. For example, within the context of T cell activation, the T cells may be exposed to a surface such as a paramagnetic bead having anti-CD3 and anti-CD28 antibodies attached thereto and subsequently concentrated by a magnetic field. Thus, in this context while cells and beads have previous contact and ligation, nevertheless, during concentration of cells additional ligation occurs.

The term "target cell", as used herein, refers to any cell that is intended to be stimulated by cell surface moiety ligation.

An "antibody", as used herein, includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'$_2$ fragments), or multimers or aggregates of intact molecules and/or fragments; and may occur in nature or be produced, e.g., by immunization, synthesis or genetic engineering; an "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof.

The term "protein", as used herein, includes proteins, polypeptides and peptides; and may be an intact molecule, a fragment thereof, or multimers or aggregates of intact molecules and/or fragments; and may occur in nature or be produced, e.g., by synthesis (including chemical and/or enzymatic) or genetic engineering.

The term "agent", "ligand", or "agent that binds a cell surface moiety", as used herein, refers to a molecule that binds to a defined population of cells. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), or the like. Within the specification and in the context of T cell stimulation, antibodies are used as a prototypical example of such an agent.

The terms "agent that binds a cell surface moiety" and "cell surface moiety", as used herein, are used in the context of a ligand/anti-ligand pair. Accordingly, these molecules should be viewed as a complementary/anti-complementary set of molecules that demonstrate specific binding, generally of relatively high affinity (an affinity constant, $K_a$, of about $10^6$ $M^{-1}$).

A "co-stimulatory signal", as used herein, refers to a signal, which in combination with a primary signal, such as TCR/CD3 ligation, leads to T cell proliferation.

A "ligand/anti-ligand pair", as used herein, refers to a complementary/anti-complementary set of molecules that demonstrate specific binding, generally of relatively high affinity (an affinity constant, $K_a$, of about $10^6$ $M^{-1}$,). Exemplary ligand/anti-ligand pairs enzyme/inhibitor, hapten/antibody, lectin/carbohydrate, ligand/receptor, and biotin/avidin or streptavidin. Within the context of the present invention specification receptors and other cell surface moieties are anti-ligands, while agents (e.g., antibodies and antibody fragments) reactive therewith are considered ligands.

"Separation", as used herein, includes any means of substantially purifying one component from another (e.g., by filtration or magnetic attraction).

"Quiescent", as used herein, refers to a cell state wherein the cell is not actively proliferating.

A "surface", as used herein, refers to any surface capable of having an agent attached thereto and includes, without limitation, metals, glass, plastics, co-polymers, colloids, lipids, cell surfaces, and the like. Essentially any surface that is capable of retaining an agent bound or attached thereto. A prototypical example of a surface used herein, is a particle such as a bead.

One aspect of the present invention is directed to the surprising finding that the combination of a force which induces the concentration of cells, ligation of cell surface moieties, and culturing cells in a rocking, closed system, results in a profound enhancement in activation and expansion of these cells. In the prototypic example set forth herein, T cells are utilized. However, one of skill in the art would readily conclude that the present invention has broad applicability to any cell type where cell surface moiety ligation or aggregation is desired or where such binding leads to a subsequent cellular signaling event (e.g., receptors). While not wishing to be bound by theory, the present invention may function by taking advantage of a phenomenon involving lipid -rafting and/or receptor polarization. The phenomena are similar in that they suggest either initiation/enhancement of signal transduction by the aggregation of lipid rafts comprising cell surface moieties or enhanced signal transduction due to localization (i.e., polarization) of receptors at one, or even several area(s) of a cell. Thus, not only does such cell surface moiety ligation lead to unexpectedly robust cell activation and proliferation in T cells but can also be applied to magnifying the signal transduction event of many cell types. Additionally, while still not wishing to be bound by theory, the present invention may function by providing optimal aeration for the expanding cells. Thus, cell surface moiety ligation combined with aeration through rocking and perfused media lead to unexpectedly robust cell activation and expansion of T cells to unexpectedly high densities and absolute numbers. Accordingly, within the context of T cells, the present invention provides a variety of unexpected advantages, first it eliminates the need for a separate monocyte-depletion step using "uncoated" particles, simplifies expansion of T cells by requiring fewer cell transfers and fewer reagents, increased level of T cell activation during activation process, significantly reduces the time to achieve cell numbers adequate for cell therapy, reduces time and labor involved in the processing of the cells, reduces the cost of manufacturing, and increases the flexibility of scheduling patient processing and infusions.

In an additional aspect of the present invention, a first and second or more surfaces are utilized with or without ligands/agents bound thereto. In this embodiment, the various surfaces may have the same or different agents attached thereto for binding cell surface moieties of target cells. For example, a paramagnetic bead may have attached thereto an antibody for a receptor on a target cell and such beads may be mixed with a population of cells containing the target cell. Further, the cell population may be mixed with a second or more bead with the same or different cell surface moiety binding agents attached thereto. Upon force induced concentration, the beads and cells are brought together in a smaller volume and thus signaling is magnified. In another example, paramagnetic beads that have an agent specific for a carbohydrate or other non-receptor cell surface moiety attached thereto are mixed with a population of cells containing the target cell. A magnetic field is then used to draw the bead attached cells to another surface that has receptor ligating agents attached thereto. Thus, the signal transduction inducing agent is on the second surface. In yet another example, an agent that binds a cell surface moiety of target cell may be attached to a particle large enough to be retained in a mesh or filter that itself may have ligands attached thereto.

As noted above, the present invention provides methods for stimulating a cell population by binding moieties on the surfaces of the cells in that population. Contacting a cell population with an agent (e.g., a ligand) that binds to a cell surface moiety can stimulate the cell population. The ligand may be in solution but also may be attached to a surface. Ligation of cell surface moieties, such as a receptor, may generally induce a particular signaling pathway. Recent studies suggest that for signaling to occur, critical concentrations of lipid rafts containing the requisite receptors must aggregate. By way of example, raft aggregation may be facilitated in vivo or in vitro by attaching ligands for particular cell surface moieties to paramagnetic particles, exposing the ligand-bearing particles to the cells, and shortly thereafter or simultaneously applying a force, such as a magnetic field to assist polarizing the ligated moieties (e.g., receptors) and concentrating cells in a small volume. The application of a magnetic force concentrates the cells as well as concentrating the cells with the surface having agents attached thereto that ligate cell surface moieties, thereby bringing greater contact of the cells with the ligands, resulting in accelerated and more potent activation. Many applications of the present invention are possible, for example, if cells have low numbers of and/or dysfunctional receptors, the method may sufficiently concentrate such receptors in the lipid rafts to overcome such defects and to permit proper signaling activity. One example of such cell surface repertoire correction is in patients with certain types of leukemia, wherein prior to cell surface moiety stimulation with agents such as anti-CD3 and anti-CD28 antibodies several normal cell surface markers are unusually low, such as the CD3/TCR complex. By stimulating these cell populations with agents such as anti-CD3 and anti-CD28 antibodies, the cell surface markers of these cells return to a level that appears normal and as such can provide a more robust immunotherapy product for cancer therapy that provides a stronger and more rapid immune response when returned to the patient. In yet other applications of this invention, cells may be efficiently concentrated and activated, including inducing receptor polarization, thereby maximizing receptor signaling events. Such applications have broad utility including the use in screening assays directed at receptors or by collecting cellular rafts on the surface of a cell to induce activation such as inducing apoptosis by ligating Fas or like molecules in a tumor cell.

In one example of such screening assays, one could use G-coupled protein receptor bearing cells and contact them with agents that bind thereto, these agents being bound to a surface that allows force induced concentration. Accordingly, as the receptors raft together the signal transduction event would be amplified. This could be important in the study of signal transduction events that are very low level in typical experiments and thus screening for drug compounds to inhibit or somehow modify such signal transduction events.

Stimulation of a Cell Population

The methods of the present invention relate to the stimulation of a target cell by introducing a ligand or agent that binds to a cellular moiety, inducing a cellular event. Binding of the ligand or agent to the cell may trigger a signaling pathway that in turn activates particular phenotypic or biological changes in the cell. The stimulation of a target cell by introducing a ligand or agent that binds to a cellular moiety as described herein may upregulate or downregulate any number of cellular processes leading to particular phenotypic or biological changes in the cell. The activation of the cell may enhance normal cellular functions or initiate normal cell functions in an abnormal cell. The method described herein provides stimulation by forcing concentration of the cells together with the ligand or agent that binds a cell surface moiety. Stimulation of a cell may be enhanced or a particular cellular event may be stimulated by introducing a second agent or ligand that ligates a second cell surface moiety. This method may be applied to any cell for which ligation of a cell surface moiety leads to a signaling event. The invention further provides means for selection or culturing the stimulated cells. The prototypic example described is stimulation of T cells, but one of ordinary skill in the art will readily appreciate that the method may be applied to other cell types. By way of example, cell types that may be stimulated and selected include fibroblasts, neuroblasts, lung cells, hematopoietic stem cells and hematopoietic progenitor cells ($CD34^+$ cells), mesenchymal stem cells, mesenchymal progenitor cells, neural and hepatic progenitor and stem cells, dendritic cells, cytolytic T cells ($CD8^+$ cells), B-cells, NK cells, other leukocyte populations, pluripotent stem cells, multi-potent stem cells, islet cells, etc. Accordingly, the present invention also provides populations of cells resulting from this methodology as well as cell populations having distinct phenotypical characteristics, including T cells with specific phenotypic characteristics.

As noted above a variety of cell types may be utilized within the context of the present invention. For example, cell types such as B cells, T cells, NK cells, other blood cells, neuronal cells, lung cells, glandular (endocrine) cells, bone forming cells (osteoclasts, etc.), germ cells (e.g., oocytes), epithelial cells lining reproductive organs, and others may be utilized. Cell surface moiety-ligand pairs could include (but not exclusively): T cell antigen receptor (TCR) and anti-CD3 mAb, TCR and major histocompatibility complex (MHC)+ antigen, TCR and peptide-MHC tetramer, TCR and superantigens (e.g., *staphylococcal* enterotoxin B (SEB), toxic shock syndrome toxin (TSST), etc.), B cell antigen receptor (BCR) and anti-Ig, BCR and LPS, BCR and specific antigens (univalent or polyvalent), NK receptor and anti-NK receptor antibodies, FAS (CD95) receptor and FAS ligand, FAS receptor and anti-FAS antibodies, CD54 and anti-CD54 antibodies, CD2 and anti-CD2 antibodies, CD2 and LFA-3 (lymphocyte function related antigen-3), cytokine receptors and their respective cytokines, cytokine receptors and anti-cytokine receptor antibodies, TNF-R (tumor necrosis factor-receptor) family members and antibodies directed against them, TNF-R family members and their respective ligands, adhesion/homing receptors and their ligands, adhesion/homing receptors and antibodies against them, oocyte or fertilized oocyte receptors and their ligands, oocyte or fertilized oocyte receptors and antibodies against them, receptors on the endometrial lining of uterus and their ligands, hormone receptors and their respective hormone, hormone receptors and antibodies directed against them, and others.

The nature of the binding of a receptor by a ligand will either result in the multimerization of the receptors, or aggregation/orientation of the receptors, such that signaling or cell response is upregulated, downregulated, accelerated, improved, or otherwise altered so as to confer a particular benefit, such as cell division, cytokine secretion, cell migration, increased cell-cell interaction, etc.

Two examples are given below that illustrate how such a multimerization, aggregation, or controlled reorientation of cell surface moieties could be of practical benefit.

In one example, normal T cell activation by antigen and antigen presenting cells usually results in aggregation of TCR rafts, cytoskeletal reorganization, polarization of "activation" signals and cell division, for example. Using man-made approaches, such as those described herein, in the absence of "normal" in-vivo T cell activation, one could accelerate, improve, or otherwise affect the functions described above, in particular through the accelerated, controlled, and spatially oriented ligation of TCR and CD28. Benefits could be improved cell expansion in vitro resulting in higher numbers of infuseable and more robust cells for therapeutic applications. In particular, the present invention provides for methods of activating and expanding T cells to very high densities (ranging from $6 \times 10^6$ cells/ml to $90 \times 10^6$ cells/ml) and results in production of very high number of cells (as many as 800 billion cells are expanded from one individual from a starting number of cells of about $0.5 \times 10^9$ cells) Other benefits could be improved receptor "aggregation" for cells with defects, such as lower-than-normal TCR density on the cell surface. Similarly, in vivo applications could be beneficial where specific T cell populations need to be activated, such as tumor-specific T cells at tumor sites. Improved receptor aggregation and orientation could provide an activation signal otherwise difficult to obtain for functionally tolerized T cells. Further, such activation could be used within the context of antigen specific T cells. In this regard T cells from a tumor could be isolated and expanded and infused into the patient. Similarly, T cells exposed to an antigen either in vivo or in vitro could be expanded by the present methodologies.

In another example, improved induction of cell death occurs via the FAS pathway: The ability to accelerate the multimerization of FAS, spatially orient "activated" FAS on target cell surfaces, or to promote a cumulative FAS ligation that would otherwise be unachievable, could provide significant benefit in vivo, particularly for treating cancer, autoimmune responses, or graft-versus-host disease. For example, a tumor cell may express low levels of FAS in vivo, and the host may express low levels of FAS-L at tumor sites (due to suppressive cytokines, etc.). Due to these low levels, an adequate FAS signal cannot be generated, allowing for tumor survival and growth. One possible way to overcome this FAS/FAS-ligand deficiency could be to target tumors/tumor sites with monovalent or multivalent ligands for FAS (FAS-L, antibodies, etc.), bound to paramagnetic particles. Application of a strong magnetic field using the present at tumor sites (e.g., melanoma, Kaposi's sarcoma, squamous cell neck carcinomas, etc.) could provide for the spatial orientation of the paramagnetic particles at tumor sites as the particles bound FAS on tumor cells, adapted for receptor activation and/or T cell activation and expansion. Increased FAS aggregation accompanied by signal polarization might provide adequate signal to now induce cell death in the tumor cells.

In one particular embodiment of the invention, a T cell population may be stimulated by simultaneously concentrating and ligating the surfaces of the T cells. In one aspect of the present invention, antibodies to CD3 and CD28 are co-immobilized on a surface. A preferred surface for such immobilization includes particles, and in certain aspects, beads, such as paramagnetic beads. In another aspect of the present invention, any ligand that binds the TCR/CD3 complex and initiates a primary stimulation signal may be utilized as a primary activation agent immobilized on the surface. Any ligand that binds CD28 and initiates the CD28 signal transduction pathway, thus causing co-stimulation of the cell with a CD3 ligand and enhancing activation of a population of T cells, is a CD28 ligand and accordingly, is a co-stimulatory agent within the context of the present invention. In a further aspect of the invention, a force is applied to the mixture of T cells and anti-CD3 and anti-CD28-conjugated surfaces to concentrate the T cells, thus maximizing T cell surface ligation. While in one particular embodiment the concentration force is magnetic force applied where the anti-CD3 and anti-CD28 coated surfaces are paramagnetic beads, other means to bring the cells and the ligands together in a concentrated fashion are available in the art. Such methods of stimulating a T cell population provides significant bead-cell and/or cell-cell contact that induces surprisingly greater activation and/or proliferation of T cells. Furthermore, the inventive methods alter the cell surface marker profile wherein the activated T cells express cell surface markers that indicate a more normal phenotype and less variable final product compared to the profile of the T cells when first isolated from a subject with a disease.

The Primary Signal

The biochemical events responsible for ex vivo T cell stimulation are set forth briefly below. Interaction between the TCR/CD3 complex and antigen presented in conjunction with either MHC class I or class II molecules on an antigen-presenting cell initiates a series of biochemical events termed antigen-specific T cell activation. Accordingly, activation of T cells can be accomplished by stimulating the T cell TCR/CD3 complex or by stimulating the CD2 surface protein. An anti-CD3 monoclonal antibody can be used to activate a population of T cells via the TCR/CD3 complex. A number of anti-human CD3 monoclonal antibodies are commercially available, exemplary are OKT3, prepared from hybridoma cells obtained from the American Type Culture Collection, and monoclonal antibody G19-4. Similarly, stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies that have been described include the following: the T11.3 antibody in combination with the T11.1 or T11.2 antibody (Meuer et al., *Cell* 36:897-906, 1984), and the 9.6 antibody (which recognizes the same epitope as T11.1) in combination with the 9-1 antibody (Yang et al., *J. Immunol.* 137:1097-1100, 1986). Other antibodies that bind to the same epitopes as any of the above described antibodies can also be used. Additional antibodies, or combinations of antibodies, can be prepared and identified by standard techniques.

A primary activation signal can also be delivered to a T cell through other mechanisms. For example, a combination that may be used includes a protein kinase C (PKC) activator, such as a phorbol ester (e.g., phorbol myristate acetate), and a calcium ionophore (e.g., ionomycin, which raises cytoplasmic calcium concentrations), or the like. The use of such agents bypasses the TCR/CD3 complex but delivers a stimulatory signal to T cells. Other agents acting as primary signals may include natural and synthetic ligands. A natural ligand may include MHC with or without a peptide presented. Other ligands may include, but are not limited to, a peptide, polypeptide, growth factor, cytokine, chemokine, glycopeptide, soluble receptor, steroid, hormone, mitogen, such as PHA, or other superantigens, peptide-MHC tetramers (Altman, et al., *Science.* 1996 Oct 4;274(5284):94-6.) and soluble MHC dimers (Dal Porto, et al. *Proc Natl Acad Sci USA* 1993 July 15;90). Within the context of the present invention, the use of concentration and stimulation may result in such high receptor polarization that no secondary signal is required to induce proliferation of T cells.

In other embodiments, signal transduction events of any kind may be magnified or analyzed by utilizing the current invention. For example, G protein-coupled receptors may stimulated and measured using the concentration methods of the present invention.

The Secondary Signal

While stimulation of the TCR/CD3 complex or CD2 molecule appears to be required for delivery of a primary activation signal in a T cell, a number of molecules on the surface of T cells, termed accessory or co-stimulatory molecules, have been implicated in regulating the transition of a resting T cell to blast transformation, and subsequent proliferation and differentiation. Thus, in addition to the primary activation signal, induction of T cell responses requires a second, co-stimulatory signal. One such co-stimulatory or accessory molecule, CD28, is believed to initiate or regulate a signal transduction pathway that is distinct from any stimulated by the TCR complex.

Therefore, to enhance activation and proliferation of a population of T cells in the absence of exogenous growth factors or accessory cells, an accessory molecule on the surface of the T cell, such as CD28, is stimulated with a ligand that binds the accessory molecule. In one embodiment, stimulation of the accessory molecule CD28 and T cell activation occur simultaneously by contacting a population of T cells with a surface to which a ligand that binds CD3 and a ligand that binds CD28 are attached. Activation of the T cells, for example, with an anti-CD3 antibody, and stimulation of the CD28 accessory molecule results in selective proliferation of CD4$^+$ T cells.

Accordingly, one of ordinary skill in the art will recognize that any agent, including an anti-CD28 antibody or fragment thereof capable of cross-linking the CD28 molecule, or a natural ligand for CD28 can be used to stimulate T cells. Exemplary anti-CD28 antibodies or fragments thereof useful in the context of the present invention include monoclonal antibody 9.3 (IgG2$_a$) (Bristol-Myers Squibb, Princeton, N.J.), monoclonal antibody KOLT-2 (IgG1), 15E8 (IgG1), 248.23.2 (IgM), and EX5.3D10 (IgG2$_a$) (ATCC HB11373).

Exemplary natural ligands include the B7 family of proteins, such as B7-1 (CD80) and B7-2 (CD86) (Freedman et al, *J. Immunol.* 137:3260-3267, 1987; Freeman et al., *J. Immunol.* 143:2714-2722, 1989; Freeman et al., *J. Exp. Med.* 174:625-631, 1991; Freeman et al., *Science* 262:909-911, 1993; Azuma et al., *Nature* 366:76-79, 1993; Freeman et al., *J. Exp. Med.* 178:2185-2192, 1993). In addition, binding homologues of a natural ligand, whether native or synthesized by chemical or recombinant techniques, can also be used in accordance with the present invention. Other agents acting as secondary signals may include natural and synthetic ligands. Agents may include, but are not limited to, other antibodies or fragments thereof, a peptide, polypeptide, growth factor, cytokine, chemokine, glycopeptide, soluble receptor, steroid, hormone, mitogen, such as PHA, or other superantigens.

In a further embodiment of the invention, activation of a T cell population may be enhanced by co-stimulation of other T cell integral membrane proteins. For example, binding of the T cell integrin LFA-1 to its natural ligand, ICAM-1, may enhance activation of cells. Another cell surface molecule that may act as a co-stimulator for T cells is VCAM-1 (CD106) that binds very-late-antigen-4 (VLA-4) on T cells. Ligation of 4-1BB, a co-stimulatory receptor expressed on activated T cells, may also be useful in the context of the present invention to amplify T cell mediated immunity.

One of skill in the art will appreciate that cells other than T cells may be stimulated by binding of an agent that ligates a cell surface moiety and induces aggregation of the moiety, which in turn results in activation of a signaling pathway. Other such cell surface moieties include, but are not limited to, GPI-anchored folate receptor (CD59), human IgE receptor (FcεRi receptor), BCR, EGF receptor, insulin receptor, ephrin B1 receptor, neurotrophin, glial-cell derived neutrophic factor (GNDF), hedgehog and other cholesterol-linked and palmitoylated proteins, H-Ras, integrins, endothelial nitric oxide synthase (eNOS), FAS, members of the TNF receptor family, GPI-anchored proteins, doubly acylated proteins, such as the Src-family kinases, the alpha-subunit of heterotrimeric G proteins, and cytoskeletal proteins.

Expansion of T Cell Population

In one aspect of the present invention, ex vivo T cell expansion can be performed by isolation of T cells and subsequent stimulation. In one embodiment of the invention, the T cells may be stimulated by a single agent. In another embodiment, T cells are stimulated with two agents, one that induces a primary signal and a second that is a co-stimulatory signal. Ligands useful for stimulating a single signal or stimulating a primary signal and an accessory molecule that stimulates a second signal may be used in soluble form, attached to the surface of a cell, or immobilized on a surface as described herein. A ligand or agent that is attached to a surface serves as a "surrogate" antigen presenting cell (APC). In a preferred embodiment both primary and secondary agents are co-immobilized on a surface. In one embodiment, the molecule providing the primary activation signal, such as a CD3 ligand, and the co-stimulatory molecule, such as a CD28 ligand, are coupled to the same surface, for example, a particle. Further, as noted earlier, one, two, or more stimulatory molecules may be used on the same or differing surfaces.

Prior to expansion, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as $CD28^+$, $CD4^+$, $CD8^+$, $CD45RA^+$, and $CD45RO^+$ T cells, can be further isolated by positive or negative selection techniques. For example, in one preferred embodiment, T cells are isolated by incubation with anti-CD3/anti-CD28 (i.e., 3'28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other timepoints during the process. Additionally, by increasing or decreasing the ratio of anti-CD3 and/or anti-CD28 antibodies on the beads or other surface, subpopulations of T cells can be preferentially selected for or against at culture initiation or at other desired timepoints. The skilled artisan would recognize that multiple rounds of selection can also be used in the context of this invention. In certain embodiments, it may be desirable to perform the selection procedure and use the "unselected" cells in the XCELLERATE™ process. "Unselected" cells can also be subjected to further rounds of selection.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$.

For isolation of a desired population of cells by positive or negative selection, the concentration of cells and surface (e.g. particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g. particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$ /ml. In other embodiments, the concentration used can be from about $1 \times 10^5$ /ml to $1 \times 10^6$ /ml, and any integer value in between.

If desired or necessary, monocyte populations (i.e., $CD14^+$ cells) may be depleted from blood preparations prior to ex vivo expansion by a variety of methodologies, including anti-CD14 coated beads or columns, or utilization of the phagocytic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Dynal AS under the trade name Dynabeads™. Exemplary Dynabeads™ in this regard are M-280, M-450, and M-500. In one aspect, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be expanded. In certain embodiments the irrelevant beads include beads coated with sheep anti-mouse antibodies, goat anti-mouse antibodies, and human serum albumin.

In brief, such depletion of monocytes is performed by preincubating PBMC isolated from whole blood or apheresed peripheral blood with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after said depletion.

T cells for stimulation can also be frozen after the washing step, which does not require the monocyte-removal step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Also contemplated in the context of the invention is the collection of blood samples or leukapheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or a leukapheresis is taken from a generally healthy subject. In certain embodiments, a blood sample or a leukapheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isloated from a blood sample or a leukapheresis from a subject prior to any number of relevant treatment modalities, including but not limited to treatment with agents such as antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxin, fludaribine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993; Isoniemi (supra)). In a further embodiment, the cells are isolated for a patient and frozen for later use in conjunction with (e.g. before, simulataneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g. Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoetic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illlustrative cell types include T cells, B cells, dendritic cells, and other cells of the immune system.

The cell population may be stimulated as described herein, such as by contact with an anti-CD3 antibody or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of $CD4^+$ cells can be contacted with an anti-CD3 antibody and an anti-CD28 antibody, under conditions appropriate for stimulating proliferation of the T cells. Similarly, to stimulate proliferation of $CD8^+$ T cells, an anti-CD3 antibody and the anti-CD28 antibody B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):1319-1328, 1999; Garland et al, *J. Immunol Meth.* 227(1-2):53-63, 1999).

The primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In a preferred embodiment, the two agents are immobilized on beads, either on the same bead, i.e., "cis," or to separate beads, i.e., "trans." By way of example, the agent providing the primary activation signal is an anti-CD3 antibody and the agent providing the co-stimulatory signal is an anti-CD28 antibody; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 0.5 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e. the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particle to cells may dependant on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include at least 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

One aspect of the present invention stems from the surprising finding that using different bead:cell ratios can lead to different outcomes with respect to expansion of antigen-specific T cells. In particular, bead:cell ratios can be varied to selectively expand or delete antigen-specific (memory) T cells. In one embodiment, the particular bead:cell ratio used selectively deletes antigen-specific T cells. In a further embodiment, the particular bead:cell ratio used selectively expands antigen-specific T cells. The skilled artisan would readily appreciate that any ratio can be used as long as the desired expansion or deletion occurs. Therefore, the compositions and methods described herein can be used to expand specific populations of T cells, or to delete specific populations of T cells, for use in any variety of immunotherapeutic settings described herein.

Using certain methodologies it may be advantageous to maintain long-term stimulation of a population of T cells following the initial activation and stimulation, by separating the T cells from the stimulus after a period of about 12 to about 14 days. The rate of T cell proliferation is monitored periodically (e.g., daily) by, for example, examining the size or measuring the volume of the T cells, such as with a Coulter Counter. In this regard, a resting T cell has a mean diameter of about 6.8 microns, and upon initial activation and stimulation, in the presence of the stimulating ligand, the T cell mean diameter will increase to over 12 microns by day 4 and begin to decrease by about day 6. When the mean T cell diameter decreases to approximately 8 microns, the T cells may be reactivated and re-stimulated to induce further proliferation of the T cells. Alternatively, the rate of T cell proliferation and time for T cell re-stimulation can be monitored by assaying for the presence of cell surface molecules, such as, CD154, CD54, CD25, CD137, CD134, which are induced on activated T cells.

In one embodiment, T cell stimulation is performed with anti-CD3 and anti-CD28 antibodies co-immobilized on beads (3×28 beads), for a period of time sufficient for the cells to return to a quiescent state (low or no proliferation) (approximately 8-14 days after initial stimulation). The stimulation signal is then removed from the cells and the cells are washed and infused back into the patient. The cells at the end of the stimulation phase are rendered "super-inducible" by the methods of the present invention, as demonstrated by their ability to respond to antigens and the ability of these cells to demonstrate a memory-like phenotype, as is evidence by the examples. Accordingly, upon re-stimulation either exogenously or by an antigen in vivo after infusion, the activated T cells demonstrate a robust response characterized by unique phenotypic properties, such as sustained CD154 expression and increased cytokine production.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, resulting in cell surface moiety ligation, thereby inducing cell stimulation.

By way of example, when T cells are the target cell population, the cell surface moieties may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e. 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain. For example, using high concentration of cells allows more efficient selection of CD8$^+$ T cells that normally have weaker CD28 expression.

In a related embodiment, it may be desirable to use lower concentrations of cells. By significantly diluting the mixture of T cells and particles, interactions between particles and cells is minimized. This selects for cells that express high amounts of desired antigens to be bound to the particles. For example, CD4$^+$ T cells express higher levels of CD28 and are more efficiently captured and stimulated than CD8$^+$ T cells in dilute concentrations. In one embodiment, the concentration of cells used is about 5×10$^6$ /ml. In other embodiments, the concentration used can be from about 1×10$^5$ /ml to about 1×10$^6$ /ml, and any integer value in between.

The buffer that the cells are suspended in may be any that is appropriate for the particular cell type. When utilizing certain cell types the buffer may contain other components, e.g. 1-5% serum, necessary to maintain cell integrity during the process. In another embodiment, the cells and beads may be combined in cell culture media. The cells and beads may be mixed, for example, by rotation, agitation or any means for mixing, for a period of time ranging from one minute to several hours. The container of beads and cells is then concentrated by a force, such as placing in a magnetic field. Media and unbound cells are removed and the cells attached to the beads are washed, for example, by pumping via a peristaltic pump, and then resuspended in media appropriate for cell culture.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (BioWhittaker)) that may contain factors necessary for proliferation and viability, including serum (e.g., fetal bovine or human serum), interleukin-2 (IL-2), insulin, IFN-γ, IL-4, GM-CSF, IL-10, IL-12, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, with added amino acids and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

When using a magnetic field as the concentrating force the magnetic field strength applied to the cells prior to cell culture may be between the range of 200 gauss to 12,000 gauss on the magnetic surface. The shape and size of the magnet may be adapted to the size and shape of the mixing or cell culture vessels or to any other parameter that facilitates or increases cell to cell contact and concentration of the cells. The magnetic force may be diffused by placing a material that acts as a buffer or spacer between the magnet and the paramagnetic beads contained within the mixture with cells. A strong magnetic force is generally considered to be at least 7500 gauss at the surface, whereas a weak magnetic force is considered to be in the range of 2000-2500 gauss at the surface. The approximate magnetic force applied by a magnet on a paramagnetic bead depends upon the volume of the paramagnetic bead and the magnetic field strength according to the following formula:

$$F_{mag} = (v)(\psi)(B)(dB/dx)$$

where $F_{mag}$ equals the magnetic force, v equals the volume of the paramagnetic bead, ψ equals the magnetic susceptibility of a paramagnetic bead (a value provided by the manufacturer), B equals the magnetic field strength, and (dB/dx) equals the field strength gradient. One of skill in the art will appreciate that the factors on the right-hand side of the equation can be obtained or measured, allowing the magnetic force applied to be calculated.

Cells stimulated by the methods of the present invention are activated as shown by the induction of signal transduction, expression of cell surface markers and/or proliferation. One such marker appropriate for T cells is CD154 which is an important immunomodulating molecule. The expression of CD154 is extremely beneficial in amplifying the immune response. CD154 interacts with the CD40 molecule expressed on many B cells, dendritic cells, monocytes, and some endothelial cells. Accordingly, this unexpected and surprising increase in CD154 expression is likely to lead to more efficacious T cell compositions. Stimulation of CD3$^+$ cells as described herein provides T cells that express a 1.1 to 20-fold increases in the levels of certain cell surface markers such as CD154 expression on days 1, 2, 3, or 4 following stimulation. (See Example V, Table 2 and FIG. 4.) Expression of another cell surface marker, CD25, also was greater on T cells after concentration and stimulation than on cells prior to culture or cells stimulated by other methods. (See Table 2.)

One of skill in the art will appreciate that any target cell that can be stimulated by cell surface moiety ligation may be combined with the agent-coated surface, such as beads. Further, the agent-coated surfaces, such as, beads may be separated from the cells prior to culture, at any point during culture, or at the termination of culture. In addition, the agent-coated surfaces ligated to the target cells may be separated from the non-binding cells prior to culture or the other cells may remain in culture as well. In one embodiment, prior to culture, the agent-coated beads and target cells are not separated but are cultured together. In a further embodiment, the beads and target cells are first concentrated by application of a force, resulting in cell surface moiety ligation, thereby inducing stimulation and subsequent activation.

Also contemplated by this invention, are other means to increase the concentration of the target cells, for example, a T cell fraction bound to a surface coated with primary and secondary stimulatory molecules. In addition to application of a magnetic force, other forces greater than gravitational force may be applied, for example, but not limited to, centrifugal force, transmembrane pressure, and a hydraulic force. Concentration may also be accomplished by filtration.

One of skill in the art will readily appreciate that contact between the agent-coated beads and the cells to be stimulated can be increased by concentration using other forces. Accordingly, any means for concentrating cells with cell surface moiety binding ligands will be sufficient as long as the concentration brings together cells and agents in a manner that exceeds gravity or diffusion.

It should be understood that in various embodiments the agent-coated surface may be a particle, such as a bead which is mixed with the cells and concentrated in a small volume in a magnetic field, thus drawing all the particles and particle bound cells into a defined and concentrated area. In certain embodiments, the agent-coated surface may be drawn together by force within thirty seconds to four hours of being exposed to the target cells. In other embodiments the time may be from 1 minute to 2 hours, or all integer ranges in between. Application of a force to a cell population with receptor bearing cells that is mixed with a surface to which at least one cell surface ligand is attached may induce cell receptor polarization, aggregating cell surface molecules. This means for inducing cell surface polarization may enhance signaling within the cell by aggregating cell surface molecules that comprise lipid rafts. Such aggregation can induce a signal pathway, which may lead to down-regulation or suppression of a cellular event. Alternatively, the aggregation of cell surface molecules may lead to up-regulation or activation of a cellular event.

A cellular event may include, for example, receptor-mediated signal transduction that induces or suppresses a particular pathway, including an apoptotic pathway, or induces phosphorylation of proteins, or stimulates or suppresses growth signals. In one embodiment, the cells may be lymphocytes, particularly a T cell, and the cell surface ligand may be an anti-CD3 antibody attached to a surface, for example, a particle. The particle may be a paramagnetic bead and the force applied a magnetic force. Application of a magnetic force to a mixture of the lymphocytes and anti-CD3-coated surface of the paramagnetic bead may cause the CD3 receptors of the T cell to polarize more quickly than would occur in the absence of an external force. This method of stimulating the T cell promotes more rapid activation of the T cell immune response pathways and proliferation of cells.

In one embodiment of the present invention, bead:cell ratios can be tailored to obtain a desired T cell phenotype. In one particular embodiment, bead:cell ratios can be vaired to selectively expand or delete antigen-specific (memory) T cells. In one embodiment, the particular bead:cell ratio used selectively deletes antigen-specific T cells. In a further embodiment, the particular bead:cell ratio used selectively expands antigen-specific T cells. The skilled artisan would readily appreciate that any ratio can be used as long as the desired expansion or deletion of antigen-specific T cells occurs. Therefore, the compositions and methods described herein can be used to expand specific populations of T cells, or to delete specific populations of T cells, for use in any variety of immunotherapeutic settings described herein.

In another embodiment, the time of exposure to stimulatory agents such as anti-CD3/anti-CD28 (i.e., 3×28)-coated beads may be modified or tailored to obtain a desired T cell phenotype. Alternatively, a desired population of T cells can be selected using any number of selection techniques, prior to stimulation. One may desire a greater population of helper T cells ($T_H$), typically CD4$^+$ as opposed to CD8$^+$ cytotoxic or regulatory T cells, because an expansion of $T_H$ cells could improve or restore overall immune responsiveness. While many specific immune responses are mediated by CD8$^+$ antigen-specific T cells, which can directly lyse or kill target cells, most immune responses require the help of CD4$^+$ T cells, which express important immune-regulatory molecules, such as GM-CSF, CD40L, and IL-2, for example. Where CD4-mediated help if preferred, a method, such as that described herein, which preserves or enhances the CD4:CD8 ratio could be of significant benefit. Increased numbers of CD4$^+$ T cells can increase the amount of cell-expressed CD40L introduced into patients, potentially improving target cell visibility (improved APC function). Similar effects can be seen by increasing the number of infused cells expressing GM-CSF, or IL-2, all of which are expressed predominantly by CD4$^+$ T cells. Alternatively, in situations where CD4-help is needed less and increased numbers of CD8$^+$ T cells are desirous, the XCELLERATE approaches described herein can also be utilized, by for example, pre-selecting for CD8$^+$ cells prior to stimulation and/or culture. Such situations may exist where increased levels of IFN-γ or increased cytolysis of a target cell is preferred. In a further embodiment, the XCELLERATE™ process can be modified or tailored to promote homing of T cells to particular sites of interest, such as lymph nodes or sites of inflammation, or to bone marrow, for example. Additionally, in certain embodiments, the XCELLERATE™ approaches described herein can also be utilized for the generation of T regulatory cells for specific immunosuppression in the case of inflammatory disease, autoimmunity, and foreign graft acceptance, or any other disease setting where regulatory T cells are desired. Classically, T regulatory cells have a CD4$^+$, CD25$^+$, CD62L$^{hi}$, GITR$^+$, and FoxP3$^+$ phenotype (see for example, Woo, et al., J Immunol. 2002 May 1;168(9):4272-6; Shevach, E. M., Annu. Rev. Immunol. 2000, 18:423; Stephens, et al., Eur. J. Immunol. 2001, 31:1247; Salomon, et al, Immunity 2000, 12:431; and Sakaguchi, et al., Immunol. Rev. 2001, 182:18). Regulatory T cells can be generated and expanded using the methods of the present invention. The regulatory T cells can be antigen-specific and/or polyclonal. Regulatory T cells can also be generated using art-recognized techniques as described for example, in Woo, et al.; Shevach, E. M.; Stephens, et al.; Salomon, et al.; and Sakaguchi, et al.; Supra.

To effectuate isolation of different T cell populations, exposure times to the to the particles may be varied. For example, in one preferred embodiment, T cells are isolated by incubation with 3×28 beads, such as Dynabeads M-450, for a time period sufficient for positive selection of the desired T cells. In one embodiment, the time period is about 30 minutes. In a further embodiment, the time period is at least 1, 2, 3, 4, 5, or 6 hours. In yet another preferred embodiment, the time period is 10 to 24 hours or more. In one preferred embodiment, the incubation time period is 24 hours. For isolation of T cells from cancer patients, use of longer incubation times, such as 24 hours, can increase cell yield.

To effectuate isolation of different T cell populations, exposure times to the concentration force may be varied or pulsed. For example when such force is a magnet, exposure to the magnet or the magnetic field strength may be varied, and/or expansion times may be varied to obtain the specific phenotype of interest. The expression of a variety of phenotypic markers change over time; therefore, a particular time point may be chosen to obtain a specific population of T cells. Accordingly, depending on the cell type to be stimulated, the stimulation and/or expansion time may be 10 weeks or less, 8 weeks or less, four weeks or less, 2 weeks or less, 10 days or less, or 8 days or less (four weeks or less includes all time ranges from 4 weeks down to 1 day (24 hours) or any value between these numbers). In some embodiments in may be desirable to clone T cells using, for example, limiting dilution or cell sorting, wherein longer stimulation time may be necessary. In some embodiments, stimulation and expansion may be carried out for 6 days or less, 4 days or less, 2 days or less, and in other embodiments for as little as 24 or less hours, and preferably 4-6 hours or less (these ranges include any integer values in between). When stimulation of T cells is carried out for shorter periods of time, the population of T cells may not increase in number as dramatically, but the population will provide more robust and healthy activated T cells that can continue to proliferate in vivo and more closely resemble the natural effector T cell pool. As the availability of T cell help is often the limiting factor in antibody responses to protein antigens, the ability to selectively expand or selectively infuse a $CD4^+$ rich population of T cells into a subject is extremely beneficial. Further benefits of such enriched populations are readily apparent in that activated helper T cells that recognize antigens presented by B lymphocytes deliver two types of stimuli, physical contact and cytokine production, that result in the proliferation and differentiation of B cells.

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In one such example, among the important phenotypic markers that reproducibly vary with time are the high affinity IL-2 receptor (CD25), CD40 ligand (CD154), and CD45RO (a molecule that by preferential association with the TCR may increase the sensitivity of the TCR to antigen binding). As one of ordinary skill in the art readily appreciates, such molecules are important for a variety of reasons. For example, CD25 constitutes an important part of the autocrine loop that allows rapid T cell division. CD154 has been shown to play a key role in stimulating maturation of the antigen-presenting dendritic cells; activating B-cells for antibody production; regulating $T_H$ cell proliferation; enhancing $T_C$ cell differentiation; regulating cytokine secretion of both $T_H$ cells and antigen-presenting cells; and stimulating expression of co-stimulatory ligands, including CD80, CD86, and CD154.

Cytokine production peaks in the first few days of the ex vivo expansion process. Accordingly, because cytokines are known to be important for mediating T cell activation and function as well as immune response modulation, such cytokines are likely critical in the development of a therapeutic T cell product, that is able to undergo reactivation upon contact with an additional antigen challenge. Cytokines important in this regard, include, but are not limited to, IL-2, IL-4, TNF-αa, and IFN-β. Thus, by obtaining a population of T cells during the first few days of expansion and infusing these cells into a subject, a therapeutic benefit may occur in which additional activation and expansion of T cells in vivo occurs.

In addition to the cytokines and the markers discussed previously, expression of adhesion molecules known to be important for mediation of T cell activation and immune response modulation also change dramatically but reproducibly over the course of the ex vivo expansion process. For example, CD62L is important for homing of T cells to lymphoid tissues and trafficking T cells to sites of inflammation. Under certain circumstances of disease and injury, the presence of activated T cells at these sites may be disadvantageous. Because down-regulation of CD62L occurs early following activation, the T cells could be expanded for shorter periods of time. Conversely, longer periods of time in culture would generate a T cell population with higher levels of CD62L and thus a higher ability to target the activated T cells to these sites under other preferred conditions. Another example of a polypeptide whose expression varies over time is CD49d, an adhesion molecule that is involved in trafficking lymphocytes from blood to tissues spaces at sites of inflammation. Binding of the CD49d ligand to CD49d also allows the T cell to receive co-stimulatory signals for activation and proliferation through binding by VCAM-1 or fibronectin ligands. The expression of the adhesion molecule CD54, involved in T cell-APC and T cell-T cell interactions as well as homing to sites of inflammation, also changes over the course of expansion. Accordingly, T cells could be stimulated for selected periods of time that coincide with the marker profile of interest and subsequently collected and infused. Thus, T cell populations could be tailored to express the markers believed to provide the most therapeutic benefit for the indication to be treated.

In the various embodiments, one of ordinary skill in the art understands removal of the stimulation signal from the cells is dependent upon the type of surface used. For example, if paramagnetic beads are used, then magnetic separation is the feasible option. Separation techniques are described in detail by paramagnetic bead manufacturers' instructions (for example, DYNAL Inc., Oslo, Norway). Furthermore, filtration may be used if the surface is a bead large enough to be separated from the cells. In addition, a variety of transfusion filters are commercially available, including 20 micron and 80 micron transfusion filters (Baxter). Accordingly, so long as the beads are larger than the mesh size of the filter, such filtration is highly efficient. In a related embodiment, the beads may pass through the filter, but cells may remain, thus allowing separation. In one particular embodiment the biocompatible surface used degrades (i.e. biodegradable) in culture during the exposure period.

Those of ordinary skill in the art will readily appreciate that the cell stimulation methodologies described herein may be carried out in a variety of environments (i.e., containers). For example, such containers may be culture flasks, culture bags, or any container capable of holding cells, preferably in a sterile environment. In one embodiment of the present invention a bioreactor is also useful. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J. Further, patents covering such bioreactors include U.S. Pat. Nos: 6,096,532; 5,985,653; 5,888,807; 5,190,878, which are incorporated herein by reference.

In one embodiment, the magnet used for simultaneous stimulation and concentration of the cells of the present invention may be incorporated into the base rocker platform of a bioreactor device, such as "The Wave" (Wave Biotech LLC, Bedminster, N.J.). The magnet, or a magnetizable element, may also be enclosed into a standard bioreactor vessel such as a cylindrical application unit. This built-in magnetic element may be capable of being switched on and off as desired at various points in the cell culture procedure. The integrated magnet, or magnetizable element, is positioned so as to allow a magnetic field emanating therefrom to pass through the culture vessel. In certain embodiments, the magnet, or magnetizable element, is incorporated within a wall, or alternatively, within the body of the culture vessel. In a further embodiment, the cells can be magnetically concentrated and/or activated, magnetically separated or isolated at a desired point during culture without the need to transfer cells to a different culture or magnetic separation unit. Use of such a built-in magnetic element can facilitate culture, stimulation and concentration, and separation processes to enable expansion and tailoring of specific functional cell populations for immunotherapeutic infusion into patients in cell or gene-based therapies. Further, this device provides an improved means for specific production of molecules both inside cells and their secretion to the outside of cells.

The integrated magnetic or magnetizable device as described above can be used to either remove magnetic particles from the culture, retaining them in the culture vessel, whilst the desired cells and/or desired molecules present in the culture media are removed. Alternatively, the cells and/or desired molecules may be specifically retained in the culture bag, or other suitable culture vessel, by interaction with magnetic particles that have been coated with specific molecules as described herein that bind to the desired cells and/or molecules. The built-in magnetic or magnetizable device enables the washing of cell populations and replacement of media in the cell culture bag by magnetically immobilizing/concentrating cells with specific particles and flowing media and or other solutions through the bag. This device effectively eliminates the need for a separate magnetic separation device by providing a fully integrated system, thereby reducing process time and manual operations for tubing connectors, reducing the number of containers used in processing and reducing the likelihood of contamination through the number of tube and container connections required. This integrated magnetic or magnetizable device-culture system also reduces the volumes needed in the culture processing and formulation.

As mentioned previously, one aspect of the present invention is directed to the surprising finding that the combination of a force which induces the concentration of cells, ligation of cell surface moieties, and culturing cells in a rocking, closed system, results in a profound enhancement in activation and expansion of these cells. Accordingly, in one embodiment, a bioreactor with a base rocker platform is used, for example such as "The Wave" (Wave Biotech LLC, Bedminster, N.J.), that allows for varying rates of rocking and at a variety of different rocking angles. The skilled artisan will recognize that any platform that allows for the appropriate motion for optimal expansion of the cells is within the context of the present invention. In certain embodiments, the methods of stimulation and expansion of the present invention provide for rocking the culture container during the process of culturing at 1, 2, 3, 4, 5, 6, 7, 8, 9, 10, 11, 12, 13, 14, 15, 16, 17, 18, 19, or 20 rocks per minute.

In certain embodiments, the capacity of the bioreactor container ranges from about 0.1 liter to about 200 liters of medium. The skilled artisan will readily appreciate that the volume used for culture will vary depending on the number of starting cells and on the final number of cells desired. In particular embodiments, the cells of the present invention, such as T cells are seeded at an initial concentration of about $0.2 \times 10^6$ cells/ml to about $5 \times 10^6$ cells/ml, and any concentration therebetween. In one particular embodiment, the cells may be cultured initially in a static environment and transferred to a bioreactor on a rocking platform after 1, 2, 3, 4, 5, 6, 7, 8, or more days of culture. In a related embodiment, the entire process of stimulation, activation, and expansion takes place in a bioreactor comprising a rocking platform and an integrated magnet, as described above. Illustrative bioreactors include, but are not limited to, "The Wave".

In one particular embodiment, the cell stimulation methods of the present invention are carried out in a closed system, such as a bioreactor, that allows for perfusion of medium at varying rates, such as from about 0.1 ml/minute to about 3 ml/minute. Accordingly, in certain embodiments, the container of such a closed system comprises an outlet filter, an inlet filter, and a sampling port for sterile transfer to and from the closed system. In other embodiments, the container of such a closed system comprises a syringe pump and control for sterile transfer to and from the closed system. Further embodiments provide for a mechanism, such as a load cell, for controlling media in-put and out-put by continuous monitoring of the weight of the bioreactor container. In one embodiment the system comprises a gas manifold. In another embodiment, the bioreactor of the present invention comprises a $CO_2$ gas mix rack that supplies a mixture of ambient air and $CO_2$ to the bioreactor container and maintains the container at positive pressure. In another embodiment, the bioreactor of the present invention comprises a variable heating element.

In one embodiment, media is allowed to enter the container starting on day 2, 3, 4, 5, or 6 at about 0.5 to 5.0 liters per day until the desired final volume is achieved. In one preferred embodiment, media enters the container at 2 liters per day starting at day 4, until the volume reaches 10 liters. Once desired volume is achieved, perfusion of media can be initiated. In certain embodiments, perfusion of media through the system is initiated on about day 2, 3, 4, 5, 6, 7, 8, 9, 10, 11, or 12 of culture. In one embodiment, perfusion is initiated when the volume is at about 0.1 lliter to about 200 liters of media. In one particular embodiment, perfusion is initiated when the final volume is at 4, 5, 6, 7, 8, 9, 10, or 20 liters.

In a further embodiment of the present invention, the cells, such as T cells, are cultured for up to 5 days in a closed, static system and then transferred to a closed system that comprises a rocking element to allow rocking of the culture container at varying speeds.

In certain aspects, the methodologies of the present invention provide for the expansion of cells, such as T cells, to a concentration of about between $6 \times 10^6$ cell/ml and about $90 \times 10^6$ cells/ml in less that about two weeks. In particular the methodologies herein provide for the expansion of T cells to a concentration of about 10, 15, 20, 25, 30, 35, 40, 45, 50, 55, 60, 65, 70, 75, 80, or $85 \times 10^6$ cells/ml and all concentrations therein. In certain embodiments, the cells reach a desired concentration, such as any of those listed above, by about day 5, 6, 7, 8, 9, 10, 11, or 12 of culture. In one embodiment, the T cells expand by at least about 1.5 fold in about 24 hours from about day 4 to about day 12 of culture. In one embodiment, the cells, such as T cells, expand from a starting number of cells of about $100 \times 10^6$ to a total of about $500 \times 10^9$ cells in less than about two weeks. In further embodiments, the T cells expand from a starting number of cells of about $500 \times 10^6$ to a total of about $500 \times 10^9$ cells in less than about two weeks. In related embodiments, the cells expand from a starting number of about $100\text{-}500 \times 10^6$ to a total of about 200, 300, or $400 \times 10^9$ cells in less than about two weeks.

In further embodiments of the present invention, the cell activation and expansion methods described herein and the conditioned medium generated using these methods can be used for the production of exosomes. In cells, vesicles can be formed by budding of the endosomal membrane into the lumen of the compartment; this process results in the formation of multivesicular bodies (MVBs). Fusion of MVBs with the plasma membrane results in secretion of the small internal vesicles, termed exosomes. The conditioned medium can be used for the culture of other T cells or for the culture of other types cells.

Although the antibodies used in the methods described herein can be readily obtained from public sources, such as the ATCC, antibodies to T cell accessory molecules and the CD3 complex can be produced by standard techniques. Methodologies for generating antibodies for use in the methods of the invention are well-known in the art and are discussed in further detail herein.

Ligand Immobilization on a Surface

As indicated above, the methods of the present invention preferably use ligands bound to a surface. The surface may be any surface capable of having a ligand bound thereto or integrated into and that is biocompatible, that is, substantially non-toxic to the target cells to be stimulated. The biocompatible surface may be biodegradable or non-biodegradable. The surface may be natural or synthetic, and a synthetic surface may be a polymer. The surface may comprise collagen, purified proteins, purified peptides, polysaccharides, glycosaminoglycans, or extracellular matrix compositions. A polysaccharide may include for example, cellulose, agarose, dextran, chitosan, hyaluronic acid, or alginate. Other polymers may include polyesters, polyethers, polyanhydrides, polyalkylcyanoacryllates, polyacrylamides, polyorthoesters, polyphosphazenes, polyvinylacetates, block copolymers, polypropylene, polytetrafluorethylene (PTFE), or polyurethanes. The polymer may be lactic acid or a copolymer. A copolymer may comprise lactic acid and glycolic acid (PLGA). Non-biodegradable surfaces may include polymers, such as poly(dimethylsiloxane) and poly(ethylene-vinyl acetate). Biocompatible surfaces include for example, glass (e.g., bioglass), collagen, metal, hydroxyapatite, aluminate, bioceramic materials, hyaluronic acid polymers, alginate, acrylic ester polymers, lactic acid polymer, glycolic acid polymer, lactic acid/glycolic acid polymer, purified proteins, purified peptides, or extracellular matrix compositions. Other polymers comprising a surface may include glass, silica, silicon, hydroxyapatite, hydrogels, collagen, acrolein, polyacrylamide, polypropylene, polystyrene, nylon, or any number of plastics or synthetic organic polymers, or the like. The surface may comprise a biological structure, such as a liposome or a cell. The surface may be in the form of a lipid, a plate, bag, pellet, fiber, mesh, or particle. A particle may include, a colloidal particle, a microsphere, nanoparticle, a bead, or the like. In the various embodiments, commercially available surfaces, such as beads or other particles, are useful (e.g., Miltenyi Particles, Miltenyi Biotec, Germany; Sepharose beads, Pharmacia Fine Chemicals, Sweden; DYNABEADS™, Dynal Inc., New York; PURABEADS™, Prometic Biosciences).

When beads are used, the bead may be of any size that effectuates target cell stimulation. In one embodiment, beads are preferably from about 5 nanometers to about 500 µm in size. Accordingly, the choice of bead size depends on the particular use the bead will serve. For example, if the bead is used for monocyte depletion, a small size is chosen to facilitate monocyte ingestion (e.g., 2.8 µm and 4.5 µm in diameter or any size that may be engulfed, such as nanometer sizes); however, when separation of beads by filtration is desired, bead sizes of no less than 50 µm are typically used. Further, when using paramagnetic beads, the beads typically range in size from about 2.8 µm to about 500 µm and more preferably from about 2.8 µm to about 50 µm. Lastly, one may choose to use super-paramagnetic nanoparticles which can be as small as about $10^{-5}$ m. Accordingly, as is readily apparent from the discussion above, virtually any particle size may be utilized.

An agent may be attached or coupled to, or integrated into a surface by a variety of methods known and available in the art. The agent may be a natural ligand, a protein ligand, or a synthetic ligand. The attachment may be covalent or noncovalent, electrostatic, or hydrophobic and may be accomplished by a variety of attachment means, including for example, chemical, mechanical, enzymatic, electrostatic, or other means whereby a ligand is capable of stimulating the cells. For example, the antibody to a ligand first may be attached to a surface, or avidin or streptavidin may be attached to the surface for binding to a biotinylated ligand. The antibody to the ligand may be attached to the surface via an anti-idiotype antibody. Another example includes using protein A or protein G, or other non-specific antibody binding molecules, attached to surfaces to bind an antibody. Alternatively, the ligand may be attached to the surface by chemical means, such as cross-linking to the surface, using commercially available cross-linking reagents (Pierce, Rockford, Ill.) or other means. In certain embodiments, the ligands are covalently bound to the surface. Further, in one embodiment, commercially available tosyl-activated DYNABEADS™ or DYNABEADS™ with epoxy-surface reactive groups are incubated with the polypeptide ligand of interest according to the manufacturer's instructions. Briefly, such conditions typically involve incubation in a phosphate buffer from pH 4 to pH 9.5 at temperatures ranging from 4 to 37 degrees C.

In one aspect, the agent, such as certain ligands may be of singular origin or multiple origins and may be antibodies or fragments thereof while in another aspect, when utilizing T cells, the co-stimulatory ligand is a B7 molecule (e.g., B7-1, B7-2). These ligands are coupled to the surface by any of the different attachment means discussed above. The B7 molecule to be coupled to the surface may be isolated from a cell expressing the co-stimulatory molecule, or obtained using standard recombinant DNA technology and expression systems that allow for production and isolation of the co-stimulatory molecule(s) as described herein. Fragments, mutants, or variants of a B7 molecule that retain the capability to trigger a co-stimulatory signal in T cells when coupled to the surface of a cell can also be used. Furthermore, one of ordinary skill in the art will recognize that any ligand useful in the activation and induction of proliferation of a subset of T cells may also be immobilized on beads or culture vessel surfaces or any surface. In addition, while covalent binding of the ligand to the surface is one preferred methodology, adsorption or capture by a secondary monoclonal antibody may also be used. The amount of a particular ligand attached to a surface may be readily determined by flow cytometric analysis if the surface is that of beads or determined by enzyme-linked immunosorbent assay (ELISA) if the surface is a tissue culture dish, mesh, fibers, bags, for example.

In a particular embodiment, the stimulatory form of a B7 molecule or an anti-CD28 antibody or fragment thereof is attached to the same solid phase surface as the agent that stimulates the TCR/CD3 complex, such as an anti-CD3 antibody. In an additional embodiment, the stimulatory form of a 4-1BB molecule or an anti-4-1BB antibody or fragment thereof is attached to the same solid phase surface as the agent that stimulates the TCR/CD3 complex, such as an anti-CD3 antibody. In addition to anti-CD3 antibodies, other antibodies that bind to receptors that mimic antigen signals may be used. For example, the beads or other surfaces may be coated with combinations of anti-CD2 antibodies and a B7 molecule and in particular anti-CD3 antibodies and anti-CD28 antibodies. In further embodiments, the surfaces may be coated with three or more agents, such as combinations of any of the agents described herein, for example, anti-CD3 antibodies, anti-CD28 antibodies, and anti-4-1BB antibodies.

When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In a preferred embodiment, the two agents are immobilized on beads, either on the same bead, i.e., "cis," or to separate beads, i.e., "trans." By way of example, the agent providing the primary activation signal is an anti-CD3 antibody and the agent providing the co-stimulatory signal is an anti-CD28 antibody; and both agents are co-immobilized to the same bead in equivalent molecular amounts. In one embodiment, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 0.5 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e. the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

In certain aspects of the present invention, three or more agents are coupled to a surface. In certain embodiments, the agents may be coupled to the same surface (i.e., in "cis" formation) or to separate surfaces (i.e., in "trans" formation). Alternatively, one or more agents may be coupled to a surface and the other agent or agents may be in solution.

Agents

Agents contemplated by the present invention include protein ligands, natural ligands, and synthetic ligands. Agents that can bind to cell surface moieties, and under certain conditions, cause ligation and aggregation that leads to signaling include, but are not limited to, lectins (for example, PHA, lentil lectins, concanavalin A), antibodies, antibody fragments, peptides, polypeptides, glycopeptides, receptors, B cell receptor and T cell receptor ligands, extracellular matrix components, steroids, hormones (for example, growth hormone, corticosteroids, prostaglandins, tetra-iodo thyronine), bacterial moieties (such as lipopolysaccharides), mitogens, antigens, superantigens and their derivatives, growth factors, cytokine, viral proteins (for example, HIV gp-120), adhesion molecules (such as, L-selectin, LFA-3, CD54, LFA-1), chemokines, and small molecules. The agents may be isolated from natural sources such as cells, blood products, and tissues, or isolated from cells propagated in vitro, or prepared recombinantly, or by other methods known to those with skill in the art.

In one aspect of the present invention, when it is desirous to stimulate T cells, useful agents include ligands that are capable of binding the CD3/TCR complex, CD2, and/or CD28 and initiating activation or proliferation, respectively. Accordingly, the term ligand includes those proteins that are the "natural" ligand for the cell surface protein, such as a B7 molecule for CD28, as well as artificial ligands such as antibodies directed to the cell surface protein. Such antibodies and fragments thereof may be produced in accordance with conventional techniques, such as hybridoma methods and recombinant DNA and protein expression techniques. Useful antibodies and fragments may be derived from any species, including humans, or may be formed as chimeric proteins, which employ sequences from more than one species.

Methods well known in the art may be used to generate antibodies, polyclonal antisera, or monoclonal antibodies that are specific for a ligand. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second distinct mammalian species. Most commonly, a chimeric antibody has murine variable region sequences and human constant region sequences. Such a murine/human chimeric immunoglobulin may be "humanized" by grafting the complementarity determining regions (CDRs), which confer binding specificity for an antigen, derived from a murine antibody into human-derived V region framework regions and human-derived constant regions. Fragments of these molecules may be generated by proteolytic digestion, or optionally, by proteolytic digestion followed by mild reduction of disulfide bonds and alkylation, or by recombinant genetic engineering techniques.

Antibodies are defined to be "immunospecific" if they specifically bind the ligand with an affinity constant, $K_a$, of greater than or equal to about $10^4$ $M^{-1}$, preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al. (*Ann. N. Y. Acad. Sci. USA* 51:660, 1949) or by surface plasmon resonance (BIAcore, Biosensor, Piscataway, N.J.) See, e.g., Wolff et al., *Cancer Res.*, 53:2560-2565, 1993).

Antibodies may generally be prepared by any of a variety of techniques known to those having ordinary skill in the art (See, e.g., Harlow et al., *Antibodies: A Laboratory Manual*, 1988, Cold Spring Harbor Laboratory). In one such technique, an animal is immunized with the ligand as antigen to generate polyclonal antisera. Suitable animals include rabbits, sheep, goats, pigs, cattle, and may include smaller mammalian species, such as, mice, rats, and hamsters.

An immunogen may be comprised of cells expressing the ligand, purified or partially purified ligand polypeptides or variants or fragments thereof, or ligand peptides. Ligand peptides may be generated by proteolytic cleavage or may be chemically synthesized. Peptides for immunization may be selected by analyzing the primary, secondary, or tertiary structure of the ligand according to methods know to those skilled in the art in order to determine amino acid sequences more likely to generate an antigenic response in a host animal (See, e.g., Novotny, *Mol. Immunol.* 28:201-207, 1991; Berzoksky, *Science* 229:932-40, 1985).

Preparation of the immunogen may include covalent coupling of the ligand polypeptide or variant or fragment thereof, or peptide to another immunogenic protein, such as, keyhole limpet hemocyanin or bovine serum albumin. In addition, the peptide, polypeptide, or cells may be emulsified in an adjuvant (See Harlow et al., *Antibodies: A Laboratory Manual*, 1988 Cold Spring Harbor Laboratory). In general, after the first injection, animals receive one or more booster immunizations according to a preferable schedule for the animal species. The immune response may be monitored by periodically bleeding the animal, separating the sera, and analyzing the sera in an immunoassay, such as an Ouchterlony assay, to assess the specific antibody titer. Once an antibody titer is established, the animals may be bled periodically to accumulate the polyclonal antisera. Polyclonal antibodies that bind specifically to the ligand polypeptide or peptide may then be purified from such antisera, for example, by affinity chromatography using protein A or using the ligand polypeptide or peptide coupled to a suitable solid support.

Monoclonal antibodies that specifically bind ligand polypeptides or fragments or variants thereof may be prepared, for example, using the technique of Kohler and Milstein (*Nature*, 256:495-497, 1975; *Eur. J. Immunol* 6:511-519, 1976) and improvements thereto. Hybridomas, which are immortal eucaryotic cell lines, may be generated that produce antibodies having the desired specificity to a the ligand polypeptide or variant or fragment thereof. An animal—for example, a rat, hamster, or preferably mouse—is immunized with the ligand immunogen prepared as described above. Lymphoid cells, most commonly, spleen cells, obtained from an immunized animal may be immortalized by fusion with a drug-sensitized myeloma cell fusion partner, preferably one that is syngeneic with the immunized animal. The spleen cells and myeloma cells may be combined for a few minutes with a membrane fusion-promoting agent, such as polyethylene glycol or a nonionic detergent, and then plated at low density on a selective medium that supports the growth of hybridoma cells, but not myeloma cells. A preferred selection media is HAT (hypoxanthine, aminopterin, thymidine). After a sufficient time, usually about 1 to 2 weeks, colonies of cells are observed. Single colonies are isolated, and antibodies produced by the cells may be tested for binding activity to the ligand polypeptide or variant or fragment thereof. Hybridomas producing antibody with high affinity and specificity for the ligand antigen are preferred. Hybridomas that produce monoclonal antibodies that specifically bind to a ligand polypeptide or variant or fragment thereof are contemplated by the present invention.

Monoclonal antibodies may be isolated from the supernatants of hybridoma cultures. An alternative method for production of a murine monoclonal antibody is to inject the hybridoma cells into the peritoneal cavity of a syngeneic mouse. The mouse produces ascites fluid containing the monoclonal antibody. Contaminants may be removed from the antibody by conventional techniques, such as chromatography, gel filtration, precipitation, or extraction.

Human monoclonal antibodies may be generated by any number of techniques. Methods include but are not limited to, Epstein Barr Virus (EBV) transformation of human peripheral blood cells (see, U.S. Pat. No. 4,464,456), in vitro immunization of human B cells (see, e.g., Boerner et al., *J. Immunol.* 147:86-95, 1991), fusion of spleen cells from immunized transgenic mice carrying human immunoglobulin genes and fusion of spleen cells from immunized transgenic mice carrying immunoglobulin genes inserted by yeast artificial chromosome (YAC) (see, e.g., U.S. Pat. No. 5,877,397; Bruggemann et al., *Curr. Opin. Biotechnol.* 8:455-58, 1997; Jakobovits et al., *Ann. N. Y. Acad. Sci.* 764:525-35, 1995), or isolation from human immunoglobulin V region phage libraries.

Chimeric antibodies and humanized antibodies for use in the present invention may be generated. A chimeric antibody has at least one constant region domain derived from a first mammalian species and at least one variable region domain derived from a second distinct mammalian species (See, e.g., Morrison et al., *Proc. Natl. Acad. Sci. USA,* 81:6851-55, 1984). Most commonly, a chimeric antibody may be constructed by cloning the polynucleotide sequences that encode at least one variable region domain derived from a non-human monoclonal antibody, such as the variable region derived from a murine, rat, or hamster monoclonal antibody, into a vector containing sequences that encode at least one human constant region. (See, e.g., Shin et al., *Methods Enzymol.* 178:459-76, 1989; Walls et al., *Nucleic Acids Res.* 21:2921-29, 1993). The human constant region chosen may depend upon the effector functions desired for the particular antibody. Another method known in the art for generating chimeric antibodies is homologous recombination (U.S. Pat. No. 5,482,856). Preferably, the vectors will be transfected into eukaryotic cells for stable expression of the chimeric antibody.

A non-human/human chimeric antibody may be further genetically engineered to create a "humanized" antibody. Such an antibody has a plurality of CDRs derived from an immunoglobulin of a non-human mammalian species, at least one human variable framework region, and at least one human immunoglobulin constant region. Humanization may yield an antibody that has decreased binding affinity when compared with the non-human monoclonal antibody or the chimeric antibody. Those having skill in the art, therefore, use one or more strategies to design humanized antibodies.

Within certain embodiments, the use of antigen-binding fragments of antibodies may be preferred. Such fragments include Fab fragments or F(ab')$_2$ fragments, which may be prepared by proteolytic digestion with papain or pepsin, respectively. The antigen binding fragments may be separated from the Fc fragments by affinity chromatography, for example, using immobilized protein A or immobilized ligand polypeptide or a variant or a fragment thereof. An alternative method to generate Fab fragments includes mild reduction of F(ab')₂ fragments followed by alkylation (See, e.g., Weir, *Handbook of Experimental Immunology*, 1986, Blackwell Scientific, Boston).

Non-human, human, or humanized heavy chain and light chain variable regions of any of the above described Ig molecules may be constructed as single chain Fv (sFv) fragments (single chain antibodies). See, e.g., Bird et al., *Science* 242: 423-426, 1988; Huston et al., *Proc. Natl. Acad. Sci. USA* 85:5879-5883, 1988. Multi-functional fusion proteins may be generated by linking polynucleotide sequences encoding an sFv in-frame with polynucleotide sequences encoding various effector proteins. These methods are known in the art, and are disclosed, for example, in EP-B1-0318554, U.S. Pat. No. 5,132,405, U.S. Pat. No. 5,091,513, and U.S. Pat. No. 5,476,786.

An additional method for selecting antibodies that specifically bind to a ligand polypeptide or variant or fragment thereof is by phage display (See, e.g., Winter et al., *Annul. Rev. Immunol.* 12:433-55, 1994; Burton et al., *Adv. Immunol.* 57:191-280, 1994). Human or murine immunoglobulin variable region gene combinatorial libraries may be created in phage vectors that can be screened to select Ig fragments (Fab, Fv, sFv, or multimers thereof) that bind specifically to a ligand polypeptide or variant or fragment thereof (See, e.g., U.S. Pat. No. 5,223,409; Huse et al., *Science* 246:1275-81, 1989; Kang et al., *Proc. Natl. Acad. Sci. USA* 88:4363-66, 1991; Hoogenboom et al., *J. Molec. Biol.* 227:381-388, 1992; Schlebusch et al., *Hybridoma* 16:47-52, 1997 and references cited therein).

Cell Populations

As discussed above, the present invention has broad applicability to any cell type having a cell surface moiety that one is desirous of ligating. In this regard, many cell signaling events can be enhanced by the methods of the present invention. Such methodologies can be used therapeutically in an ex vivo setting to activate and stimulate cells for infusion into a patient or could be used in vivo, to induce cell signaling events on a target cell population. However, as also noted above, the prototypic example provided herein is directed to T cells, but is in no way limited thereto.

With respect to T cells, the T cell populations resulting from the various expansion methodologies described herein may have a variety of specific phenotypic properties, depending on the conditions employed. Such phenotypic properties include enhanced expression of CD25, CD154, IFN-γ and GM-CSF, as well as altered expression of CD137, CD134, CD62L, and CD49d. The ability to differentially control the expression of these moieties may be very important. For example, higher levels of surface expression of CD154 on "tailored T cells," through contact with CD40 molecules expressed on antigen-presenting cells (such as dendritic cells, monocytes, and even leukemic B cells or lymphomas), will enhance antigen presentation and immune function. Such strategies are currently being employed by various companies to ligate CD40 via antibodies or recombinant CD40L. The approach described herein permits this same signal to be delivered in a more physiological manner, e.g., by the T cell. The ability to increase IFN-γ secretion by tailoring the T cell activation (XCELLERATE) process could help promote the generation of TH1-type immune responses, important for anti-tumor and anti-viral responses. Like CD154, increased expression of GM-CSF can serve to enhance APC function, particularly through its effect on promoting the maturation of APC progenitors into more functionally competent APC, such as dendritic cells. Altering the expression of CD137 and CD134 can effect a T cell's ability to resist or be susceptible to apoptotic signals. Controlling the expression of adhesion/ homing receptors, such as CD62L and/or CD49d may determine the ability of infused T cells to home to lymphoid organs, sites of infection, or tumor sites.

An additional aspect of the present invention provides a T cell population or composition that has been depleted of CD8⁺ or CD4⁺ cells prior to expansion. In one embodiment, CD8⁺ cells are depleted by antibodies directed to the CD8⁺ marker. One of ordinary skill in the art would readily be able to identify a variety of particular methodologies for depleting a sample of CD8⁺ or CD4⁺ cells or conversely enriching the CD4⁺ or CD8⁺ cell content. With respect to enriching for CD4⁺ cells, one aspect of the present invention is focused on the identification of an extremely robust CD154 expression profile upon stimulation of T cell populations wherein $T_C$ (CD8⁺) cells have been depleted. As indicated above, CD154 is an important immunomodulating molecule whose expression is extremely beneficial in amplifying the immune response. Accordingly an increase in CD154 expression is likely to lead to more efficacious T cell compositions.

An additional aspect of the present invention provides a T cell population or composition that has been depleted or enriched for populations of cells expressing a variety of markers, such as CD62L, CD45RA or CD45RO, cytokines (e.g. IL-2, IFN-γ, IL-4, IL-10), cytokine receptors (e.g. CD25), perforin, adhesion molecules (e.g. VLA-1, VLA-2, VLA-4, LPAM-1, LFA-1), and/or homing molecules (e.g. L-Selectin), prior to expansion. In one embodiment, cells expressing any of these markers are depleted or positively selected by antibodies or other ligands/binding agents directed to the marker. One of ordinary skill in the art would readily be able to identify a variety of particular methodologies for depleting or positively selecting for a sample of cells expressing a desired marker.

The phenotypic properties of T cell populations of the present invention can be monitored by a variety of methods including standard flow cytometry methods and ELISA methods known by those skilled in the art.

Methods of Use

Generally, the cells stimulated and/or activated by the methods described herein may be utilized in the treatment and prevention of cancer, infectious diseases, autoimmune diseases, immune disfunction related to aging, or any other disease state where such cells are desired for treatment.

In addition to the methods described above, cells stimulated and/or activated by the methods herein described may be utilized in a variety of contexts. With respect to the prototypic example of T cells, the methodologies described herein can be used to selectively expand a population of CD28⁺, CD4⁺, CD8⁺, CD45RA⁺, or CD45RO⁺T cells for use in the treatment of infectious diseases, cancer, and immunotherapy. As a result, a phenotypically unique population of T cells, which is polyclonal with respect to antigen reactivity, but essentially homogeneous with respect to either CD4⁺ or CD8⁺ can be produced. In addition, the method allows for the expansion of a population of T cells in numbers sufficient to reconstitute an individual's total CD4⁺ or CD8⁺ T cell population (the population of lymphocytes in an individual is approximately $3-5 \times 10^{11}$). The resulting T cell population can also be genetically transduced and used for immunotherapy or can be used in methods of in vitro analyses of infectious agents. For example, a population of tumor-infiltrating lymphocytes can be obtained from an individual afflicted with cancer and the T cells stimulated to proliferate to sufficient numbers. The resulting T cell population can be genetically transduced to express tumor necrosis factor (TNF) or other proteins (for example, any number of cytokines, inhibitors of apoptosis (e.g. Bcl-2), genes that protect cells from HIV infection such as RevM10 or intrakines, and the like, targeting molecules, adhesion and/or homing molecules and any variety of antibodies or fragments thereof (e.g. Scfv)) and given to the individual.

One particular use for the CD4+ T cells populations of the invention is the treatment of HIV infection in an individual. Prolonged infection with HIV eventually results in a marked decline in the number of CD4+ T lymphocytes. This decline, in turn, causes a profound state of immunodeficiency, rendering the patient susceptible to an array of life threatening opportunistic infections. Replenishing the number of CD4+ T cells to normal levels may be expected to restore immune function to a significant degree. Thus, the method described herein provides a means for selectively expanding CD4+ T cells to sufficient numbers to reconstitute this population in an HIV infected patient. It may also be necessary to avoid infecting the T cells during long-term stimulation or it may desirable to render the T cells permanently resistant to HIV infection. There are a number of techniques by which T cells may be rendered either resistant to HIV infection or incapable of producing virus prior to restoring the T cells to the infected individual. For example, one or more anti-retroviral agents can be cultured with CD4+ T cells prior to expansion to inhibit HIV replication or viral production (e.g., drugs that target reverse transcriptase and/or other components of the viral machinery, see e.g., Chow et al. *Nature* 361:650-653, 1993).

Several methods can be used to genetically transduce T cells to produce molecules which inhibit HIV infection or replication. For example, in various embodiments, T cells can be genetically transduced to produce transdominant inhibitors, "molecular decoys", antisense molecules, intrakines, or toxins. Such methodologies are described in further detail in U.S. patent application Ser. Nos. 08/253,751, 08/253,964, and PCT Publication No. WO 95/33823, which are incorporated herein by reference in their entirety.

The methods for stimulating and expanding a population of antigen specific T cells are useful in therapeutic situations where it is desirable to up-regulate an immune response (e.g., induce a response or enhance an existing response) upon administration of the T cells to a subject. For example, the method can be used to enhance a T cell response against tumor-associated antigens. Tumor cells from a subject typically express tumor-associated antigens but may be unable to stimulate a co-stimulatory signal in T cells (e.g., because they lack expression of co-stimulatory molecules). Thus, tumor cells can be contacted with T cells from the subject in vitro and antigen specific T cells expanded according to the method of the invention and the T cells returned to the subject.

Accordingly, in one embodiment malignancies such as non-Hodgkins Lymphoma (NHL) and B-cell chronic lymphocytic leukemia (B-CLL) can be treated. While initial studies using expanded T cells have been tested in NHL, (see Liebowitz et al., *Curr. Opin. Onc.* 10:533-541, 1998), the T cell populations of the present invention offer unique phenotypic characteristics that can dramatically enhance the success of immunotherapy by providing increased engraftment (likely supplied by stimulation of the CD28 signal) and reactivity. However, patients with B-CLL present special difficulties, including low relative T cell numbers with high leukemic cell burden in the peripheral blood, accompanied by a general T cell immunosuppression. The T cell populations of the present invention can provide dramatically improved efficacy in treating this disease and especially when combined with stem cell transplantation therapy. Accordingly, increasing T cell function and anti-CLL T cell activity with anti-CD3× anti-CD28 co-immobilized beads would be beneficial.

For example, given that deficient expression of CD154, the ligand for CD40, on T cells of B-CLL patients has been cited as a major immunological defect of the disease, the T cell populations of the present invention, which may provide sustained high levels of CD154 expression upon re-infusion, could aid in its treatment. Investigators report that in CLL the capability of a patient's T cells' to express CD154 is defective as well as the capability of the leukemic B-cells to express CD80 and CD86. The failure of leukemic B-cells in CLL to adequately express the ligands for CD28, could result in failure to fully activate tumor-responsive T cells and, therefore, may represent the mechanism underlying the T cells' apparent state of tolerance. Studies in which CD40 is engaged on CLL B cells, either via soluble anti-CD40 antibodies or via CD154-transduced leukemic B-cells, appears to correct the defect in CD80 and CD86 expression and up-regulates MHC surface expression. Kato et al., *J. Clin. Invest.* 101:1133-1141, 1998; Ranheim and Kipps, *J. Exp. Med.* 177:925-935, 1993. Cells treated in this way were able to stimulate specific T cell anti-tumor responses.

With the enhanced expression of CD154 on the surface of the T cell population of the present invention such T cells would be expected to interact with autologous B-CLL cells, and would thus increase that tumor's immunogenicity by driving up expression of MHC, CD80, and CD86. This, in turn, should lead to a strong anti-tumor response. Further, one of ordinary skill in the art would readily understand that treatment of a patient with ex vivo expanded T cells of the present invention may be combined with traditional cancer therapies such as chemotherapy. In this regard, for example, a patient may be treated with an agent such as Fludarabine or Campath (Berlex Laboratories, Montville, N.J., USA), followed by infusion with T cell populations of the present invention or both.

The invention further provides methods to selectively expand a specific subpopulation of T cells from a mixed population of T cells. In particular, the invention provides specifically enriched populations of T cells that have much higher ratio of CD4+ and CD8+ double positive T cells.

Another embodiment of the invention, provides a method for selectively expanding a population of $T_{H1}$ cells from a population of CD4+ T cells. In this method, CD4+ T cells are co-stimulated with an anti-CD28 antibody, such as the monoclonal antibody 9.3, inducing secretion of $T_{H1}$-specific cytokines, including IFN-γ, resulting in enrichment of $T_{H1}$ cells over $T_{H2}$ cells.

The observation herein that phenotypic traits of activated T cells vary over time during the expansion process, combined with the fact that T cells have been demonstrated to be activated within a few hours (Iezzi et al., Immunity 8:89-95, 1998). Accordingly, in combination with the methodologies herein described, this provides the ability to expand a tailor made subset of a T cell population in a short period of time. In one embodiment, this technique can be utilized at the bedside of a subject, in an outpatient modality, or at a subject's home, similar to the use of kidney dialysis. For example, a method or device wherein T cells are incubated in contact with activation signals (e.g., anti-CD3 and anti-CD28 antibodies, and the like) and returned to the patient immediately in a continuous flow or after a few hour expansion period. In one aspect, such techniques of expansion could use isolated chambers with filter components, such that 3×28 beads or similarly coated microparticles are mixed with a continuous flow of blood/concentrated cells. In another embodiment, solid surfaces within an apparatus may be coated or conjugated directly (including covalently) or indirectly (e.g., streptavidin/biotin and the like) with antibodies or other components to stimulate T cell activation and expansion. For example, a continuous fluid path from the patient through a blood/cell collection device and/or a disposable device containing two or more immobilized antibodies (e.g., anti-CD3 and anti-CD28) or other components to stimulate receptors required for T cell activation prior to cells returning to the subject can be utilized (immobilized on plastic surfaces or upon separable microparticles). Such a system could involve a leukapheresis instrument with a disposable set sterile docked to the existing manufacturers disposable set, or be an adaptation to the manufacturer's disposable set (e.g., the surface platform on which the antibodies/activation components are immobilized/contained is within the bag/container for collection of peripheral blood mononuclear cells during apheresis). Further, the solid surface/surface platform may be a part of a removal insert which is inserted into one of the device chambers or physically present within one of the disposable components. In another embodiment of the continuous flow aspect discussed above, the system may comprise contacting the cells with the activating components at room temperature or at physiologic temperature using a chamber within a blood collection device or an incubation chamber set up in series with the flow path to the patient.

In another example, blood is drawn into a stand-alone disposable device directly from the patient that contains two or more immobilized antibodies (e.g., anti-CD3 and anti-CD28) or other components to stimulate receptors required for T cell activation prior to the cells being administered to the subject (e.g., immobilized on plastic surfaces or upon separable microparticles). In one embodiment, the disposable device may comprise a container (e.g., a plastic bag, or flask) with appropriate tubing connections suitable for combining/docking with syringes and sterile docking devices. This device will contain a solid surface for immobilization of T cell activation components (e.g., anti-CD3 and anti-CD28 antibodies); these may be the surfaces of the container itself or an insert and will typically be a flat surface, an etched flat surface, an irregular surface, a porous pad, fiber, clinically acceptable/safe ferro-fluid, beads, etc.). Additionally when using the stand-alone device, the subject can remain connected to the device, or the device can be separable from the patient. Further, the device may be utilized at room temperature or incubated at physiologic temperature using a portable incubator.

As devices and methods for collecting and processing blood and blood products are well known, one of skill in the art would readily recognize that given the teachings provided herein, that a variety of devices that fulfill the needs set forth above may be readily designed or existing devices modified. Accordingly, as such devices and methods are not limited by the specific embodiments set forth herein, but would include any device or methodology capable of maintaining sterility and which maintains blood in a fluid form in which complement activation is reduced and wherein components necessary for T cell activation (e.g., anti-CD3 and anti-CD28 antibodies or ligands thereto) may be immobilized or separated from the blood or blood product prior to administration to the subject. Further, as those of ordinary skill in the art can readily appreciate a variety of blood products can be utilized in conjunction with the devices and methods described herein. For example the methods and devices could be used to provide rapid activation of T cells from cryopreserved whole blood, peripheral blood mononuclear cells, other cyropreserved blood-derived cells, or cryopreserved T cell lines upon thaw and prior to subject administration. In another example, the methods and devices can be used to boost the activity of a previously ex vivo expanded T cell product or T cell line prior to administration to the subject, thus providing a highly activated T cell product. Lastly, as will be readily appreciated the methods and devices above may be utilized for autologous or allogeneic cell therapy simultaneously with the subject and donor.

The methods of the present invention may also be utilized with vaccines to enhance reactivity of the antigen and enhance in vivo effect. Further, given that T cells expanded by the present invention have a relatively long half-life in the body, these cells could act as perfect vehicles for gene therapy, by carrying a desired nucleic acid sequence of interest and potentially homing to sites of cancer, disease, or infection. Accordingly, the cells expanded by the present invention may be delivered to a patient in combination with a vaccine, one or more cytokines, one or more therapeutic antibodies, etc. Virtually any therapy that would benefit by a more robust T cell population is within the context of the methods of use described herein.

In certain embodiments the cells stimulated and expanded cells using the methods described herein, or other methods known in the art wherein T cells are stimulated and expanded to therapeutic levels, can be used to prevent or treat diseases caused by infectious organisms. T cells can be stimulated and expanded as described herein or using other methods known in the art wherein T cells are stimulated and expanded to therapeutic levels, to induce or enhance responsiveness to infectious organisms, such as viruses, bacteria, parasites and fungi. Infectious organisms may comprise viruses, (e.g., RNA viruses, DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as *Plasmodia* species, *Leishmania* species, *Schistosoma* species, *Trypanosoma* species), bacteria (e.g., *Mycobacteria,* in particular, *M. tuberculosis, Salmonella, Streptococci, E. coli, Staphylococci*), fungi (e.g., *Candida* species, *Aspergillus* species), *Pneumocystis carinii,* and prions (known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI)). As used herein "prion" includes all forms of prions causing all or any of these diseases or others in any animals used—and in particular in humans and domesticated farm animals.

T cells can be stimulated and expanded as described herein or using other methods known in the art wherein T cells are stimulated and expanded to therapeutic levels, to induce or enhance immune responsiveness in a subject for the prevention or treatment of a variety of cancers. T cells of the present invention are useful for preventing or treating melanoma, non-Hodgkin's lymphoma, cutaneous T cell lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers.

In certain embodiments, T cells stimulated and activated using the methods of the present invention, or other methods known in the art wherein T cells are stimulated and expanded to therapeutic levels, can be used for the treatment of lymph-node bearing diseases. In this regard, such disease include a variety of cancers and infectious diseases as described herein. Illustrative conditions include, but are not limited to, non-Hodgkin's lymphoma, Hodgkin's disease, angioimmunoblastic lymphadenopathy and chronic lymphocytic leukemia. Illustrative infectious diseases include, but are not limited to, toxoplasmosis, histoplasmosis, CMV, EBV, coccidiomycosis, tuberculosis, HIV, and the like. Non-infectious diseases that involve the lymph nodes can also benefit from treatment with the cells described herein, such as sarcoidosis. Target cancers include solid tumors that have metastasized from a primary site to a lymph node and that may have spread systemically (e.g., solid tumors from any number of cancers as described herein). In certain embodiments, treatment is for patients with disease documented by standard techniques such as CT scans, or for patients known to be at high risk for having lymph node disease. In certain embodiments, T cells stimulated and activated using the methods of the present invention, or other methods known in the art wherein T cells are stimulated and expanded to therapeutic levels, are given in conjunction with agents that home to (target) lymph nodes. In certain embodiments, vaccines, adjuvants, or dendritic cells can be administered near or in a lymph node followed by administration of T cells. In an additional embodiment, T cells are used as a carrier to deliver agents to lymph nodes (e.g., DNA, RNA, proteins, toxins, chemotherapy agents, etc).

In certain embodiments, T cells stimulated and activated using the methods of the present invention, or other methods known in the art wherein T cells are stimulated and expanded to therapeutic levels, can be used for the treatment of autoimmune diseases such as, but not limited to, rheumatoid arthritis, multiple sclerosis, insulin dependent diabetes, Addison's disease, celiac disease, chronic fatigue syndrome, inflammatory bowel disease, ulcerativecolitis, Crohn's disease, Fibromyalgia, systemic lupus erythematosus, psoriasis, Sjogren's syndrome, hyperthyroidism/Graves disease, hypothyroidism/Hashimoto's disease, Insulin-dependent diabetes (type 1), Myasthenia Gravis, endometriosis, scleroderma, pernicious anemia, Goodpasture syndrome, Wegener's disease, glomerulonephritis, aplastic anemia, paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis and rheumatic fever.

Pharmaceutical Compositions

Target cell populations, such as T cell populations of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The immune response induced in a subject by administering T cells stimulated and activated using the methods described herein, or other methods known in the art wherein T cells are stimulated and expanded to therapeutic levels, may include cellular immune responses mediated by cytotoxic T cells, capable of killing tumor and infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Coligan et al. Current Protocols in Immunology, John Wiley & Sons Inc. (1994).

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^7$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

Typically, in adoptive immunotherapy studies, antigen-specific T cells are administered approximately at $2 \times 10^9$ to $2 \times 10^{11}$ cells to the patient. (See, e.g., U.S. Pat. No. 5,057,423). In some aspects of the present invention, particularly in the use of allogeneic or xenogeneic cells, lower numbers of cells, in the range of $10^6$/kilogram ($10^6$-$10^{11}$ per patient) may be administered. In certain embodiments, T cells are administered at $1 \times 10^5$, $1 \times 10^6$, $1 \times 10^7$, $1 \times 10^8$, $2 \times 10^8$, $2 \times 10^9$, $1 \times 10^{10}$, $2 \times 10^{10}$, $1 \times 10^{11}$, $5 \times 10^{11}$, or $1 \times 10^{12}$ cells to the subject. T cell compositions may be administered multiple times at dosages within these ranges. The cells may be autologous or heterologous to the patient undergoing therapy. If desired, the treatment may also include administration of mitogens (e.g., PHA) or lymphokines, cytokines, and/or chemokines (e.g., GM-CSF, IL-4, IL-13, Flt3-L, RANTES, MIP1α, etc.) as described herein to enhance induction of the immune response.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramdullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In yet another embodiment, the pharmaceutical composition can be delivered in a controlled release system. In one embodiment, a pump may be used (see Langer, 1990, Science 249:1527-1533; Sefton 1987, CRC Crit. Ref. Biomed. Eng. 14:201; Buchwald et al., 1980; Surgery 88:507; Saudek et al., 1989, N. Engl. J. Med. 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, N.Y.; Ranger and Peppas, 1983; J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, thus requiring only a fraction of the systemic dose (see, e.g., Medical Applications of Controlled Release, 1984, Langer and Wise (eds.), CRC Pres., Boca Raton, Fla., vol. 2, pp. 115-138).

The T cell compositions of the present invention may also be administered using any number of matrices. Matrices have been utilized for a number of years within the context of tissue engineering (see, e.g., Principles of Tissue Engineering (Lanza, Langer, and Chick (eds.)), 1997. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos: 5,980,889; 5,913,998; 5,902,745; 5,843,069; 5,787,900; or 5,626,561 are utilized. Matrices comprise features commonly associated with being biocompatible when administered to a mammalian host. Matrices may be formed from both natural or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

In certain embodiments of the present invention, cells activated and expanded using the methods described herein, or other methods known in the art where T cells are expanded to therapeutic levels, are administered to a patient in conjunction with (e.g. before, simultaneously or following) any number of relevant treatment modalities, including but not limited to treatment with agents such as antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993; Isoniemi (supra)). In a further embodiment, the cell compositions of the present invention are administered to a patient in conjunction with (e.g. before, simulataneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g. Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In a further embodiment, the cell compositions comprising T cells stimulated and activated using the methods described herein, or other methods known in the art wherein T cells are stimulated and expanded to therapeutic levels, are administered to a patient in conjunction with allogeneic stem cell transplantation (such as in a mini-transplant setting) or organ transplantation. Without being bound by theory, such T cells may enhance and promote engraftment and anti-tumor effects. These T cells may have enhanced stem cell graft promoting effects and anti-tumor effects that allow a much reduced and less toxic transplant conditioning regimen to be utilized.

All references referred to within the text are hereby incorporated by reference in their entirety. Moreover, all numerical ranges utilized herein explicitly include all integer values within the range and selection of specific numerical values within the range is contemplated depending on the particular use. Further, the following examples are offered by way of illustration, and not by way of limitation.

EXAMPLES

Example I

T Cell Stimulation

In certain experiments described herein, the process referred to as XCELLERATE I™ was utilized. In brief, in this process, the XCELLERATED™ T cells are manufactured from a peripheral blood mononuclear cell (PBMC) apheresis product. After collection from the patient at the clinical site, the PBMC apheresis are washed and then incubated with "uncoated" DYNABEADS® M-450 Epoxy T. During this time phagocytic cells such as monocytes ingest the beads. After the incubation, the cells and beads are processed over a MaxSep Magnetic Separator in order to remove the beads and any monocytic/phagocytic cells that are attached to the beads. Following this monocyte-depletion step, a volume containing a total of $5\times10^8$ CD3$^+$ T cells is taken and set-up with $1.5\times10^9$ DYNABEADS® M-450 CD3/CD28 T to initiate the XCELLERATE™ process (approx. 3:1 beads to T cells). The mixture of cells and DYNABEADS® M-450 CD3/CD28 T are then incubated at 37° C., 5% $CO_2$ for approximately 8 days to generate XCELLERATED T cells for a first infusion. The remaining monocyte-depleted PBMC are cryopreserved until a second or further cell product expansion (approximately 21 days later) at which time they are thawed, washed and then a volume containing a total of $5\times10^8$ CD3$^+$ T cells is taken and set-up with $1.5\times10^9$ DYNABEADS® M-450 CD3/CD28 T to initiate the XCELLERATE Process for a second infusion. During the incubation period of ≈8 days at 37° C., 5% $CO_2$, the CD3$^+$ T cells activate and expand. The anti-CD3 mAb used is BC3 (XR-CD3; Fred Hutchinson Cancer Research Center, Seattle, Wash.), and the anti-CD28 mAb (B-T3, XR-CD28) is obtained from Diaclone, Besançon, France.

Figure 5A:
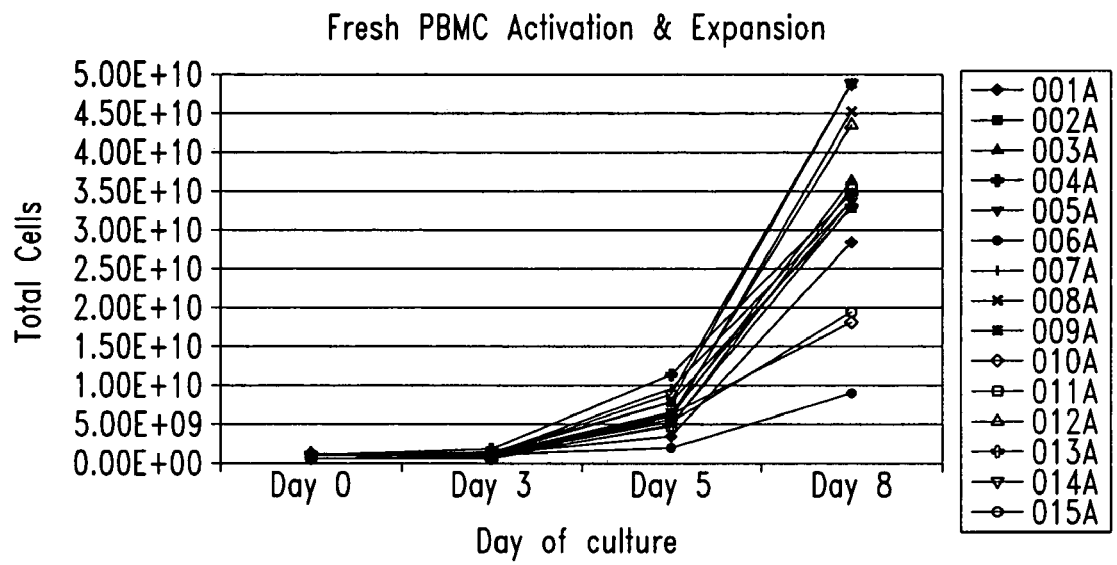
FIGS. 5A-5B are plots depicting T cell activation and expansion with XCELLERATE I™ PBMC (5A) or PBMC having been frozen and thawed (5B) to initiate the XCELLERATE I™ process.
Figure 5B:
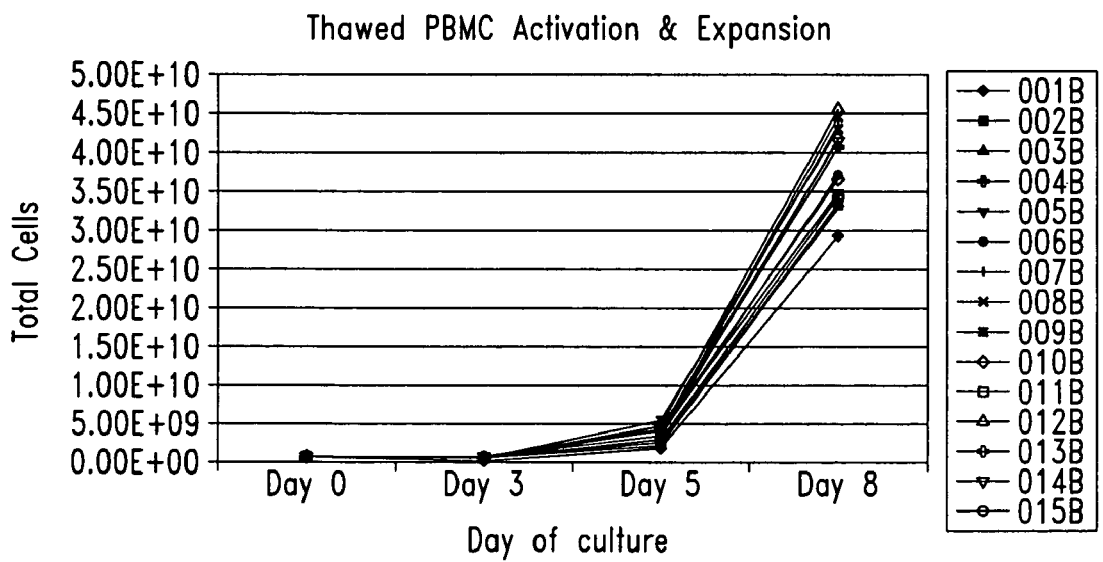

With a modified process referred to as XCELLERATE II™ the process described above was utilized with some modifications in which no separate monocyte depletion step was utilized and in certain processes the cells were frozen prior to initial contact with beads and further concentration and stimulation were performed. (See FIGS. 5A and 5B). In one version of this process T cells were obtained from the circulating blood of a donor or patient by apheresis. Components of an apheresis product typically include lymphocytes, monocytes, granulocytes, B cells, other nucleated cells (white blood cells), red blood cells, and platelets. A typical apheresis product contains $1-2\times10^{10}$ nucleated cells. The cells are washed with calcium-free, magnesium-free phosphate buffered saline to remove plasma proteins and platelets. The washing step was performed by centrifuging the cells and removing the supernatant fluid, which is then replaced by PBS. The process was accomplished using a semi-automated "flow through" centrifuge (COBE 2991 System, Baxter). The cells are maintained in a closed system as they are processed.

The cells may be further processed by depleting the non-binding cells, including monocytes, (enriched for activated cells) and then continuing with the stimulation. Alternatively, the washed cells can be frozen, stored, and processed later, which is demonstrated herein to increase robustness of proliferation as well as depleting granulocytes. In one example, to freeze the cells, a 35 ml suspension of cells is placed in a 250 ml Cryocyte freezing bag along with 35 ml of the freezing solution. The 35 ml cell suspension typically contains $3.5\times10^9$ to $5.0\times10^9$ cells in PBS. An equal volume of freezing solution (20% DMSO and 8% human serum albumin in PBS) is added. The cells are at a final concentration of $50\times10^6$ cells/ml. The Cryocyte bag may contain volumes in the range of 30-70 ml, and the cell concentration can range from 10 to $200\times10^6$ cells/ml. Once the Cryocyte bag is filled with cells and freezing solution, the bag is placed in a controlled rate freezer and the cells are frozen at 1° C./minute down to −80° C. The frozen cells are then placed in a liquid nitrogen storage system until needed.

The cells are removed from the liquid nitrogen storage system and are thawed at 37° C. To remove DMSO, the thawed cells are then washed with calcium-free, magnesium-free PBS on the COBE 2991 System. The washed cells are then passed through an 80 micron mesh filter.

The thawed cells, approximately $0.5\times10^9$ CD3$^+$ cells, are placed in a plastic 1 L Lifecell bag that contains 100 ml of calcium-free, magnesium-free PBS. The PBS contains 1%-5% human serum. $1.5\times10^9$ 3×28 beads (DYNABEADS® M-450 CD3/CD28 T) are also placed in the bag with the cells (3:1 DYNABEADS M-450 CD3/CD28 T:CD3$^+$ T cells). The beads and cells are mixed at room temperature at ~1 RPM (end-over-end rotation) for about 30 minutes. The bag containing the beads and cells is placed on the MaxSep Magnetic Separator (Nexell Therapeutics, Irvine, CAb. Between the bag and the MaxSep, a plastic spacer (approximately 6 mm thick) is placed. (To increase the magnetic strength the spacer is removed.) The beads and any cells attached to beads are retained on the magnet while the PBS and unbound cells are pumped away.

The 3×28 beads and concentrated cells bound to the beads are rinsed with cell culture media (1 liter containing X-Vivo 15, BioWhittaker; with 50 ml heat inactivated pooled human serum, 20 ml 1 M Hepes, 10 ml 200 mM L-glutamine with or without about 100,000 I.U. IL-2) into a 3L Lifecell culture bag. After transferring the 3×28 beads and positively selected cells into the Lifecell bag, culture media is added until the bag contains 1000 ml. The bag containing the cells is placed in an incubator (37° C. and 5% $CO_2$) and cells are allowed to expand.

Cells were split 1 to 4 on each of days 3 and 5. T cell activation and proliferation were measured by harvesting cells after 3 days and 8 days in culture. Activation of T cells was assessed by measuring cell size, the level of cell surface marker expression, particularly the expression of CD25 and CD154 on day 3 of culture. On day 8 cells were allowed to flow under gravity (approx. 150 ml/min) over the MaxSep magnet to remove the magnetic particles and the cells are washed and concentrated using the COBE device noted above and resuspended in a balanced electrolyte solution suitable for intravenous administration, such as Plasma-Lyte A® (Baxter-Healthcare).

As described within the specification XCELLERATE I™ refers to conditions similar to that above, except that stimulation and concentration were not performed and monocyte depletion was performed prior to stimulation.

Both XCELLERATE I™ and II™ processes were performed and T cell proliferation was measured after 8 days in culture. The yield of expanded T cells was greater when CD3$^+$ cells were concentrated prior to cell culture. (See Table 1). In addition, the cell population had greater than 90% CD3$^+$ cells.

TABLE 1

T cell Yield Expansion at Day 8

| Experiment | No CD3+ Concentration (XCELLERATE I ™) | CD3+ Concentration (XCELLERATE II ™) |
|---|---|---|
| NDa079 | $33 \times 10^9$ | $36 \times 10^9$ |
| NDa081 | $38 \times 10^9$ | $42 \times 10^9$ |
| NDa082 | $28 \times 10^9$ | $38 \times 10^9$ |
| Average | $33 \pm 5 \times 10^9$ | $39 \pm 3 \times 10^9$ |

Figure 2:
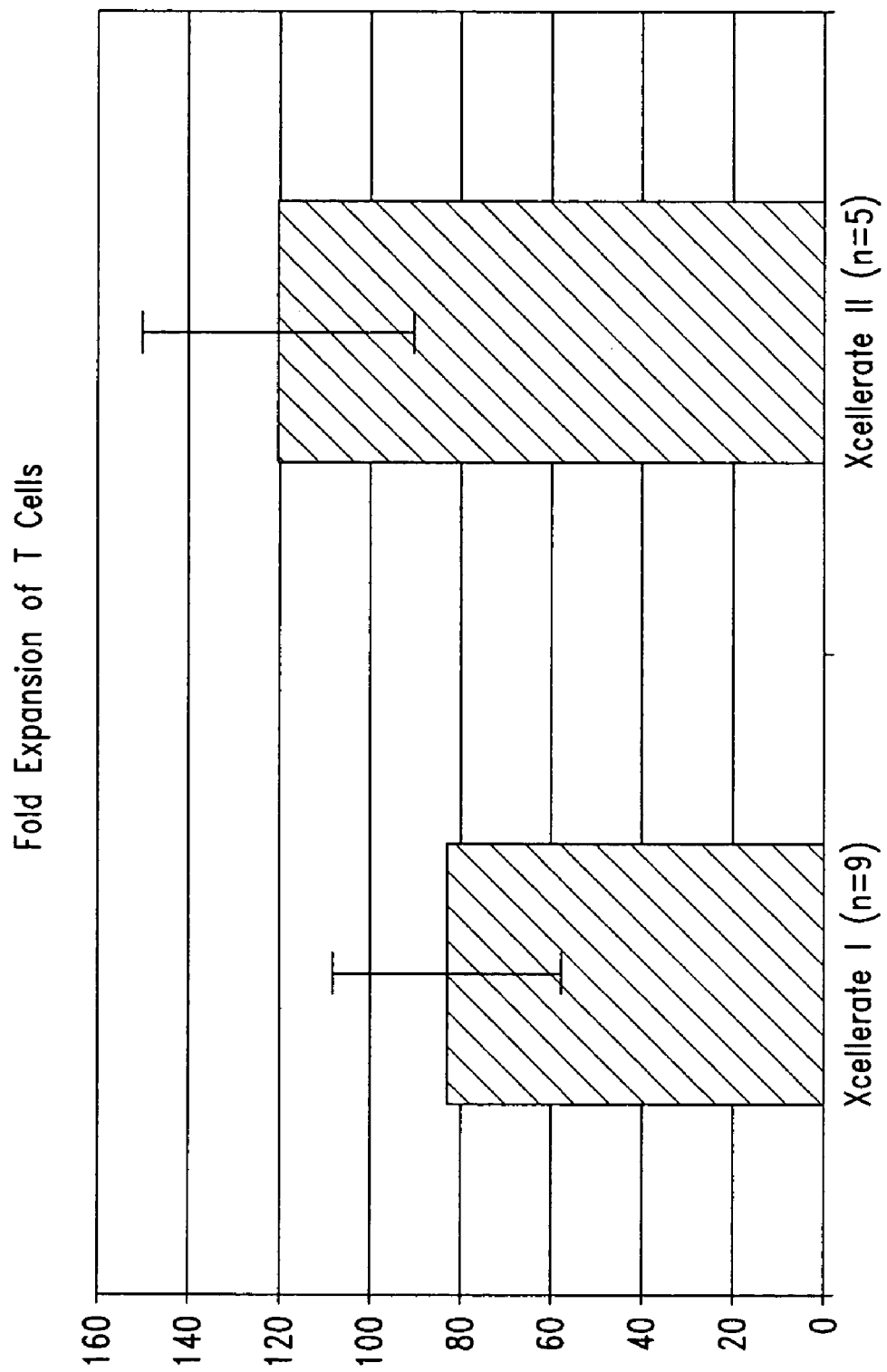
FIG. 2 is a plot comparing fold expansion of activated and expanded T cells measured at day 8 with (XCELLERATE II™) or without (XCELLERATE I™) magnetic concentration and stimulation.

Further experiments were performed in this regard and depict total number of expanded cells as well as the fold expansion of nine batches of cells stimulated without CD3+ concentration and five batches of cells stimulated with CD3+ concentration. (See FIGS. 1 and 2).

Figure 3:
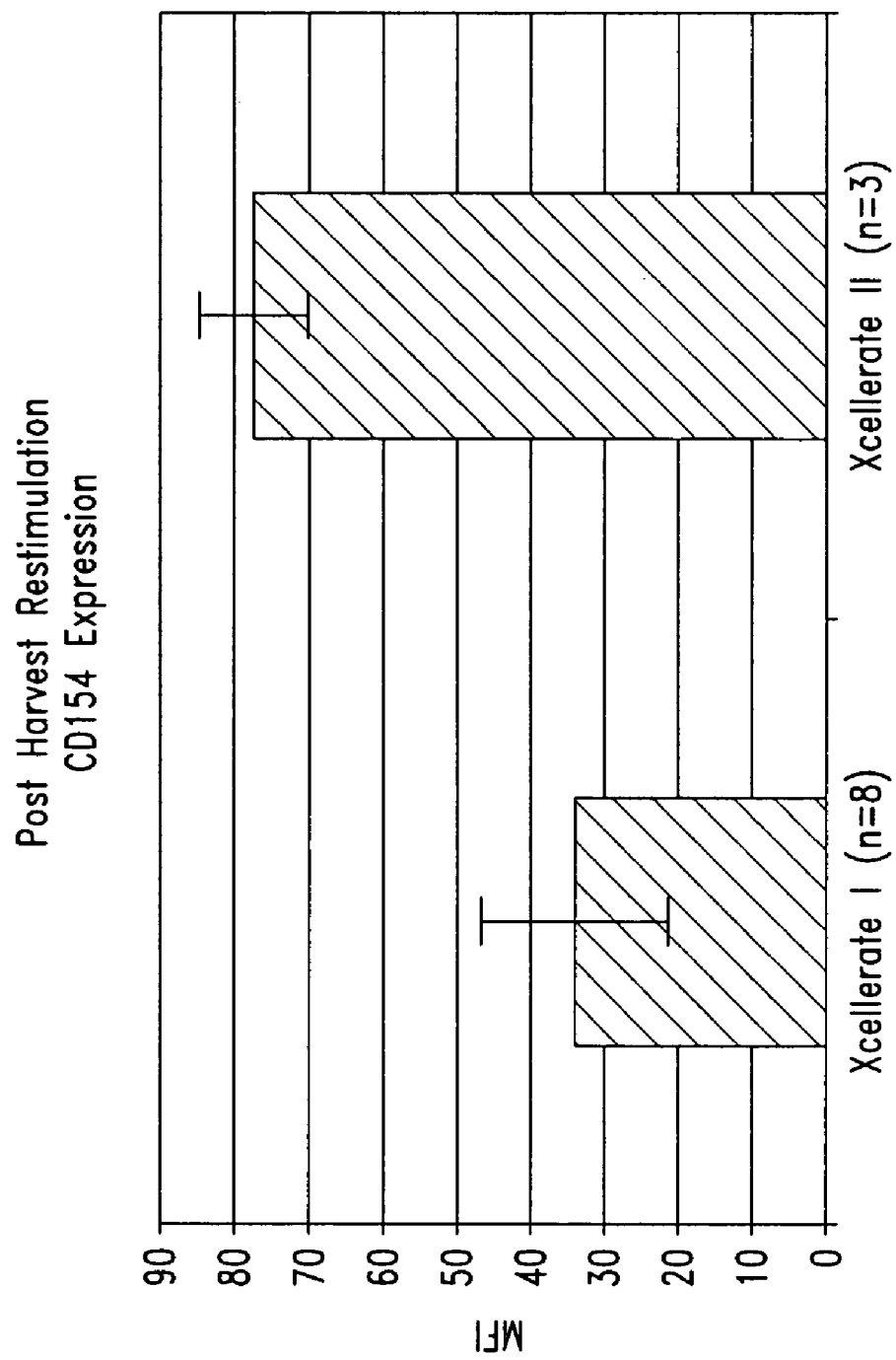
FIG. 3 is a plot representing flow cytometry analysis of CD154 expression comparing restimulation of T cells previously cultured for 8 days after magnetic concentration and stimulation (XCELLERATE II™) or without magnetic concentration and stimulation (XCELLERATE I™).
Figure 4:
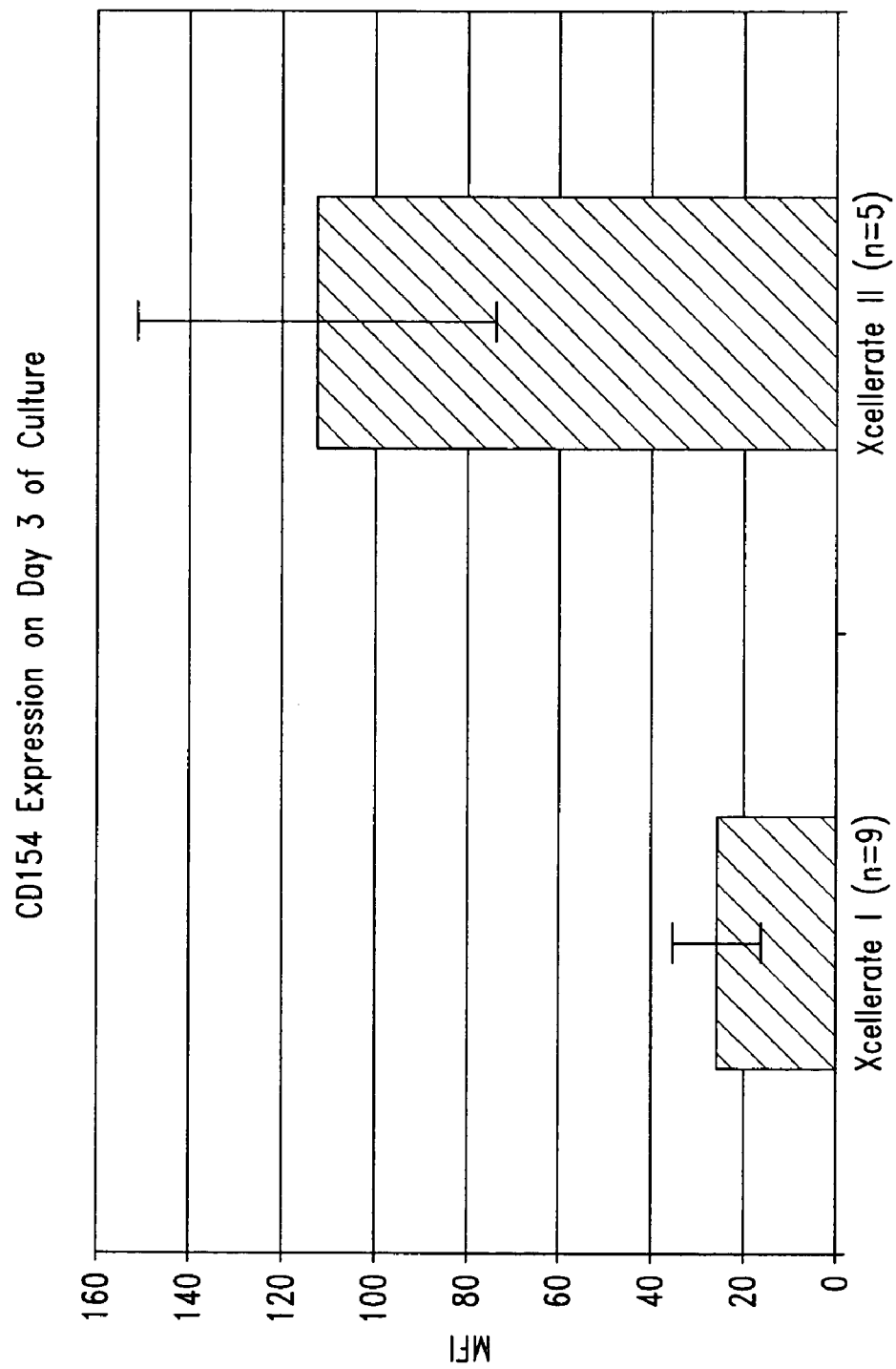
FIG. 4 is a plot representing flow cytometry analysis of CD154 expression following 3 days in culture comparing magnetic concentration and stimulation (XCELLERATE II™) with cells activated without magnetic concentration and stimulation (XCELLERATE I™).

Concentration of the cells by application of a magnetic force prior to culture effectively increases the purity of the CD3+ cells as well as increasing CD154 levels. (Table 2, FIGS. 3 and 4 depict CD154 levels graphically). Furthermore, comparison of T cell proliferation where populations of T cells were exposed to magnets of differing strengths showed that exposure to a stronger magnet resulted in greater yield of CD3+ cells. (Table 2.)

TABLE 2

Comparison of T cell Proliferation and Cell Surface Markers after Concentration Using Weak and Strong Magnets

| Experiment | Magnet | Day | CD3% | Size (FSC) | CD25 (MFI) | CD154 (MFI) | CD3# $\times 10^9$ |
|---|---|---|---|---|---|---|---|
| NDa087 | | | | | | | |
| Pre-Selection | | 0 | 47% | 318 | 8 | 4 | 0.5 |
| Post-Selection | Weak | 0 | 56% | | | | 0.37 |
| Post-Selection | Strong | 0 | 61% | | | | 0.35 |
| No Selection | None | 3 | | 533 | 758 | 19 | |
| Post-Selection | Weak | 3 | 90% | 570 | 846 | 41 | |
| Post-Selection | Strong | 3 | 92% | 558 | 1006 | 45 | |
| Post-Culture | None | | | | | | |
| Post-Culture | Weak | 8 | 92% | 412 | 110 | 9 | 17.7 |
| | Strong | 8 | 93% | 413 | 89 | 7 | 37.8 |
| NDa089 | | | | | | | |
| Pre-Selection | | 0 | 44% | 312 | 6 | 4 | 0.5 |
| Post-Selection | Weak | 0 | 46% | | | | 0.39 |
| Post-Selection | Strong | 0 | 55% | | | | 0.3 |
| Post-Selection | Weak | 3 | 83% | 589 | 685 | 67 | |
| Post-Selection | Strong | 3 | 83% | 600 | 720 | 115 | |
| Post-Culture | Weak | 8 | 89% | 409 | 58 | 18 | 25.3 |
| | Strong | 8 | 87% | 371 | 65 | 13 | 42.1 |

| Experiment | Magnet | CD25 on Day 0 (MFI) | CD25 on Day 3 (MFI) | CD154 on Day 0 (MFI) | CD154 on Day 3 (MFI) | CD3 Cell # On Day 8 $\times 10^9$ |
|---|---|---|---|---|---|---|
| NDa087 | | | | | | |
| No Selection | None | 8 | 758 | 4 | 19 | 31 |
| Selection | Weak | 8 | 846 | 4 | 41 | 18 |
| Selection | Strong | 8 | 1006 | 4 | 45 | 38 |
| NDa089 | | | | | | |
| No Selection | None | 6 | 309 | 4 | 12 | 26 |
| Selection | Weak | 6 | 685 | 4 | 67 | 25 |
| Selection | Strong | 6 | 720 | 4 | 115 | 42 |

Five additional experiments were performed comparing the process of XCELLERATE I™ to that of XCELLERATE II™. For the cells activated and culture-expanded according to the two processes, cell activation markers (cell size, CD25 expression, and CD154 expression) on days 3 and 8 of culture are shown below in Table 3 and in FIGS. 6-7.

TABLE 3

Cell Activation Markers on Day 3

| Experiment Number (Donor) | Process | Cell Size (FSC) Day 0 | Cell Size (FSC) Day 3 | CD25 (MFI) Day 0 | CD25 (MFI) Day 3 | CD154 (MFI) Day 0 | CD154 (MFI) Day 3 |
|---|---|---|---|---|---|---|---|
| NDa104 (PC071) | XCELLERATE I | 282 | 526 | 7 | 625 | 5 | 50 |
| | XCELLERATE II | 315 | 531 | 7 | 750 | 5 | 162 |
| NDa107 (PC074) | XCELLERATE I | 243 | 578 | 5 | 287 | 4 | 23 |
| | XCELLERATE II | 272 | 587 | 6 | 311 | 5 | 120 |
| NDa110 (PC076) | XCELLERATE I | 262 | 588 | 6 | 497 | 4 | 59 |
| | XCELLERATE II | 284 | 615 | 6 | 580 | 5 | 197 |
| NDa113 (PC060) | XCELLERATE I | 271 | 662 | 5 | 726 | 4 | 54 |
| | XCELLERATE II | 291 | 660 | 6 | 741 | 5 | 177 |
| NDa115 (PC073) | XCELLERATE I | 253 | 560 | 6 | 202 | 6 | 25 |
| | XCELLERATE II | 252 | 582 | 6 | 448 | 6 | 83 |

TABLE 3-continued

| | | Cell Activation Markers on Day 3 | | | | | |
|---|---|---|---|---|---|---|---|
| | | Cell Size (FSC) | | CD25 (MFI) | | CD154 (MFI) | |
| Experiment Number (Donor) | Process | Day 0 | Day 3 | Day 0 | Day 3 | Day 0 | Day 3 |
| Average ± Std Dev | XCELLERATE I | 262 ± 15 | 583 ± 50 | 6 ± 1 | 467 ± 221 | 5 ± 1 | 42 ± 17 |
| | XCELLERATE II | 283 ± 23 | 595 ± 47 | 6 ± 1 | 566 ± 189 | 5 ± 1 | 148 ± 17 |

All cultures in Table 3 were initiated with cells that were frozen/thawed.

Figure 6A:
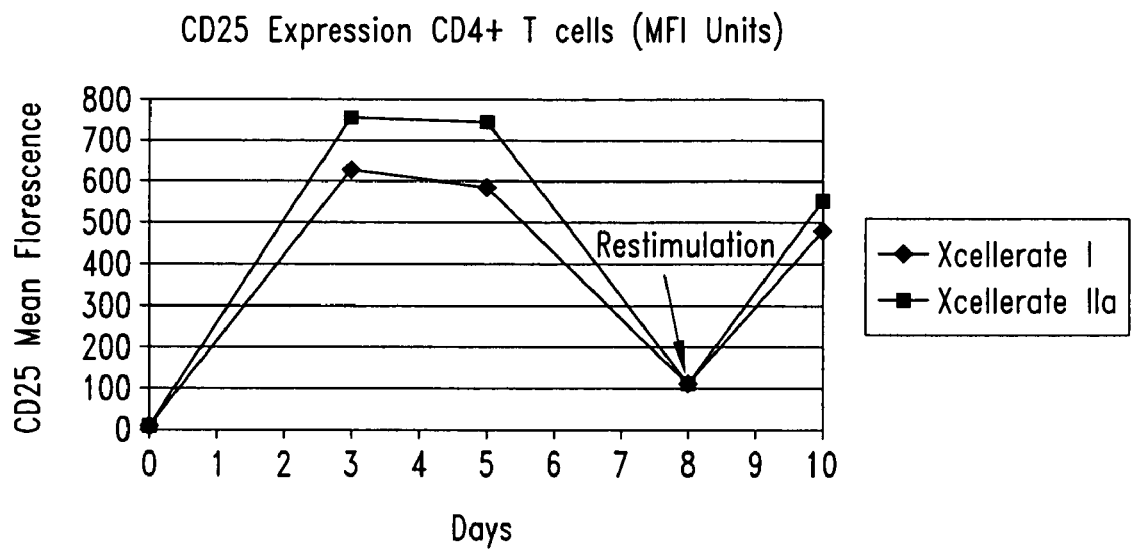
FIGS. 6A-6B are plots depicting time course analysis of CD25 expression following activation of T cells in one donor sample (PC071) during the XCELLERATE I or II™ process. Restimulation was performed at the 8 day mark to simulate in vivo activation.
Figure 6B:
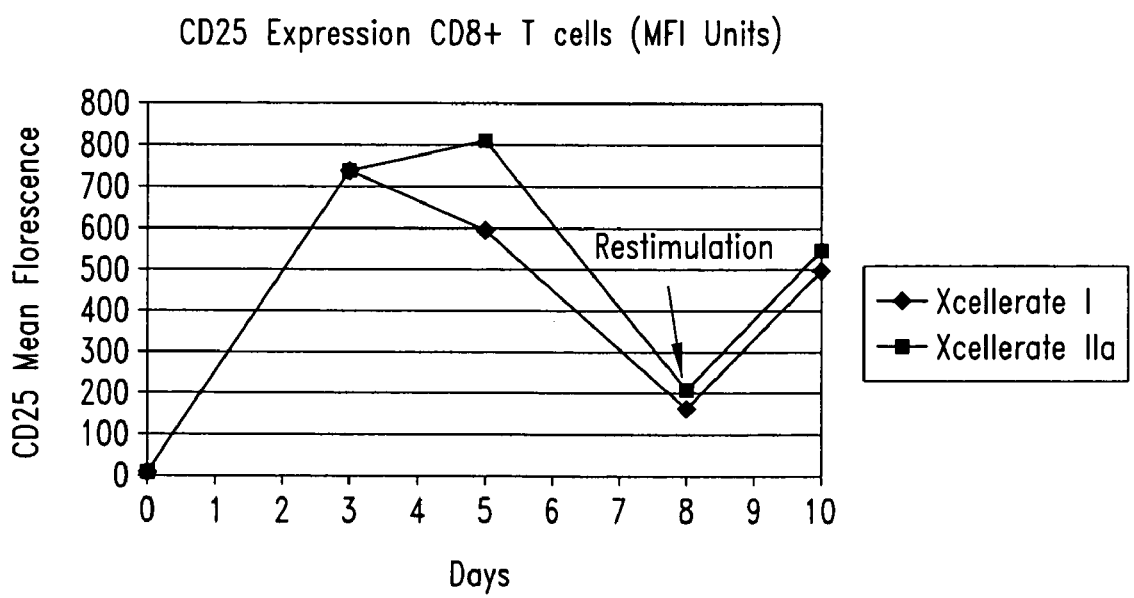
Figure 7A:
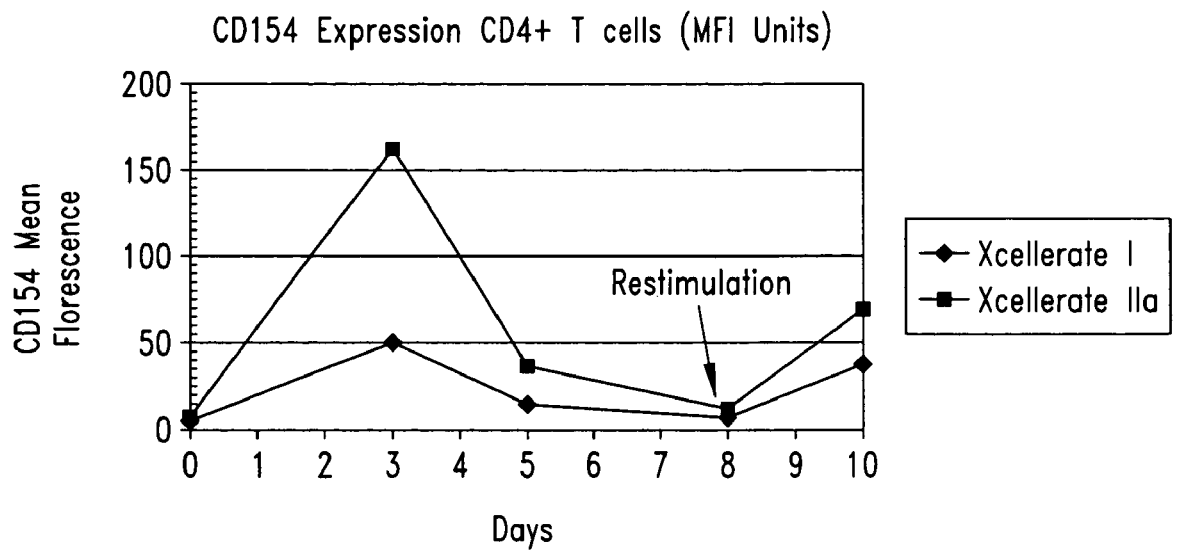
FIGS. 7A-7B are plots depicting time course analysis of CD154 expression following activation of T cells in one donor sample (PC071) during the XCELLERATE I or II™ process. Restimulation was performed at the 8 day mark to simulate in vivo activation.
Figure 7B:
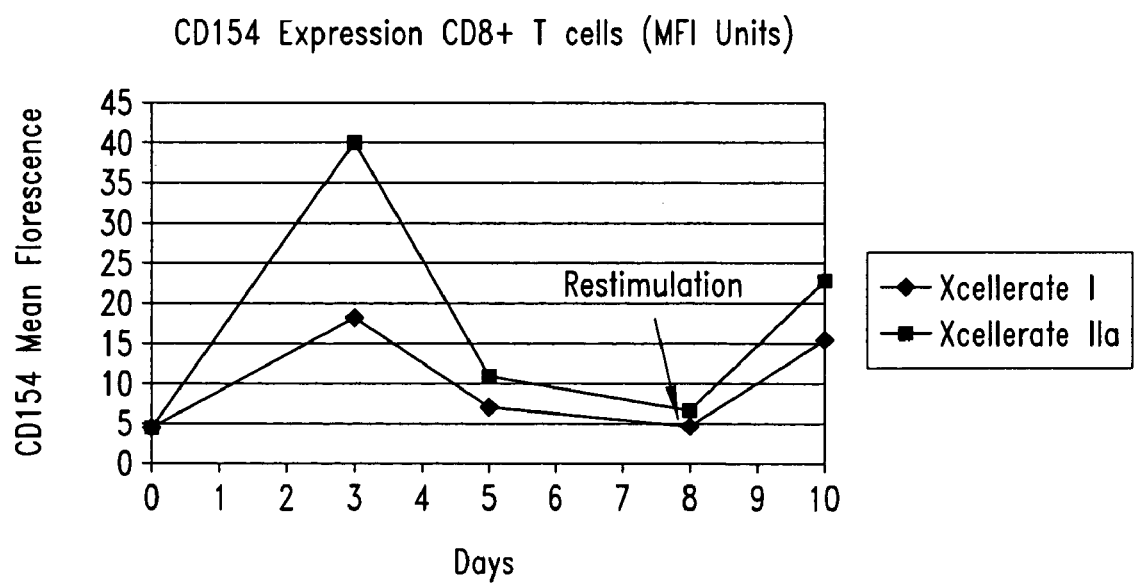

The data in Table 3 and FIGS. 6-7 show that the XCELLERATE II™ process generated cells whose cell size and CD25 expression activation markers on day 3 were on average similar, but typically higher and continued to be higher following stimulation. However, the CD154 activation marker on day 3 for T cells from the XCELLERATE II™ process was much greater than for those of T cells from the XCELLERATE I™ process. Further, as demonstrated above, the XCELLERATE II™ process generated CD25 and CD154 levels that were consistently higher per donor than other methods.

The expression of CD154 on Day 3 of the XCELLERATE II™ process is actually much higher than for XCELLERATE I™. This observation suggests that the T cells are in a higher state of activation during the XCELLERATE II™ process than in the XCELLERATE I™ process. It is predicted that this may translate into a more effective product when administered in vivo.

$CD3^+$ Cell Purity, CD4 Cell/CD8 cell ratio, and cell viability on Day 3 of culture were also determined for five patient samples. The phenotype and viability of cells used subjected to the XCELLERATE I™ process and the XCELLERATE II™ process are shown below in Table 4 as measured by Flow Cytometry or Trypan blue staining.

TABLE 4

| NDa # | Day 0 $CD3^+$ Cell Purity (%)* | Day 0 Cell Viability (%) | Day 0 CD4:CD8 ratio$^\Psi$ | Day 3 $CD3^+$ Cell Purity (%) | Day 3 Cell Viability (%) | Day 3 CD4:CD8 ratio |
|---|---|---|---|---|---|---|
| 103 XCELLERATE I | 70 | 92 | 1.91 | 79 | 82 | 1.3 |
| 103 XCELLERATE II | 85 | 99 | 2.3 | 91 | 95 | 2.4 |
| 104 XCELLERATE I | 67 | 95 | 3.2 | 84 | 78 | 2.7 |
| 104 XCELLERATE II | 110 | 99 | 3.7 | 93 | 87 | 2.9 |
| 107 XCELLERATE I | 69 | 99 | 2.3 | 85 | 82 | 2.3 |
| 107 XCELLERATE II | 119 | 99 | 2.7 | 95 | 92 | 2.8 |
| 110 XCELLERATE I | 63 | 99 | 2.9 | 91 | 82 | 2.6 |
| 110 XCELLERATE II | 83 | 99 | 3.9 | 93 | 92 | 4.5 |
| 115 XCELLERATE I | 60 | 99 | 1.9 | 92 | 91 | 2.7 |
| 115 XCELLERATE II | 72 | 99 | 2.2 | 96 | 94 | 2.8 |

*= Purity of $CD3^+$ T cells on day 0 after monocyte-depletion in the XCELLERATE I process or after magnetic concentration in the XCELLERATE II process $\Psi$ = ratio of $CD4^+$:$CD8^+$ T cells on day 0 after monocyte-depletion in the XCELLERATE I process or after magnetic concentration in the XCELLERATE II process

Example II

Efficiency of CD3+ T Cell Enrichment, Monocyte-Depletion and Granulocyte-Depletion For this study, upon receipt at the Xcyte Therapies Development laboratory, the incoming PBMC apheresis product was washed, split and:

1. For the XCELLERATE I process, a monocyte-depletion step was carried out and the CD14+ monocyte-depleted PBMC were cryopreserved and stored in the vapor phase of a $LN_2$ freezer (as noted in Example I). On the day of set-up of the XCELLERATE I process, the CD14+ monocyte-depleted PBMC were thawed and the XCELLERATE process initiated with DYNABEADS M-450 CD3/CD28 T as detailed in Example I. The average cellular composition and the average efficiency of CD3+ T cell enrichment, CD14+ monocyte-depletion and granulocyte-depletion for the N=5 donors in these initial steps is shown in Table 5.1 and the data for each individual donor is shown in Table 5.2.

2. For the XCELLERATE II process, the PBMC apheresis product cells cryopreserved and stored in the vapor phase of a $LN_2$ freezer. On the day of set-up of the XCELLERATE II process, the cryopreserved PBMC apheresis product cells were thawed and the CD3+ T cells magnetically concentrated and the XCELLERATE II process initiated with DYNABEADS M-450 CD3/CD28 T as detailed in Example I. The average cellular composition and the average efficiency of CD3+ T cell enrichment, CD14+ monocyte-depletion and granulocyte-depletion for the N=5 donors in these initial steps is shown in Table 5.1 and the data for each individual donor is shown in Table 5.2.

As demonstrated in Tables 5.1 and 5.2, the combination of freeze/thawing of the PBMC apheresis product followed by magnetic concentration of CD3+ T cells direct from the thawed PBMC apheresis product in the XCELLERATE II process configuration results in efficient elimination of CD14+ monocytes and granulocytes (Table 5.1 and Table 5.2). The efficiency of the elimination of the CD14+ monocytes and the granulocytes in the XCELLERATE II process is as good as that of the XCELLERATE I process with the benefit that it eliminates the need for a separate depletion step using the additional "uncoated" DYNABEADS M-450 T reagent and consistently leads to a higher CD4/CD8 ratio.

TABLE 5.1

Average (N = 5) efficiency of CD3+ T cell enrichment, CD14+ monocyte-depletion and granulocyte-depletion in the Initial Steps of the XCELLERATE I and the XCELLERATE II Process Configurations

| | Average ± Std. Dev Cellular Composition (%) | | | |
|---|---|---|---|---|
| Cell Preparation | CD3+ | CD14+ | Granulocytes | CD4/CD8* |
| Incoming PBMC apheresis product XCELLERATE I | 49 ± 6 | 16 ± 3 | 8 ± 7 | 2.2 ± 0.3 |
| Monocyte-depleted PBMC | 51 ± 6 | 5.5 ± 3 | 5.7 ± 5 | 2.4 ± 0.6 |
| Freeze/thawed Monocyte-depleted PBMC XCELLERATE II | 64 ± 4 | 6 ± 3 | 0.4 ± 0.5 | 2.4 ± 0.6 |
| Freeze-thawed PBMC apheresis product | 56 ± 5 | 11 ± 2 | 0.4 ± 0.5 | 2.4 ± 0.8 |
| Post- CD3+ magnetic concentration | 92 ± 22 | 2.4 ± 3.7 | 0 ± 0 | 2.86 ± 0.86 |

Cellular compositions were determined by flow cytometry according to standard protocols.

TABLE 5.2

Comparison of the efficiency of CD3+ T cell enrichment, CD14+ monocyte-depletion and granulocyte-depletion in the initial steps of the XCELLERATE I and the XCELLERATE II process configurations

| Experiment Number (Donor) | Cell Preparation | Cellular Composition (%) | | | |
|---|---|---|---|---|---|
| | | CD3+ | CD14+ | Granulocytes | CD4/CD8* |
| NDa104 (PC071) | Incoming PBMC apheresis product XCELLERATE I | 43% | 11% | 14% | 2.2 |
| | Monocyte-depleted PBMC | 54% | 5% | 12.5% | 3.2 |
| | Freeze/thawed Monocyte-depleted PBMC XCELLERATE II | 67% | 4% | 0% | 3.2 |
| | Freeze-thawed PBMC apheresis product | 64% | 7% | 0% | 3.1 |
| | Post-CD3+ magnetic concentration | 110% | 1% | 0% | 3.7 |

TABLE 5.2-continued

Comparison of the efficiency of CD3+ T cell enrichment,
CD14+ monocyte-depletion and granulocyte-depletion
in the initial steps of the XCELLERATE I and the
XCELLERATE II process configurations

| Experiment Number (Donor) | Cell Preparation | Cellular Composition (%) | | | |
|---|---|---|---|---|---|
| | | CD3+ | CD14+ | Granulocytes | CD4/CD8* |
| NDa107 (PC074) | Incoming PBMC apheresis product<br>XCELLERATE I | 51% | 16% | 1% | 2.1 |
| | Monocyte-depleted PBMC | 64% | 5% | 1% | 2.3 |
| | Freeze/thawed Monocyte-depleted PBMC<br>XCELLERATE II | 69% | 3% | 0% | 2.3 |
| | Freeze-thawed PBMC apheresis product | 55% | 11% | 0% | 2.0 |
| | Post- CD3+ magnetic concentration | 120% | 0% | 0% | 2.7 |
| NDa110 (PC076) | Incoming XCELLERATE I | 44% | 18% | 15% | 2.5 |
| | Monocyte-depleted PBMC | 63% | 3.5% | 10% | 2.9 |
| | Freeze/thawed Monocyte-depleted PBMC<br>XCELLERATE II | 63% | 7% | 0% | 2.9 |
| | Freeze-thawed PBMC apheresis product | 55% | 13% | 0% | 3.2 |
| | Post- CD3+ magnetic concentration | 83% | 1% | 0% | 3.8 |
| NDa113 (PC060) | Incoming PBMC apheresis product<br>XCELLERATE I | 47% | 17% | 6% | 2.3 |
| | Monocyte-depleted PBMC | 61% | 4% | 3% | 1.8 |
| | Freeze/thawed Monocyte-depleted PBMC<br>XCELLERATE II | 63% | 4% | 1% | 1.8 |
| | Freeze-thawed PBMC apheresis product | 51% | 13% | 1% | 1.5 |
| | Post- CD3+ magnetic concentration | 76% | 1% | 0% | 1.9 |
| NDa115 (PC073) | Incoming PBMC apheresis product<br>XCELLERATE I | 59% | 17% | 2% | 1.7 |
| | Monocyte-depleted PBMC | 60% | 10% | 2% | 1.8 |
| | Freeze/thawed Monocyte-depleted PBMC<br>XCELLERATE II | 60% | 11% | 1% | 1.9 |
| | Freeze-thawed PBMC apheresis product | 53% | 12% | 1% | 2.0 |
| | Post- CD3+ magnetic concentration | 72% | 9% | 0% | 2.2 |

Cellular compositions were determined by flow cytometry according to standard protocols.

In addition to the simplification and streamlining of the process by elimination of the CD14+ monocyte-depletion step and the associated reagents, the magnetic concentration step in the XCELLERATE II™ process also provides a higher purity of CD3+ T cells and a higher ratio of CD3+CD4+:CD3+ CD8+ T cells at the initiation of T cell activation (Table 5.1 and Table 5.2).

Yield, Purity, Viability and Composition of Activated CD3+ T cells Pre-harvest on Day 8 of the XCELLERATE I™ process and the XCELLERATE II™ process were also compared.

As shown in Table 5.3, the average yield, purity and viability of the CD3+ T cells prior to harvest on day 8 are typically improved for the XCELLERATE II™ compared to the XCELLERATE I™ process.

TABLE 5.3

Yield, purity, viability and composition of activated CD3+ T cells pre-harvest on day 8 of the XCELLERATE I process and the XCELLERATE II process

| Experiment Number (Donor) | XCELLERATE Process Configuration | # CD3+ T cells | Purity CD3+ T cells (%) | Viability (%) | CD4/CD8 Ratio* |
|---|---|---|---|---|---|
| NDa104 | XCELLERATE I | $65 \times 10^9$ | 95 | 97 | 1.2 |
| (PC071) | XCELLERATE II | $50 \times 10^9$ | 97 | 97 | 1.7 |
| NDa107 | XCELLERATE I | $57 \times 10^9$ | 98 | 98 | 0.8 |
| (PC074) | XCELLERATE II | $52 \times 10^9$ | 98 | 98 | 1.5 |
| NDa110 | XCELLERATE I | $41 \times 10^9$ | 96 | 96 | 1.6 |
| (PC076) | XCELLERATE II | $41 \times 10^9$ | 99 | 99 | 2.4 |
| NDa113 | XCELLERATE I | $41 \times 10^9$ | 96 | 96 | 1.3 |
| (PC060) | XCELLERATE II | $43 \times 10^9$ | 98 | 98 | 2.0 |
| NDa115 | XCELLERATE I | $31 \times 10^9$ | 96 | 96 | 1.3 |
| (PC073) | XCELLERATE II | $48 \times 10^9$ | 97 | 97 | 1.4 |
| Average ± Std Dev | XCELLERATE I | 47 ± 14 | 96 ± 2 | 97 ± 1 | 1.2 ± 0.3 |
| | XCELLERATE II | 45 ± 6 | 98 ± 1 | 98 ± 1 | 1.8 ± 0.4 |

*= Ratio of CD3+CD4+:CD3+CD8+ T cells.

Also, as shown in Table 5.3, the XCELLERATE II™ process maintains a higher ratio of CD3+CD4+:CD3+CD8+ T cells throughout the process. This may be due to preferential concentration of CD3+CD4+ cells during the magnetic concentration step (Tables 5.1 and 5.2).

"Incoming" refers to fresh, washed incoming apheresis cells. The starting cells listed in Table 5.2 for the XCELLERATE I™ process were apheresed cells that had been washed, monocyte depleted, and/or frozen/thawed. The starting cells listed in Table 5.2 for the XCELLERATE II™ process were apheresis cells that had been washed and frozen/thawed.

*=Ratio of *CD3+ CD4+:CD3+ CD8+ T* cells

Table 5.3 shows that the XCELLERATE II™ process resulted in a cell product that was more pure (in terms of % CD3+ cells) than the cell product from the XCELLERATE I™ process. That is, the product cells from the XCELLERATE II™ process had an average (±std dev) CD3+ cell purity of 96%±1% while the cells from the XCELLERATE I™ process had an average purity of 93%±2%.

Also, as shown in Table 5.3, the XCELLERATE II™ process maintained a higher ratio of CD4/CD8 cells. The incoming cells had an average CD4/CD8 cell ratio of 2.2 and the product cells from the XCELLERATE II™ process had a CD4/CD8 ratio of 1.8, while the product cells from the XCELLERATE I™ process had a CD4/CD8 ratio of 1.2.

The data of Table 5.3 also shows that the XCELLERATE II™ process resulted in product cells with an average viability of 98% while the XCELLERATE I™ process resulted in product cells with an average viability of 97%.

Example III

Monocyte Depletion

Monocytes (CD14+ phagocytic cells) are removed from T cell preparations via magnetic depletion using a variety of "irrelevant" (i.e., non-antibody coated or non-target antibody coated) Dynal beads. Depletion was performed by pre-incubating either whole blood after separation in ficol or apheresed peripheral blood with Dynal Sheep anti-mouse M-450 beads, or Dynal human serum albumin-coated beads (M-450), or with Dynal Epoxy (M-450) beads at roughly a 2:1 bead to cell ratio. The cells and beads were incubated for periods of 1-2 hours at 22-37 degrees C., followed by magnetic removal of cells that had attached to beads or that had engulfed beads. The remaining cells were placed into culture alongside un-manipulated cells. Cells were characterized by flow cytometry for cell phenotype before and after depletion.

Example IV

Flow Cytometry Settings

A Becton Dickinson FACSCALIBUR cytometer was used for all the data collected and presented. Any flow cytometer capable of performing 3-color analysis could be used by an experienced operator to acquire identical data. For example, a FACSCAN, Vantage Cell Sorter, or other BD product would work to collect similar data. Also, Coulter products, such as the Coulter Epic Sorter would work as well.

The instrument setting given below can be used as a general guideline for instrument conformation to gather data as was done in these studies. These settings were used for the Examples provided herein; however, modifications to these settings can and should be made by an experienced instrument handler to adjust appropriately for compensation and detector voltages. Also, the use of different detection antibodies with different fluorescent tags requires unique adjustment to any particular instrument to give optimal signal separation (voltage) with minimal "bleeding-over" into other channels (e.g., compensation). A skilled flow operator, well-versed in using compensation controls, isotype controls, and with a general understanding of T cell biology should be able to reproduce any of the data presented below.

Further it should be noted that various settings, particularly voltage settings, may vary, depending upon the efficiency of the instrument laser. For example, older lasers may require more voltage to generate a signal comparable to a newer laser. However, the data obtained, whether with more or less voltage, should reflect similar patterns in biology.

Settings used on the FACSCALIBUR™ (Becton Dickinson):

Detector/Amps:

| Parameter | Detector | Voltage | Amp/Gain | Mode |
|-----------|----------|---------|----------|------|
| P1 | FSC | E00 | 1.30 | Lin |
| P2 | SSC | 370 | 1.00 | Lin |
| P3 | FL1 | 610 | 1.00 | Log |
| P4 | FL2 | 550 | 1.00 | Log |
| P5 | FL3 | 520 | 1.00 | Log |

Although the parameter voltages are generally constant, P3, P4, and P5 may be adjusted slightly up or down in order to achieve maximum signal separation, while maintaining a negative control signal value in or near the first decade (0-10) in signal strength in the log mode.

Threshold:

Primary parameter: FSC (forward scatter)

Value: 52

Secondary parameter: none

Compensation:

FL1—4.0% FL2

FL2—21.4% FL1

FL2—2.6% FL3

FL3—15.2% FL2

While the settings provided approximate the settings used to collect most of the data presented below, the settings may be altered and roughly equivalent data on stimulated T cells should be generated. The general acceptable ranges for compensation at the voltages listed above are as shown below:

| FL1-FL2 | 0.4-4% |
|---------|--------|
| FL2-FL1 | 18-27% |
| FL2-FL3 | 2-8% |
| FL3-FL2 | 10-16% |

The determination of the particular compensation or voltage values has to be made by an experienced flow cytometer operator with the following goals:

1) Voltage: Maximization of signal separation between positive and negative signals (e.g., surface antigen marker negative vs. low levels surface antigen vs. high levels surface antigen).

2) Compensation: Minimization of interchannel interference (bleed-over) by use of compensation controls.

As voltage settings change, so do compensation settings.

Example V

Cell Proliferation and Viability Assays

Cell proliferation and viability was measured by standard Trypan Blue staining and cell counting using a hemocytometer. See FIGS. 5A-5B.

Example VI

Activation Marker Assays

CD154 is expressed on activated T cells in a temporal manner and has been shown to be a key element in T cells interactions via CD40 on APCs. Blocking the interaction of these two receptors can effectively alter, and even shut-off, an immune response. Aliquots of T cells that were stimulated by concentration with 3×28 paramagnetic beads were removed from cell culture at days 3, 5, and 8 and analyzed for the level of CD154 expression. The level of CD154 expression was compared with T cells that were depleted of monocytes but were not incubated with 3×28 paramagnetic beads (that is, the T cells were not magnetically concentrated at culture initiation). Significant activation of the T cells stimulated by magnetic concentration with anti-CD3 and anti-CD28 beads was shown by a three-fold increase in the level of CD 154 expression on the third day of culture compared with cells that were not similarly stimulated at culture initiation. (See FIGS. 4 and 7). CD25 levels measured in a similar manner (FIG. 6) show a trend toward higher activation.

In general, marker expression was monitored over various times. In this regard cells are labeled with anti-human CD4 (Immunotech, Fullerton, Calif.), FITC coupled anti-human CD11a (Pharmingen), FITC coupled anti-human CD26 (Pharmingen), FITC coupled anti-human CD49d (Coulter), FITC coupled anti-human CD54 (Pharmingen and Becton Dickinson), FITC coupled anti-human CD95 (Pharmingen), FITC coupled anti-human CD134 (Pharmingen), FITC coupled anti-human CD25 Ab (Becton Dickinson, Fullerton, Calif.), FITC coupled anti-human CD69 Ab (Becton Dickinson), FITC or PE coupled anti-human CD154 Ab (Becton Dickinson), or FITC or PE coupled IgG1 isotype control Ab. Cells, $2\times10^5$ are labeled for 20 minutes at 4° C. with 2 µl of each antibody in a final volume of 30 µl, washed and resuspended in 1% parformaldehyde (Sigma, St. Louis, Mo.).

Comparison of cell surface marker molecule expression levels may be carried out by a variety of methods and thus absolute values may differ. However, when comparing two values the relative fold values may be readily calculated. For example, CD154 expression levels on T cells generated by different "activation" methods can be measured with relative accuracy by flow cytometric means. Using a reagent, such as Becton Dickinson's anti-CD154 -PE conjugate (catalogue # 340477), one can stain T cells in resting or activated states and gauge expression levels for this marker (or others by means well known to experienced flow cytometer operators). Described herein are methods which provide for increased expression of CD154 on T cells, both $CD4^+$ and $CD8^+$. By simultaneously stimulating and concentrating T cells at the initiation of culture, as described herein, expression levels can be driven up beyond values obtained by standard 3×28 activation, on the order of a 20% to over a 100% increase in levels, as measured by mean fluorescent intensity (MFI)

using flow cytometry (BD FACSCalibur and antibody described above). For example, an unstimulated CD4+ T cell would be negative for CD154 and would therefore yield MFI values between 1-10. Upon activation by XCELLERATE I™, at 3 days post-activation, MFI values for CD154 on CD4+ T cells might be in the 20-40 range, while the XCELLERATE II™ process might yield CD154 MFI values of 60-200. While these are not absolute values in terms of the number of CD154 molecules expressed on T cells, there are sufficient to determine relative levels of increased expression. Accordingly, it can be demonstrated that an approximate 1.1 to 20 fold increase in CD154 levels between 1-4 days, post-activation can be demonstrated with the XCELLERATE II™ process as compared to the XCELLERATE I™ process.

Example VII

Cytokine Assays

Cells are prepared as described above. Supernatants from cells stimulated for various times are subjected to an IL-2, IL-4, INF-gamma or TNF-α ELISA according to the manufacturer's instructions (Biosource International, Sunnyvale, Calif.).

In an alternative assay, IL-2 is measured by intracellular staining of CD4 T cells using flow cytometry. For intracellular labeling of IL-2 or IFN-γ, cells are first incubated with 1 μml Monensin (Calbiochem) for 4 hours prior to assay. The cells are subsequently stained for surface proteins as described above, fixed and permeabilized using Becton Dickinson intracellular staining-kit, labeled with PE-coupled anti-human IL-2 Ab and FITC coupled anti-human IFN-γ or the corresponding control Abs as described by the manufacturer. Data acquisition and flow cytometric analysis is performed on a Becton Dickinson FACSCalibur flow cytometer using Cellquest software following the manufacturer's protocol (Becton Dickinson).

IFN-gamma concentrations were about 2, 3, 4, and in some cases 5 fold higher at day 3 when using the XCELLERATE II™ methodology as opposed to XCELLERATE I™ (data not shown). Further, TNF-alpha levels were also markedly higher (between 1.5 to 3 fold higher) up to day 5 following stimulation (data not shown) as compared with XCELLERATE I™.

Example VIII

Phenotypical Cell Analysis after Restimulation

For restimulation analysis about $5\times10^6$ cells are taken from the culture at the day of termination. In several examples, the date of termination is day 8 of culture. The cells are placed into 5 mL of X-vivo 15 media with serum and with or without IL-2 as indicated above, in one well of a six well plate. About $5\times10^6$ Dynabeads M-450 CD3/CD28 T beads to the well containing the cells and the cells and beads are placed in a 37° C., 5% $CO_2$ incubator. After two days, the samples are removed and tested for viability and analyzed by FACS to determine cell size, and cell marker and/or cytokine expression levels, such as CD25 expression levels, CD154 expression levels. Table 6 demonstrates these results below for five patient samples subject to the XCELLERATE I™ and the XCELLERATE II™ process.

TABLE 6

Results of the Re-stimulation Assay for XCELLERATED T cells Produced Using the XCELLERATE I ™ and the XCELLERATE II ™ Processes

| Experiment Number (Donor) | Process Configuration | Cell Size (FSC) | | CD25 (MFI) | | CD154 (MFI) | |
|---|---|---|---|---|---|---|---|
| | | T = 0 | T = 48 hr | T = 0 | T = 48 hr | T = 0 | T = 48 hr |
| NDa104 (PC071) | XCELLERATE I | 393 | 607 | 104 | 478 | 6 | 37 |
| | XCELLERATE II | 404 | 659 | 115 | 544 | 12 | 70 |
| NDa107 (PC074) | XCELLERATE I | 386 | 596 | 59 | 585 | 6 | 121 |
| | XCELLERATE II | 380 | 607 | 62 | 721 | 10 | 109 |
| NDa110 (PC076) | XCELLERATE I | 425 | 501 | 111 | 600 | 10 | 39 |
| | XCELLERATE II | 390 | 445 | 97 | 434 | 15 | 36 |
| NDa113 (PC060) | XCELLERATE I | 399 | 630 | 66 | 659 | 8 | 32 |
| | XCELLERATE II | 411 | 633 | 113 | 816 | 12 | 145 |
| NDa115 (PC073) | XCELLERATE I | 433 | 514 | 105 | 247 | 13 | 10 |
| | XCELLERATE II | 408 | 569 | 81 | 369 | 20 | 36 |
| Average ± Std Dev (n = 5) | XCELLERATE I | 407 ± 21 | 570 ± 58 | 89 ± 24 | 514 ± 163 | 9 ± 3 | 48 ± 43 |
| | XCELLERATE II | 399 ± 13 | 583 ± 84 | 94 ± 22 | 577 ± 189 | 14 ± 4 | 79 ± 48 |

Example IX

Alternative Cell Collection and Culture Protocols

XCELLERATE™

Cells isolated from human blood are grown in X-vivo media (Biowhittaker Inc., Walkersville, Md.) and depending on use supplemented with or without 20 U/ml IL-2 (Boehringer Mannheim, Indianapolis, Ind.) and supplemented with 5% human serum (Biowhittaker), 2 mM Glutamine (Life Technologies, Rockville, Md.) and 20 mM HEPES (Life Technology). Jurkat E6-1 cells (ATCC, Manassas, Va.) are grown in RPMI 1640 (Life Technologies) supplemented with 10% FBS (Biowhittaker), 2 mM glutamine (Life Technologies), 2 mM Penicillin (Life Technologies), and 2 mM Streptomycin (Life Technologies).

Buffy coats from healthy human volunteer donors are obtained (American Red Cross, Portland, Oreg.). Peripheral blood mononuclear cells (PBMC) are obtained using Lymphocyte Separation Media (ICN Pharmaceuticals, Costa Mesa, Calif.) according to the manufacturers' instructions.

Peripheral blood lymphocytes (PBL) are obtained from the PBMC fraction by incubation in culture flask (Costar, Pittsburgh, Pa.) with uncoated Dynabeads (Dynal, Oslo, Norway), $10^8$ cells/ml, 2 beads/cell, 2h at 37° C. Monocytes and macrophages can be removed by adherence to the culture flask. Alternatively, they can be removed by phagocytosing the paramagnetic beads and then depleting these cells by magnetic cell separation according to the manufacture's instruction (Dynal). CD4$^+$ cells are purified from the PBL fraction by incubation with 10 μg/ml of monoclonal antibodies against CD8 (clone G10-1), CD20 (clone IF5), CD14 (clone F13) and CD16 (Coulter), $10^8$ cells/ml, 20 min at 4° C. After washing, cells are treated with sheep anti-mouse Ig-coupled Dynabeads ($10^6$ cells/ml, 6 beads/cell, 20 min at 4° C.) and then depleted twice via magnetic cell separation. The purity of CD4$^+$ cells are routinely 91-95% as measured by Flow cytometry.

Dendritic cells are generated by first adhering PBMC to a culture flask (Costar), $10^8$ cells/ml, 2 h at 37° C. (without Dynabeads). After extensive washing, adherent cells are cultured for 7 days in media containing 500 U/ml GM-CSF (Boehringer Mannheim) and 12.5 U/ml IL-4 (Boehringer Mannheim). The resulting cell population is weakly adherent and expresses surface markers characteristic of dendritic cells (e.g., expresses HLA-DR, CD86, CD83, CD11c and lacks expression of CD4). (All antibodies obtained from Becton Dickinson, San Jose, Calif.).

Other techniques can utilize human peripheral blood lymphocytes containing T cells that are incubated in tissue culture plates and/or tissue culture flasks (Baxter bags), or other common culture vessels in media, which could be composed of RPMI, X-Vivo 15, or some other T cell culture media. Although not required for the activation and growth of T cells, glutamine and HEPES are added to the culture media. Fetal bovine serum (10% final), human A/B serum (5%), or autologous human serum (5%) is added to culture media. The percentage of serum may vary without greatly affecting T cell biology or culture outcome. In some instances, recombinant human IL-2 is added to cultures. In some instances, phagocytic CD14$^+$ cells and other phagocytic cells are remove by magnetic depletion as described, infra. Beads having co-immobilized upon their surface anti-CD3 and anti-CD28 (3×28 beads) are added at a 3:1 bead:cell ratio. In some instances, 3×28 beads are added at a 1:1 bead:cell ratio. In other instances, the 3×28 beads are added sequentially over the first 5 days of culture with final ratios of 1:1 at day 1, 1:5 at days 3 and 5. Cultures are maintained at 37 degrees C. at 5-7% $CO_2$. Cells are removed at several timepoints over a 14 day period to determine cell density (cell number), cell size, and cell surface phenotype as measured via flow cytometric analysis of a variety of surface antigens. Supernatants are also collected from cultures to determine cytokine secretion profiles, including, but not limited to: IL-2, IL-4, IFN-γ, TNF-α. As activated cells grow and divide, cultures are maintained at 0.2-2×10$^6$ CD3$^+$ T cells/ml. When T cell density exceeds roughly 1.5×10$^6$ /ml, cultures are split and fed with fresh media so as to give a cell density in the 0.2-1.4×10$^6$ /ml range. At roughly 2 hours to about 14 days following initial stimulation, when activated T cells are shown to be entering a more quiescent phase (e.g., CD25 levels diminishing, cell size as determined by forward scatter is diminishing, rate of cell division may be reduced), cells are either infused into the subject or re-stimulated with one of the following stimuli:

1) No stimulus
2) Phytohemagglutinin (PHA) 2 μg/ml
3) (3×28 beads) at a 1:1 bead/cell ratio Cells are again analyzed over time for cell phenotype and activation/functional state. Supernatants are again collected for secreted cytokine analysis.

Cells were stimulated by three different methodologies 1) Dynabeads (M-450) covalently coupled to anti-CD3 (OKT-3) and anti-CD28 (9.3) antibodies (3×28 beads) according to the manufacturer's instructions (Dynal), 3 beads/cell, 2) Ionomycin (Calbiochem, La Jolla, Calif.) (100 ng/ml) and phorbol 12-myristate-13-acetate (PMA) (Calbiochem) (10 ng/ml), 3) allogeneic dendritic cells (25,000 dendritic cells/200,000 CD4 cells). All cells are stimulated at a concentration of $10^6$ cell/ml. Proliferation assays are conducted in quadruplicate in 96 well flat-bottom plates. Cells are stimulated at $10^6$ cells/ml in a final volume of 200 μl. Proliferation is measured by MTT assay (MTT assay kit, Chemicon International Inc., Temecula, Calif.) at day 3 (stimulation method 1 and 2) or at day 6 (stimulation method 3), and results are presented as mean value of quadruplicates. PBL cultures or purified CD4$^+$ cell cultures are stimulated with 3×28 beads, ionomycin/PMA, or allogeneic dendritic cells.

Figure 8A:
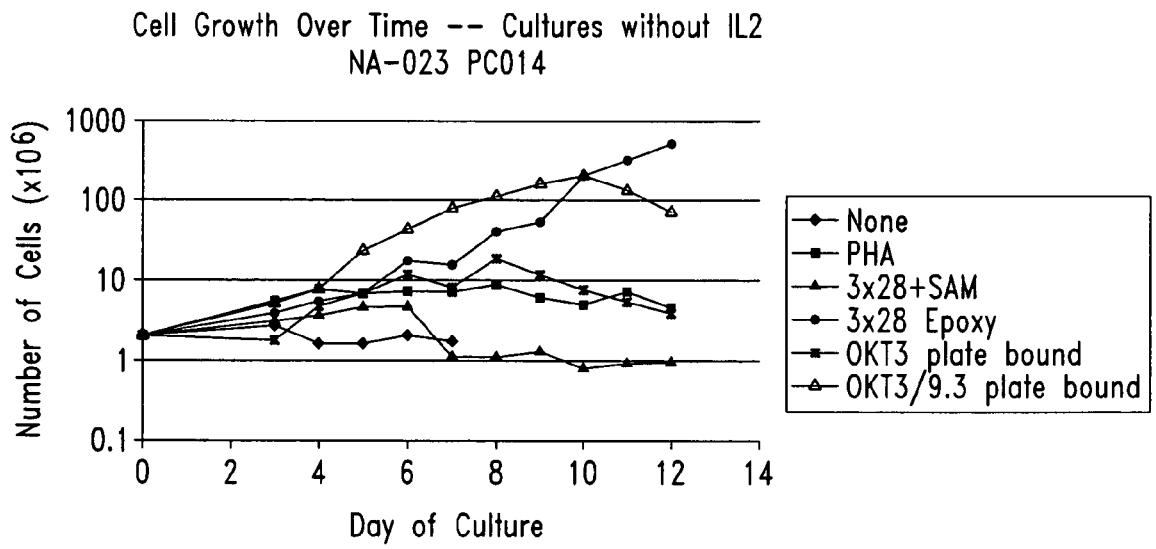
FIGS. 8A and 8B are plots illustrating growth of human peripheral blood T cells following stimulation with anti-CD3 and anti-CD28 co-immobilized beads utilizing process set forth in Example IX.
Figure 8B:
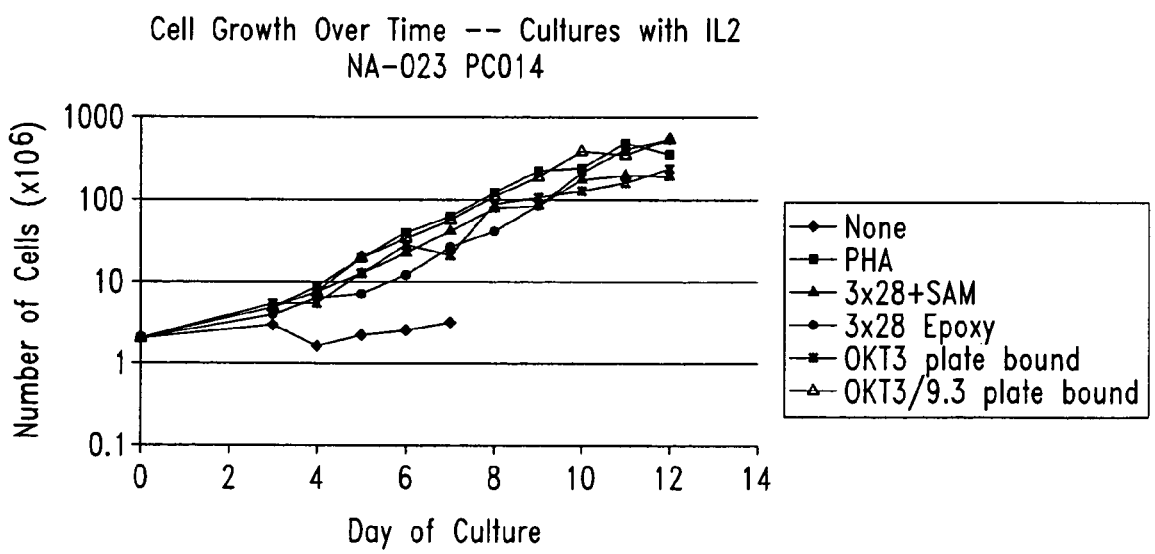
Figure 9:
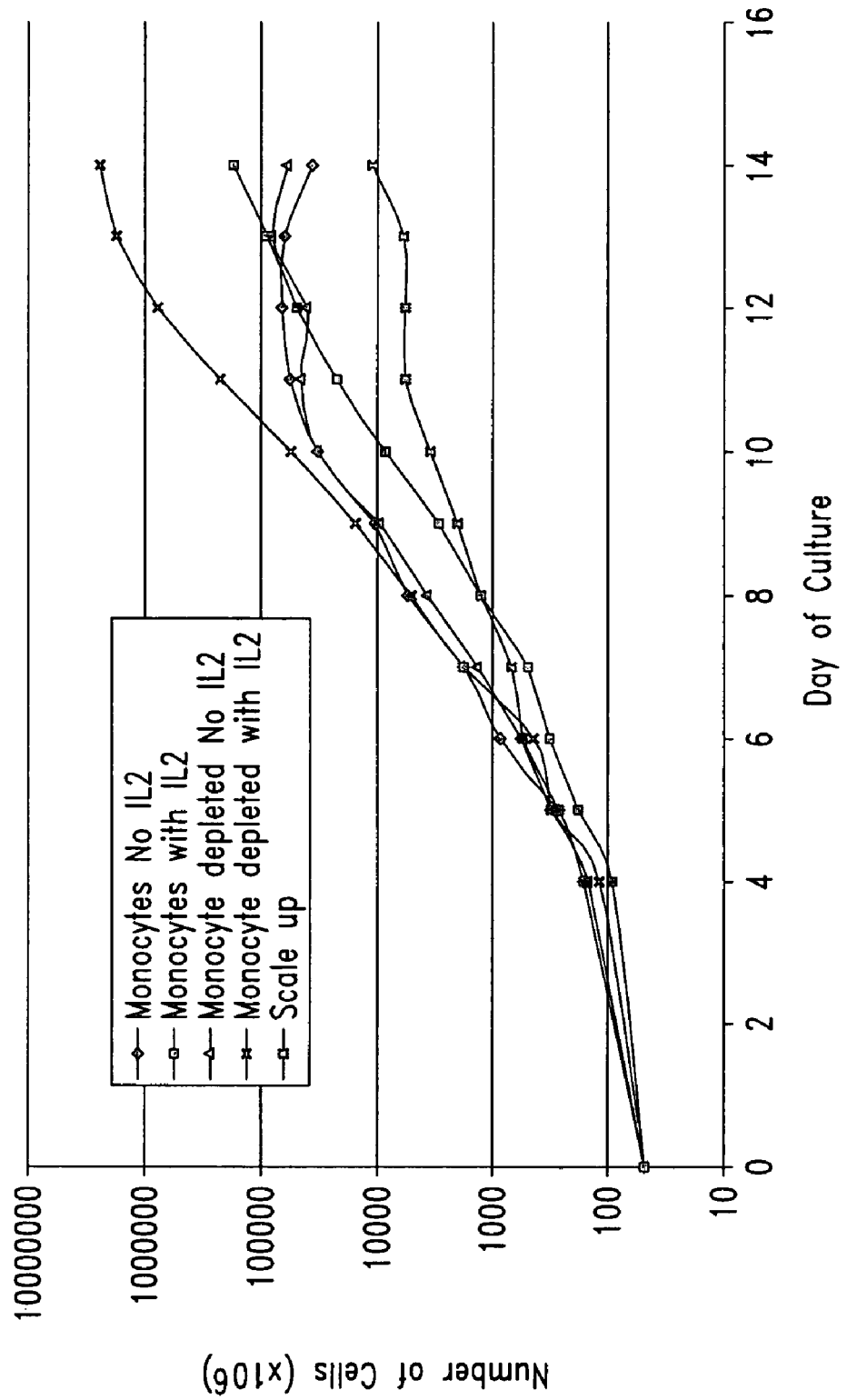
FIG. 9 is a plot illustrating growth of human peripheral blood T cells following stimulation with anti-CD3 and anti-CD28 co-immobilized beads±recombinant human IL-2 at 10 u/ml and ±monocyte depletion. All cells were cultured in Baxter Lifecell Flasks (300 ml). Scale up refers to a 300 ml flask culture (No IL-2/Monocyte depleted) that was expanded up to a Baxter Lifecell 3 Liter flask.

As demonstrated by FIGS. 8A-8B, cell numbers (Coulter counter) increase dramatically following stimulation with PHA, 3×28 beads (anti-CD3 and anti-CD28 co-immobilized on beads) attached to the beads via sheep anti-mouse (SAM), 3×28 beads with the antibodies covalently attached to the beads, or antibodies singly or dually immobilized on a plate. FIG. 9 also demonstrates increases in cell numbers following stimulation with covalently immobilized anti-CD3 and anti-CD28 on beads±monocyte depletion and ±20 units of IL-2.

Example X

Monocyte Depletion Via Magnetic Depletion

Monocytes (CD14$^+$ phagocytic cells) are removed from T cell preparations via magnetic depletion using a variety of "irrelevant" (i.e., non-antibody coated or non-target antibody coated) Dynal beads. Depletion was performed by pre-incubating ficolled whole blood, or apheresed peripheral blood with roughly 2:1 bead to cell ratio of Dynal Sheep anti-mouse M-450 beads, or Dynal human serum albumin-coated beads (M-450), or with Dynal Epoxy (M-450) beads for periods of 1-2 hours at 22-37 degrees C., followed by magnetic removal of cells which had attached to beads or engulfed beads. The remaining cells were placed into culture alongside un-manipulated cells. Cells were characterized by flow cytometry for cell phenotype before and after depletion. FIG. 9 demonstrates increased proliferation in the absence of monocytes.

Example XI

Pre-Activation and Post-Activation Kinetic Timecourse Studies

A series of experiments were performed in which human T cells, isolated either from whole blood or from apheresed peripheral blood, were cultured under a variety of conditions. Those conditions include:

1) No stimulation
2) Stimulation with phytohemagglutinin (PHA) at 2 μg/ml.
3) Stimulation with 3×28 Dynabeads (beads having anti-CD3 and anti-C28 beads conjugated thereto) at 3:1 or 1:1 bead-to-T cell ratio.
4) Stimulation or culture in the presence or absence of exogenously added recombinant human IL-2 at 10 U/ml (5 ng/ml).

5) Culture in the presence of monocytes (CD14+ phagocytic cells) or cultured following removal of aforementioned cells via magnetic depletion using a variety of "irrelevant" Dynabeads. Depletion was performed as illustrated in Example II.

The following cell surface markers were analyzed by flow cytometry to determine cell phenotype and activation state: CD2, CD3, CD4, CD8, CD14, CD19, CD20, CD25, CD45RA, CD45RO, CD54, CD62L, CDw137 (41BB), CD154. Cell size is also examined, as determined by forward scatter profiles via flow cytometry.

Markers, such as CD2, CD3, CD4, CD8, CD14, CD19, CD20, CD45RA, and CD45RO are used to determine T, B, and monocyte lineages and subpopulations, while forward scatter, CD25, CD62L, CD54, CD137, CD154 are used to determine activation state and functional properties of cells.

Human peripheral blood lymphocytes containing T cells were prepared as described in Example IX. Cells are analyzed over time for cell phenotype and activation/functional state. Supernatants are collected for secreted cytokine analysis. FIGS. 8 and 9 demonstrates general growth characteristics of human T cells following activation with 3×28 beads+/−recombinant human IL-2 at 10 u/ml and +/−monocyte depletion. All cells were cultured in Baxter Lifecell Flasks (300 ml). The one plot labeled "Scale up" refers to a 300 ml flask culture (No IL-2/Monocyte depleted) that was expanded up to a Baxter Lifecell 3 liter flask. The graph demonstrates an approximate 2-4 log expansion of human T cells under the various conditions.

Figure 10:
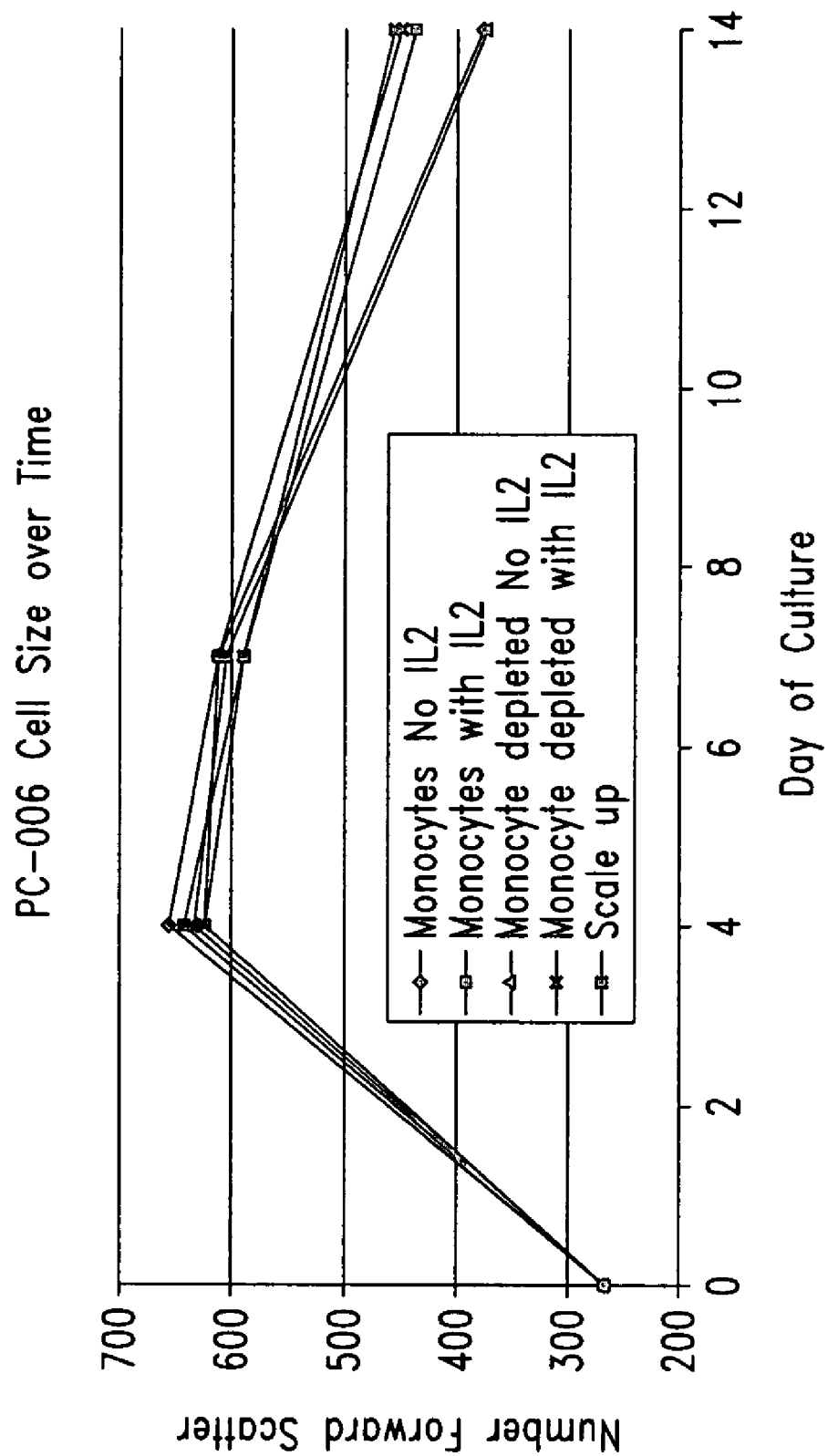
FIG. 10 is a plot demonstrating the kinetic analysis of cell size as determined by forward scatter flow cytometry profiles over time.

FIG. 10 shows the kinetic analysis of cell size as determined by forward scatter flow cytometry profiles over time. T cell are seen to increase in size shortly after activation and subsequently decrease in size so that by day 14 they demonstrate smaller forward scatter profiles, indicating a more quiescent state.

Figure 11A:
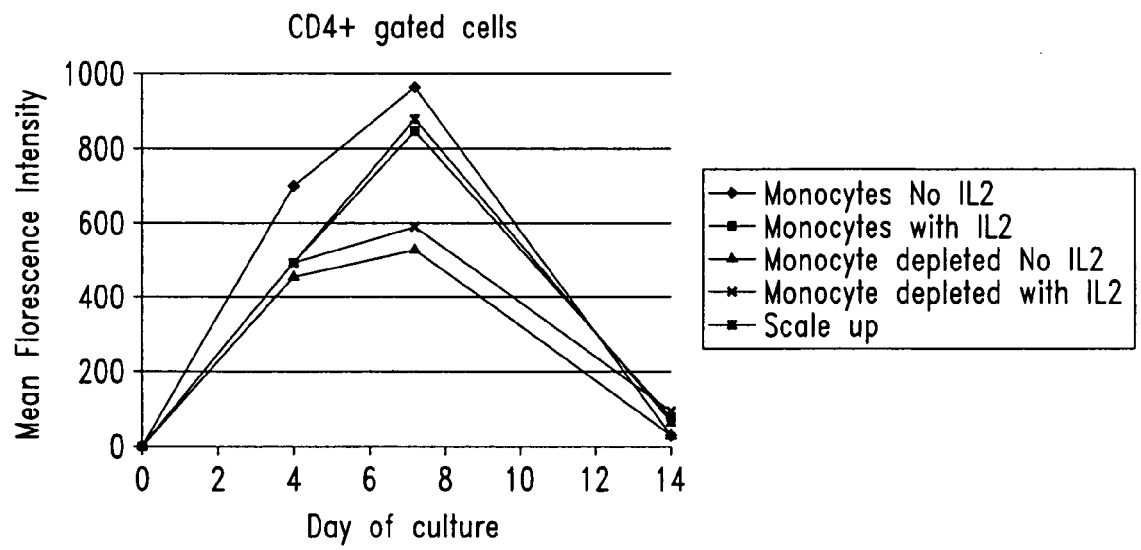
FIGS. 11A and 11B are plots representing CD25 expression over time following initial stimulation with anti-CD3 and anti-CD28 co-immobilized beads.
Figure 11B:
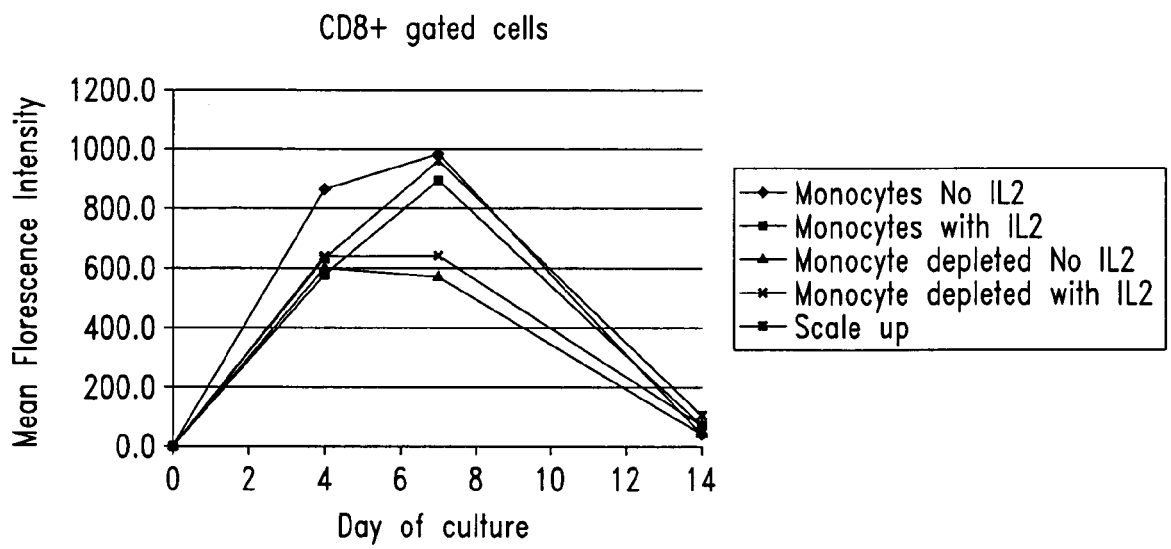

FIG. 11 shows IL-2 receptor (CD25) expression over time following 3×28 bead stimulation. Both CD4+ and CD8+ T cells show an early increase in receptor level. By day 14, CD25 expression levels are greatly reduced on a majority of T cells, indicating a more quiescent state.

Figure 12:
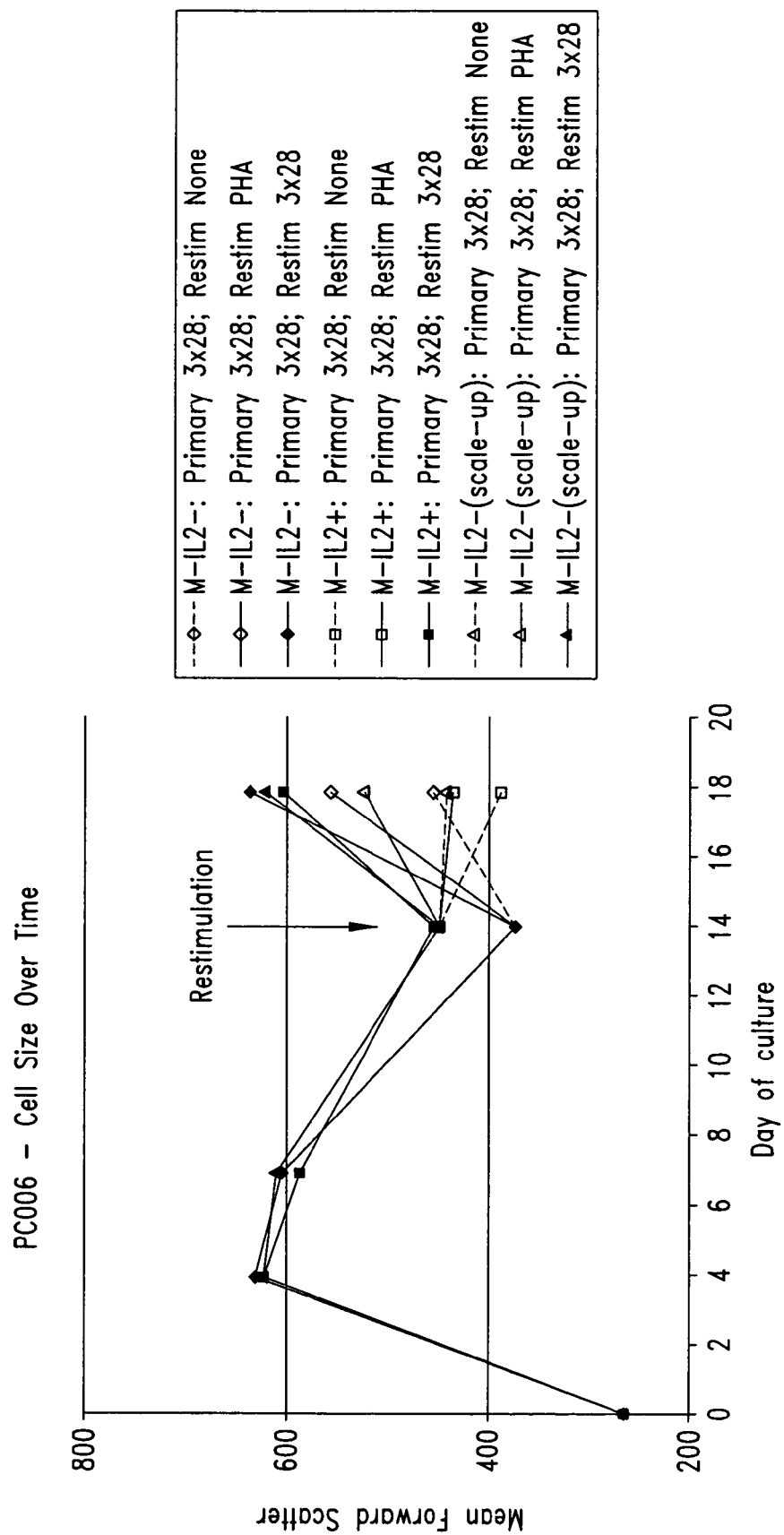
FIG. 12 is a plot illustrates changes in cell size as determined by forward scatter flow cytometry profiles over time following primary and secondary stimulation.
Figure 13A:
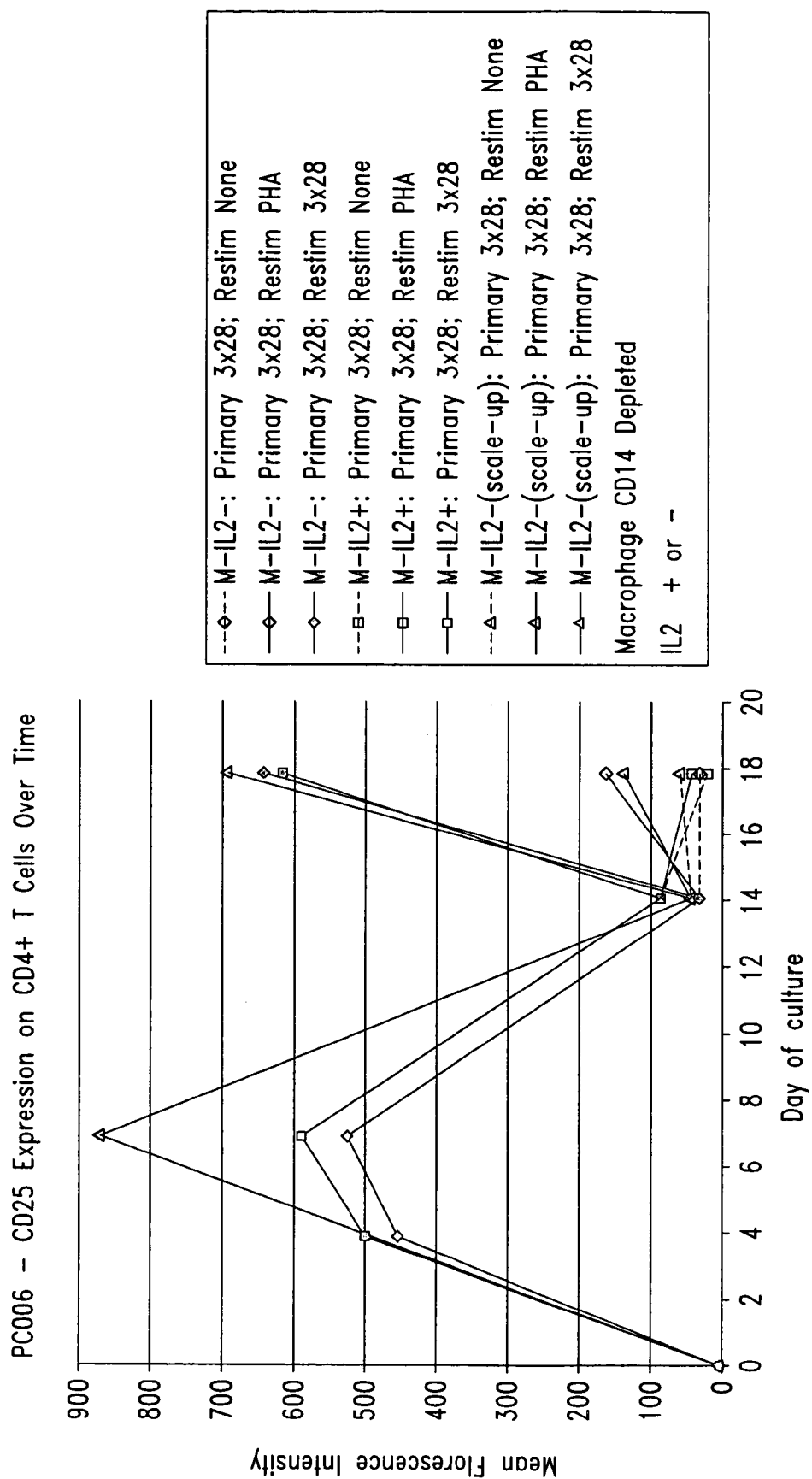
FIGS. 13A and 13B are plots representing CD25 expression over time following primary and secondary stimulation.
Figure 13B:
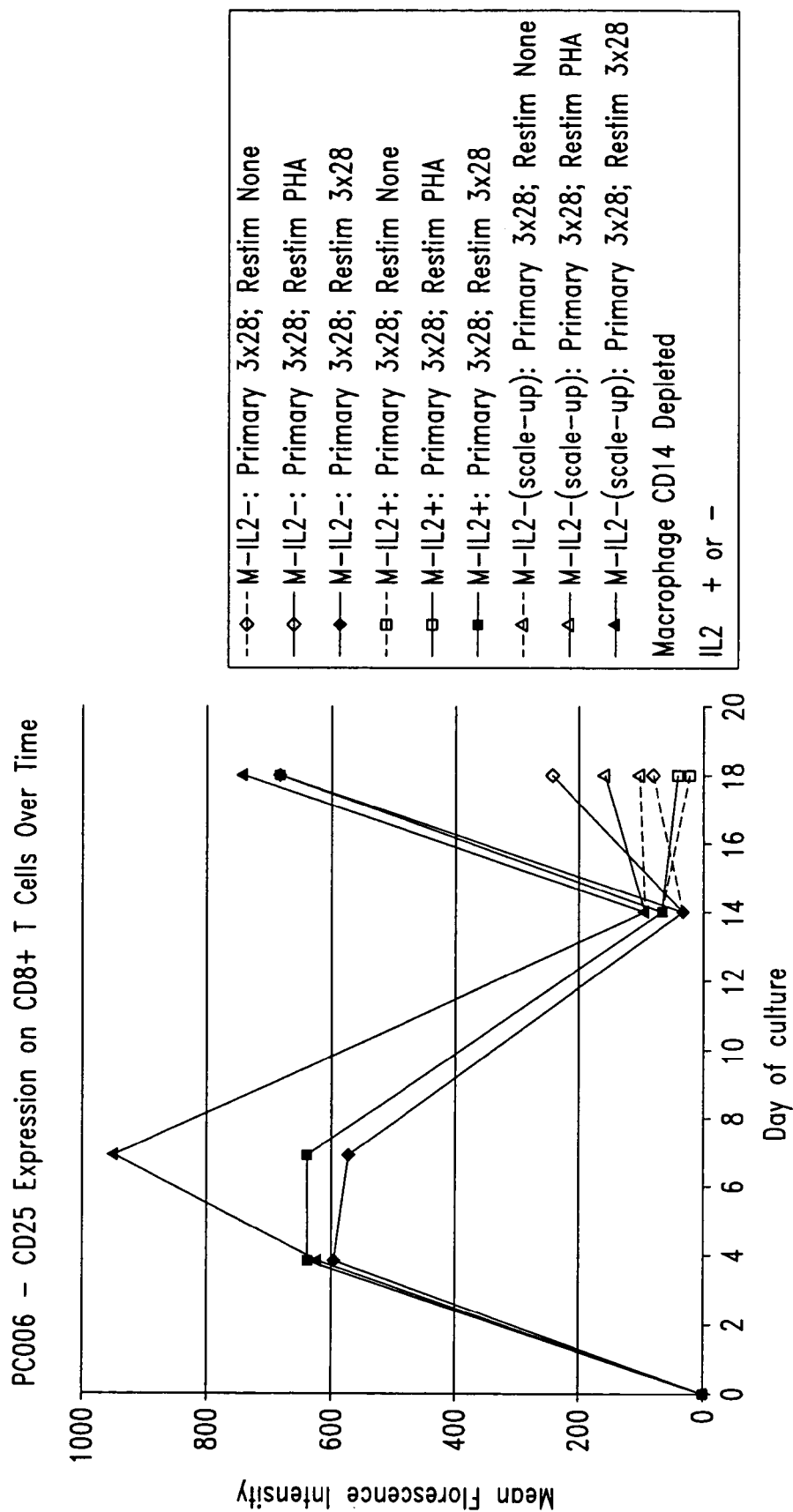
Figure 14A:
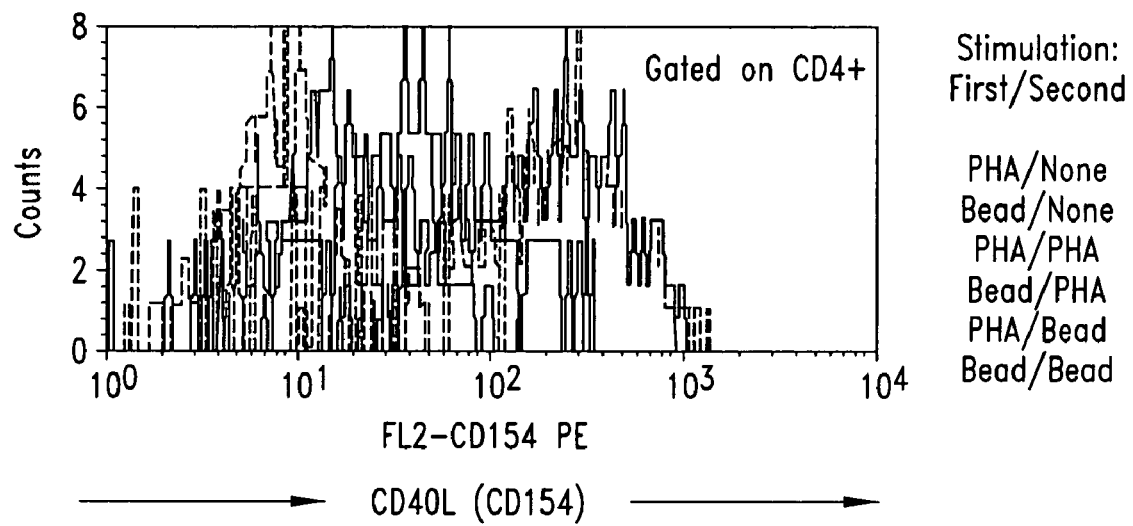
FIGS. 14A and 14B are flow cytometry data plots representing CD154 expression following secondary stimulation, wherein primary and secondary stimulation sources were varied.
Figure 14B:
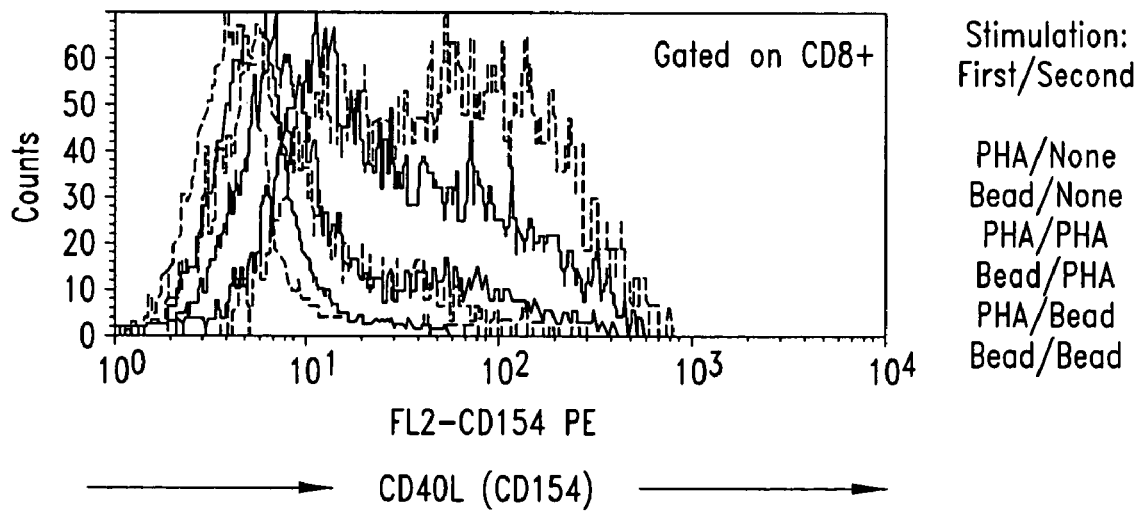
Figure 15:
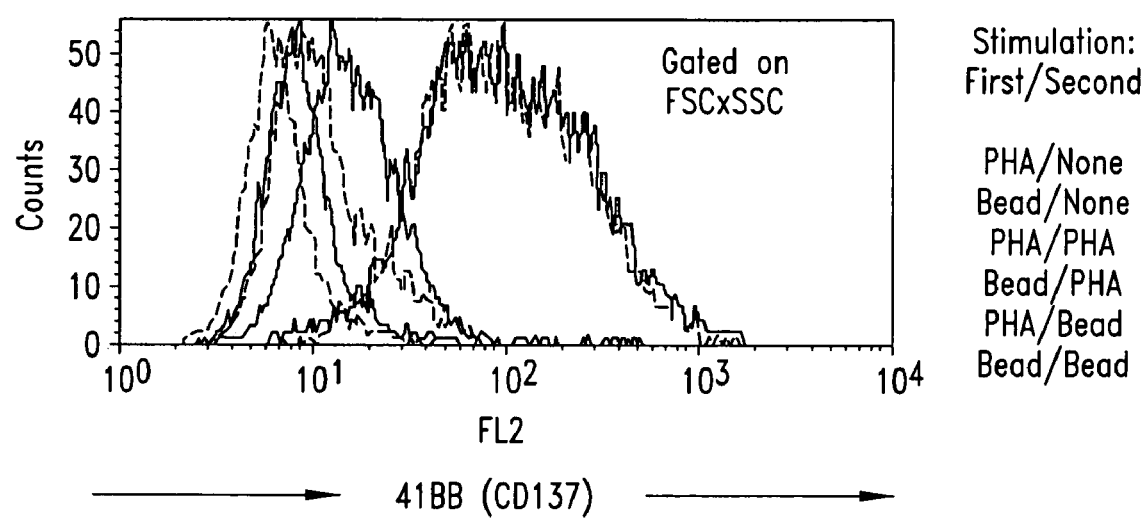
FIG. 15 is a flow cytometry data plot representing CD137 expression on all expanded T cells in sample following secondary stimulation.
Figure 16A:
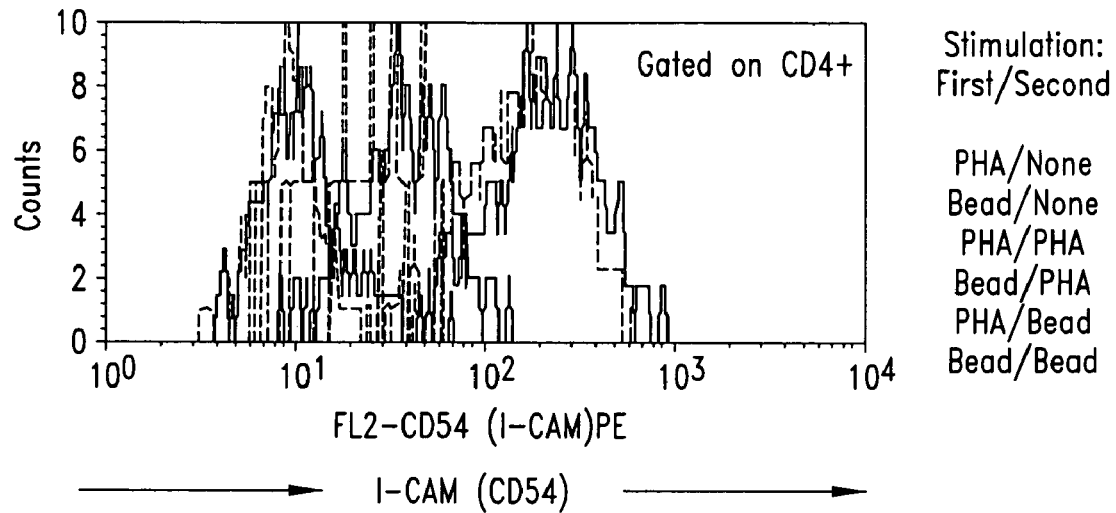
FIGS. 16A and 16B are flow cytometry data plots representing CD54 expression following secondary stimulation, wherein secondary stimulation sources were varied.
Figure 16B:
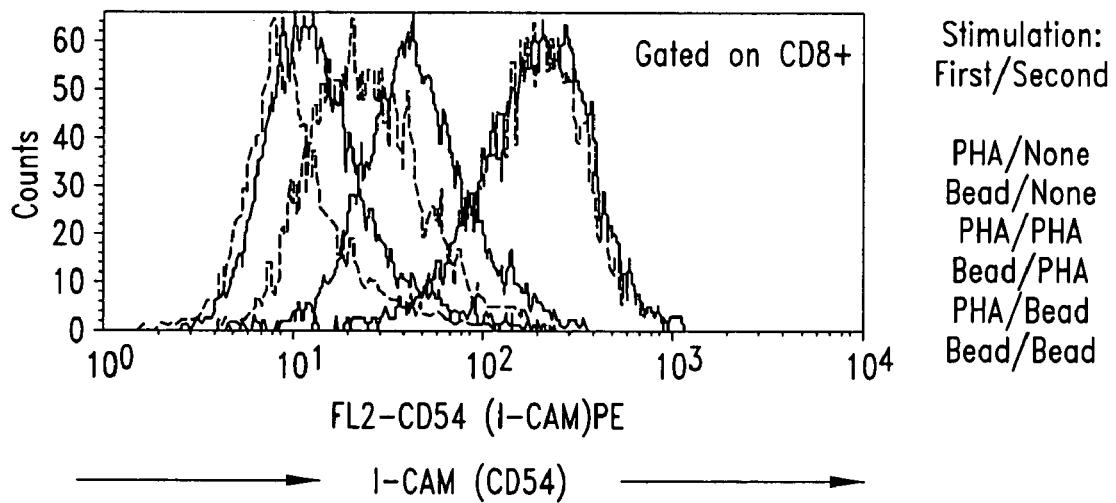
Figures 17A, 17B:
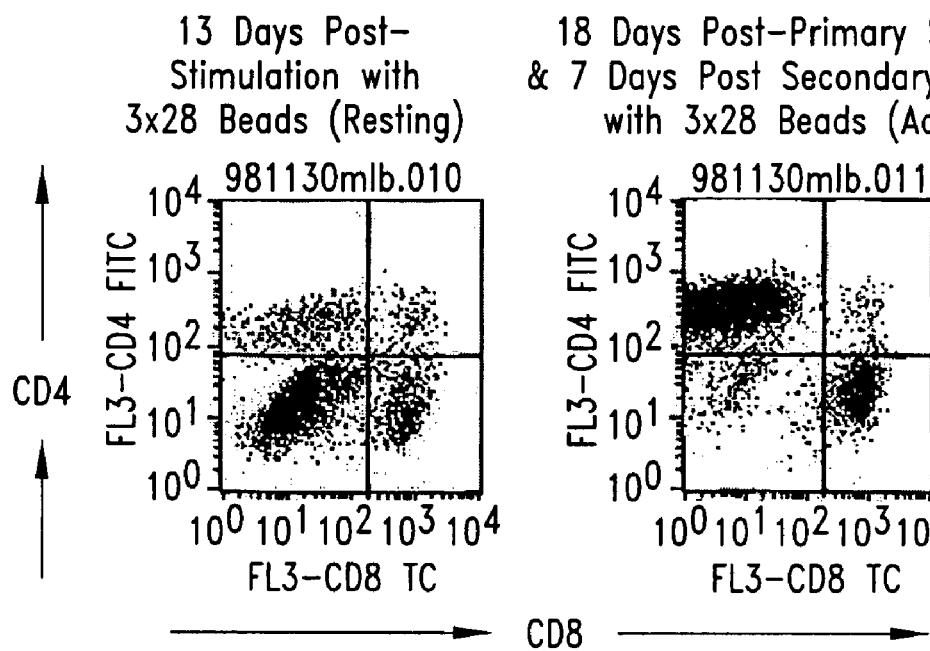
FIGS. 17A-17D are flow cytometry data plots representing cell phenotypes as well as CD154 and CD137 expression following secondary stimulation by anti-CD3 and anti-CD28 coupled beads of T cells obtained from a patient with B-cell chronic lymphocytic leukemia.
Figure 17C:
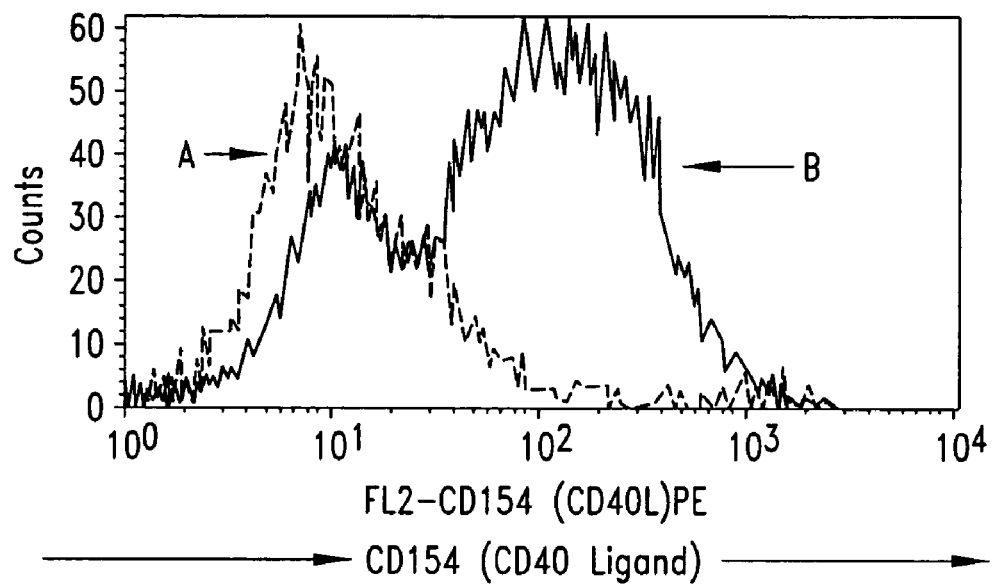
Figure 17D:
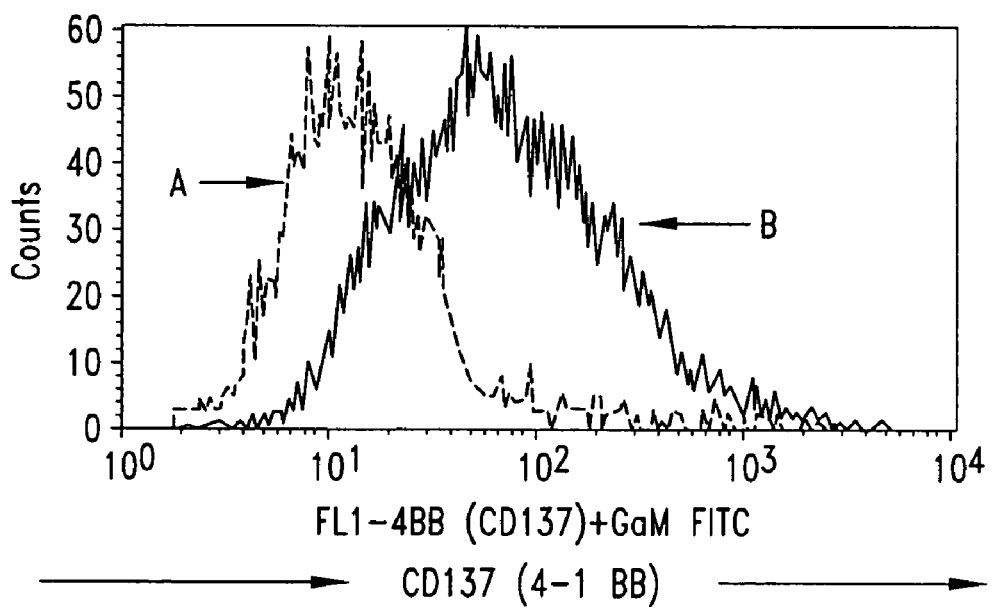
Figure 18A:
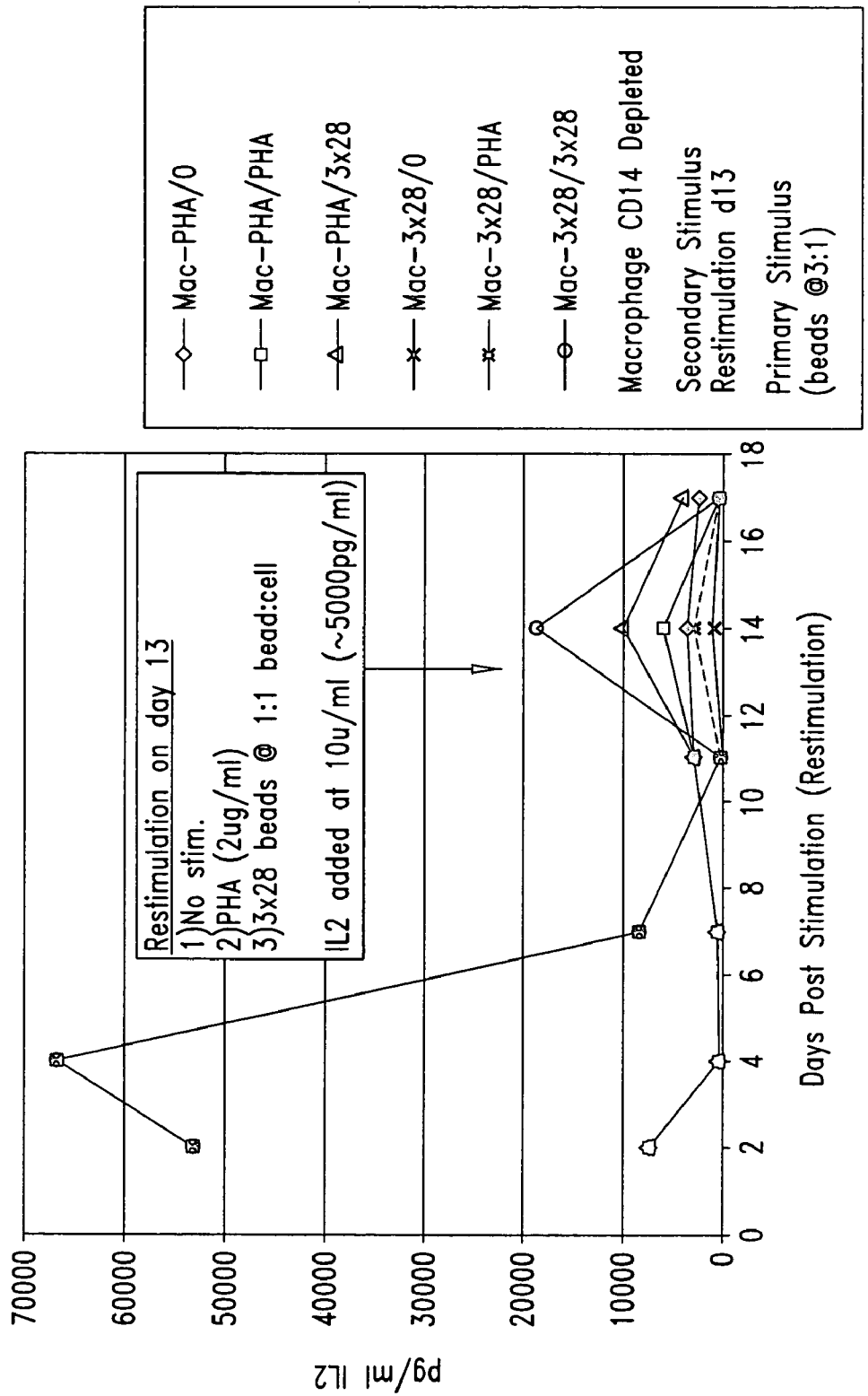
FIGS. 18A-18C are plots representing the expression over time of IL-2 (18A), Interferon gamma (IFN-γ) (18B), and IL-4 (18C) following primary and secondary stimulation of T cells from normal donors.
Figure 18B:
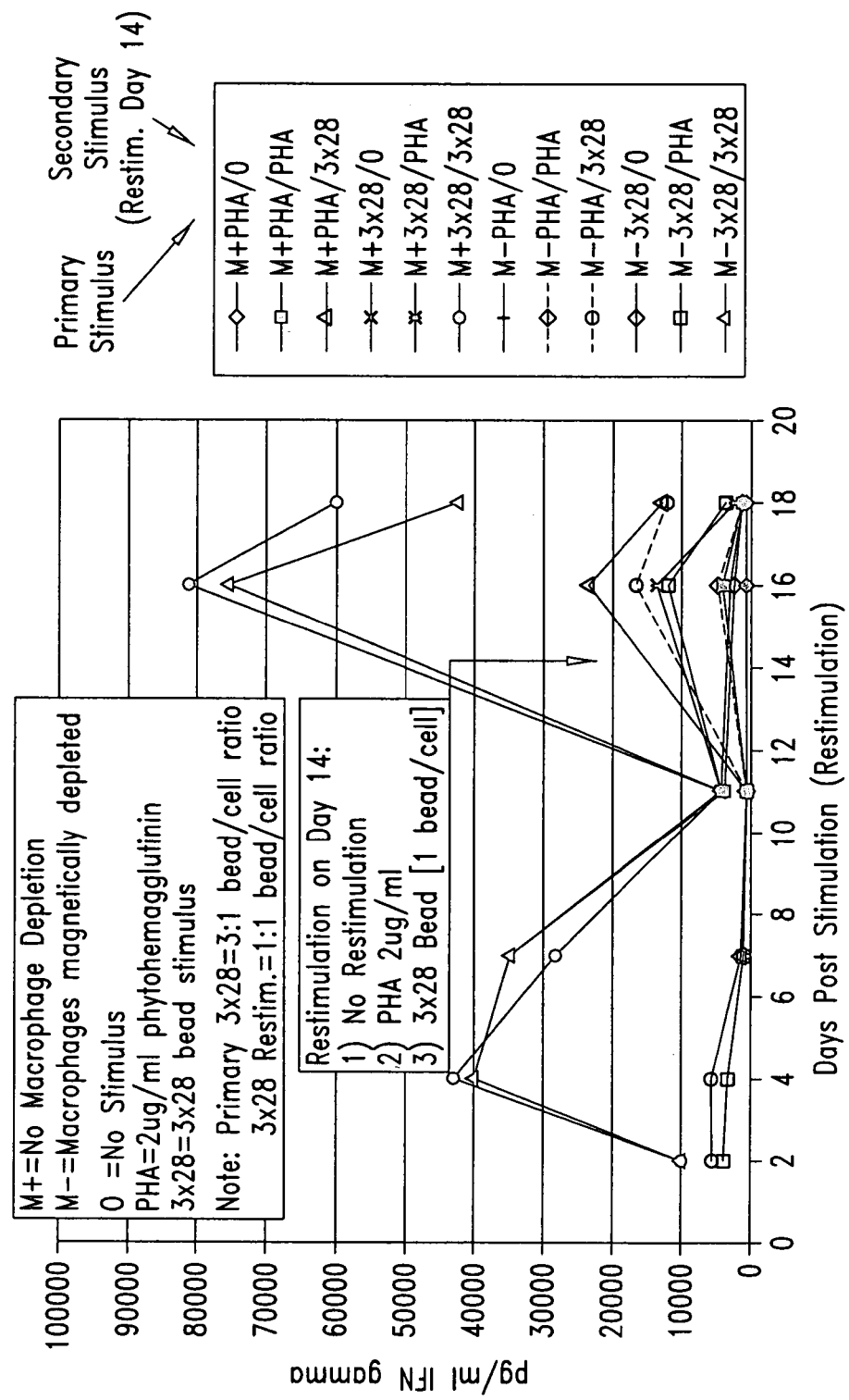
Figure 18C:
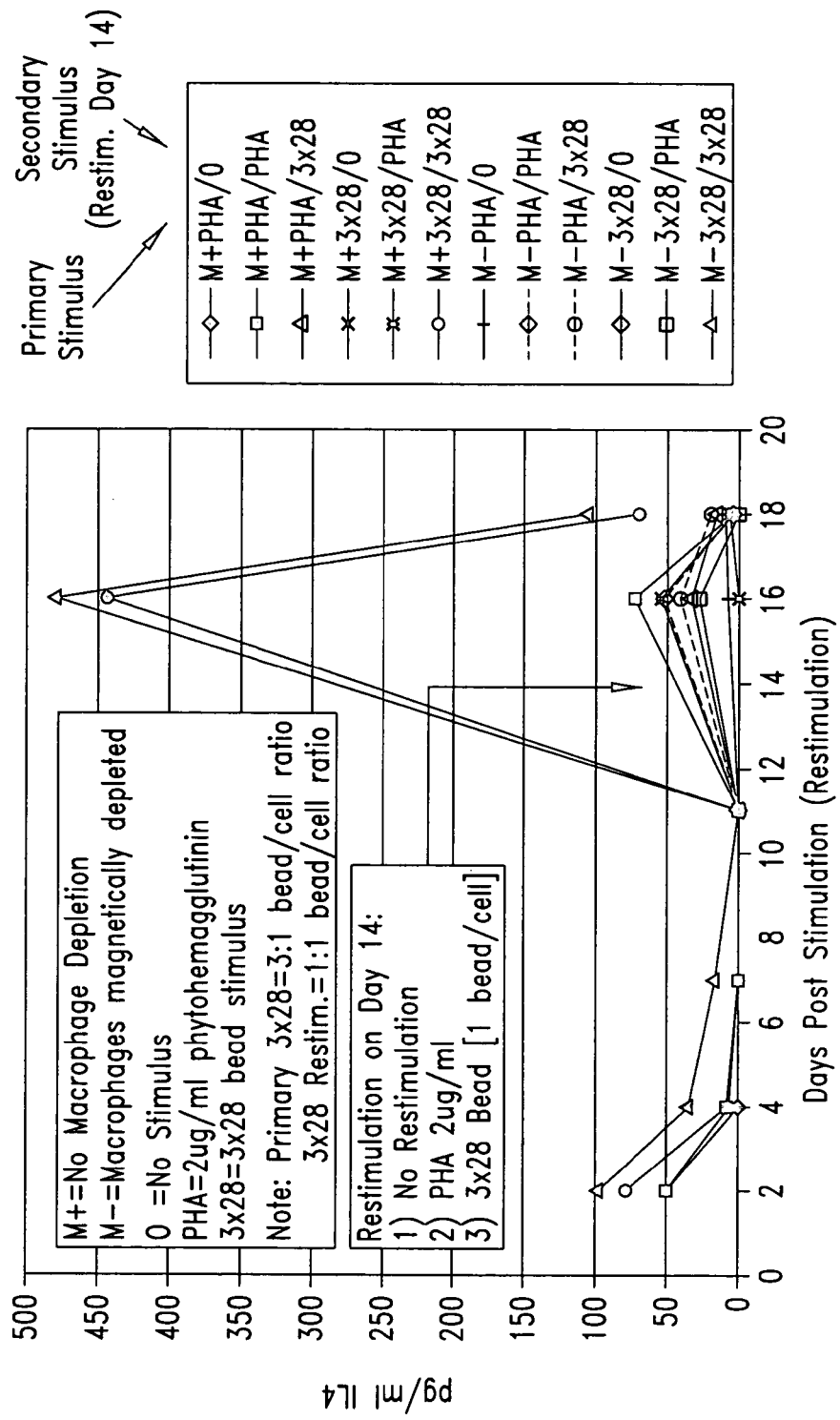
Figure 19A:
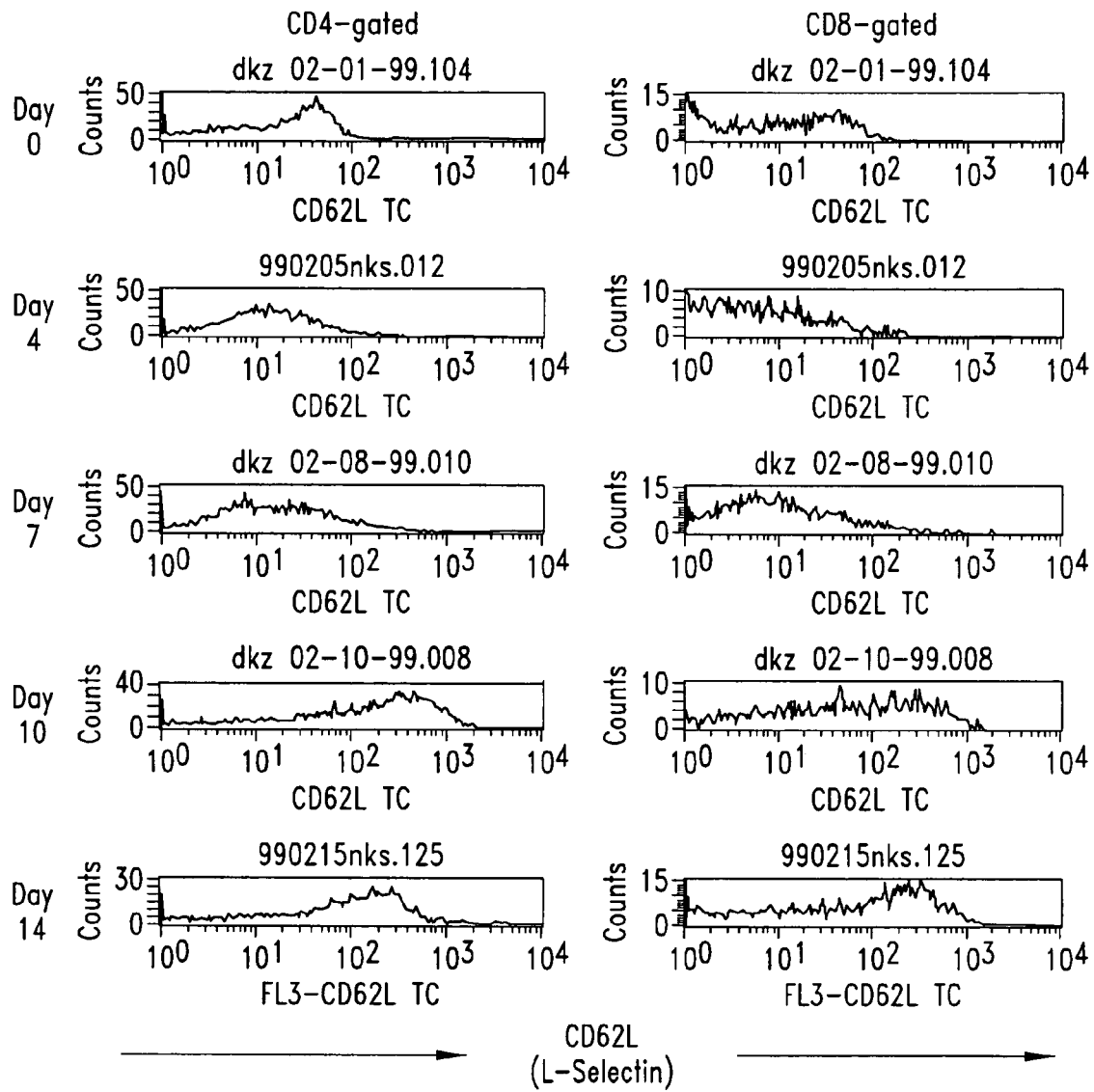
FIGS. 19A-19B are plots representing expression over time of CD62L following stimulation with anti-CD3 and anti-CD28 coupled beads.
Figure 19B:
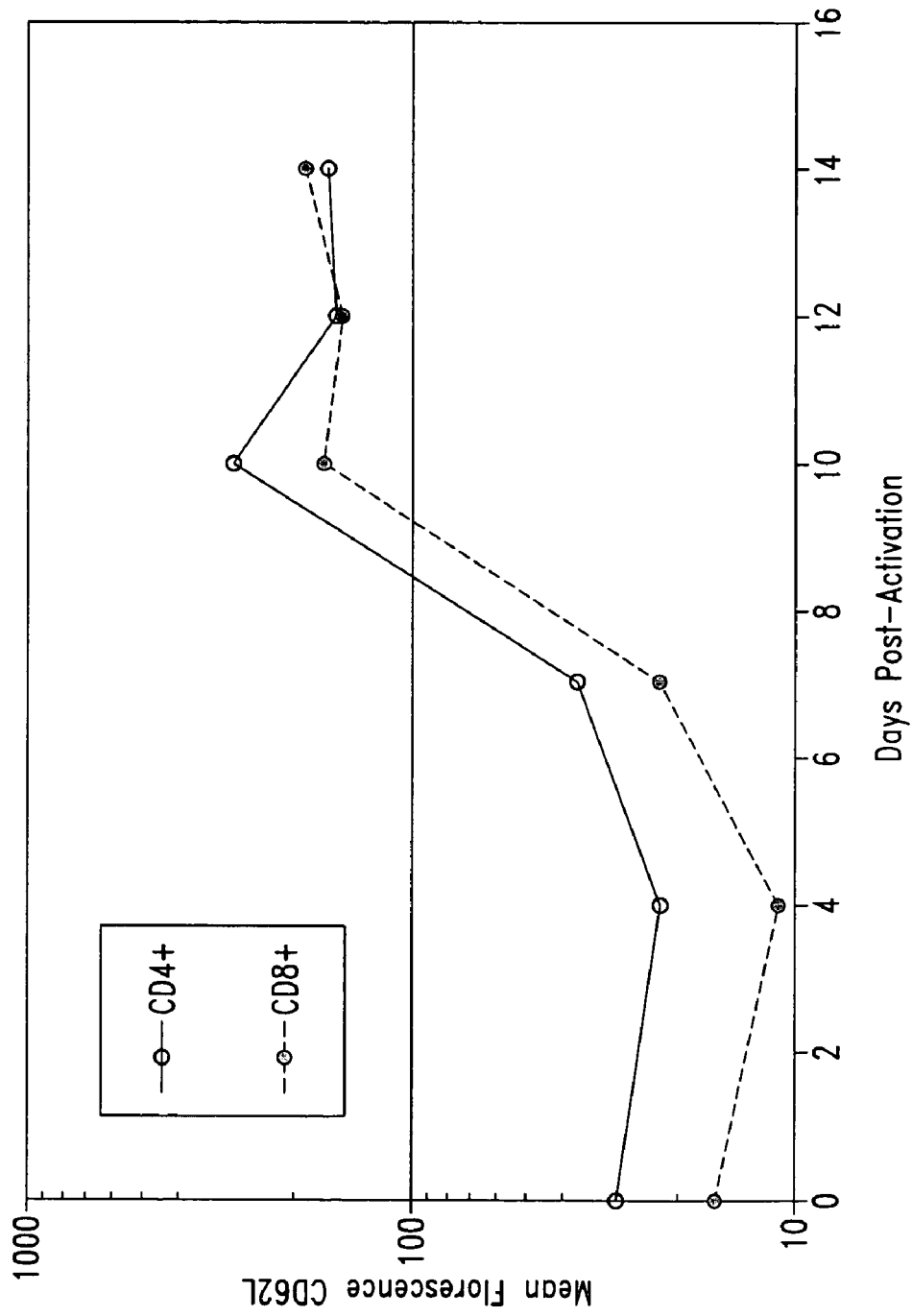
Figure 20:
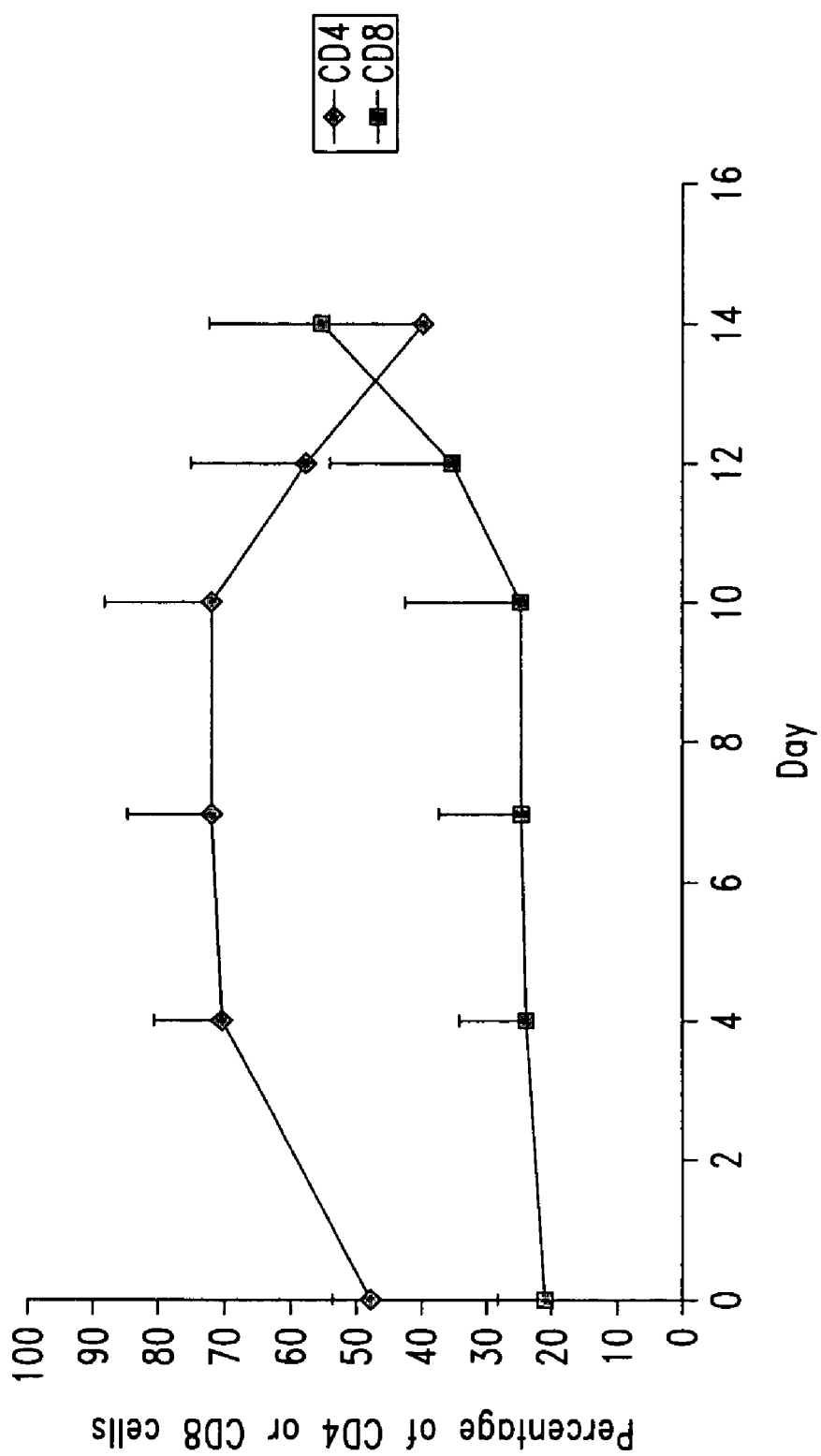
FIG. 20 is a plot depicting the percentage of CD4 or CD8 cells following stimulation with anti-CD3 and anti-CD28 co-immobilized beads.
Figure 21A:
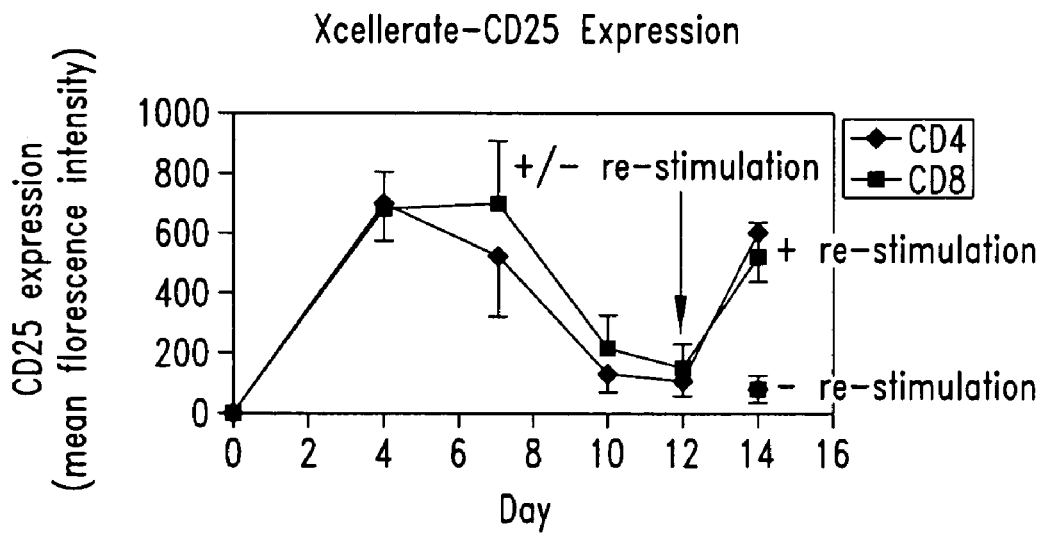
FIGS. 21A-21B are plots representing flow cytometry data as a function of mean fluorescence intensity of CD25 and CD154 expression, respectively following stimulation with anti-CD3 and anti-CD28 co-immobilized beads and ±re-stimulation utilizing process in Example IX.
Figure 21B:
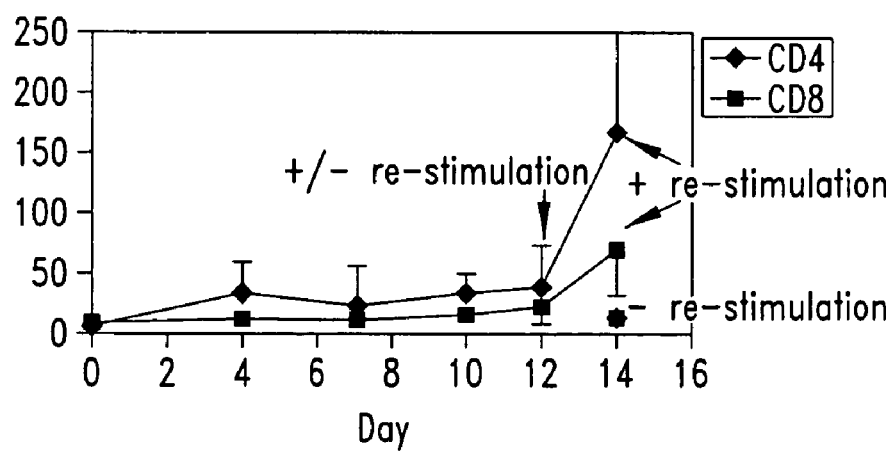
Figure 22A:
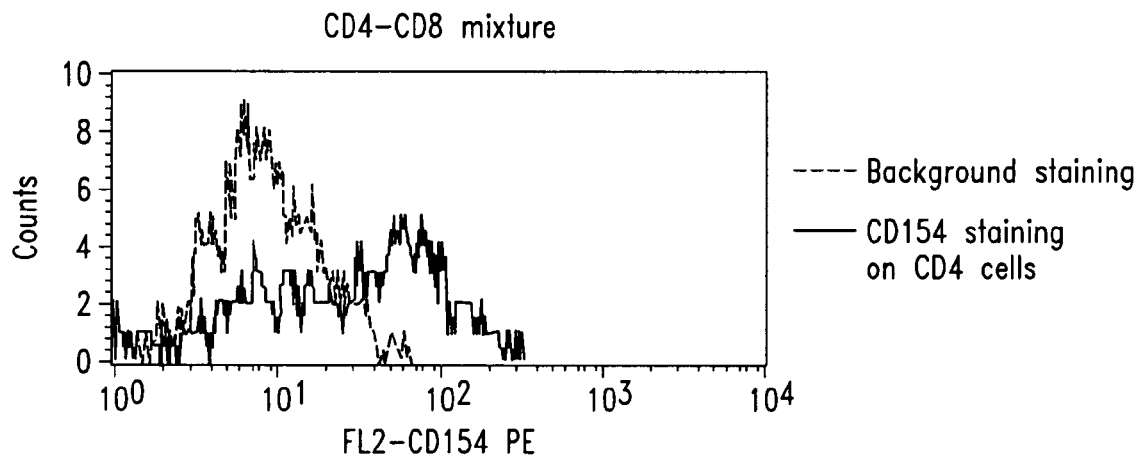
FIGS. 22A-22B are plots representing flow cytometry analyses of CD154 staining versus control staining (e.g., background) in cells with both CD4 and CD8 sub-populations (22A) or CD4-enriched populations (22B), prior to anti-CD3 and anti-CD28 co-immobilized bead stimulation.
Figure 22B:
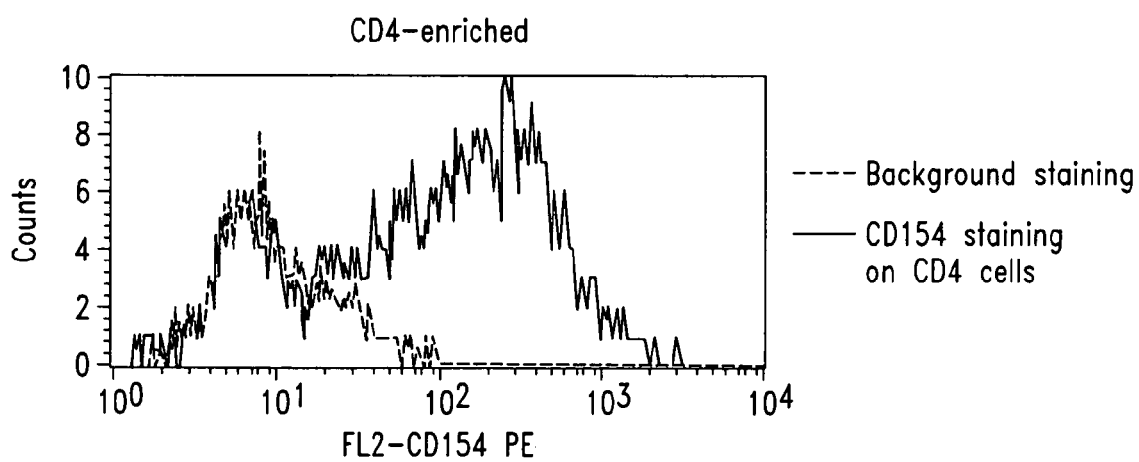
Figure 23A:
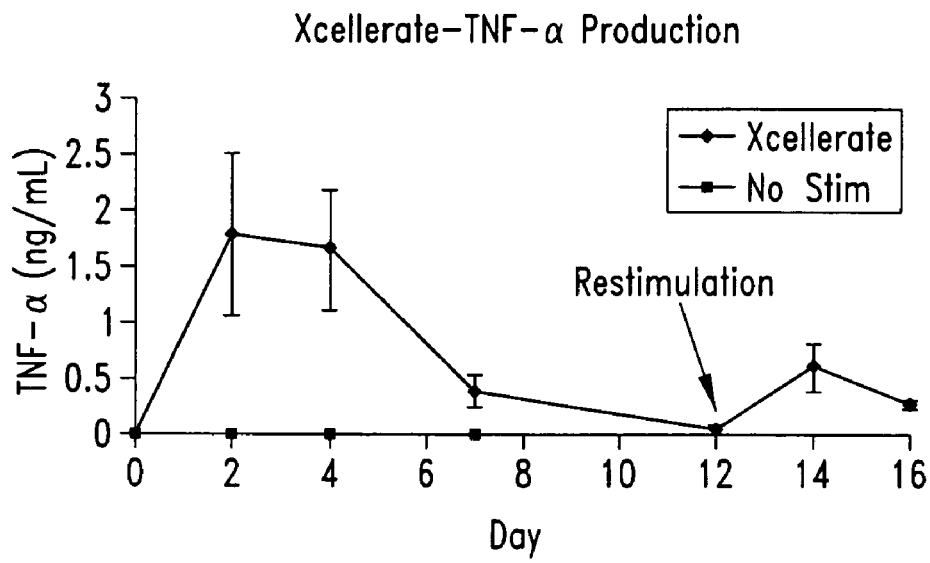
FIGS. 23A-23B are plots representing ELISA analysis of TNF-α (23A) and IFN-γ (23B) in media following stimulation of peripheral blood lymphocytes with anti-CD3 and anti-CD28 co-immobilized beads.
Figure 23B:
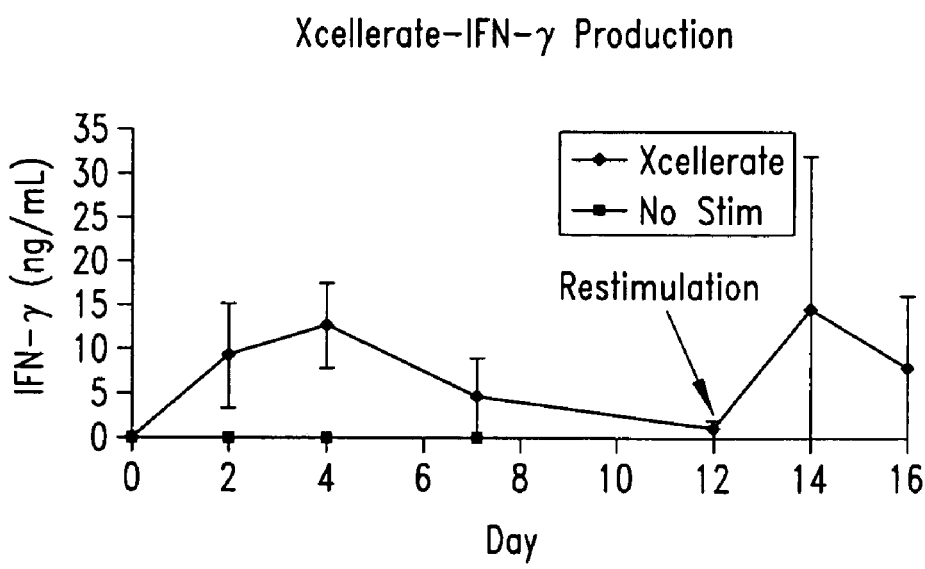
Figure 24A:
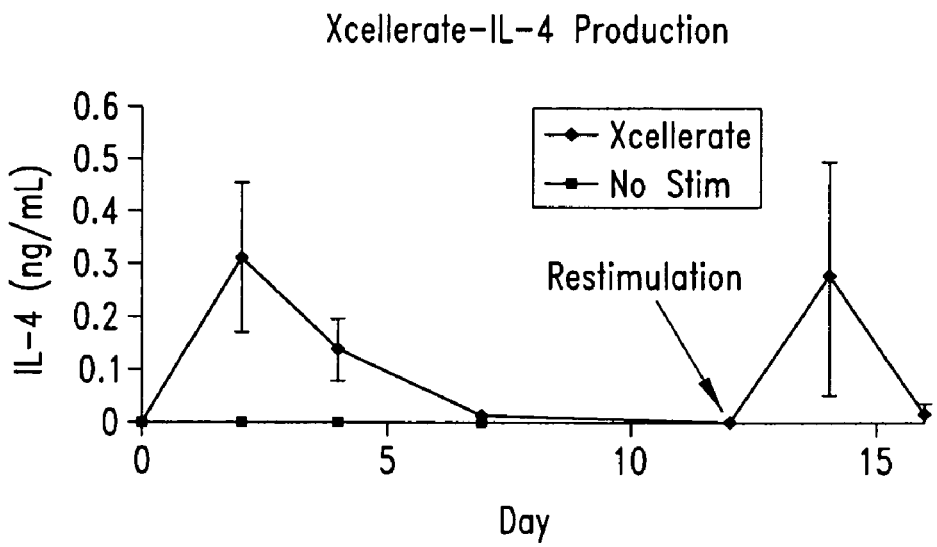
FIGS. 24A-24B are plots representing ELISA analysis of IL-4 (24A) and IL-2 (24B) in media following stimulation of peripheral blood lymphocytes with anti-CD3 and anti-CD28 co-immobilized beads.
Figure 24B:
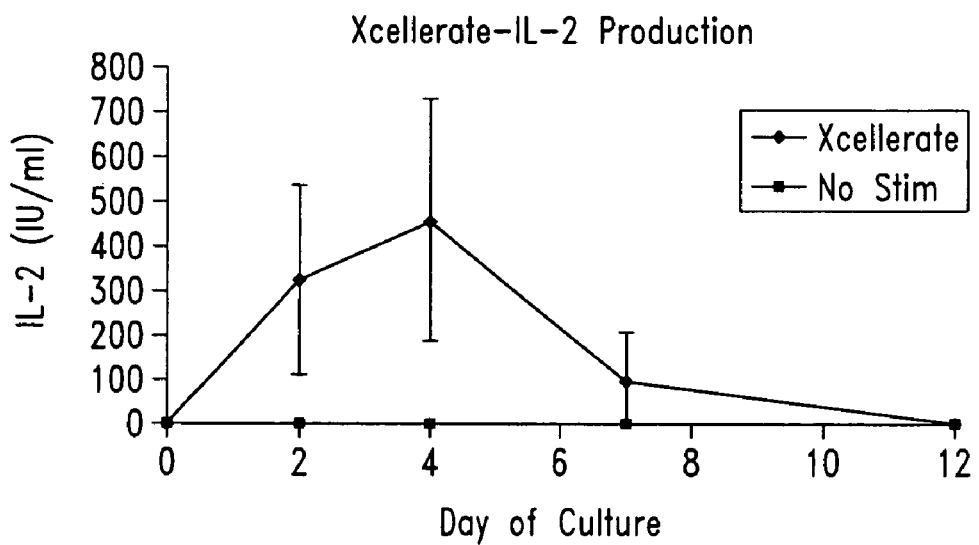
Figure 25:
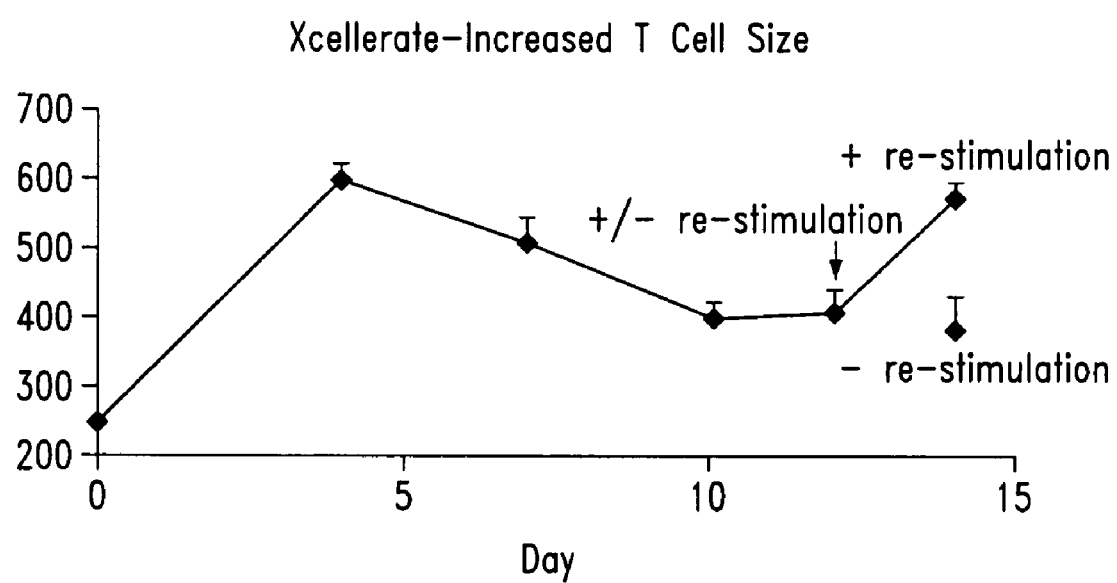
FIG. 25 is a plot depicting increase in T cell size following stimulation of peripheral blood lymphocytes with anti-CD3 and anti-CD28 co-immobilized beads and using forward scatter analysis.
Figure 26B:
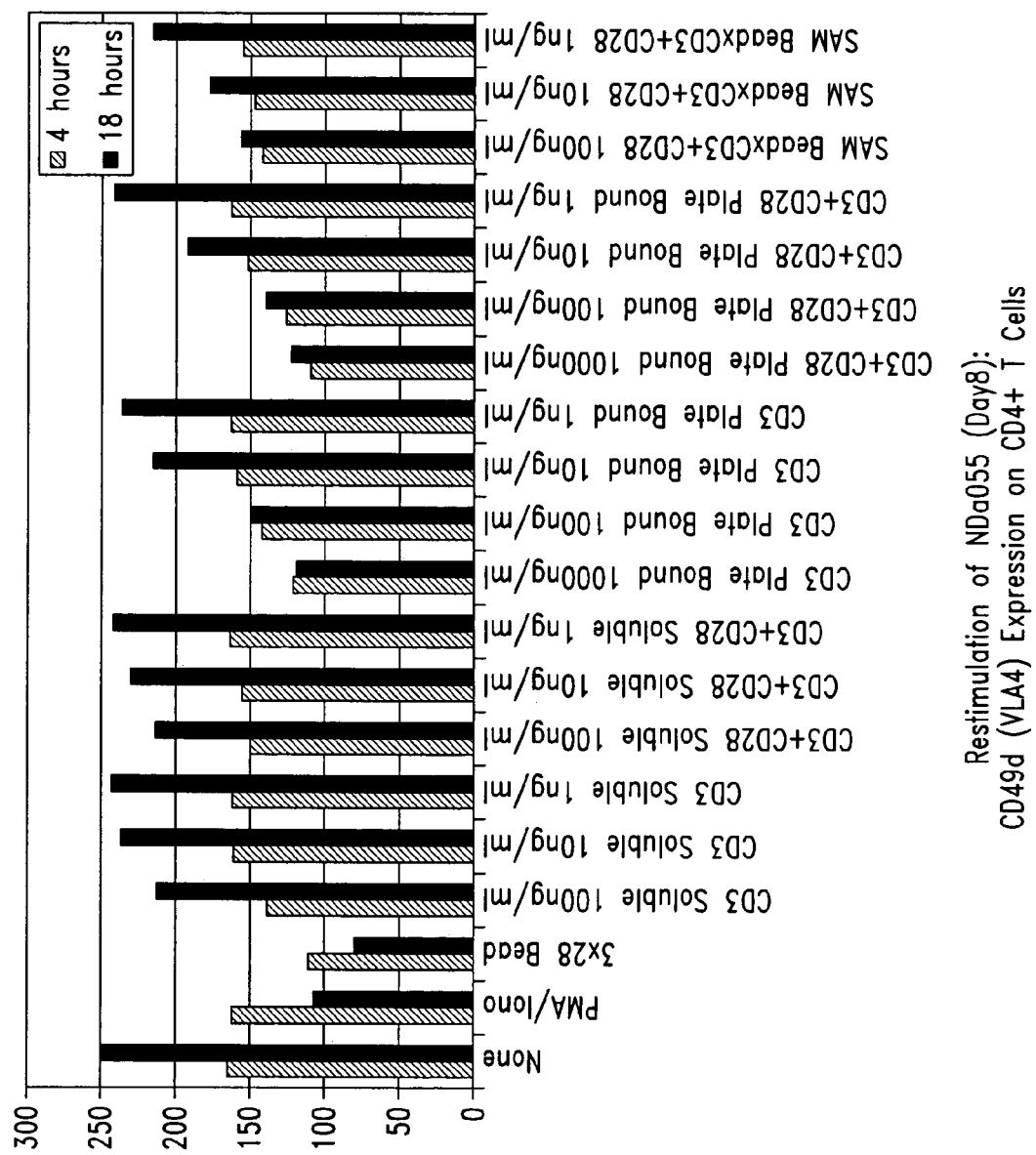
Figure 26C:
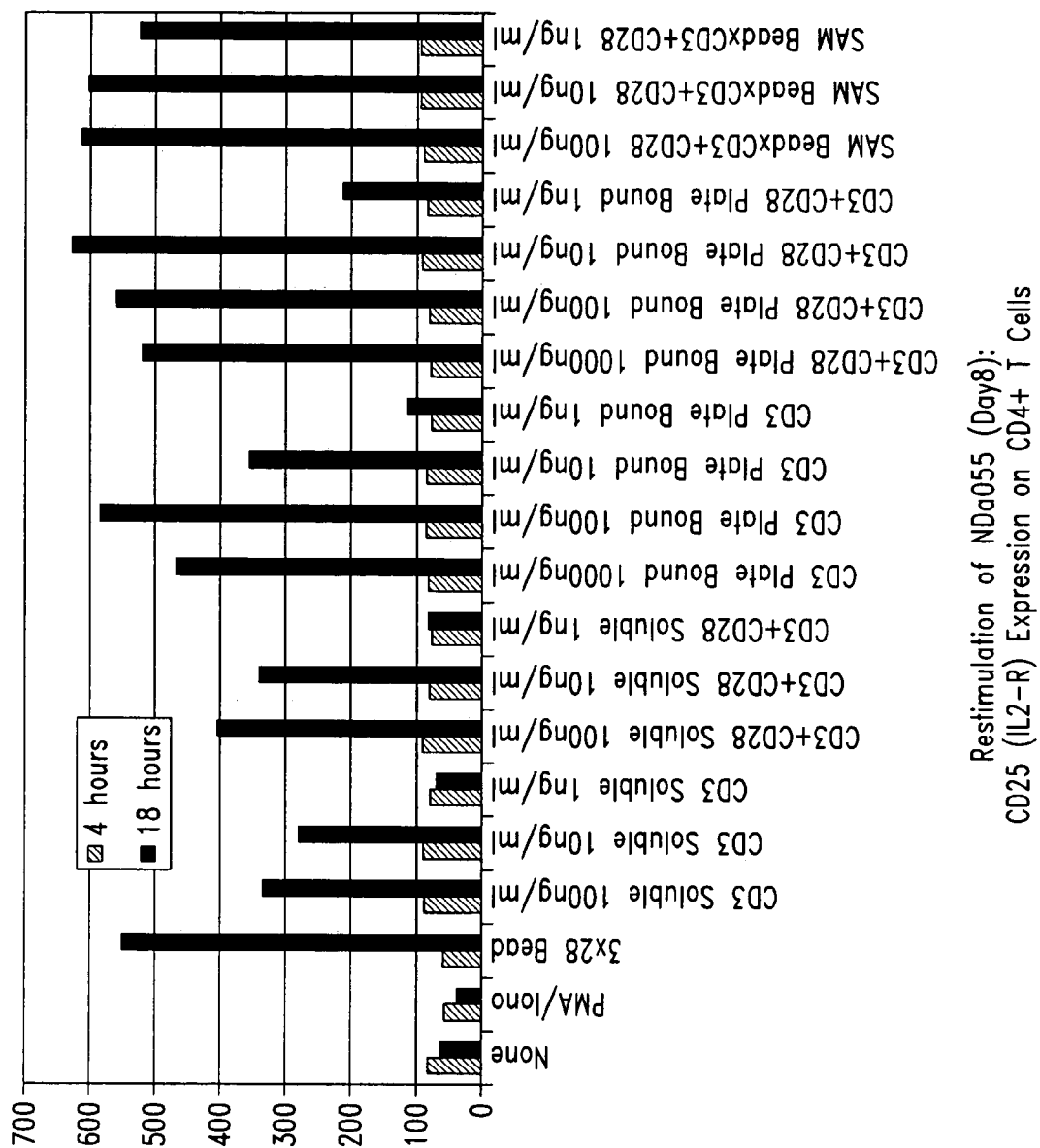
Figure 26D:
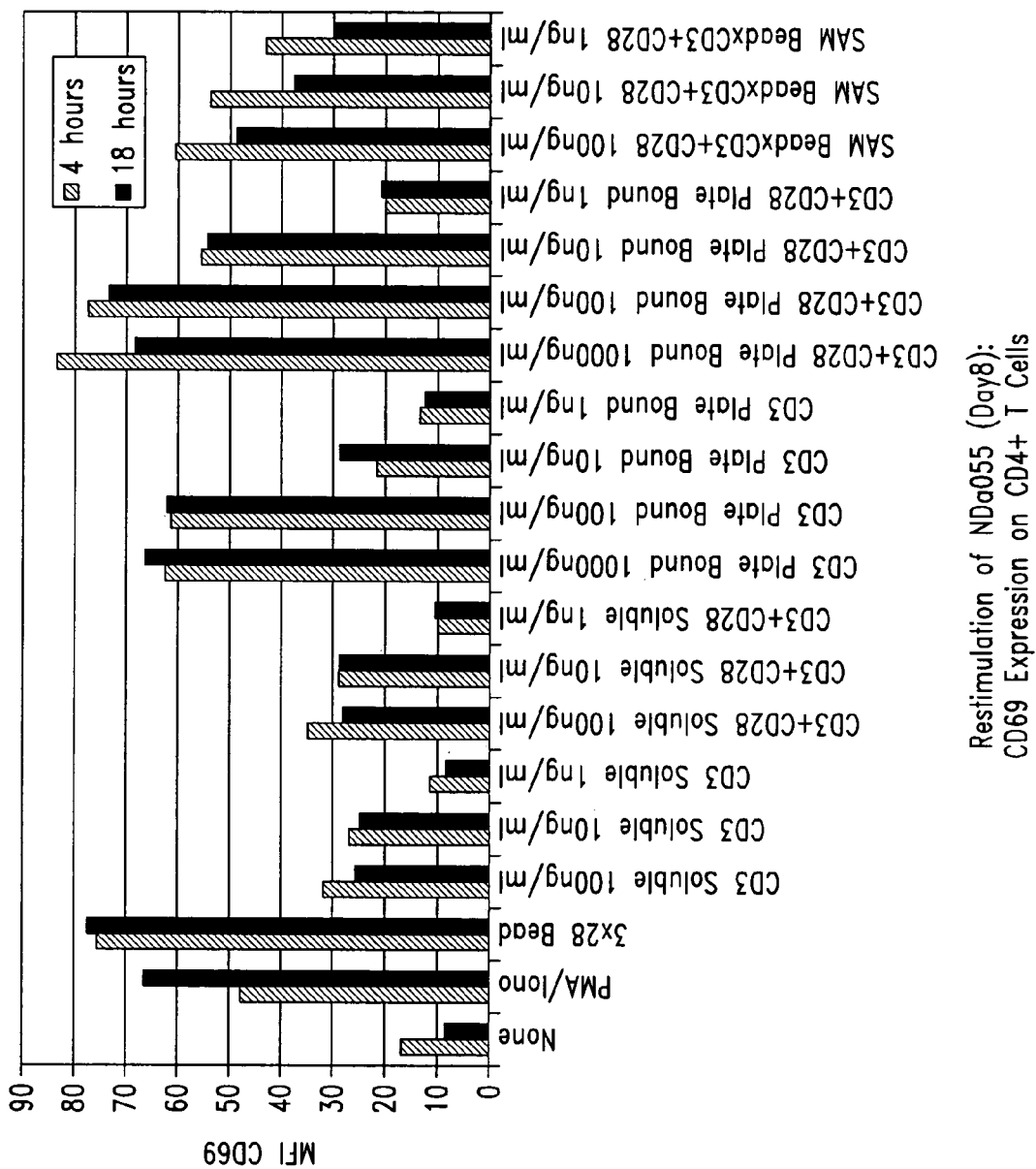
Figure 26E:
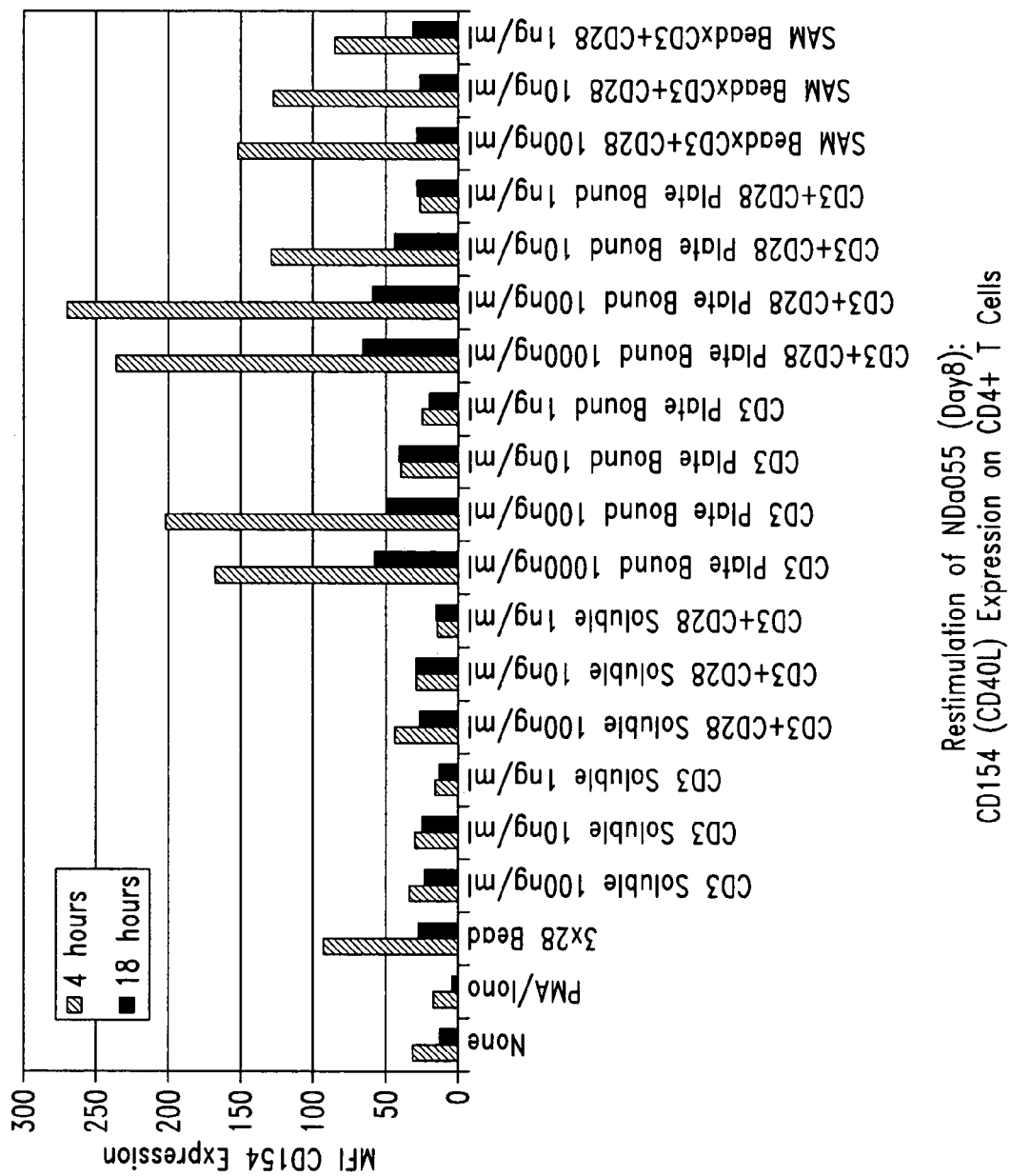
Figure 26G:
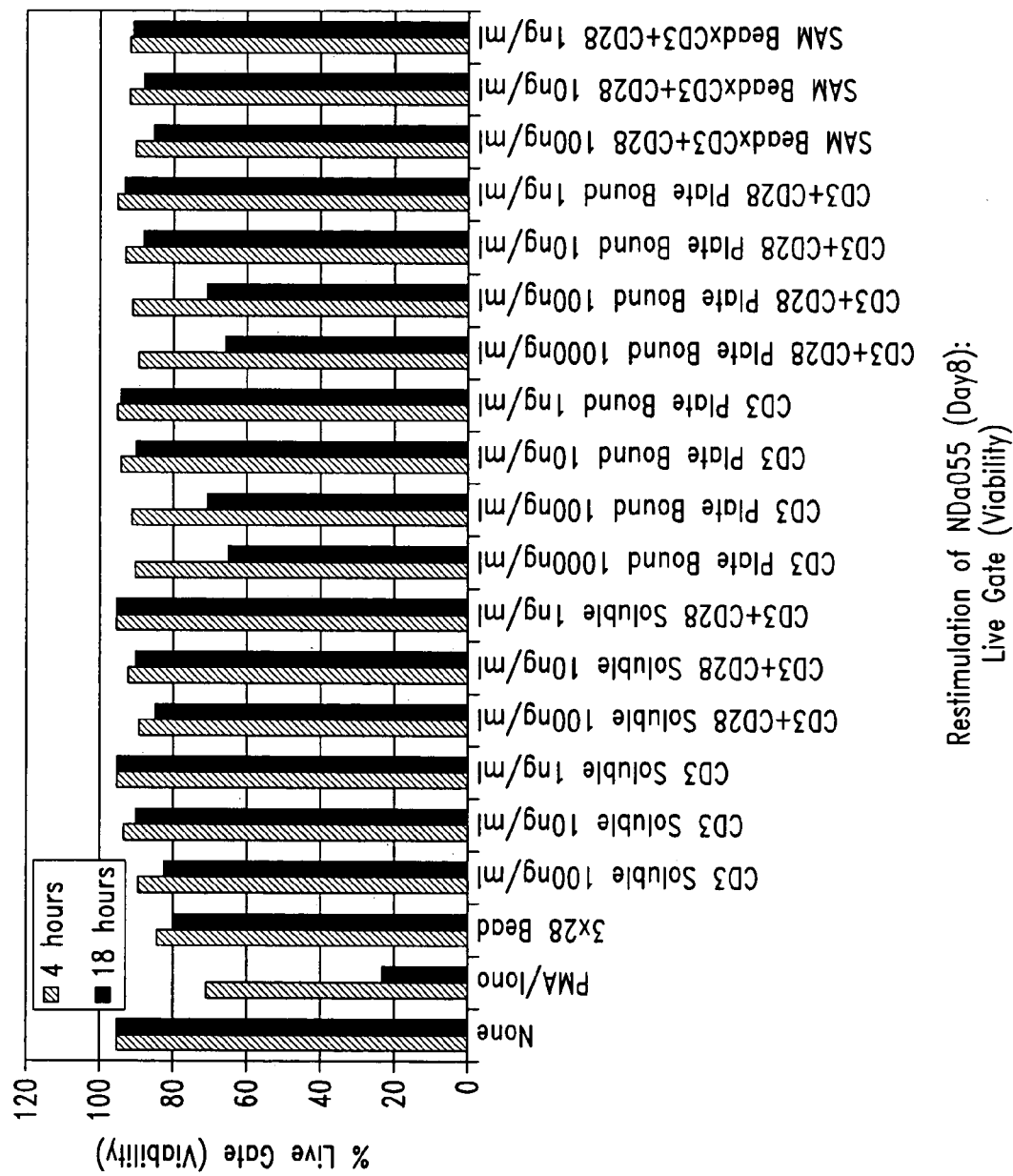
Figure 26H:
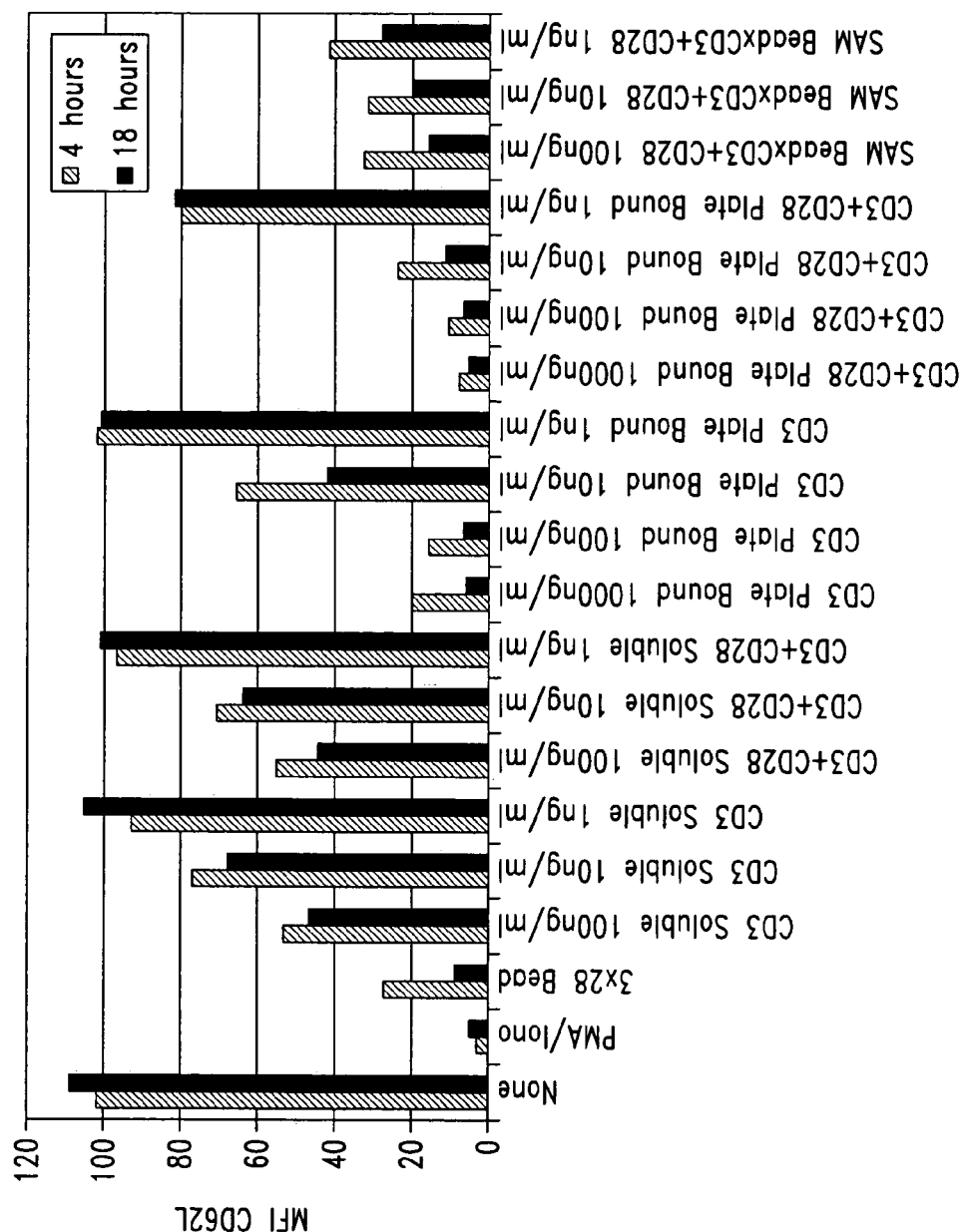
Figure 26I:
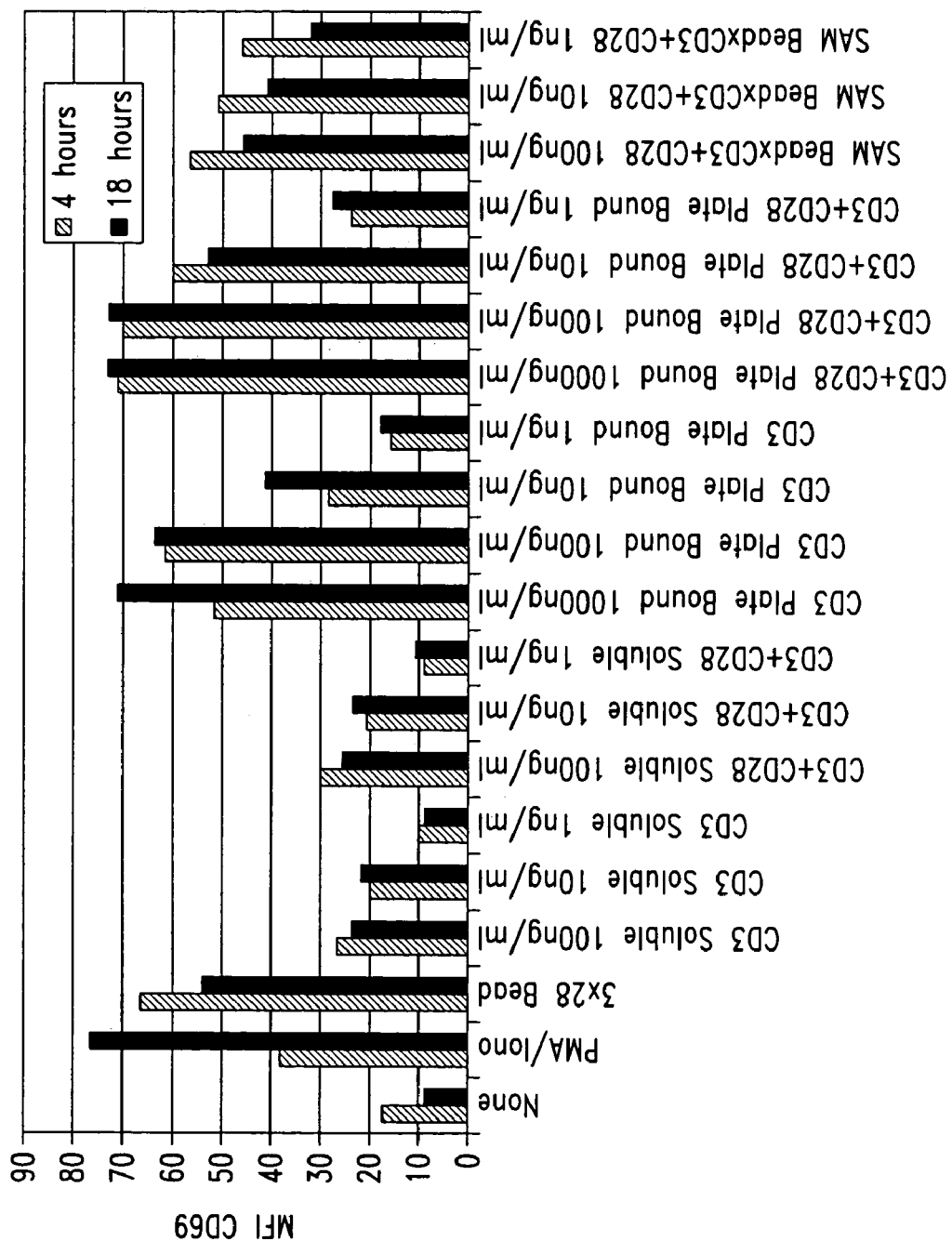
Figure 26J:
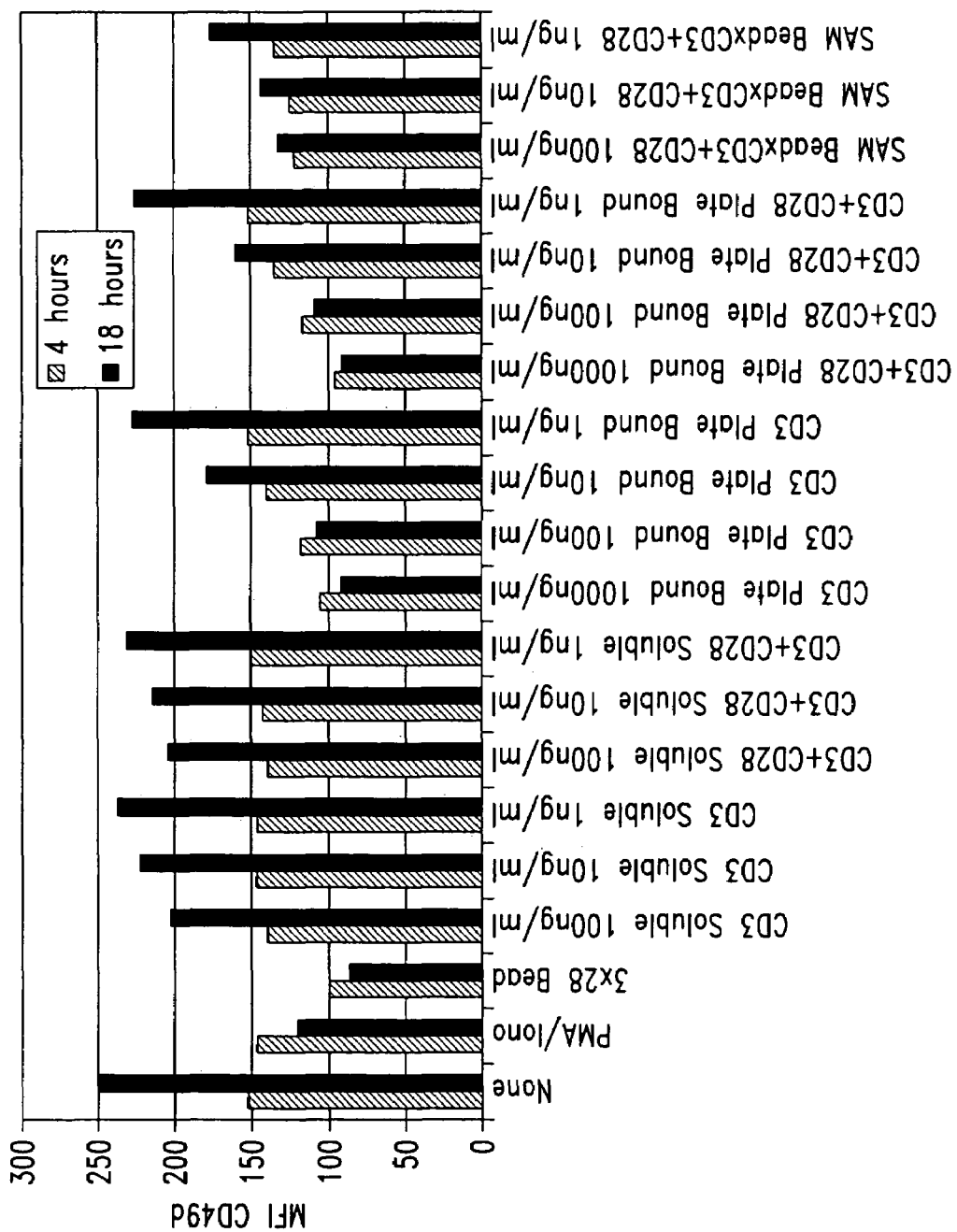
Figure 26K:
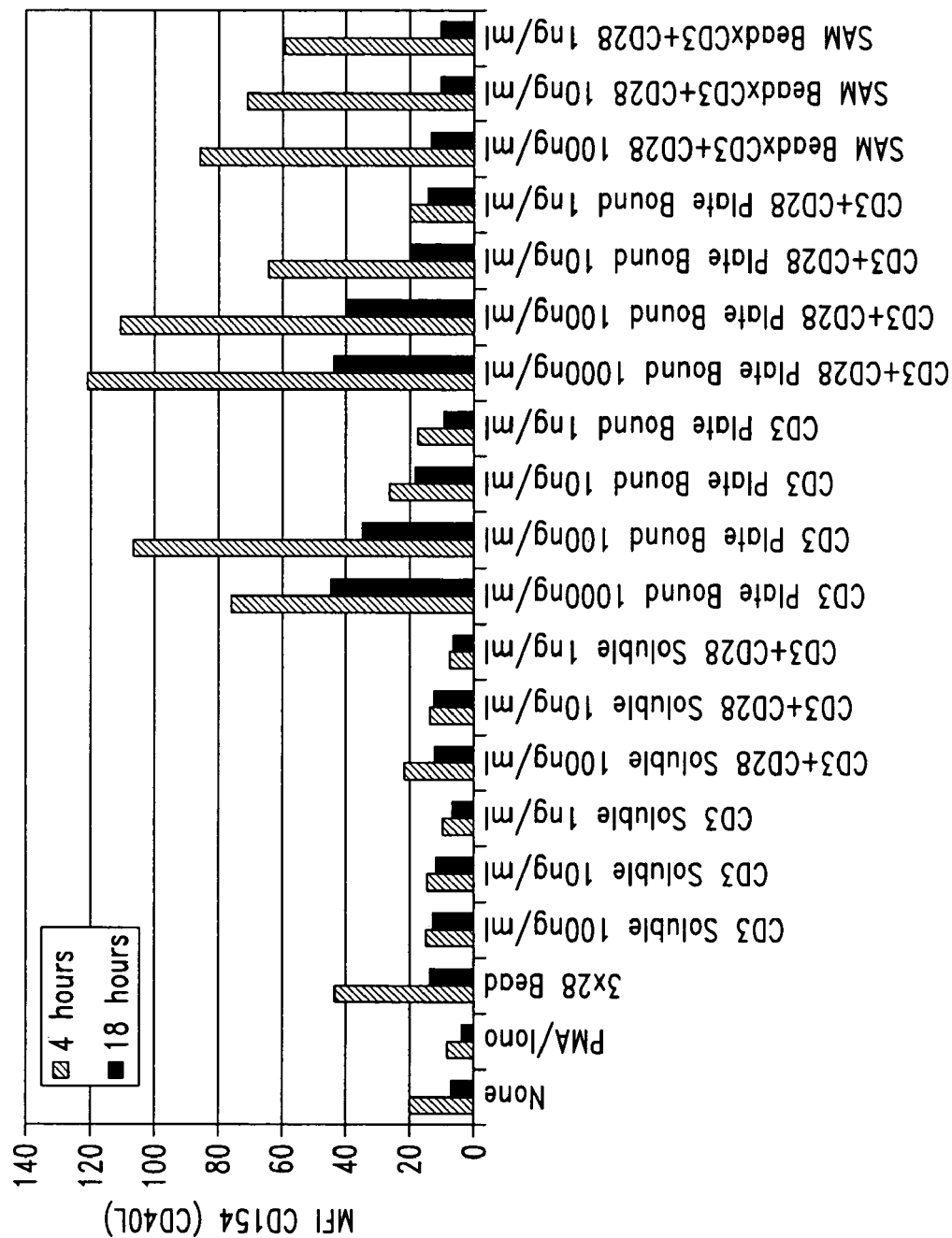
Figure 26L:
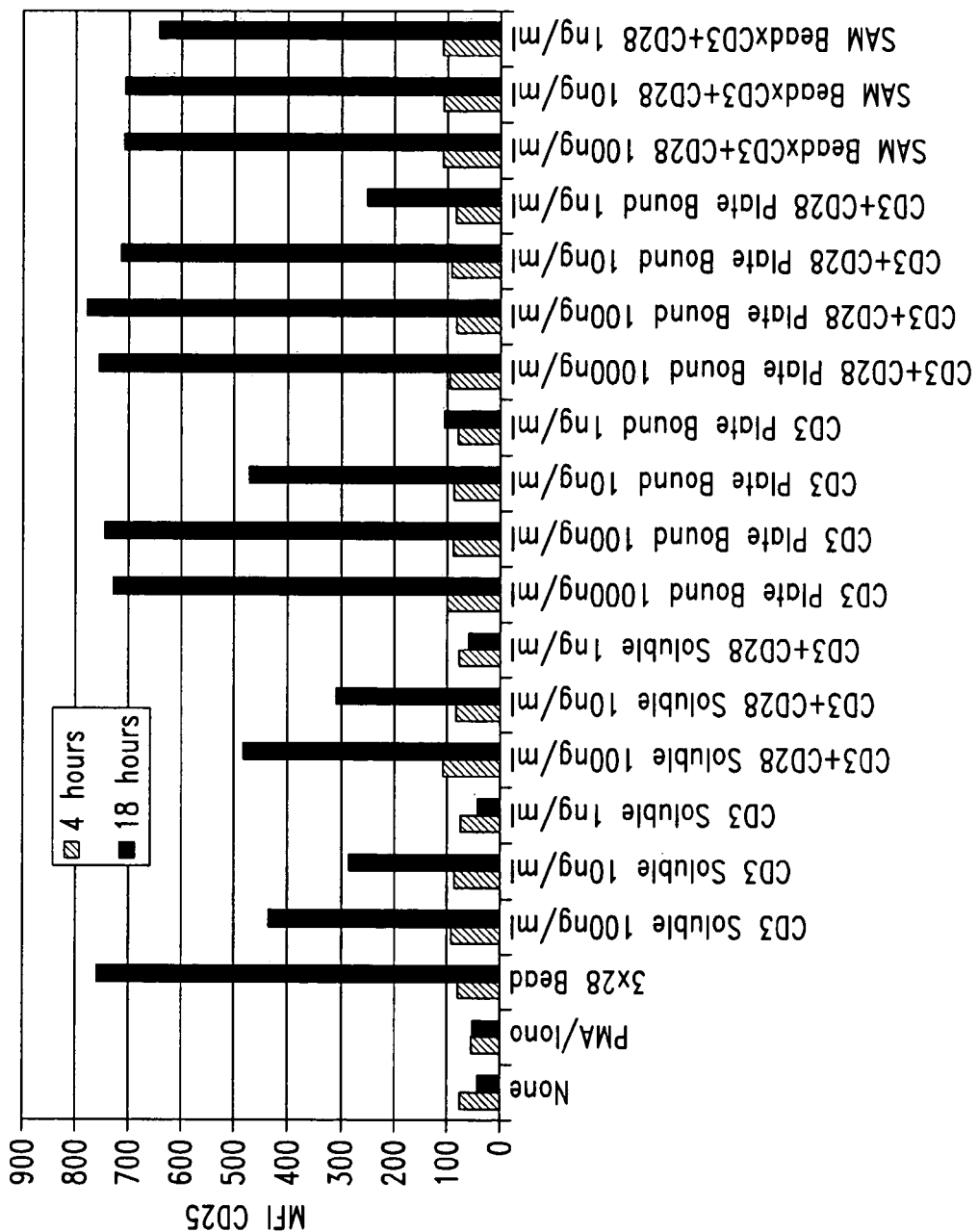

When 3×28-stimulated T cells became more quiescent (low CD25, low forward scatter), they were re-stimulated as shown below:
1) No stimulation
2) PHA 2 ug/ml
3) 3×28 (Xcellerate) bead stimulation at 1 bead/CD3+ T cell A kinetic analysis of cell size (forward scatter), surface phenotype, activation marker expression, and cytokine secretion was then performed. FIG. 12 shows forward scatter (cell size) kinetics following primary and secondary stimulation. FIG. 13 shows CD25 (IL-2-Receptor) expression kinetics following primary and secondary stimulation. FIG. 16 shows CD54 (I-CAM) expression following secondary stimulation, on CD4+ T cells (A) and on CD8+ T cells (B), where the primary stimulation was either PHA or 3×28 beads, and re-stimulation was either: none, PHA, or 3×28 beads. Markers delineating between CD4 and CD8 positive cells were also used to determine their relative proportion during 3×28 antibody bead activation (FIGS. 19 and 22).

Example XII

Analysis of Cytokine Expression Patterns of Co-Stimulated T Cells

The role of a variety of cytokines, including IL-2, IFN-γ, TNF-α, and IL-4 have been extensively studied as they relate to T cell maintenance, expansion, and differentiation. Notably, IL-2 has been shown to be supportive of T cell maintenance and expansion. IFN-γ has been implicated in driving T cells to differentiate into $T_{H1}$-type immune responder, while IL-4 has been implicated for driving T cells to $T_{H2}$-type responses. Cytokine release levels in primary human T cells activated by either PHA or 3×28 beads were analyzed by stimulating T cells as in Example IX, including kinetic studies of responses to primary stimulation and responses to a secondary stimulus. The data are shown in FIGS. 18A-C and FIGS. 23-24 demonstrate a unique feature of 3×28 bead stimulation. Between day 2 and day 4 following initial stimulation (day one was not assessed), extremely high levels of both IL-2 and IFN-γ were observed. A nearly 5-fold increase in absolute secreted IL-2 levels was seen for 3×28 bead-stimulated T cells as compared to levels observed for cells stimulated with PHA. An approximate 7-fold increase in IFNγ levels was also observed in 3×28 stimulated T cells as compared to their PHA counterparts. In the case of IL-4, the increase was not as dramatic for primary stimulation. Interestingly, and of possibly great significance, is that after cells became quiescent (no longer dividing or secreting the three cytokines mentioned above) following primary stimulation, they were re-stimulated with either 3×28 beads, PHA, or left un-stimulated. T cells which had received an initial activation/expansion signal through 3×28 beads secreted even higher levels of IFN-γ than observed following primary stimulation. In contrast, cells that were initially stimulated with PHA secreted IFN-γ levels much lower than seen for their 3×28 counterparts. Similar difference were also observed for IL-4 levels.

These data suggest that cells obtained following activation/expansion mediated through 3×28 beads are functionally different than those obtained from other means of expansion, such as PHA. The resultant cells appear to have an altered cytokine secretion response, one that promotes very high levels of both $T_{H1}$ and $T_{H2}$ cytokines, with a possible favoring of the $T_{H1}$-type profile (IFN-γ). Secretion of such high levels of these cytokines in culture can have many effects, including: driving T cells into a $T_{H1}$ differentiation pathway, which is one that favors anti-tumor and anti-viral responses; and also by altering the basic functionality of resultant T cells (such as lowering threshold of activation and inhibiting programmed cell death pathways).

Example XIII

Analysis of CD54 Expression of Co-Stimulated T Cells

FIG. 16 shows CD54 (I-CAM) expression following secondary stimulation, on CD4+ T cells (A) and on CD8+ T cells (B), where the primary stimulation was either PHA or 3×28 beads, and re-stimulation was either: none, PHA, or 3×28 beads.

Example XIV

Short Term Activation Marker Assays

Marker expression was monitored over various times following stimulation of T cells as set forth in Example IX. In this regard cells are labeled with anti-human CD4 (Immunotech, Fullerton, Calif.), FITC-coupled anti-human CD11a (Pharmingen), FITC-coupled anti-human CD26 (Pharmingen), FITC-coupled anti-human CD49d (Coulter), FITC-coupled anti-human CD54 (Pharmingen and Becton Dickinson), FITC-coupled anti-human CD95 (Pharmingen), FITC-coupled anti-human CD134 (Pharmingen), FITC-coupled anti-human CD25 Ab (Becton Dickinson, Fullerton, Calif.), FITC-coupled anti-human CD69 Ab (Becton Dickinson), FITC- or PE-coupled anti-human CD154 Ab (Becton Dickinson), or FITC-or PE-coupled IgG1 isotype control Ab. Cells, $2 \times 10^5$ are labeled for 20 minutes at 4° C. with 2 µl of each antibody in a final volume of 30 µl, washed and resuspended in 1% paraformaldehyde (Sigma, St. Louis, Mo.). See FIGS. 21-22, and 26A-26L, as is demonstrated by these figures there appear significant differences over activation time as well as between CD4+ and CD8+ cells.

Example XV

T Cell Expansion Using Varying CD3:CD28 Ratios

Figure 27:
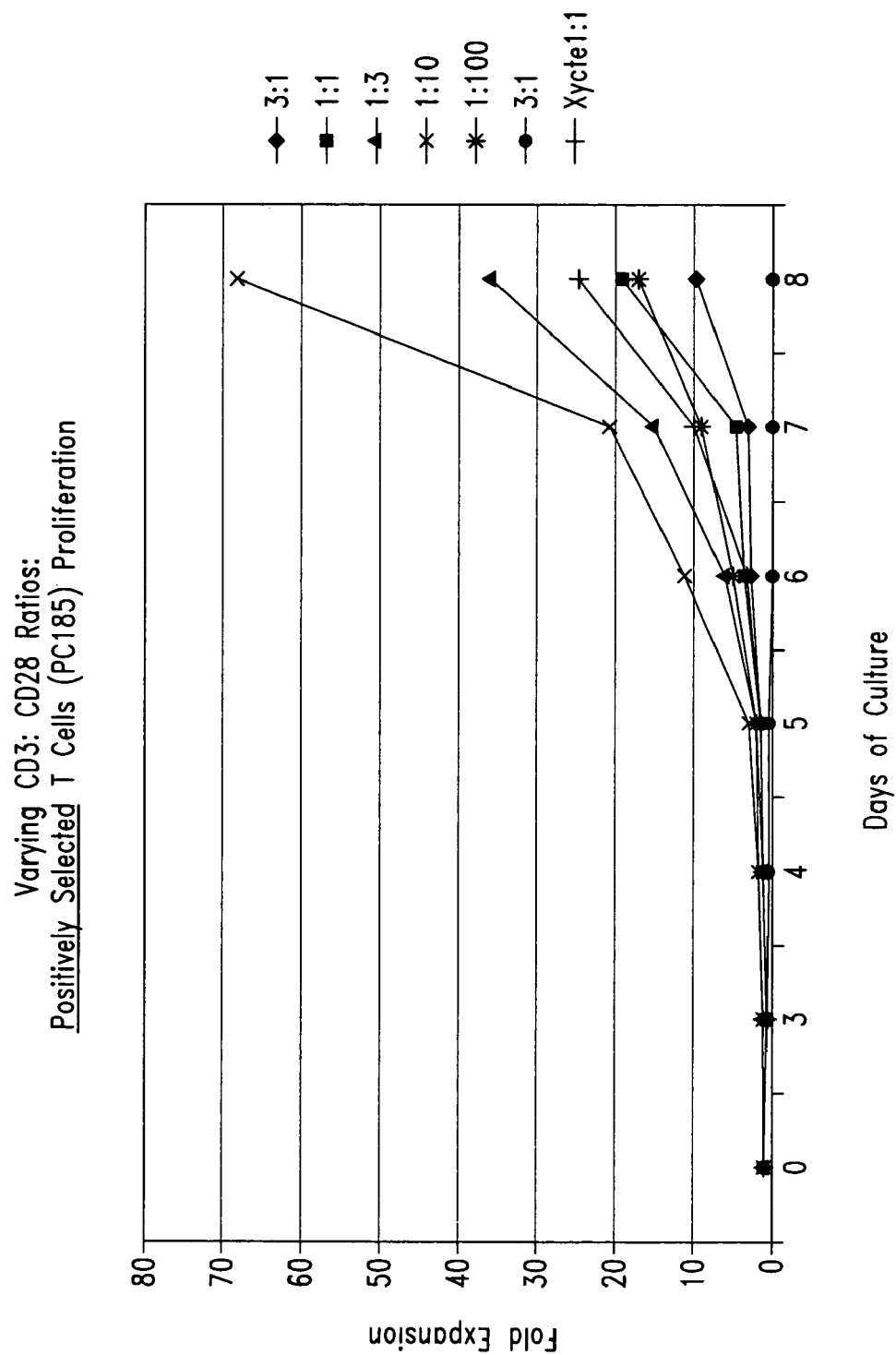
FIG. 27 is a graph depicting the fold increase of T cells over time following stimulation with anti-CD3 and anti-CD28 co-immobilized beads with varying ratios of CD3:CD28.

T cell expansion was evaluated using varying concentrations of CD3:CD28 ratios on the 3×28 DYNABEADS® M-450. In the experiments described herein, the process referred to as XCELLERATE II™ was used, as described in Example I. As shown in FIG. 27, surprisingly, about a 68-fold expansion after 8 days of culture was observed with a CD3:CD28 ratio of 1:10 on the beads. A 35-fold expansion of T cells was seen after 8 days of culture with a CD3:CD28 ratio of 1:3 on the beads. At a 1:1 ratio, about a 24-fold expansion was seen.

Example XVI

T Cell Expansion Using Varying Bead:T Cell Ratios for Positive Selection Followed by Varying Amounts of Sequential Addition of Beads This example describes modifications to the EXCELLERATE II™ process (see Example I) to determine the most effective bead:T cell ratios for positive selection and for optimal T cell expansion through the first 10 days of stimulation.

In the first experiment, comparisons were made of cells positively selected with a 1:1 ratio of 3×28 beads:cells and stimulated with varying ratios of sequentially added 3×28 beads in the first 10 days of stimulation. Cells were positively selected with 3×28 DYNABEADS® M-450 at bead:T cell ratios of 3:1 and 1:1. For the 3:1 ratio, $20 \times 10^6$ cells (assuming 50-60% T cells) were isolated and resuspended in 1 ml PBS+ 5% human serum. $30 \times 10^6$ washed beads were added for a total volume of 2 mls. For the 1:1 ratio, $10 \times 10^6$ washed beads were added to the $10 \times 10^6$ total cells. The cells were cultured in T-25 flasks and on day 3, counted and split into 6-well plates in 5 ml volume. On day 5, all wells were split to $1.25 \times 10^6$ cells/well. On days 3, 4, and 6-9, all wells were split to $2.5 \times 10^6$ cells/well. 3×28 beads were then sequentially added to those cells positively selected at 1:1 ratio beads: cells. As summarized in Table 7, cell yields on day 10 were highest with sequential addition of beads on days 3, 4, and 5 at a final ratio of 0.2:1.

TABLE 7

Cell Yield on Day 10 Following Varying Sequential 3 × 28 Bead Addition

| Positive Selection Ratio (beads:cells) | Ratio of Sequentially Added Beads (beads:cells) | Cell Yield × 10⁶ on Day 10 |
|---|---|---|
| 3:1 Selection | None | 4,300 |
| 1:1 Selection | None | 2,600 |

TABLE 7-continued

Cell Yield on Day 10 Following Varying Sequential 3 × 28 Bead Addition

| Positive Selection Ratio (beads:cells) | Ratio of Sequentially Added Beads (beads:cells) | Cell Yield × 10⁶ on Day 10 |
|---|---|---|
| 1:1 Selection | 0.33:1 on D1 &2 | 6,700 |
| 1:1 Selection | 0.2:1 on D1 &2 | 4,000 |
| 1:1 Selection | 0.2:1 on D1-5 | 9,600 |
| 1:1 Selection | 0.2:1 on D3-5 | 11,400 |

In a second experiment, positive selection times were varied from 0.5-1.0 hour and the bead:cell ratios varied from 3:1 to 1:1. As summarized in Table 8, the highest cell yield at day 10 was obtained with a 1:1 bead:cell ratio selection for 60 minutes and sequential addition of beads at 0.2:1 ratio on days 3 and 5. It should be noted however, that selecting with a bead:cell ratio of 3:1 for 30 minutes gave the highest positive selection yields.

TABLE 8

Cell Yield on Day 10 Following Varying Positive Selection Ratios, Times, and Sequential 3 × 28 Bead Addition

| Positive Selection Bead:Cell Ratio | Positive Selection Time | Ratio of Sequentially Added Beads (Beads:Cells) | Cell Yield × 10⁶ on Day 10 |
|---|---|---|---|
| 3:1 | 30 minutes | 0.2:1 on D3 | 5,100 |
| 1:1 | 30 minutes | None | 3,300 |
| 1:1 | 30 minutes | 0.2:1 on D3 | 4,400 |
| 1:1 | 30 minutes | 0.2:1 on D3 &D5 | 5,700 |
| 1:1 | 30 minutes | 0.2:1 on D3, 4, &5 | 6,700 |
| 1:1 | 60 minutes | None | 3,400 |
| 1:1 | 60 minutes | 0.2:1 on D3 | 4,800 |
| 1:1 | 60 minutes | 0.2:1 on D3 &D5 | 9,000 |
| 1:1 | 60 minutes | 0.2:1 on D3, 4, &5 | 7,900 |

Example XVII

T Cell Expansion Using Xcellerate II and the Wave Bioreactor

This example describes the T cells expansion using the Xcellerate IIb process followed by seeding cells into the Wave Bioreactor.

Day 0 of the Xcellerate Process—On the first day of the Xcellerate process essentially as described in Example I, the required number of cryopreserved Cryocte™ containers from were removed from the storage freezer, thawed washed and filtered.

Day 0—A volume of cells containing approximately 0.5× 10⁹ CD3+ cells was then mixed with Dynabeads M-450 CD3/ CD28 T at a ratio of 3:1 Dynabeads M-450 CD3/CD28 T:CD3+ T cells and incubated with rotation. After the incubation, the CD3+ T cells were magnetically concentrated and simultaneously activated. The CD3+ T cells were then resuspended in complete medium in a Lifecell Cell Culture Bag. The bag containing the cells and beads was then placed in a patient-dedicated incubator (37° C., 5% $CO_2$).

On or around Day 3—The CD3+ cells were culture-expanded for ≅3 days at which point the contents of the single bag are split into 4 new Lifecell bags. The 4 bags were then returned to the patient-dedicated incubator (37° C., 5% $CO_2$).

On or around Day 5—The CD3+ cells were culture-expanded for ≅2 additional days at which point the contents of the culture bags were then seeded into a 20 L Wave Bioreactor containing a 10 L volume of media. The cells were then cultured at 37° C., 5% $CO_2$ with the wave motion at 15 rocks/minute and with perfusion at 1 ml/minute.

Figure 28:
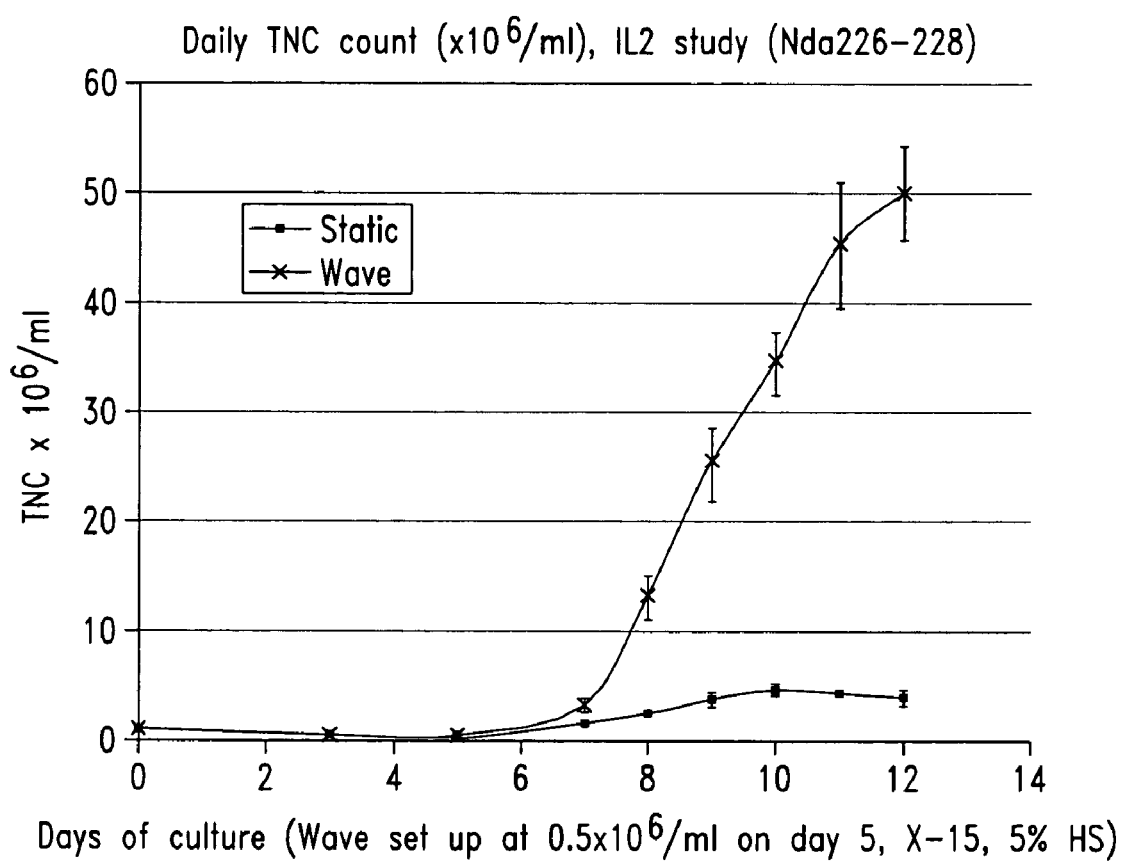
FIG. 28 is a graph comparing expansion of T cells in a static system to expansion of T cells in the Wave Bioreactor.

Cell counts were determined each day and compared to cells stimulated and expanded using the static Xcellerate II process. As shown in FIG. 28, expansion was dramatically improved when cells were cultured in The Wave Bioreactor. Further, cell densities reached as high as $50\times10^6$ cells/ml in The Wave Bioreactor, as compared to a maximum cell density of $5\times10^6$ observed in the static Xcellerate II process. A total cell count of about 800 billion was achieved at day 12 of culture from a starting cell count of about $0.5\times10^9$ cells using The Wave Bioreactor.

Thus, The Wave Bioreactor provides an unexpected and dramatic improvement to the expansion process. Furthermore, hitherto unobserved cell densities and final absolute cell yields were achieved using The Wave Bioreactor.

Example XVIII

Alternative Protocols for T Cell Expansion Using the Wave Bioreactor

Alternative T cell stimulation/activation and expansion strategies using The Wave Bioreactor, or comparable bioreactor systems, are developed to achieve high cell densities and high final cell yields.

In one strategy, cells are thawed and washed and positive selection is initiated as described in the Xcellerate II process. The positively selected cells are transferred to a 2 liter Wave bag on the Rocker platform. The volume is increased to 1 liter by introducing complete medium into the bag via the outlet tube. The bag is then incubated on the Wave platform, without rocking, at 37° C., 5% $CO_2$. On day 3, gentle rocking (5-10 rocks/minute) is initiated. On day 4-5, the contents are transferred to a 20 liter Wave bag, and the volume is increased to 4 liters. The fluid delivery system is set to increase the volume of the bag by 2 liters per day. On day 7 -8, perfusion is initiated at from about 0.5-3 mls/minute and the outlet pump is set to maintain the volume of the bag at 10 liters. On day 9 to day 12, cells are harvested: the fluid delivery system is disconnected and 5 liters of supernatant is removed through the outlet pump. The angular magnet is attached to the out-put line. The expanded cell product is allowed to flow out of the 20 liter bag into transfer packs. The de-beaded expanded cell product is processed and cryopreserved.

In an alternative strategy, cells are thawed and washed and positively selected as described in the Xcellerate II process but at twice the cell and bead concentration. The positively selected cells are transferred to a 20 liter Wave bag on the rocker platform. The volume is increased to 2 liter by introducing complete medium into the bag via the outlet tube. The bag is then incubated on the Wave platform, without rocking, at 37° C., 5% $CO_2$. On day 3, gentle rocking (5-10 rocks/minute) is initiated and the volume is increased to 6 liters. On day 4, the fluid delivery system is set to increase the volume of the bag by 2 liters per day. On day 6, perfusion is initiated at from about 0.5-3mls/minute and the outlet pump is set to maintain the volume of the bag at 10 liters. On day 9 to day 12, cells are harvested: the fluid delivery system is disconnected and 5 liters of supernatant is removed through the outlet pump. The angular magnet is attached to the out-put line. The expanded cell product is allowed to flow out of the 20 liter bag into transfer packs. The de-beaded expanded cell product is processed and cryopreserved.

Example XIX

Varying Bead:Cell Ratios can Selectively Expand or Delete Memory CD8 T Cells

This example shows that the bead:cell ratio can have a profound effect on expansion of different populations of T cells. In particular, a high bead:cell ratio (3:1-10:1) tends to induce death in antigen-specific T cells while a lower bead:cell ratio (1:1-1:10) leads to expansion of antigen-specific T cells. Further, the data described below show that lower bead:cell ratios lead to improved cell expansion in polyclonal cell populations as well. Thus, this example shows that lower bead:cell ratios improve overall cell expansion.

Cells were prepared and stimulated using the XCELLERATE I™ process essentially as described in Example 1. Prior to plating and culturing, the monocyte-depleted cells were mixed by rotation for 30 minutes with varying amounts of beads as summarized below in Table 9. The beads used in this Example comprised the DYNABEADS® M-450 CD3/CD28 T with a 1:1 CD3:CD28 antibody ratio bound on the beads.

TABLE 9

Varying Bead:Cell Ratios can Selectively Expand or Delete Memory CD8 T cells

| Bead:Cell Ratio | Fold Increase | |
|---|---|---|
| | Polyclonal T cells | CMV Antigen-Specific T cells |
| 10:1 | 149 | 0 |
| 5:1 | 294 | 0 |
| 3:1 | 346 | 1.4 |
| 1:1 | 562 | 20.6 |
| 1:5 | 113 | 53 |
| 1:10 | 79 | 45.8 |

Figure 29:
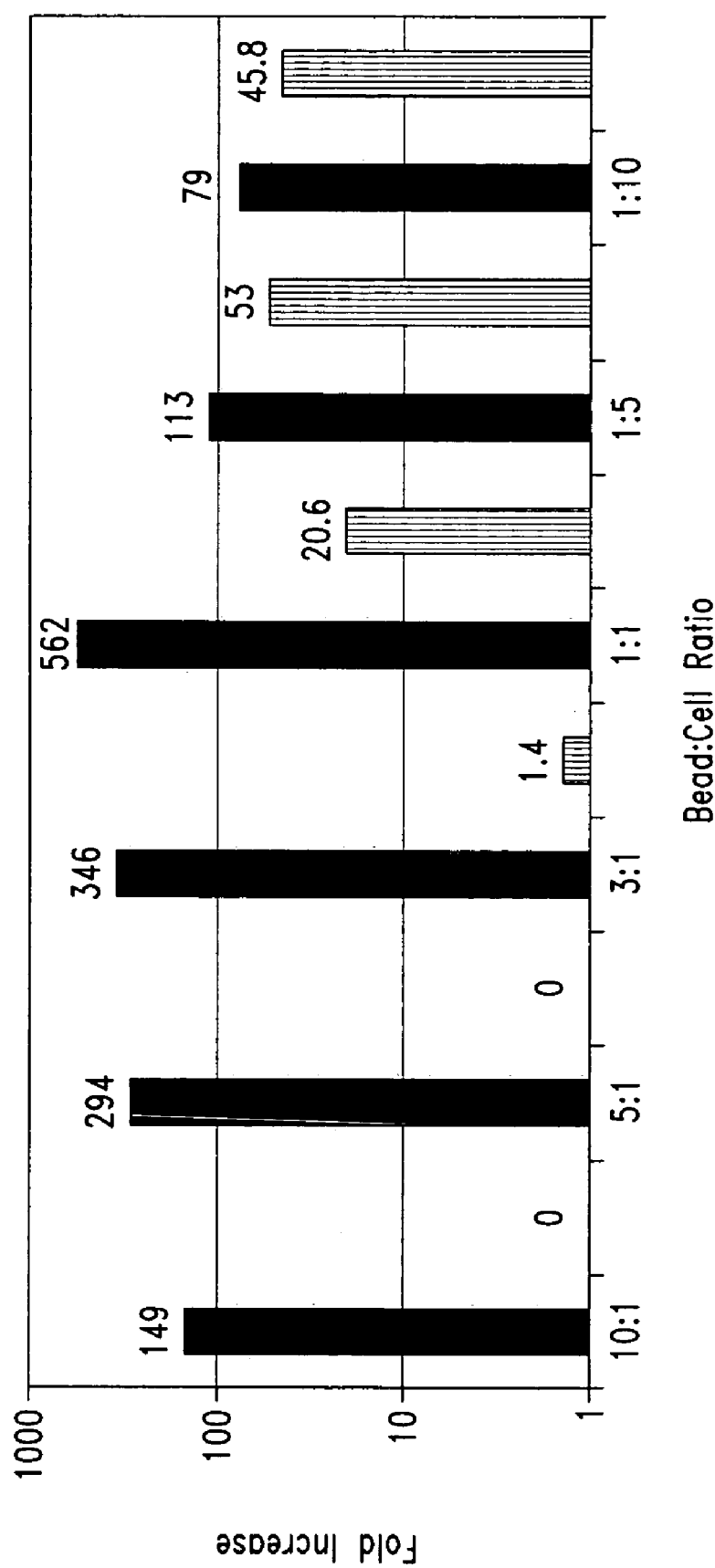
FIG. 29 is a graph comparing fold increase of polyclonal T cells to the fold increase of CMV pp65 A2-tetramer+(antigen-specific) T cells using varying bead:cell ratios. Solid bars represent polyclonal T cells. Striped bars represent CMV-specific T cells.

The results summarized in Table 9 and shown graphically in FIG. 29 demonstrate that antigen-specific T cells can be selectively deleted by using high bead:cell ratios and expanded using low bead:cell ratios. Without being bound by theory, it is thought that the antigen-specific T cells are sensitized to further stimulation. Stimulation with high bead:cell ratios provides a high concentration of stimulating antibody, leading to over-stimulation of antigen-specific T cells, causing them to die, either by apoptosis or other mechanisms. Using lower bead:cell ratios provides a stimulation signal to antigen-specific T cells that does not over-stimulate, but rather induces rapid proliferation of these cells. An increase in proliferation is also observed in the polyclonal population of T cells using lower bead:cell ratios. In particular, the results indicate that a bead:cell ratio of 1:1 is optimal for polyclonal T cell expansion.

Therefore, in this Example, evidence is provided to support the use of differing bead:cell ratios depending on the outcome desired. For expansion of antigen-specific T cells, a lower bead:cell ratio is preferable. A higher bead:cell ratio is preferred if deletion of antigen-specific T cells is the desired outcome.

Example XX

The XCELLERATE™ III Process

This example describes further qualification studies carried out using what is referred to as the XCELLERATE™ III process. This process is essentially as described in Examples XVII and XVIII. In brief, PBMC leukapheresis product is processed as described for the XCELLERATE™ II process.

However, the magnetically concentrated CD3+ T cells are transferred into a 20 L culture bag (such as a 20 L Cellbag™, Wave Biotech, Bridgewater, N.J.), on a rocking platform (such as the WaveBioreactor™ 20XE platform, Wave Biotech, Bridgewater, N.J.) in X-VIVO™ 15 (phenol red-free and gentamycin-free) media in the presence of recombinant IL-2. The T cells activate and expand at 37° C. over a 10-day period with rocking motion and perfusion. The Xcyte™ Dynabeads® are then removed and the XCELLERATED™ T cells are harvested, formulated and cryopreserved.

The XCELLERATE™ III Process was developed using PBMC apheresis products from healthy donors. During development and then qualification for use in GMP manufacturing operations, a comparison of the XCELLERATE™ III Process with the static XCELLERATE™ II Process with healthy donors was carried out. As shown in Table 10, the purity and viability of final XCELLERATED™ T Cell products produced by the different processes are very similar. However, the cell density achieved in the XCELLERATE™ III Process is 5-fold higher than that in the XCELLERATE™ II Process giving a yield of $188 \pm 50 \times 10^9$ XCELLERATED™ T Cells in a 10 L volume compared to $223.2 \pm 47.4 \times 10^9$ XCELLERATED™ T Cells in a 60 L volume. The high yield of XCELLERATED™ T Cells in a small volume with the XCELLERATE™ III Process enables a number of efficiencies including reduction of: (a) overall labor; (b) number of culture containers required from 60 to 1; (c) number of sterile connections and (d) process volume from 60 L to 10 L, while increasing: (a) final cell density $\geq$ 4-fold and (b) facility capacity 2-fold. In addition, there is also a significant reduction in the cost of goods.

Figure 30A:
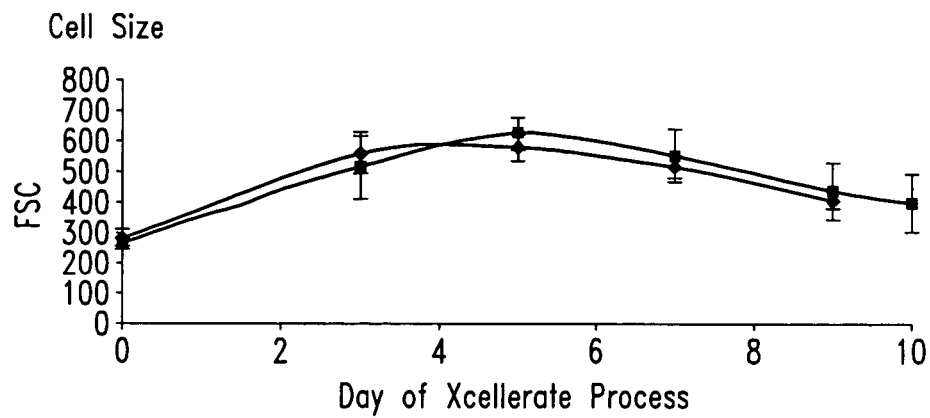
FIG. 30, panels a, b, and c is a graph showing the comparison of in-process T cell activation markers during the static XCELLERATE™ II process and the WaveBioreactor-based XCELLERATE™ III process.
Figure 30B:
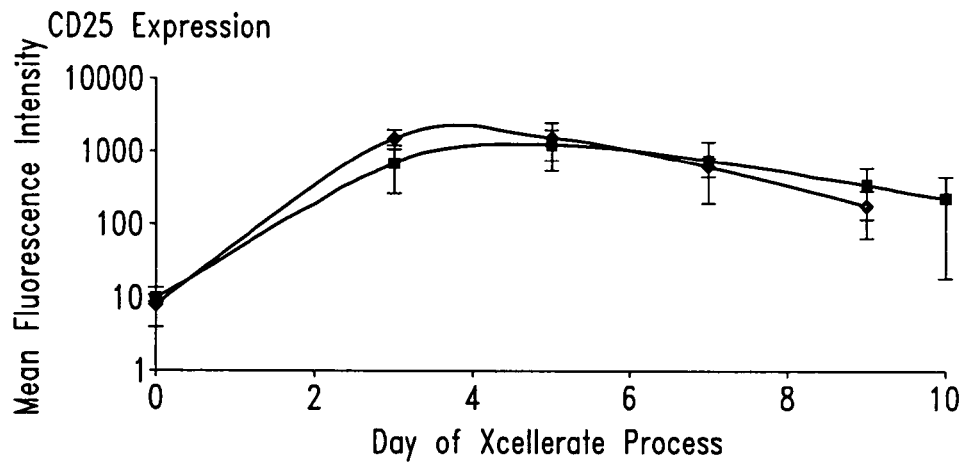
Figure 30C:
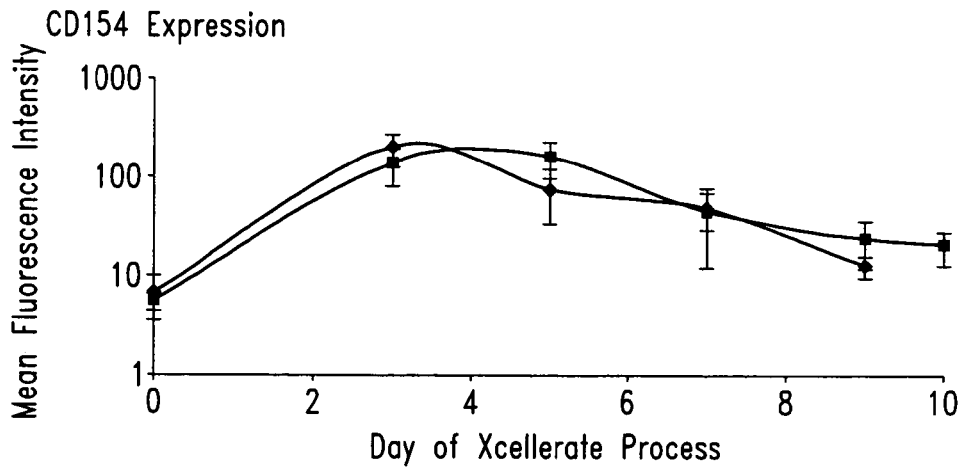
Figure 31A:
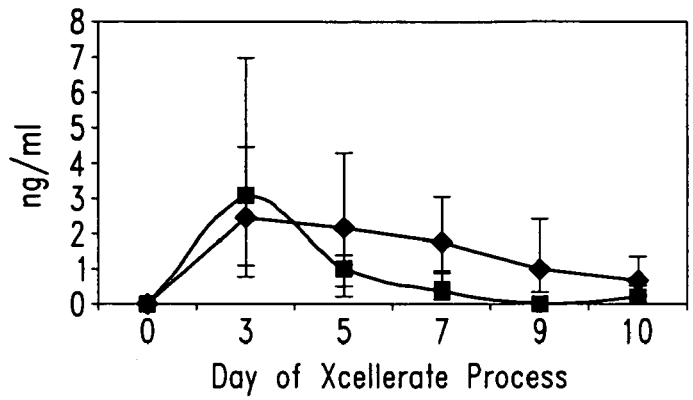
FIG. 31, panels a, b, and c is a graph showing the comparison of in-process soluble cytokine concentrations during the static XCELLERATE™ II process and the WaveBioreactor-based XCELLERATE™ III process.
Figure 31B:
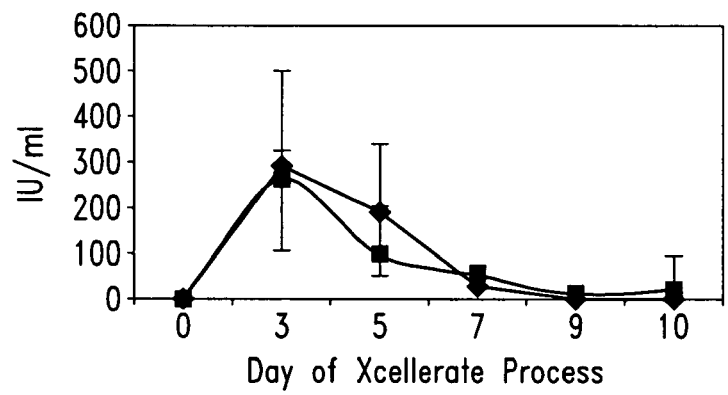
Figure 31C:
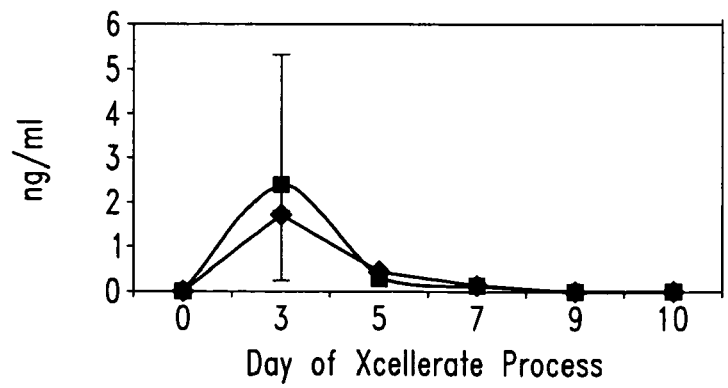
Figure 32A:
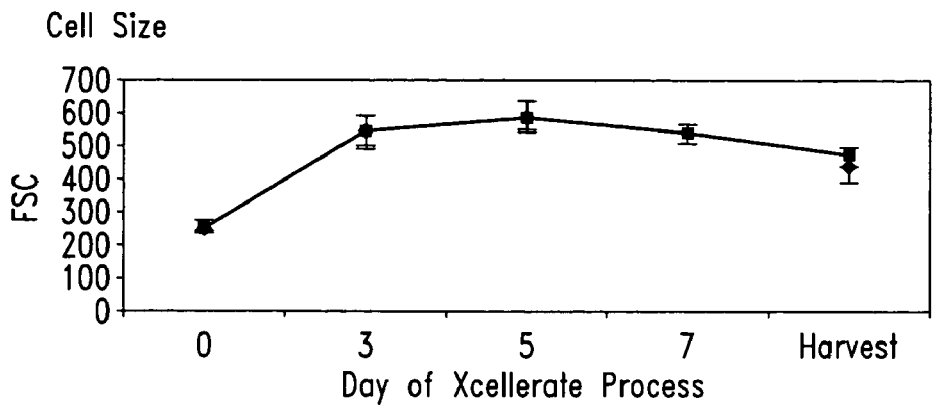
FIG. 32, panels a, b, and c is a graph showing the comparison of in-process T Cell activation during the manufacture of XCELLERATED™ T Cells for infusion into multiple myeloma patients using the static XCELLERATE™ II Process and the WaveBioreactor-based XCELLERATE™ III Process.
Figure 32B:
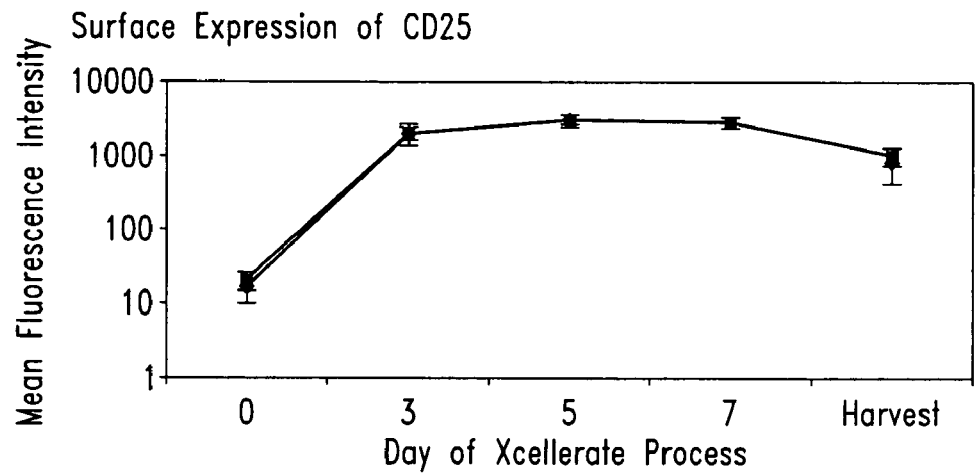
Figure 32C:
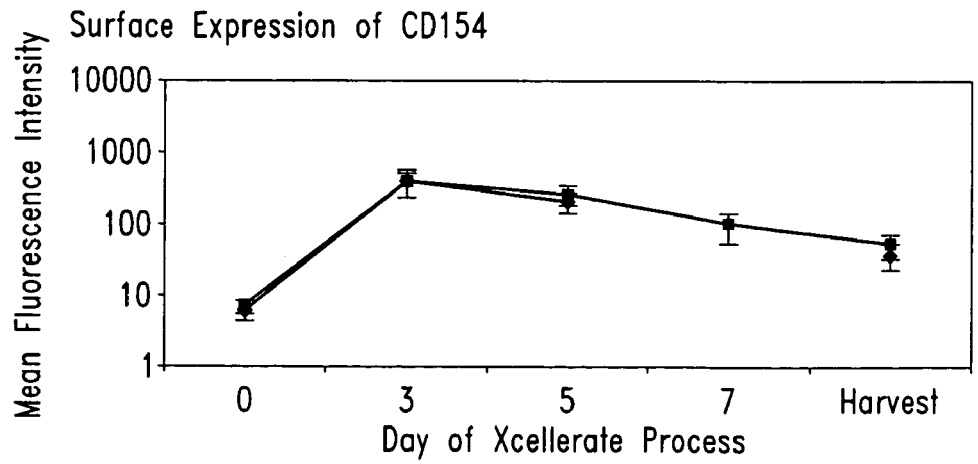
Figure 33A:
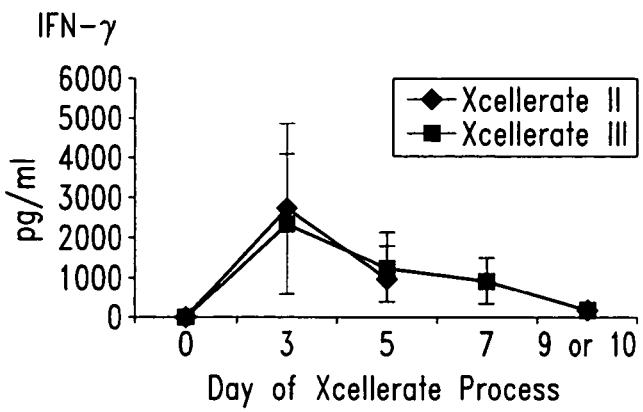
FIG. 33, panels a, b, and c, is a graph showing the comparison of in-process soluble cytokine concentrations during the manufacture of Xcellerated T Cells using the Xcellerate II Process and the Xcellerate III Process for the treatment of patients with multiple myeloma.
Figure 33B:
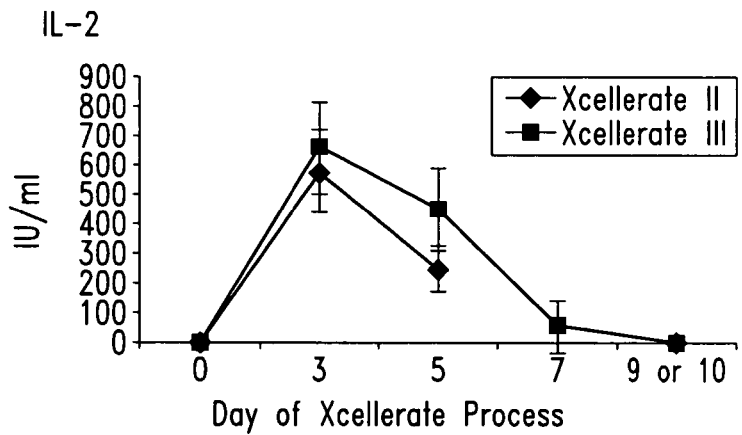
Figure 33C:
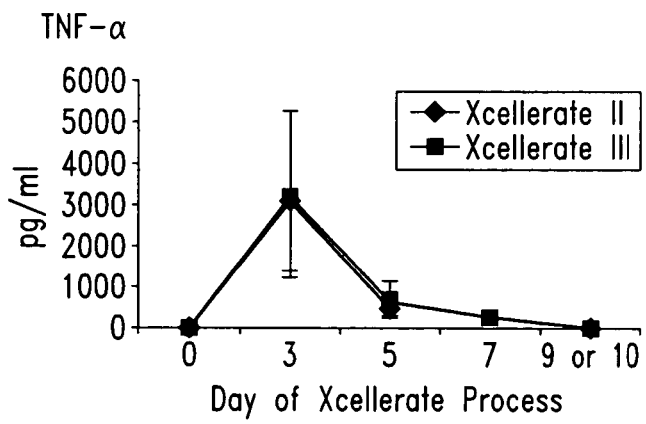

Upon activation in the ex vivo XCELLERATE™ Process, T cells undergo physical, biological and phenotypic changes that parallel those observed during the initial stimulation and activation of naive resting T cells in the lymph node. These characteristics provide useful in-process tools with which to monitor the activation of T cells during the ex vivo XCELLERATE™ Process. As shown in FIGS. 30 and 31 the activation of T cells in the XCELLERATE™ III Process is very similar to that in the XCELLERATE™ II Process as determined by cell size, CD25 expression, CD154 expression and cytokine expression. As shown in FIGS. 32 and 33, the in-process kinetics and magnitude of activation observed for multiple myeloma patients during GMP manufacture for clinical trials is essentially identical. In terms of final product composition, the purity, viability and ratio of CD4+ helper: CD8+ cytotoxic T cells is closely similar for XCELLERATED™ T Cells manufactured using the different processes.

Figure 34A:
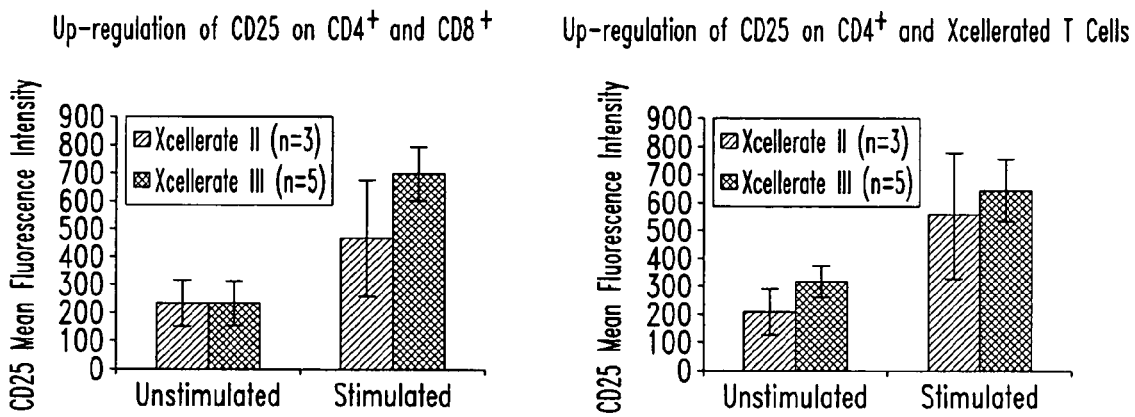
FIG. 34 panels a, b, and c, is a bar graph showing the comparison of the biological activity of Xcellerated T Cells manufactured using the static Xcellerate II Process (n=3) and the WaveBioreactor-based Xcellerate III process (n=5) following In Vitro re-stimulation.
Figure 34B:
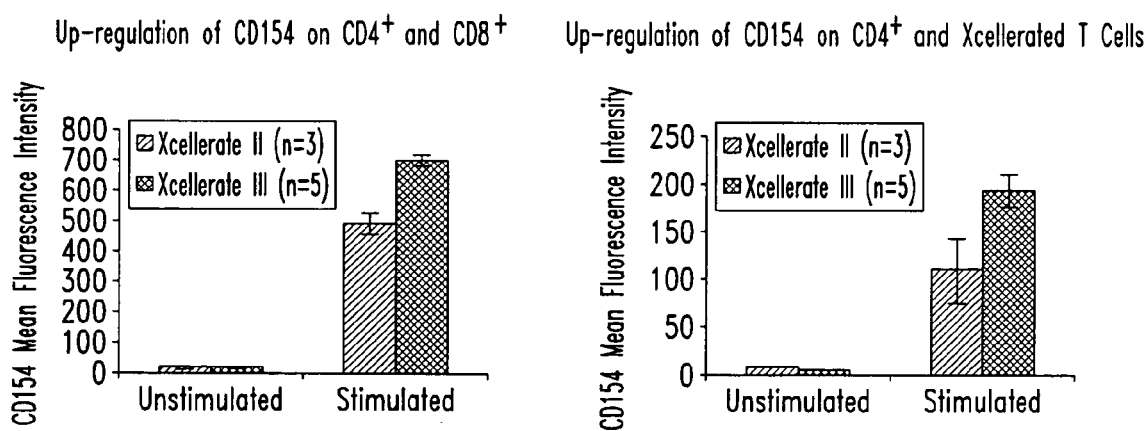
Figure 34C:
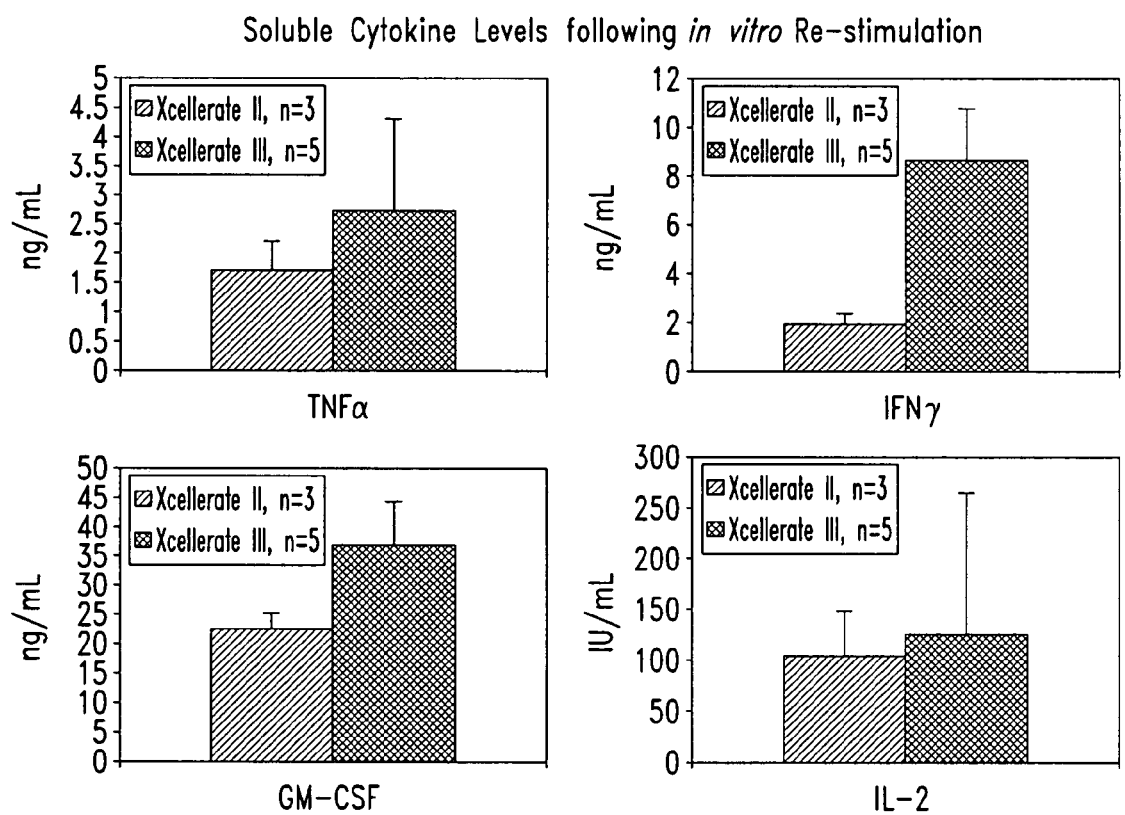
Figure 35:
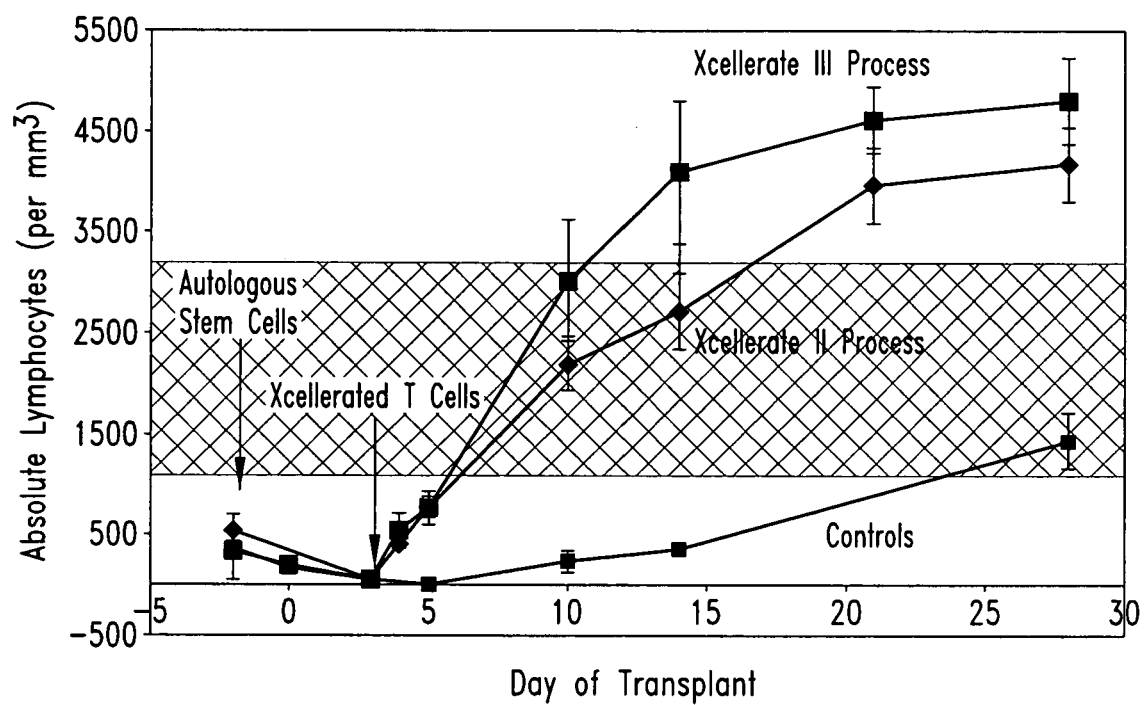
FIG. 35 is a graph showing lymphocyte recovery in multiple myeloma patients following high-dose chemotherapy, an autologous stem cell transplant with (Xcellerate II Process or Xcellerate III Process) or without (Control) a single infusion of Xcellerated T Cells.

Since re-stimulation of activated T cells is the natural biological event during an effective immune response, a re-stimulation assay was used to assess the in vitro biological activity of XCELLERATED™ T Cells. In this assay XCELLERATED™ T Cells were either re-stimulated with XR-CD3 & XR-CD28, or stimulated with Phorbol Myristate Acetate (PMA)/ionomycin, and the up-regulation of cytokine secretion, CD25 expression and CD154 expression was measured. The results in FIG. 34 indicate that, surprisingly, upon re-stimulation, XCELLERATED™ T Cells produced in the bioreactor-based XCELLERATE™ III Process exhibit higher levels of cytokine secretion, and greater CD154 and CD25 up-regulation/induction than those produced in the static XCELLERATE™ II Process. Additionally, the increase in the in vitro biological activity of XCELLERATED™ T Cells manufactured using the XCELLERATE™ III Process appears to correlate with increased in vivo biological effect following infusion into multiple myeloma patients (FIG. 35).

A decreased diversity of T cell receptors expressed on the surface of T cells is observed in the peripheral blood of patients in many diseases, including cancer (Peggs K S, et al. *Brit J Haematol* 2003: 120; 154-165.; Mariani S, et al., *Brit J Haematol*. 2001: 113; 1051-1059; Roux E, et al. *Blood* 2000: 96; 2299-2303.; Claret E J, et al., *J Clin Invest* 1997: 100; 855-866.; Kluin-Nelemans H C, et al., *Blood* 1998: 91; 4224-4231.; Eyrich M, et al.; *Blood* 2002: 100; 1915-1918.; Gorski J, et al.; *J Immunol* 1994: 152; 5109-5119.), human immunodeficiency virus (HIV) (Gorochov G, et al.; *Nature Med* 1998: 4; 215-221) and autoimmune diseases (Kuchroo V K, et al.; *Annu Rev Immunol* 2002: 20; 101-123.; Ria F, et al.; *Curr Mol Med* 2001: 1; 297-304.; Vergelli M, et al.; *J Neurosci Res* 2001: 66; 517-524.; Wong S, et al.; *Autoimmunity* 1994: 18; 77-83.). This decreased spectrum of T cell receptors narrows

TABLE 10

Comparison of the Yield, Purity, and Viability of XCELLERATED ™ T Cells Produced from the Static XCELLERATE ™ II Process and the WaveBioreactor-based XCELLERATE ™ III Process using Healthy Donors

| | | Pre-harvest XCELLERATED ™ T Cell Product Properties | | | | |
|---|---|---|---|---|---|---|
| | XCELLERATE ™ Process Configuration | Density of CD3+ T Cells ($\times 10^6$ mL) | Culture Volume | Yield of CD3+ T Cells ($\times 10^9$) | Purity of CD3+ T Cells (%) | Cell Viability (%) |
| Average ± Std Dev | XCELLERATE ™ II Healthy Donors (n = 12) | 3.7 ± 0.8 | 60 L | 223.2 ± 47.4 | 99.0 ± 2.0 | 97.0 ± 3.0 |
| | XCELLERATE ™ III Healthy Donors (n = 10) | 18.8 ± 5.0 | 10 L | 188 ± 50.2 | 100 ± 0.0 | 96.0 ± 2.0 |

XCELLERATED ™ T Cells were manufactured from healthy donor PBMC using either the XCELLERATE ™ II Process or the XCELLERATE ™ III Process (n = 10). Prior to harvest, cultures were evaluated for cell number, viability, and CD3+ T cell purity. CD3+ T cell density and yield were calculated from these values.

the ability of T cells to recognize a broad array of antigens, which may reduce a patient's ability to respond to and eliminate cancer and infectious diseases. The ability of the XCELLERATE™ Technology to broaden the diversity of the narrow T cell repertoire has previously been demonstrated in patients with chronic lymphocytic leukemia (CLL) (see for example, U.S. patent application Ser. No. 10/360,507). Both the XCELLERATE™ II Process and the XCELLERATE™ III Process restore a broad T cell receptor repertoire from the narrow skewed pattern that is characteristic of the starting PBMC for almost all of the multiple myeloma patients processed to date for this clinical trial.

To date, the infusion of XCELLERATED™ T Cells manufactured with either process into patients with multiple myeloma has been well tolerated with no serious adverse events or toxicity. Previous clinical studies have shown that the recovery of peripheral blood lymphocyte counts to $\geq 500/mm^3$ on or before day 14 following high-dose chemotherapy and an autologous stem cell transplant (with no T cell infusion) correlates with increased survival. As shown in FIG. 35, infusion of XCELLERATED™ T Cells leads to a very rapid recovery of peripheral blood lymphocytes to $>500/mm^3$ by day 4-5 following chemotherapy and autologous stem cell transplant (day 1-2 following infusion of the XCELLERATED™ T Cells) that is sustained for an extended period.

Surprisingly, the data in FIG. 35 show that the recovery of peripheral blood lymphocyte counts is in fact faster following infusion of XCELLERATED™ T Cells manufactured using the XCELLERATE™ III Process (n=10 patients infused to date) compared to those manufactured using the XCELLERATE™ II Process (n=18 patients infused). These data correlate with the higher in vitro biological activity observed for healthy donors during the development and qualification of the XCELLERATE™ III Process and suggest that XCELLERATED™ T Cells manufactured using the WaveBioreactor™ may have improved biological activity.

All of the above U.S. patents, U.S. patent application publications, U.S. patent applications, foreign patents, foreign patent applications and non-patent publications referred to in this specification and/or listed in the Application Data Sheet, including but not limited to U.S. patent application Ser. No. 09/960,264, filed Sep. 20, 2001; which is a continuation-in-part of U.S. application Ser. No. 09/794,230, filed Feb. 26, 2001; which claims the benefit of Provisional Application Nos. 60/184,788, filed Feb. 24, 2000, and 60/249,902, filed Nov. 17, 2000, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims. All of references, patents, patent applications, etc. cited above, are incorporated herein in their entirety. Further, all numerical ranges recited herein explicitly include all integer values within the range.

What is claimed is:

1. A method for activating and expanding a population of regulatory T cells by simultaneous T cell concentration and cell surface moiety ligation, comprising:
    a. contacting a population of cells wherein at least a portion thereof comprises regulatory T cells with a surface, wherein said surface is a surface of a paramagnetic particle and wherein said surface has attached thereto a first agent that ligates a first T cell surface moiety of a regulatory T cell, and the same surface has attached thereto a second agent that ligates a second moiety of said regulatory T cell; and
    b. applying a magnetic force that predominantly drives T cell concentration and T cell surface moiety ligation;
    thereby inducing activation and expansion of said regulatory T cell.

2. The method according to claim 1 wherein the first agent is an anti-CD3 antibody or an antigen-binding fragment thereof and the second agent is an anti-CD28 antibody or an antigen-binding fragment thereof.

* * * * *